(12) United States Patent
Edelman

(10) Patent No.: US 11,845,924 B1
(45) Date of Patent: Dec. 19, 2023

(54) METHODS OF PREPARING NUCLEIC ACID SAMPLES FOR SEQUENCING

(71) Applicant: CS GENETICS LIMITED, Cambridge (GB)

(72) Inventor: Lucas Brandon Edelman, Cambridge (GB)

(73) Assignee: CS Genetics Limited, Cambridge (GB)

(*) Notice: Subject to any disclaimer, the term of this patent is extended or adjusted under 35 U.S.C. 154(b) by 0 days.

(21) Appl. No.: 18/185,904

(22) Filed: Mar. 17, 2023

Related U.S. Application Data

(63) Continuation of application No. 16/471,941, filed as application No. PCT/GB2017/053816 on Dec. 19, 2017.

(30) Foreign Application Priority Data

Dec. 23, 2016 (GB) .................. 1622222.6

(51) Int. Cl.
C12N 15/10 (2006.01)
C12Q 1/6806 (2018.01)
C12Q 1/6869 (2018.01)

(52) U.S. Cl.
CPC ....... C12N 15/1065 (2013.01); C12Q 1/6806 (2013.01); C12Q 1/6869 (2013.01)

(58) Field of Classification Search
None
See application file for complete search history.

(56) References Cited

U.S. PATENT DOCUMENTS

| | | |
|---|---|---|
| 10,011,872 B1 | 7/2018 | Beigrader et al. |
| 2006/0040286 A1 | 2/2006 | Mirkin et al. |
| 2007/0054288 A1 | 3/2007 | Su et al. |
| 2012/0220494 A1 | 8/2012 | Samuels et al. |
| 2015/0337298 A1 | 11/2015 | Xi et al. |
| 2015/0376609 A1 | 12/2015 | Hindson et al. |
| 2016/0010078 A1 | 1/2016 | Shirai et al. |
| 2016/0046985 A1 | 2/2016 | Drmanac et al. |
| 2016/0138011 A1 | 5/2016 | Dewitt et al. |
| 2016/0289740 A1 | 10/2016 | Fu et al. |
| 2019/0316182 A1* | 10/2019 | Edelman .............. C12Q 1/6806 |

FOREIGN PATENT DOCUMENTS

| | | |
|---|---|---|
| WO | WO 2005001113 | 1/2005 |
| WO | WO 2012087736 | 6/2012 |
| WO | WO 2014071361 | 5/2014 |
| WO | WO 2015073693 | 5/2015 |
| WO | WO 2015091207 | 6/2015 |
| WO | WO 2016100976 | 6/2016 |
| WO | WO 2016145416 | 9/2016 |
| WO | WO 2016168351 | 10/2016 |
| WO | WO 2016168584 | 10/2016 |
| WO | WO 2016207639 | 12/2016 |
| WO | WO 2017053905 | 3/2017 |
| WO | WO 2017060316 | 4/2017 |
| WO | 2018203141 | 11/2018 |

OTHER PUBLICATIONS

Extended European Search Report dated Oct. 21, 2021, Appl. No. EP21168174.7, 7 pp.
Examination Report dated Oct. 31, 2017, Appl. No. GB1622222.6, 8 pp.
International Preliminary Report on Patentability dated Nov. 13, 2018, Appl. No. PCT/GB2017/053816, 8 pp.
International Search Report dated Mar. 16, 2018, Appl. No. PCT/GB2017/053816, 16 pp.
Notice of Allowance dated May 5, 2020, Appl. No. EP17817859.6, 250 pp.
Stoeckius et al. (2017) "Large-scale simultaneous measurement of epitopes and transcriptomes in single cells" bioRxiv preprint doi: https://doi.org/10.1101/113068.
Text intended for grant, Appl. No. EP17817859.6, 243 pp. dated Aug. 28, 2018.
Notice of Allowance dated Jan. 26, 2023, Appl. No. EP21168174.7, 7 pp.
Selden et al. (2012) "Chemically Programmed Cell Adhesion with Membrane-Anchored Oligonucleotides" J. Am. Chem.Soc., 134:765-768.

* cited by examiner

Primary Examiner — Teresa E Strzelecka
(74) Attorney, Agent, or Firm — Brian E. Davy; Bozicevic, Field & Francis LLP

(57) ABSTRACT

Reagents and methods for preparing nucleic acid samples for sequencing are provided. The reagents include multimeric barcoding reagents that comprise barcode regions linked together and a cell-binding moiety. The methods comprise contacting a nucleic acid sample comprising cells with a library of multimeric barcoding reagents, wherein each multimeric barcoding reagent comprises barcode regions linked together, and appending barcode sequences of a first multimeric barcoding reagent to sub-sequences of a target nucleic acid of a first cell, and appending barcode sequences of a second multimeric barcoding reagent to sub-sequences of a target nucleic acid of a second cell. Methods are also provided that comprise steps of internalising multimeric barcoding reagents into cells (e.g. by endocytosis) or exposing multimeric barcoding reagents to target nucleic acids by lysing cells or permeabilizing cell membranes.

11 Claims, 30 Drawing Sheets
Specification includes a Sequence Listing.

FIGURE 15

| | Annealed to Genomic DNA Overnight | Annealed to Genomic DNA Overnight; Barcoding Reagents Denatured First | Annealed to Genomic DNA for 3 Hours | Annealed to Genomic DNA for 3 Hours; Barcoding Reagents Denatured First |
|---|---|---|---|---|
| HLA-A_Exon2 | 153 | 62 | 103 | 50 |
| HLA-A_Exon3 | 2548 | 341 | 818 | 106 |
| HLA-A_Exon4 | 489 | 235 | 400 | 108 |
| DQB1_Exon2 | 557 | 627 | 285 | 635 |
| DQB1_Exon3 | 2186 | 1614 | 1085 | 221 |
| BRCA1_US1 | 1771 | 941 | 1047 | 544 |
| BRCA1_SNP7 | 2524 | 1261 | 90 | 43 |
| BRCA1_SNP6 | 731 | 537 | 245 | 339 |
| BRCA1_SNP1 | 10033 | 5787 | 2905 | 1813 |
| BRCA1_DS1 | 4 | 103 | 5 | 0 |
| BRCA_AMP6 | 81 | 69 | 37 | 24 |
| BRCA_AMP7 | 731 | 391 | 40 | 472 |
| On-Target Fraction: | 81% | 76% | 82% | 70% |

Schematic of Sequence Read from Barcoding
of genomic DNA loci
(In 5' to 3' Direction)

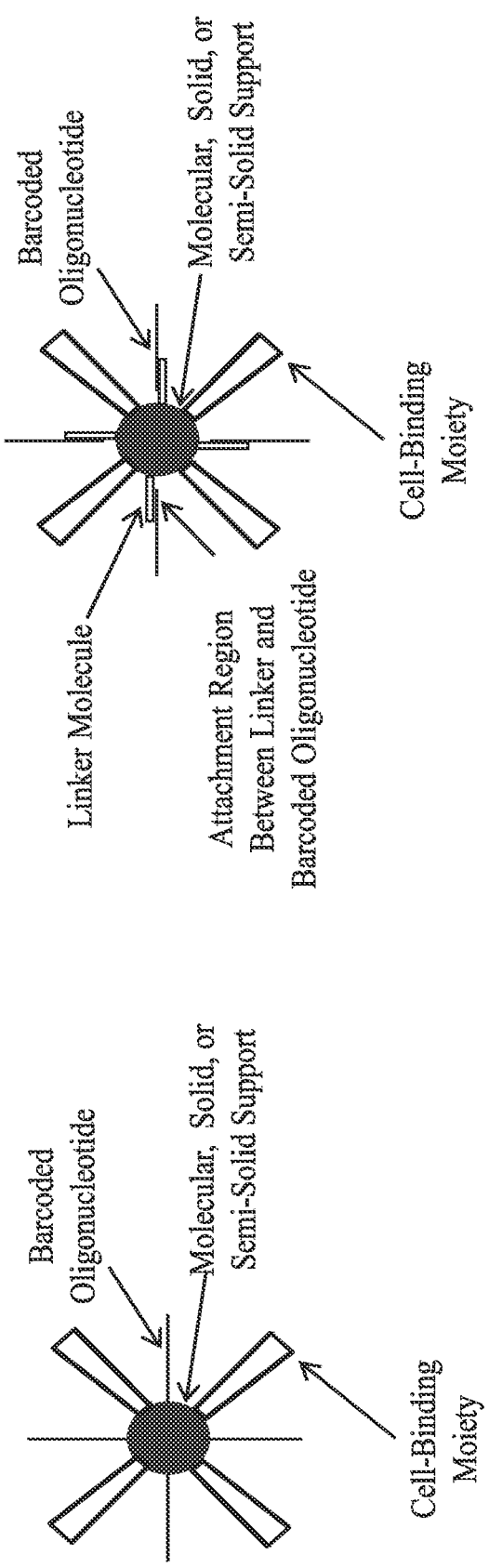

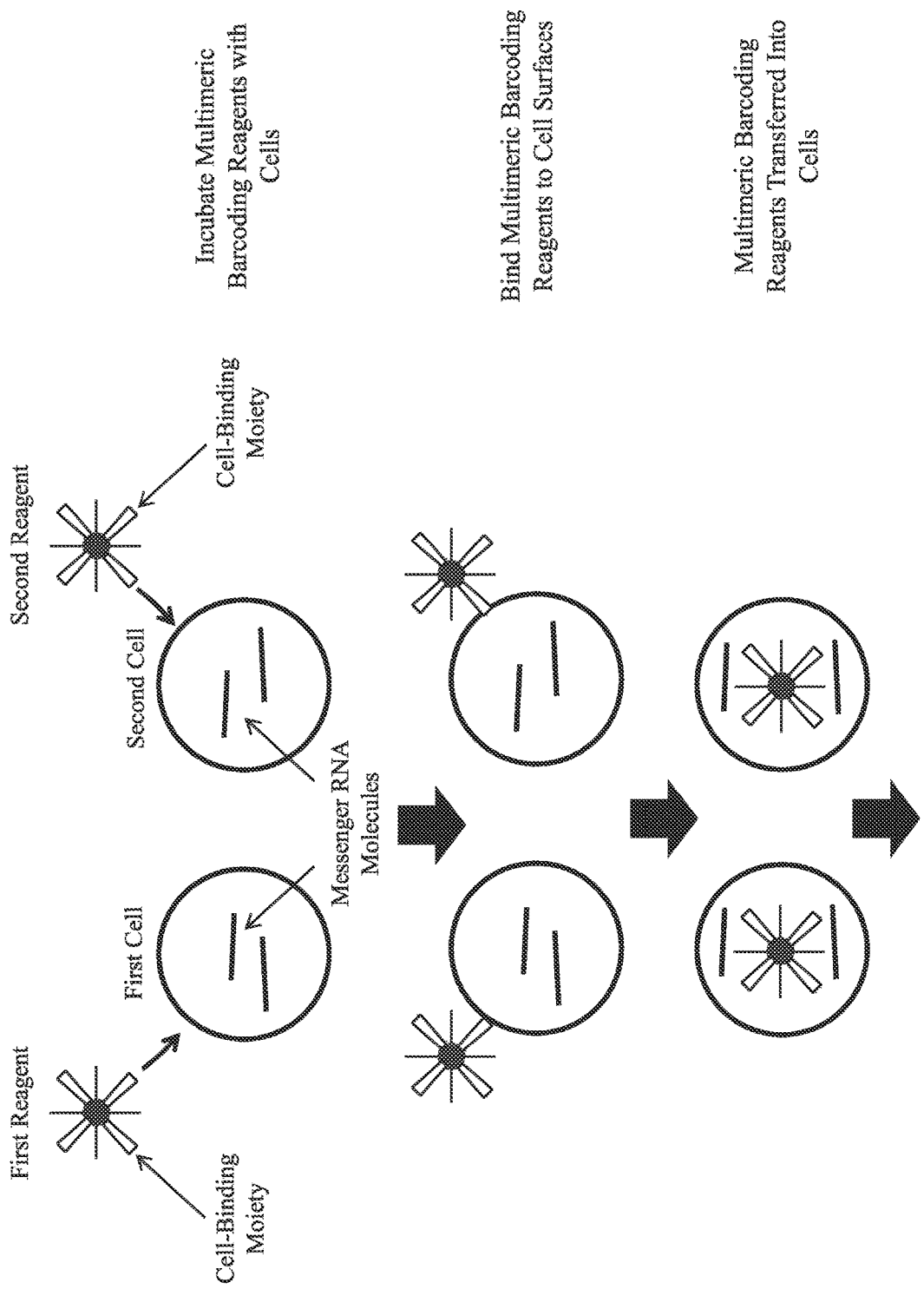

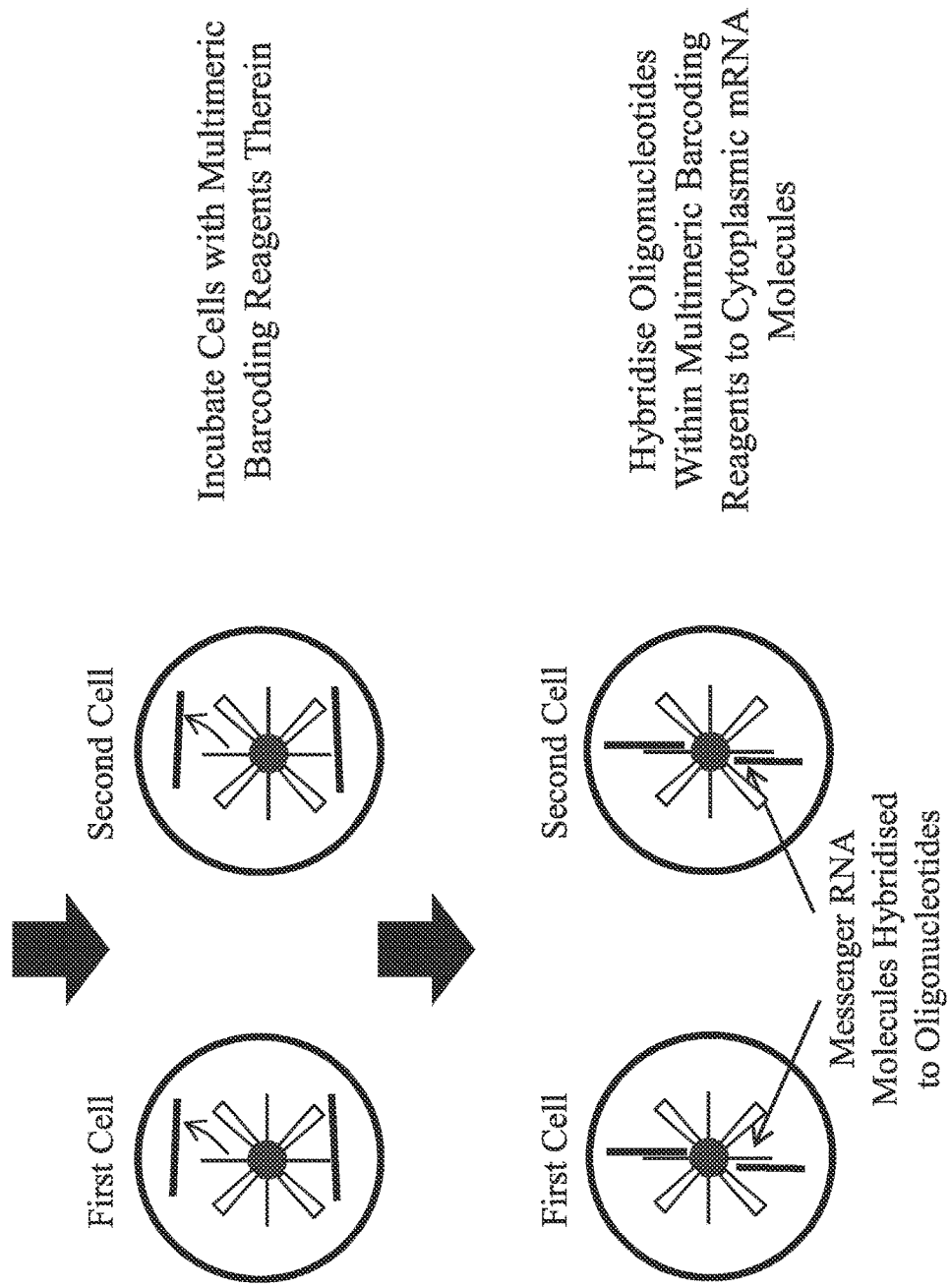

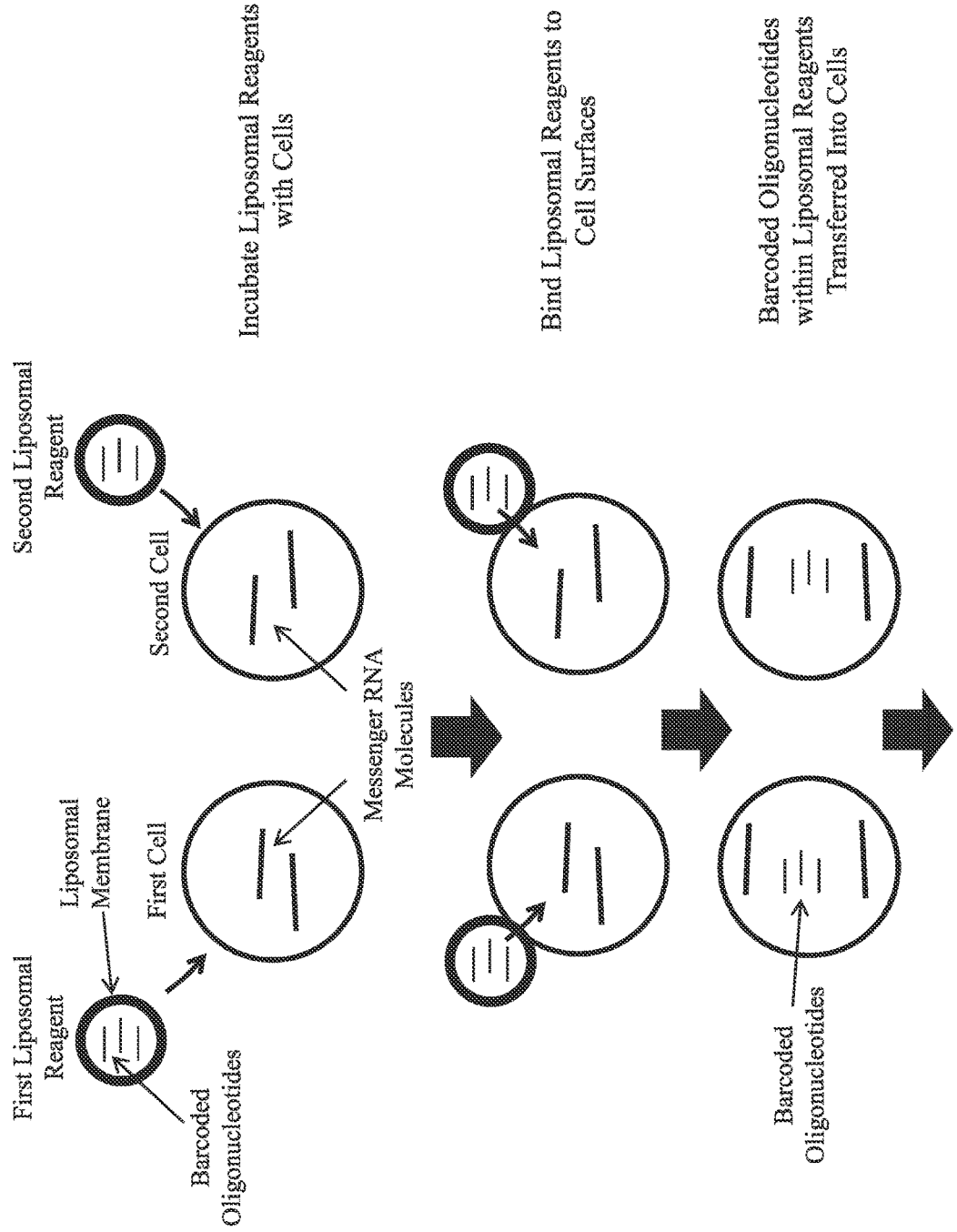

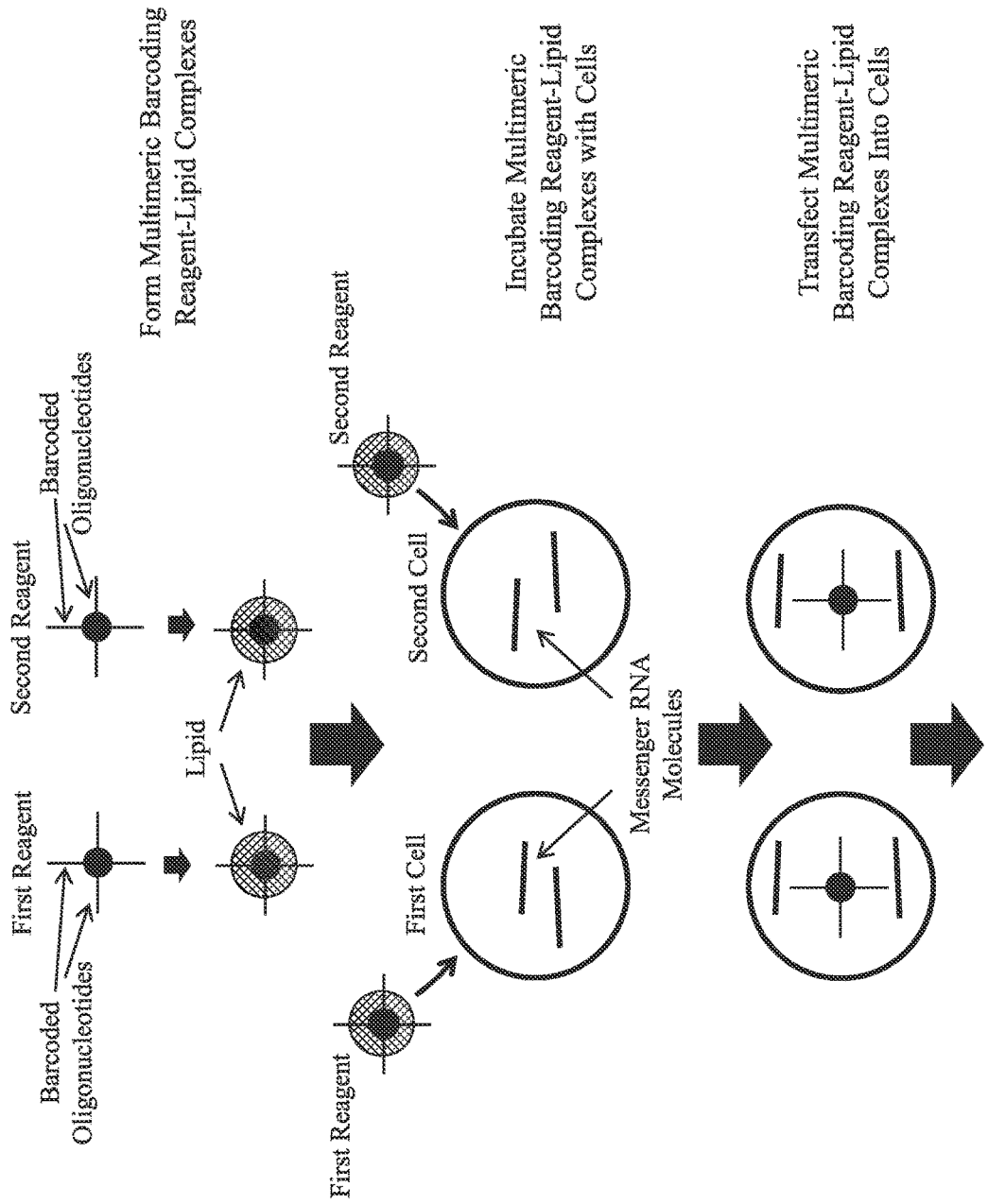

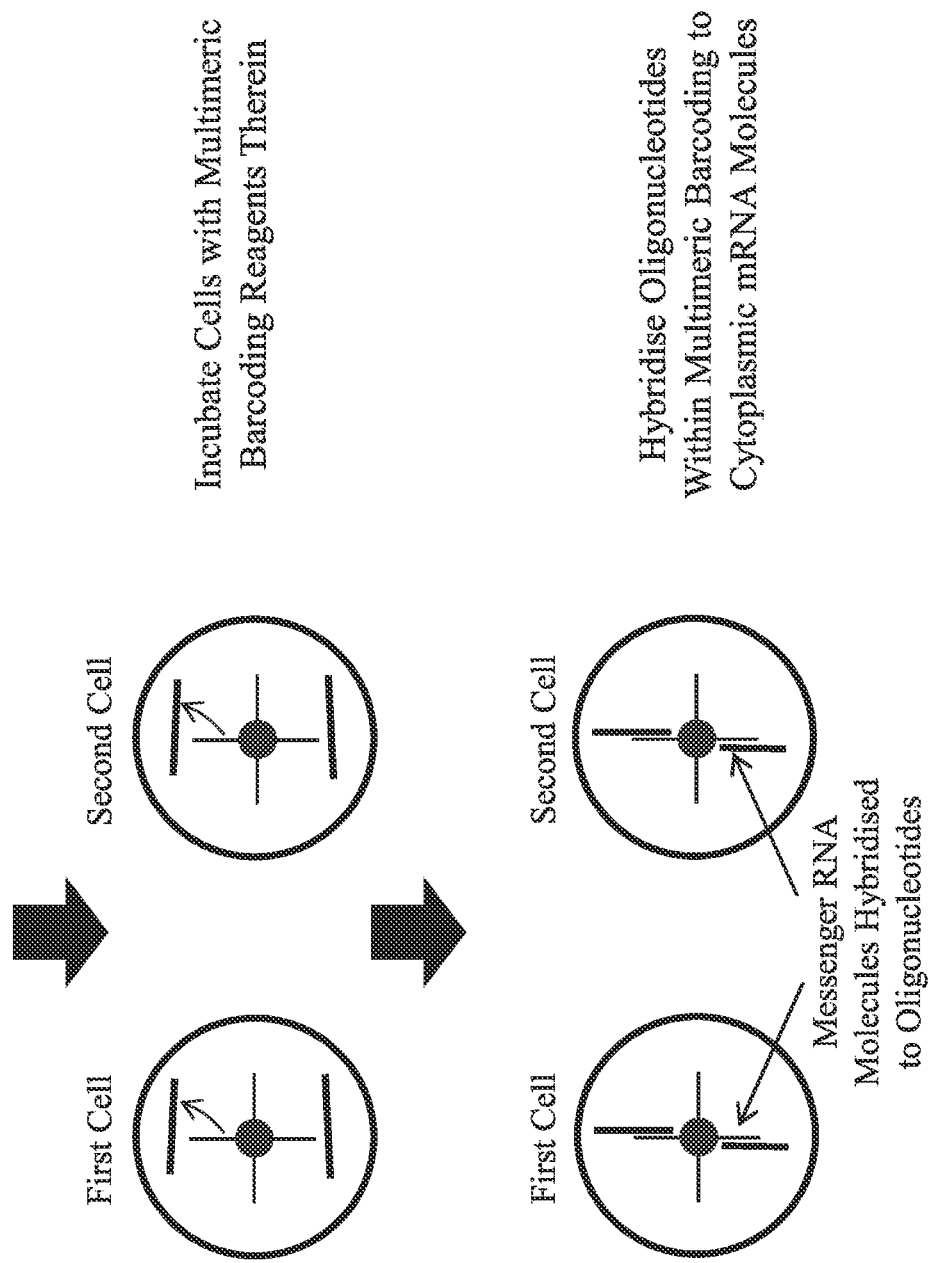

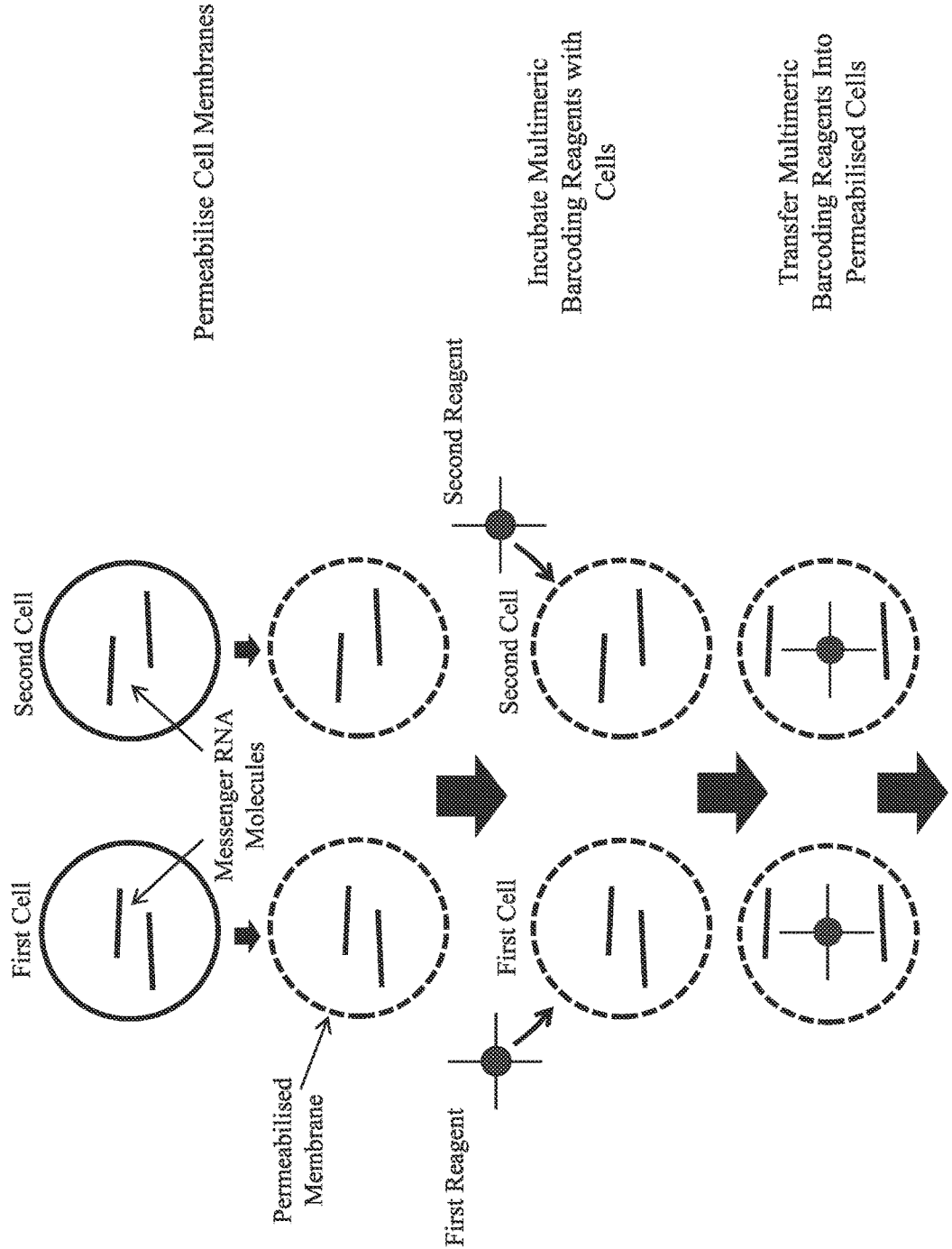

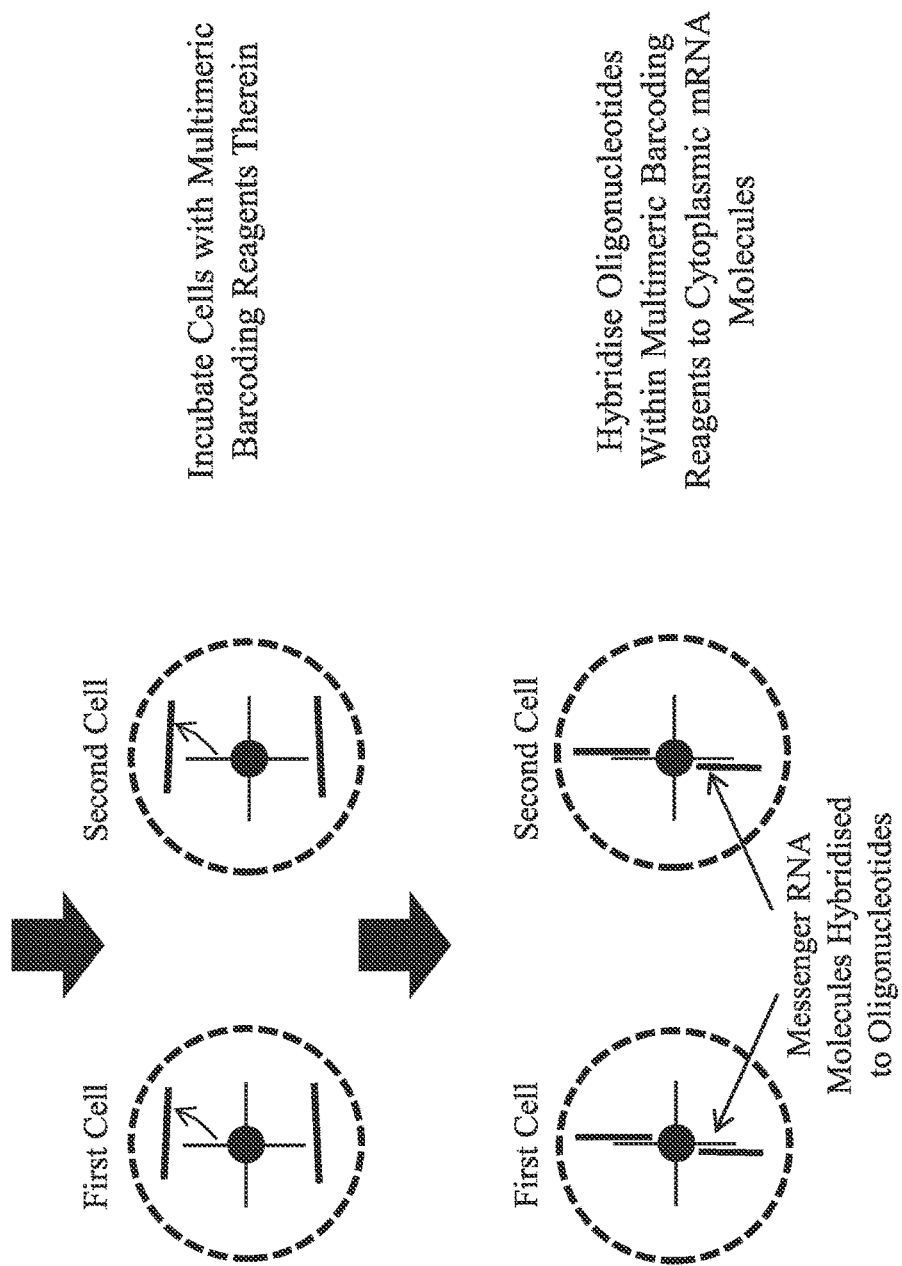

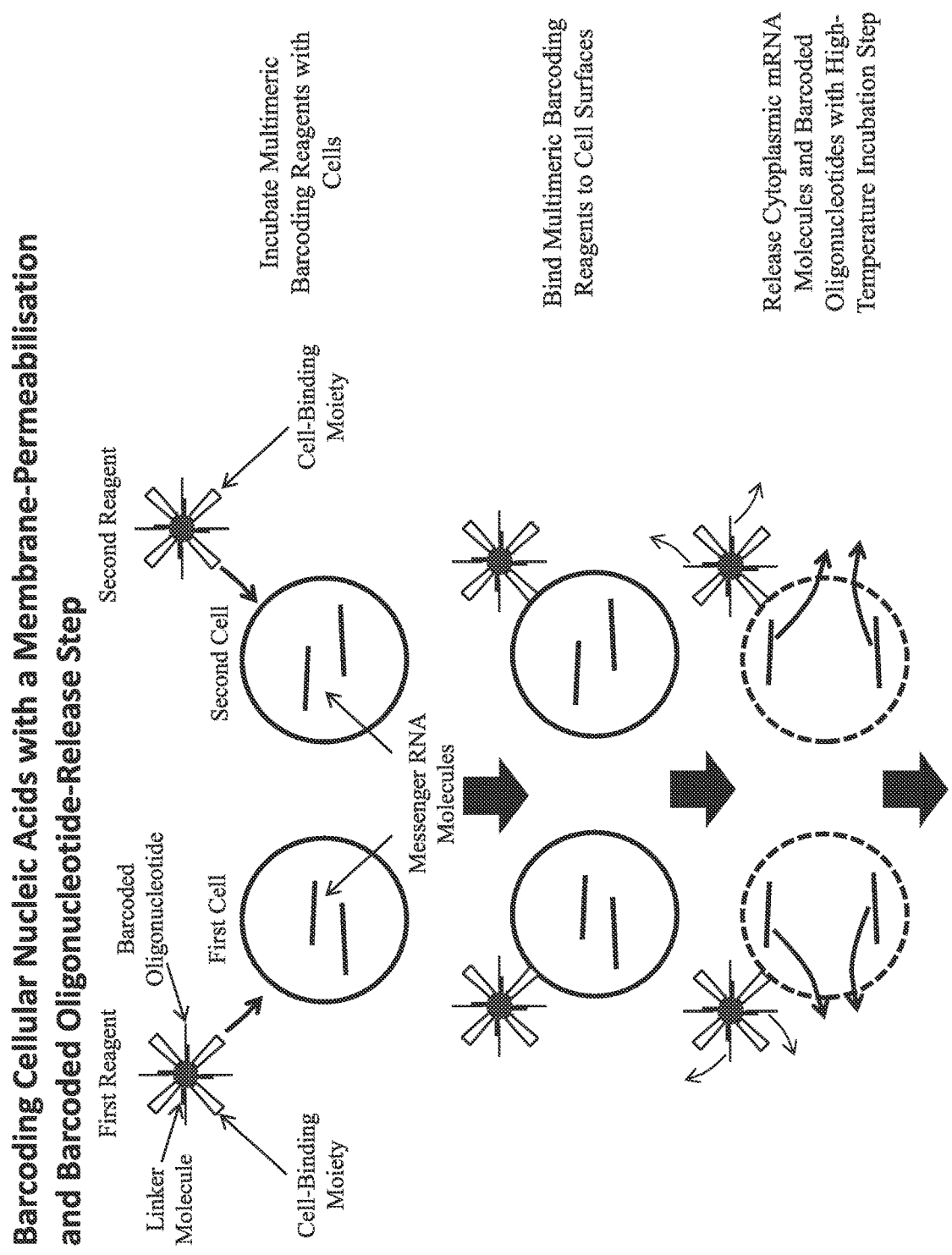

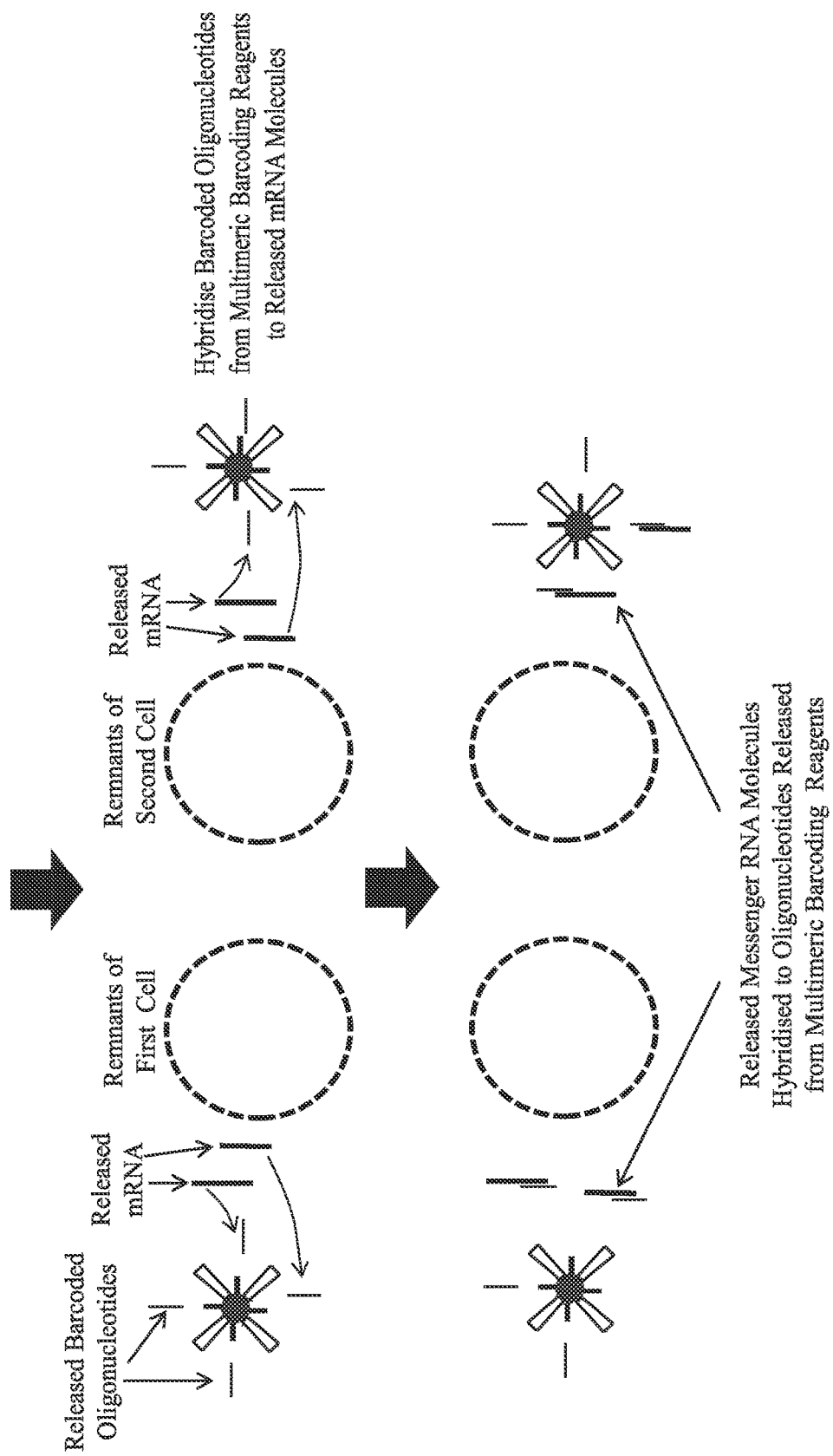

METHODS OF PREPARING NUCLEIC ACID SAMPLES FOR SEQUENCING

TECHNICAL FIELD

The present invention relates to molecular barcoding. Provided are libraries of multimeric barcoding reagents and methods for their use in barcoding nucleic acids of single cells.

INCORPORATION BY REFERENCE OF SEQUENCE LISTING PROVIDED AS A SEQUENCE LISTING XML FILE

A Sequence Listing is provided herewith as a Sequence Listing XML, BOULT_SEQ_LIST, created on Mar. 17, 2023 and having a size of 413,422 bytes. The contents of the Sequence Listing XML are incorporated herein by reference in their entirety.

BACKGROUND

'Molecular barcoding' was developed to address problems generated by raw error rates intrinsic to DNA sequence machines (synthetic accuracy), and also problems related to counting individual nucleic acid molecules within a sample (molecular counting).

Molecular barcoding generally involves attaching (for example, by ligation or by primer-extension) a unique nucleic acid label (a 'barcode') to several single target molecules (DNA or RNA) in a solution containing a large number of such molecules. These labelled molecules are then sequenced, which for each reveals both the sequence of the molecular barcode, and at least part of the sequence of the labelled target molecule itself.

This barcoding is typically used towards two different ends. First, it can be used to enable 'redundant sequencing'. For example, imagine a nucleic acid sample containing 1000 copies of a particular gene in a DNA sample; 999 of the copies hold sequences identical to each other, but a single copy has a particular single-nucleotide mutation. Without barcoding, the sequencer will be unable to detect this mutated copy, since the sequencer makes random errors at a higher rate than 1:1000—i.e. the mutation is so rare in the population of sequenced molecules that it falls below the sequencer's intrinsic background noise threshold.

However, if the 1000 copies have each been labelled with a unique molecular barcode, and each individual labelled molecule is sequenced several times by the sequencing machine (redundant sequencing), you would observe that every time (or, at least 99% of the time, equivalent to the raw accuracy of the sequencer) that the labelled mutated molecule was redundantly sequenced (i.e., every time the target gene sequence was observed to be labelled with that one particular unique barcode that was attached to the mutated starting molecule), that the same apparent mutation would in fact be observed. By contrast, that particular mutation would only be observed approximately 1% of the time (the raw error rate of the sequencer) when the labelled but non-mutated gene copies were redundantly sequenced, as per their respective alternative barcodes.

The barcode thus serves to identify individual input molecules across all their respective multiple copies within the sequencing reaction, allowing a sequence-detection algorithm to specifically focus on their respective reads within a sequencing dataset, and thus avoiding the large amount of stochastic sequence noise (in the form of sequence errors) that is present across the remainder of the dataset. This thus enables 'synthetic accuracy', through redundant sequencing, which is potentially much higher than the raw accuracy of the sequencer itself.

Barcoding can also be used to enable digital 'molecular counting' of input DNA or RNA molecules. In this process, a large number of unique barcodes are attached to input molecules, for example, cDNA copies that have been made from a particular mRNA species. Each input cDNA molecule is labelled (for example, by primer extension) with a single, unique barcode. The molecules are then sequenced, which, as with redundant sequencing, reveals the unique barcode and at least part of each associated labelled input molecule; these molecules are then also each sequenced more than once.

Instead of using this redundant sequencing to reduce sequencing errors, in molecular counting it is used to digitally quantify how many individual molecules of the given target molecule (cDNA in this case) were present in the original sample, by simply counting the total number of unique barcodes that were sequenced and found to be associated with the particular target. Barcode-directed redundant sequencing in this way reduces the chance that any input molecule is stochastically left unsequenced by the sequencing reaction (since each labelled molecule on average is sequenced several times), whilst retaining an accurate measure of input quantity (since redundantly sequenced starting molecules are only counted once, as discriminated by repeated copies of their unique barcode).

Examples of the use of molecular barcodes are provided in U.S. Pat. Nos. 8,728,766, 8,685,678, 8,722,368, Kinde et al., 2011 (PNAS, 108, 23, 9530-9535) and US 20140227705 A1.

A 'synthetic long read' is generated when a long, contiguous sequence of DNA (longer than the readlength attainable on a DNA sequencer) is converted into two or more shorter 'sub-sequences' that are short enough to be read by a DNA sequencer, and which are somehow labelled such that it can be deduced (after sequencing) that the sub-sequences were generated from the same original long DNA sequence. For example, if you want to sequence a particular human gene which is 1000 nucleotides long, but do so with a short-read DNA sequencer with a readlength of 100 nucleotides, you could separate the long sequence into 10 different sub-sequences of 100 nucleotide length, then label each of these 10 sub-sequences with a synthetic, informative 'label' DNA sequence that identifies each of the 10 sub-sequences as coming from the same original 1000 nucleotide DNA molecule, then perform high-throughput DNA sequencing with these 10 resulting DNA molecules, and thus (for each of the 10 resulting DNA molecules) attain both the 100 nucleotide sub-sequence, and the associated identifying DNA label. With this high-throughput DNA data an algorithm can be used which detects these identifying labels and uses them to associate the 10 different 100-nucleotide sub-sequences with each other as a collective sub-sequence 'grouping', and therewith estimate that the 10 sub-sequences came from a longer, 1000-nucleotide gene, and therewith estimate the total 1000-nucleotide long genetic sequence by 'stitching' the 10 sub-sequences together in silico into a single 1000-nucleotide long gene.

At least two general synthetic long read technologies have been described in the literature: a partitioning-based approach which is described in US 20130079231 A1 and US 2014378345 A1; and a barcode-copying approach which is described in Casbon et al., 2013 (Nucleic Acids Research, 2013, 41, 10, e112), U.S. Pat. Nos. 8,679,756 and 8,563,274.

'Spatial sequencing' is considered to be the sequencing of nucleic acids with the inclusion of some information about where each sequenced nucleic acid is located within a particular space (for example, within a particular sample, or within a particular cell). However, very few spatial sequencing methods are known. The main known technology is the fluorescent in situ RNA sequencing (FISSEQ) technique. In FISSEQ a sample of cells are cross-linked, and while the cells are still intact, RNA is reverse transcribed into cDNA, and amplified whilst still in the crosslinked cells. Then, each amplified cDNA molecule is sequenced optically whilst still in the cells, with a high-powered and sensitive optical detection system. This method is described in Lee et al., 2014 (Science, 343, 6177, 1360-1363). Current techniques for performing nucleic acid analysis of single cells are generally limited in throughput (i.e., the number of cells that may be simultaneously analysed within a single experiment, or analysed per unit time), and also require relatively complex experimental instrumentation, such as microfluidic equipment, and may furthermore involve relatively complex and/or length experimental procedures to carry out.

The invention addresses two main types of problem in the sequencing field: 1) specific analytic limitations of DNA sequencing machines; and 2) biophysical challenges associated with common types of experimental DNA samples.

Current high-throughput DNA-sequencing machines are powerful platforms used to analyse large amounts of genetic material (from thousands to billions of DNA molecules) and function as systems for both basic research and applied medical applications. However, all current DNA sequencing machines are subject to certain analytic limitations which constrain the scientific and medical applications in which they can be effectively used. The chief such limitations include finite raw readlengths and finite raw accuracy, both of which are described below.

With regard to finite raw readlengths, each DNA sequencing platform is characterised by a typical 'readlength' that it can attain, which is the 'length' in nucleotides of DNA that it can 'read' of each sequenced molecule. For most sequencing machines, this ranges from 100 to ~500 nucleotides.

With regard to finite raw accuracy, each sequencing platform is also characterised by an attainable 'raw accuracy', typically defined as the likelihood that each given nucleotide it sequences has been determined correctly. Typical raw accuracy for the most popular sequencing platforms range between 98 and 99.5%. The related quantity, the 'raw error' rate, is essentially the converse of raw accuracy, and is the per-nucleotide likelihood that the sequencer randomly reports an incorrect nucleotide in a particular sequenced DNA molecule.

In addition, certain common experimental DNA samples pose biophysical challenges for sequencing. These challenges arise from the unique (and troublesome) molecular state of DNA in these samples, which makes it difficult to sequence them or to extract important pieces of genetic information therefrom, irrespective of the sequencing machine employed. For example, Formalin-Fixed Paraffin-Embedded (FFPE) samples are the standard experimental tool for performing molecular pathology from human biopsy specimens. However, the process of creating an FFPE sample—in which the biopsy specimen is fixed (crosslinked and kept physically together and stable at the molecular level) by a harsh chemical, and then embedded in a wax—creates significant damage to the DNA and RNA contained therein. DNA and RNA from FFPE samples is thus heavily fragmented (generally into small fragments between 50 and 200 nucleotides), and also includes sporadic damage to individual nucleotides which makes it essentially impossible to amplify or isolate long, contiguous sequences.

DESCRIPTION

The invention provides multimeric barcoding reagents and methods for their use in preparing nucleic acid samples containing cells for sequencing. In the methods, the multimeric barcoding reagents are used to barcode target nucleic acids of cells in the samples. Barcode sequences may be appended from a single multimeric barcoding reagent to sub-sequences of a target nucleic acid of a single cell to produce a set of barcoded target nucleic acid molecules. Such molecules may be sequenced to produce sets of sequence reads, each set of sequence reads corresponding to nucleic acid molecules of a single cell (i.e. single-cell sequencing). In addition, the methods may be performed on many cells in parallel enabling high throughput single-cell sequencing.

The invention provides a library comprising at least two multimeric barcoding reagents, wherein each multimeric barcoding reagent comprises: (a) first and second barcoded oligonucleotides linked together and a cell-binding moiety, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library.

The invention provides a library of multimeric barcoding reagents comprising at least 2 multimeric barcoding reagents for labelling target nucleic acids for sequencing, wherein each multimeric barcoding reagent comprises: (a) first and second hybridization molecules linked together, wherein each of the hybridization molecules comprises a nucleic acid sequence comprising a hybridization region; (b) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule, wherein the barcoded oligonucleotides each comprise a barcode region; and (c) a cell-binding moiety; wherein the barcode regions of the first and second barcoded oligonucleotides of a first multimeric barcoding reagent of the library are different to the barcode regions of the first and second barcoded oligonucleotides of a second multimeric barcoding reagent of the library.

A cell-binding moiety may be attached to each of the barcode molecules. Additionally or alternatively, a cell-binding moiety may be attached to each of the barcoded oligonucleotides.

The multimeric barcoding reagents may be for labelling sub-sequences of a target nucleic acid in a cell.

Each multimeric barcoding reagent in the library may be for labelling the target nucleic acids of a single cell. Each multimeric barcoding reagent in the library may be for labelling the target nucleic acids in a single cell.

The first and second hybridization molecules may be comprised within a (single) nucleic acid molecule. Alternatively, the first and second hybridization molecules may be linked together by a support e.g. a macromolecule, solid support or semi-solid support, as described herein.

The first and second barcoded oligonucleotides may take any form described herein. For example, each barcoded oligonucleotide may further comprise a target region.

The library may comprise at least 10 multimeric barcoding reagents. The barcode regions of the first and second barcoded oligonucleotides of each multimeric barcoding reagent may be different to the barcode regions of the barcoded oligonucleotides of at least 9 other multimeric barcoding reagents in the library.

The invention provides a library of multimeric barcoding reagents comprising at least 10 multimeric barcoding reagents for labelling target nucleic acids for sequencing, wherein each multimeric barcoding reagent comprises: (a) first and second hybridization molecules comprised within a nucleic acid molecule, wherein each of the hybridization molecules comprises a nucleic acid sequence comprising a hybridization region; (b) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule, wherein the barcoded oligonucleotides each comprise a barcode region; and (c) a cell-binding moiety; wherein the barcode regions of the first and second barcoded oligonucleotides of each multimeric barcoding reagent of the library are different to the barcode regions of the barcoded oligonucleotides of at least 9 other multimeric barcoding reagents of the library.

The library may comprise at least two multimeric barcoding reagents each comprising: (a) first and second barcode molecules linked together, wherein each of the barcode molecules comprises a nucleic acid sequence comprising a barcode region; (b) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (c) a cell-binding moiety; wherein the barcode regions of the first and second barcoded oligonucleotides of a first multimeric barcoding reagent of the library are different to the barcode regions of the first and second barcoded oligonucleotides of a second multimeric barcoding reagent of the library.

A cell-binding moiety may be attached to each of the barcode molecules. Additionally or alternatively, a cell-binding moiety may be attached to each of the barcoded oligonucleotides.

The library may comprise at least 10 multimeric barcoding reagents, wherein each multimeric barcoding reagent comprises: (a) first and second barcode molecules comprised within a nucleic acid molecule, wherein each of the barcode molecules comprises a nucleic acid sequence comprising a barcode region; (b) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (c) a cell-binding moiety; wherein the barcode regions of the first and second barcoded oligonucleotides of each multimeric barcoding reagent of the library are different to the barcode regions of the barcoded oligonucleotides of at least 9 other multimeric barcoding reagents of the library.

In the libraries, each multimeric barcoding reagent may be comprised within a different (or separate) lipid carrier. The lipid carrier may be a micelle or a liposome. Alternatively, the lipid carrier may take any of the forms described herein.

The invention provides a kit for labelling target nucleic acids for sequencing, wherein the kit comprises: (a) a library of multimeric barcoding reagents comprising at least two multimeric barcoding reagents, wherein each multimeric barcoding reagent comprises (i) first and second barcode molecules linked together, wherein each of the barcode molecules comprises a nucleic acid sequence comprising, optionally in the 5' to 3' direction, an adapter region and a barcode region, (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; wherein the barcode regions of the first and second barcoded oligonucleotides of a first multimeric barcoding reagent of the library are different to the barcode regions of the first and second barcoded oligonucleotides of a second multimeric barcoding reagent of the library; and (b) first and second adapter oligonucleotides for each of the multimeric barcoding reagents, wherein the first adapter oligonucleotide comprises an adapter region capable of annealing to the adapter region of the first barcode molecule and wherein the second adapter oligonucleotide comprises an adapter region capable of annealing to the adapter region of the second barcode molecule, and wherein a cell-binding moiety is attached to each of the adapter oligonucleotides.

The kit may be for labelling target nucleic acids of (or in) at least two cells for sequencing.

The multimeric barcoding reagents may each comprise a cell-binding moiety. A cell-binding moiety may be attached to each of the barcode molecules. A cell-binding moiety may be attached to each of the barcoded oligonucleotides.

The invention provides a kit for labelling target nucleic acids for sequencing, wherein the kit comprises: (a) a library of multimeric barcoding reagents comprising at least two multimeric barcoding reagents, wherein each multimeric barcoding reagent comprises first and second barcoded oligonucleotides linked by a support, wherein the barcoded oligonucleotides each comprise a barcode region and a target region, and wherein the barcode regions of the first and second barcoded oligonucleotides of a first multimeric barcoding reagent of the library are different to the barcode regions of the first and second barcoded oligonucleotides of a second multimeric barcoding reagent of the library; and (b) a cell-binding moiety for each multimeric barcoding reagent in the library, wherein each such cell-binding moiety is capable of binding to a multimeric barcoding reagent within the library The invention provides a kit for labelling target nucleic acids for sequencing, wherein the kit comprises: (a) a library of multimeric barcoding reagents comprising at least two multimeric barcoding reagents, wherein each multimeric barcoding reagent comprises at least first and second barcoded oligonucleotides linked by a support, wherein the barcoded oligonucleotides each comprise a barcode region and a poly(T) target region, and wherein the barcode regions of the first and second barcoded oligonucleotides of a first multimeric barcoding reagent of the library are different to the barcode regions of the first and second barcoded oligonucleotides of a second multimeric barcoding reagent of the library; and (b) a cell-binding moiety for each multimeric barcoding reagent in the library, wherein each such cell-binding moiety is capable of binding to a multimeric barcoding reagent within the library The invention provides a kit for labelling target nucleic acids for sequencing, wherein the kit comprises: (a) a library of multimeric barcoding reagents comprising at least two multimeric barcoding reagents, wherein each multimeric barcoding reagent comprises at least first and second barcoded oligonucleotides linked by a support, wherein the barcoded oligonucleotides each comprise a barcode region and a target region, and wherein the barcode regions of the first and second barcoded oligonucleotides of a first multimeric barcoding reagent of the library are different to the barcode regions of the first and second barcoded oligonucleotides of a second multimeric barcoding reagent of the library; (b) a cell-binding moiety for each multimeric barcoding reagent in the library, wherein each such cell-binding moiety is capable of binding to a multimeric barcoding reagent within the library; and (c) blocking oligonucleotides (e.g. a solution of blocking oligonucleotides), wherein each blocking oligonucleotide comprises a sequence complementary to all or part of a barcoded oligonucleotide, and/or comprises a sequence complementary to all or part of a target nucleic acid.

The invention provides a kit for labelling target nucleic acids for sequencing, wherein the kit comprises: (a) a library of multimeric barcoding reagents comprising at least two multimeric barcoding reagents, wherein each multimeric barcoding reagent comprises at least first and second barcoded oligonucleotides linked by a support, wherein the barcoded oligonucleotides each comprise a barcode region and a poly(T) target region, and wherein the barcode regions of the first and second barcoded oligonucleotides of a first multimeric barcoding reagent of the library are different to the barcode regions of the first and second barcoded oligonucleotides of a second multimeric barcoding reagent of the library; (b) a cell-binding moiety for each multimeric barcoding reagent in the library, wherein each such cell-binding moiety is capable of binding to a multimeric barcoding reagent within the library; and (c) blocking oligonucleotides (e.g. a solution of blocking oligonucleotides), wherein each blocking oligonucleotide comprises a sequence complementary to all or part of a barcoded oligonucleotide, and/or comprises a sequence complementary to all or part of a target nucleic acid.

In any kit comprising a library of multimeric barcoding reagents and cell-binding moieties, two or more cell-binding moieties may be provided (e.g. in a solution of cell-binding moieties) separately to a library of multimeric barcoding reagents (e.g. a solution of a library of multimeric barcoding reagents).

In any kit comprising a library of multimeric barcoding reagents and cell-binding moieties, the library of multimeric barcoding reagents and the cell-binding moieties may be provided together in a single solution.

In any kit comprising a library of multimeric barcoding reagents, cell-binding moieties and blocking oligonucleotides, each of the three components of the kit may be provided separately (e.g. in a separate solution) to the other two components of the kit. Optionally, two components of the kit may be provided together (e.g. in a single solution). Optionally, all three components of the kit may be provided together (e.g. in a single solution).

The invention provides a kit for labelling target nucleic acids for sequencing, wherein the kit comprises: (a) a library of multimeric barcoding reagents comprising at least 10 multimeric barcoding reagents, wherein each multimeric barcoding reagent comprises (i) first and second barcode molecules comprised within a nucleic acid molecule, wherein each of the barcode molecules comprises a nucleic acid sequence comprising, optionally in the 5' to 3' direction, an adapter region and a barcode region, (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; wherein the barcode regions of the first and second barcoded oligonucleotides of each multimeric barcoding reagent of the library are different to the barcode regions of the barcoded oligonucleotides of at least 9 other multimeric barcoding reagent of the library; and (b) first and second adapter oligonucleotides for each of the multimeric barcoding reagents, wherein the first adapter oligonucleotide comprises an adapter region capable of annealing to the adapter region of the first barcode molecule and wherein the second adapter oligonucleotide comprises an adapter region capable of annealing to the adapter region of the second barcode molecule, and wherein a cell-binding moiety is attached to each of the adapter oligonucleotides.

In the kits, the adapter oligonucleotides for each multimeric barcoding reagent may be comprised within a different (or separate) lipid carrier. The lipid carrier may be a micelle or a liposome. Alternatively, the lipid carrier may take any of the forms described herein. The lipid carriers may each further comprise a multimeric barcoding reagent e.g. the first lipid carrier comprises the first multimeric barcoding reagent and the adapter oligonucleotides for the first multimeric barcoding reagent.

In the libraries or kits, the barcoding reagents may each comprise a solid support or semi-solid support, and wherein a cell-binding moiety is attached to the solid support or semi-solid support (e.g. by a covalent or non-covalent bond).

A cell-binding moiety may be attached to each barcoded oligonucleotide, hybridization molecule, barcode molecule and/or adapter oligonucleotide by a linker molecule. Optionally, said linker may be a flexible linker. Optionally, said linker may be comprised of one or more units of ethylene glycol and/or poly(ethylene) glycol, such as hexa-ethylene glycol or penta-ethylene glycol.

Optionally, said linker may be comprised of one or more ethyl groups, such as a C3 (three-carbon) spacer, C6, C12, or C18. Optionally, any other spacer may be used.

The cell-binding moiety (or moieties) may capable of initiating endocytosis on binding to a cell membrane.

The cell-binding moiety may comprise one or more moieties selected from: a peptide, a cell penetrating peptide, an aptamer, a DNA adptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a cationic lipid, a cationic polymer, poly(ethylene) glycol, spermine, a spermine derivatives or analogue, a poly-lysine, a poly-lysine derivative or analogue, polyethyleneimine, diethylaminoethyl (DEAE)-dextran, cholesterol, a sterol moiety, a cationic molecule, a hydrophobic molecule and an amphiphilic molecule.

The cell-binding moiety may interact with one or more specific molecule(s) on the cell surface (as in the case of e.g. an antibody, an antibody fragment and an aptamer). Alternatively or additionally, the cell-binding moiety may alter the overall charge and/or charge distribution of multimeric barcoding reagents (as in the case of e.g. a cationic polymer). Alternatively or additionally, the cell-binding moiety may alter the lipophilic/lipophobic and/or hydrophilic/hydrophobic character and/or balance of the multimeric barcoding reagents (as in the case of e.g. a lipid or cholesterol).

The cell-binding moiety may be a molecule that has a net positive charge in a solution comprising a cell and that enables binding of a multimeric barcoding reagent to the cell.

A multimeric barcoding reagent, adapter oligonucleotide, barcoded oligonucleotide, hybridization molecule or barcode molecule may comprise at least 2, at least 3, at least 5, at least 10, at least 20, at least 50, at least 100, at least 500, or at least 1000 cell binding moieties.

A cell-binding moiety may be attached to a multimeric barcoding reagent, adapter oligonucleotide, barcoded oligonucleotide, hybridization molecule or barcode molecule by a covalent linkage or by a non-covalent linkage.

The invention provides a method of preparing a nucleic acid sample for sequencing, wherein the sample comprises a cell, and wherein the method comprises the steps of: (a) contacting the sample with a multimeric barcoding reagent, wherein the multimeric barcoding reagent comprises first and second barcode regions linked together and a cell-binding moiety, wherein each barcode region comprises a nucleic acid sequence, wherein the cell-binding moiety of the multimeric barcoding reagent binds to the cell membrane of the cell and the first and second barcode regions of the multimeric barcoding reagent are internalized into the cell; and (b) appending barcode sequences to each of the first and second sub-sequences of a target nucleic acid of the cell to produce first and second barcoded target nucleic acid molecules for the cell, wherein the first barcoded target nucleic acid molecule comprises the nucleic acid sequence of the first barcode region of the multimeric barcoding reagent and the second barcoded target nucleic acid molecule comprises the nucleic acid sequence of the second barcode region of the multimeric barcoding reagent.

The invention provides a method of preparing a nucleic acid sample for sequencing, wherein the sample comprises at least two cells, and wherein the method comprises the steps of: (a) contacting the sample with a library comprising at least two multimeric barcoding reagents, wherein each multimeric barcoding reagent comprises first and second barcode regions linked together and a cell-binding moiety, wherein each barcode region comprises a nucleic acid sequence and wherein the first and second barcode regions of a first multimeric barcoding reagent are different to the first and second barcode regions of a second multimeric barcoding reagent of the library, wherein the cell-binding moiety of the first multimeric barcoding reagent from the library binds to the cell membrane of a first cell of the sample and the first and second barcode regions of the first multimeric barcoding reagent are internalized into the first cell, and wherein the cell-binding moiety of the second multimeric barcoding reagent from the library binds to the cell membrane of a second cell of the sample and the first and second barcode regions of the second multimeric barcoding reagent are internalized into the second cell; and (b) appending barcode sequences to each of first and second sub-sequences of a target nucleic acid of the first cell to produce first and second barcoded target nucleic acid molecules for the first cell, wherein the first barcoded target nucleic acid molecule comprises the nucleic acid sequence of the first barcode region of the first multimeric barcoding reagent and the second barcoded target nucleic acid molecule comprises the nucleic acid sequence of the second barcode region of the first multimeric barcoding reagent, and appending barcode sequences to each of first and second sub-sequences of a target nucleic acid of the second cell to produce first and second barcoded target nucleic acid molecules from the second cell, wherein the first barcoded target nucleic acid molecule comprises the nucleic acid sequence of the first barcode region of the second multimeric barcoding reagent and the second barcoded target nucleic acid molecule comprises the nucleic acid sequence of the second barcode region of the second multimeric barcoding reagent.

The method may comprise the steps of: (a) contacting the sample with a library comprising first and second multimeric barcoding reagents, wherein each multimeric barcoding reagent comprises first and second barcode molecules linked together and a cell-binding moiety, wherein each of the barcode molecules comprises a nucleic acid sequence comprising a barcode region and an adapter region and wherein the first and second barcode regions of a first multimeric barcoding reagent are different to the first and second barcode regions of a second multimeric barcoding reagent of the library, and wherein the cell-binding moiety of the first multimeric barcoding reagent from the library binds to the cell membrane of a first cell of the sample and the first and second barcode molecules of the first multimeric barcoding reagent are internalized into the first cell, and wherein the cell-binding moiety of the second multimeric barcoding reagent from the library binds to the cell membrane of a second cell of the sample and the first and second barcode molecules of the second multimeric barcoding reagent are internalized into the second cell; (b) appending a coupling sequence to each of first and second sub-sequences of a target nucleic acid of a first cell, and appending a coupling sequence to each of first and second sub-sequences of a target nucleic acid of a second cell; (c) for each of the multimeric barcoding reagents, annealing the coupling sequence of the first sub-sequence to the adapter region of the first barcode molecule, and annealing the coupling sequence of the second sub-sequence to the adapter region of the second barcode molecule; and (d) appending barcode sequences to each of the first and second sub-sequences of the target nucleic acid of the first cell to produce first and second barcoded target nucleic acid molecules for the first cell, wherein the first barcoded target nucleic acid molecule comprises the nucleic acid sequence of the barcode region of the first barcode molecule of the first multimeric barcoding reagent and the second barcoded target nucleic acid molecule comprises the nucleic acid sequence of the barcode region of the second barcode molecule of the first multimeric barcoding reagent, and appending barcode sequences to each of the first and second sub-sequences of a target nucleic acid of the second cell to produce first and second barcoded target nucleic acid molecules from the second cell, wherein the first barcoded target nucleic acid molecule comprises the nucleic acid sequence of the barcode region of the first barcode molecule of the second multimeric barcoding reagent and the second barcoded target nucleic acid molecule comprises the nucleic acid sequence of the barcode region of the second barcode molecule of the second multimeric barcoding reagent.

The invention provides a method of preparing a nucleic acid sample for sequencing, wherein the sample comprises a cell, and wherein the method comprises the steps of: (a) contacting the sample with a multimeric barcoding reagent, wherein the multimeric barcoding reagent comprises first and second barcoded oligonucleotides linked together and a cell-binding moiety, wherein the barcoded oligonucleotides each comprise a barcode region, and wherein the cell-binding moiety of the multimeric barcoding reagent binds to the cell membrane of the cell and the first and second barcoded oligonucleotides of the multimeric barcoding reagent are internalized into the cell; and (b) annealing or ligating the first and second barcoded oligonucleotides of the multimeric barcoding reagent to first and second sub-sequences of a target nucleic acid of the cell to produce first and second barcoded target nucleic acid molecules.

The invention provides a method of preparing a nucleic acid sample for sequencing, wherein the sample comprises at least two cells, and wherein the method comprises the steps of: (a) contacting the sample with a library comprising at least two multimeric barcoding reagents, wherein each multimeric barcoding reagent comprises first and second barcoded oligonucleotides linked together and a cell-binding moiety, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library, wherein the cell-binding moiety of a first multimeric barcoding reagent from the library binds to the cell membrane of a first cell of the sample and the first and second barcoded oligonucleotides of the first multimeric barcoding reagent are internalized into the first cell, and wherein the cell-binding moiety of a second multimeric barcoding reagent from the library binds to the cell membrane of a second cell of the sample and the first and second barcoded oligonucleotides of the second multimeric barcoding reagent are internalized into the second cell; and (b) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules.

In the methods, the cell binding and internalisation step may comprise an incubation period, wherein said incubation takes place for at least 5 seconds, at least 10 seconds, at least 30 seconds, at least 60 seconds, at least 2 minutes, at least 5 minutes, at least 10 minutes, at least 15 minutes, at least 30 minutes, at least 60 minutes, at least 2 hours, or at least 4 hours, optionally for 5 seconds to 4 hours, 10 seconds to 2 hours, 30 seconds to 60 minutes, 60 seconds to 30 minutes, 2 to 15 minutes or 5 to 10 minutes. Optionally, said incubation takes place at a temperature of at least 4 degrees Celsius, at least 12 degrees Celsius, at least 20 degrees Celsius, at least 30 degrees Celsius, at least 37 degrees Celsius, at least 40 degrees Celsius, at least 45 degrees Celsius, or at least 50 degrees Celsius, optionally at 4 to 50 degrees Celsius, 12 to 45 degrees Celsius, 20 to 40 degrees Celsius or 30 to 37 degrees Celsius.

The step of annealing or ligating (step (b)) may comprise: (i) annealing the first and second barcoded oligonucleotides of the first multimeric barcoding reagent to first and second sub-sequences of a target nucleic acid of the first cell, and annealing the first and second barcoded oligonucleotides of the second multimeric barcoding reagent to first and second sub-sequences of a target nucleic acid of the second cell; and (ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the target nucleic acid as a template.

A cell-binding moiety may be attached to each of the barcoded oligonucleotides.

The multimeric barcoding reagents may each comprise: (i) first and second hybridization molecules linked together, wherein each of the hybridization molecules comprises a nucleic acid sequence comprising a hybridization region; and (ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule; optionally wherein the first multimeric barcoding reagent is internalized into the first cell and the second multimeric barcoding reagent is internalized into the second cell.

A cell-binding moiety may be attached to each of the hybridization molecules.

The multimeric barcoding reagents may each comprise: (i) first and second barcode molecules linked together, wherein each of the barcode molecules comprises a nucleic acid sequence comprising a barcode region; and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; optionally wherein the first multimeric barcoding reagent is internalized into the first cell and the second multimeric barcoding reagent is internalized into the second cell.

A cell-binding moiety may be attached to each of the barcode molecules.

In the methods, the first multimeric barcoding reagent may be comprised within a first lipid carrier and the second multimeric barcoding reagent may be comprised within a second lipid carrier, optionally wherein in step (a) the first lipid carrier merges with the cell membrane of the first cell and the first and second barcoded oligonucleotides of the first multimeric barcoding reagent are internalized into the first cell, and the second lipid carrier merges with the cell membrane of the second cell and the first and second barcoded oligonucleotides of the first multimeric barcoding reagent are internalized into the second cell. Optionally, the barcoded oligonucleotides are released into the cell e.g. into the cytoplasm. The lipid carrier may be a liposome or a micelle. Alternatively, the lipid carrier may take any of the forms described herein.

The invention provides a method of preparing a nucleic acid sample for sequencing, wherein the sample comprises a cell, and wherein the method comprises the steps of: (a) contacting the sample with a multimeric barcoding reagent, wherein the multimeric barcoding reagent comprises: (i) first and second barcode molecules linked together, wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule and wherein the second barcoded oligonucleotide comprises a barcode region annealed to the barcode region of the second barcode molecule; wherein the sample is further contacted with first and second adapter oligonucleotides for the multimeric barcoding reagent, wherein the first and second adapter oligonucleotides each comprise an adapter region, wherein a cell-binding moiety is attached to each of the adapter oligonucleotides, and wherein the cell-binding moieties of the first and second adapter oligonucleotides bind to the cell membrane of the cell and the first and second adapter oligonucleotides for the first multimeric barcoding reagent are internalized into the cell; (b) annealing or ligating the first and second adapter oligonucleotides for the multimeric barcoding reagent to sub-sequences of a target nucleic acid of the first cell; (c) annealing the adapter region of the first adapter oligonucleotide to the adapter region of the first barcode molecule, and annealing the adapter region of the second adapter oligonucleotide to the adapter region of the second barcode molecule; and (d) ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.

In the methods, step (b) may comprise annealing the first and second adapter oligonucleotides to sub-sequences of a target nucleic acid of the cell, and wherein either: (i) step (d) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the target nucleic acid as a template, or (ii) before step (d), the method comprises extending the first and second adapter oligonucleotides to produce first and second different target nucleic acid molecules each of which comprises at least one nucleotide synthesised from the target nucleic acid as a template.

The invention provides a method of preparing a nucleic acid sample for sequencing, wherein the sample comprises at least two cells, and wherein the method comprises the steps of: (a) contacting the sample with a library comprising first and second multimeric barcoding reagents, wherein each multimeric barcoding reagent comprises: (i) first and second barcode molecules linked together, wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule and wherein the second barcoded oligonucleotide comprises a barcode region annealed to the barcode region of the second barcode molecule, and wherein the barcode regions of the first and second barcoded oligonucleotides of the first multimeric barcoding reagent of the library are different to the barcode regions of the first and second barcoded oligonucleotides of the second multimeric barcoding reagent of the library; wherein the sample is further contacted with first and second adapter oligonucleotides for each of the multimeric barcoding reagents, wherein the first and second adapter oligonucleotides each comprise an adapter region, wherein a cell-binding moiety is attached to each of the adapter oligonucleotides, and wherein the cell-binding moieties of the first and second adapter oligonucleotides for the first multimeric barcoding reagent bind to the cell membrane of a first cell of the sample and the first and second adapter oligonucleotides for the first multimeric barcoding reagent are internalized into the first cell, and wherein the cell-binding moieties of the first and second adapter oligonucleotides for the second multimeric barcoding reagent bind to the cell membrane of a second cell of the sample and the first and second adapter oligonucleotides for the second multimeric barcoding reagent are internalized into the second cell; (b) annealing or ligating the first and second adapter oligonucleotides for the first multimeric barcoding reagent to sub-sequences of a target nucleic acid of the first cell, and annealing or ligating the first and second adapter oligonucleotides for the second multimeric barcoding reagent to sub-sequences of a target nucleic acid of the second cell; (c) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and (d) for each of the multimeric barcoding reagents, ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.

In the methods, step (b) may comprise annealing the first and second adapter oligonucleotides for the first multimeric barcoding reagent to sub-sequences of a target nucleic acid of the first cell, and annealing the first and second adapter oligonucleotides for the second multimeric barcoding reagent to sub-sequences of a target nucleic acid of the second cell, and wherein either: (i) for each of the multimeric barcoding reagents, step (d) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the target nucleic acid as a template, or (ii) for each of the multimeric barcoding reagents, before step (d), the method comprises extending the first and second adapter oligonucleotides to produce first and second different target nucleic acid molecules each of which comprises at least one nucleotide synthesised from the target nucleic acid as a template.

The multimeric barcoding reagents may each comprise a cell-binding moiety, optionally wherein: (i) the cell-binding moiety of the first multimeric barcoding reagent binds to the cell membrane of the first cell of the sample and the multimeric barcoding reagent is internalized into the first cell and (ii) the cell-binding moiety of the second multimeric barcoding reagent binds to the cell membrane of the second cell of the sample and the second multimeric barcoding reagent is internalized into the second cell.

A cell-binding moiety may be attached to each of the barcode molecules. Additionally or alternatively, a cell-binding moiety may be attached to each of the barcoded oligonucleotides.

In the methods, the first and second adapter oligonucleotides for the first multimeric barcoding reagent may be comprised within a first lipid carrier and the first and second adapter oligonucleotides for the second multimeric barcoding reagent may be comprised within a second lipid carrier, optionally wherein in step (a) the first lipid carrier merges with the cell membrane of the first cell and the first and second adapter oligonucleotides for the first multimeric barcoding reagent are internalized into the first cell, and the second lipid carrier merges with the cell membrane of the second cell and the first and second adapter oligonucleotides for the second multimeric barcoding reagent are internalized into the second cell. Optionally, the adapter oligonucleotides are released into the cell e.g. into the cytoplasm.

The first lipid carrier may further comprise the first multimeric barcoding reagent and the second lipid carrier may further comprise the second multimeric barcoding reagent.

The lipid carrier may be a liposome or a micelle. Alternatively, the lipid carrier may take any of the forms described herein.

A cell-binding moiety may be attached to a multimeric barcoding reagent, adapter oligonucleotide, barcoded oligonucleotide, hybridization molecule or barcode molecule by a covalent linkage or by a non-covalent linkage.

A cell-binding moiety may be attached to each barcoded oligonucleotide, hybridization molecule, barcode molecule and/or adapter oligonucleotide by a linker molecule. Optionally, said linker may be a flexible linker. Optionally, said linker may be comprised of one or more units of ethylene glycol and/or poly(ethylene) glycol, such as hexa-ethylene glycol or penta-ethylene glycol. Optionally, said linker may be comprised of one or more ethyl groups, such as a C3 (three-carbon) spacer, C6, C12, or C18. Optionally, any other spacer may be used.

The cell-binding moiety (or moieties) may capable of initiating endocytosis on binding to a cell membrane.

The cell-binding moiety may comprise one or more moieties selected from: a peptide, a cell penetrating peptide, an aptamer, a DNA adptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a cationic lipid, a cationic polymer, poly(ethylene) glycol, spermine, a spermine derivatives or analogue, a poly-lysine, a poly-lysine derivative or analogue, polyethyleneimine, diethylaminoethyl (DEAE)-dextran, cholesterol, a sterol moiety, a cationic molecule, a hydrophobic molecule and an amphiphilic molecule.

The cell-binding moiety may interact with one or more specific molecule(s) on the cell surface or membrane (as in the case of e.g. an antibody, an antibody fragment and an aptamer). Alternatively or additionally, the cell-binding moiety may alter the overall charge and/or charge distribution of multimeric barcoding reagents (as in the case of e.g. a cationic polymer). Alternatively or additionally, the cell-binding moiety may alter the lipophilic/lipophobic and/or hydrophilic/hydrophobic character and/or balance of the multimeric barcoding reagents (as in the case of e.g. a lipid or cholesterol).

The cell-binding moiety may be a molecule that has a net positive charge in a solution comprising a cell and that enables binding of a multimeric barcoding reagent to the cell.

A multimeric barcoding reagent, adapter oligonucleotide, barcoded oligonucleotide, hybridization molecule or barcode molecule may comprise at least 2, at least 3, at least 5, at least 10, at least 20, at least 50, at least 100, at least 500, or at least 1000 cell binding moieties.

The invention provides a method of preparing a nucleic acid sample for sequencing, wherein the sample comprises at least two cells, and wherein the method comprises the steps of: (a) contacting the sample with a library comprising at least two multimeric barcoding reagents, wherein each multimeric barcoding reagent comprises first and second barcode regions linked together, wherein each barcode region comprises a nucleic acid sequence and wherein the first and second barcode regions of a first multimeric barcoding reagent are different to the first and second barcode regions of a second multimeric barcoding reagent of the library;

(b) transferring the first and second barcode regions of the first multimeric barcoding reagent from the library into a first cell of the sample and transferring the first and second barcode regions of the second multimeric barcoding reagent from the library into a second cell of the sample; and (c) appending barcode sequences to each of first and second sub-sequences of a target nucleic acid of the first cell to produce first and second barcoded target nucleic acid molecules for the first cell, wherein the first barcoded target nucleic acid molecule comprises the nucleic acid sequence of the first barcode region of the first multimeric barcoding reagent and the second barcoded target nucleic acid molecule comprises the nucleic acid sequence of the second barcode region of the first multimeric barcoding reagent, and appending barcode sequences to each of first and second sub-sequences of a target nucleic acid of the second cell to produce first and second barcoded target nucleic acid molecules from the second cell, wherein the first barcoded target nucleic acid molecule comprises the nucleic acid sequence of the first barcode region of the second multimeric barcoding reagent and the second barcoded target nucleic acid molecule comprises the nucleic acid sequence of the second barcode region of the second multimeric barcoding reagent.

The method of preparing a nucleic acid sample for sequencing, wherein the sample comprises at least two cells, may comprise the steps of: (a) contacting the sample with a library comprising at least two multimeric barcoding reagents, wherein each multimeric barcoding reagent comprises first and second barcoded oligonucleotides linked together, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library; (b) transferring the first and second barcoded oligonucleotides of the first multimeric barcoding reagent from the library into a first cell of the sample and transferring the first and second barcoded oligonucleotides of the second multimeric barcoding reagent from the library into a second cell of the sample; and (c) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules.

In the methods, the step of annealing or ligating (step (c)) may comprise: (i) annealing the first and second barcoded oligonucleotides of the first multimeric barcoding reagent to first and second sub-sequences of a target nucleic acid of the first cell, and annealing the first and second barcoded oligonucleotides of the second multimeric barcoding reagent to first and second sub-sequences of a target nucleic acid of the second cell; and (ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the target nucleic acid as a template.

In the methods, the multimeric barcoding reagents may each comprise: (i) first and second hybridization molecules linked together, wherein each of the hybridization molecules comprises a nucleic acid sequence comprising a hybridization region; and (ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule; optionally wherein step (b) comprises transferring the first multimeric barcoding reagent into the first cell and transferring the second multimeric barcoding reagent into the second cell.

In the methods, the multimeric barcoding reagents may each comprise: (i) first and second barcode molecules linked together, wherein each of the barcode molecules comprises a nucleic acid sequence comprising a barcode region; and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; optionally wherein step (b) comprises transferring the first multimeric barcoding reagent into the first cell and transferring the second multimeric barcoding reagent into the second cell.

The invention provides a method of preparing a nucleic acid sample for sequencing, wherein the sample comprises at least two cells, and wherein the method comprises the steps of: (a) contacting the sample with a library comprising first and second multimeric barcoding reagents, wherein each multimeric barcoding reagent comprises: (i) first and second barcode molecules linked together, wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule, wherein the second barcoded oligonucleotide comprises a barcode region annealed to the barcode region of the second barcode molecule, and wherein the barcode regions of the first and second barcoded oligonucleotides of the first multimeric barcoding reagent of the library are different to the barcode regions of the first and second barcoded oligonucleotides of the second multimeric barcoding reagent of the library; wherein the sample is further contacted with first and second adapter oligonucleotides for each of the multimeric barcoding reagents, wherein the first and second adapter oligonucleotides each comprise an adapter region; (b) transferring the first and second adapter oligonucleotides for the first multimeric barcoding reagent into the first cell and transferring the first and second adapter oligonucleotides for the second multimeric barcoding reagent into the second cell, optionally wherein the step further comprises transferring the first multimeric barcoding reagent into the first cell and transferring the second multimeric barcoding reagent into the second cell; (c) annealing or ligating the first and second adapter oligonucleotides for the first multimeric barcoding reagent to sub-sequences of a target nucleic acid of the first cell, and annealing or ligating the first and second adapter oligonucleotides for the second multimeric barcoding reagent to sub-sequences of a target nucleic acid of the second cell; (d) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and (e) for each of the multimeric barcoding reagents, ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.

In the methods, the step of annealing or ligating (step (c)) may comprise annealing the first and second adapter oligonucleotides for the first multimeric barcoding reagent to sub-sequences of a target nucleic acid of the first cell, and annealing the first and second adapter oligonucleotides for the second multimeric barcoding reagent to sub-sequences of a target nucleic acid of the second cell, and wherein either:

(i) for each of the multimeric barcoding reagents, step (e) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the target nucleic acid as a template, or (ii) for each of the multimeric barcoding reagents, before step (e), the method comprises extending the first and second adapter oligonucleotides to produce first and second different target nucleic acid molecules each of which comprises at least one nucleotide synthesised from the target nucleic acid as a template.

In the methods, prior to the step of transferring (step (b)), the cell membrane of the cells may be permeabilised by contact with a chemical surfactant. Optionally, the barcoded oligonucleotides, adapter oligonucleotides and/or multimeric barcoding reagents are transferred into the cells through the permeabilised membrane.

The chemical surfactant may be a non-ionic surfactant. The chemical surfactant may be one or more of Triton X-100 ($C_{14}H_{22}O(C_2H_4O)n(n=9-10)$), Brij 35, Brij 58, Digitonin, IGEPAL CA-630, Saponin, TWEEN 20, TWEEN 40 and/or TWEEN 80.

The chemical surfactant may be in solution at a concentration of less than 1.0 micromolar, less than less than 5 micromolar, 10 micromolar, less than 25 micromolar, less than 50 micromolar, less than 100 micromolar, less than 200 micromolar, or less than 500 micromolar, less than 1.0 milimolar or less than 5.0 milimolar.

The cell(s) may be permeabilised by a mixture of two or more different chemical surfactants.

In the methods, after the step of permeabilising the cell membranes, the concentration of the chemical surfactant in the solution may be reduced by addition of a second solution to the sample comprising the cells and the chemical surfactant. Optionally, this second solution may not contain a chemical surfactant.

In the methods, after the step of permeabilising the cell membranes, the sample of cells may be pelleted by a centrifugation step, the supernatant (containing the chemical surfactant but not the cells) may be removed, and the pelleted cells may be resuspended in a second solution. Optionally, this second solution may not contain a chemical surfactant.

In the methods, prior to the step of transferring (step (b)), the cell membrane of the cells may be permeabilised by contact with a solvent or molecular solvent (capable of disturbing the lipid bilayer of the cell membrane). Optionally, the barcoded oligonucleotides, adapter oligonucleotides and/or multimeric barcoding reagents are transferred into the cells through the permeabilised membrane.

The solvent may be one or more of betaine, formamide, and/or dimethyl sulfoxide (DMSO)

The solvent may be used at a concentration of at least 1% by weight or by volume, at least 5% by weight or by volume, at least 10% by weight or by volume, at least 20% by weight or by volume, at least 30% by weight or by volume, at least 40% by weight or by volume, or at least 50% by weight or by volume.

In the methods, prior to the step of transferring (step (b)), the cell membrane of the cells may be permeabilised by a high-temperature thermal incubation step. Optionally, barcoded oligonucleotides, adapter oligonucleotides and/or multimeric barcoding reagents are transferred into the cells through the permeabilised membrane.

The thermal incubation step may be performed at a temperature of at least 37 degrees Celsius, at least 40 degrees Celsius, at least 45 degrees Celsius, at least 50 degrees Celsius, at least 55 degrees Celsius, at least 60 degrees Celsius, at least 65 degrees Celsius, at least 70 degrees Celsius, at least 75 degrees Celsius, at least 80 degrees Celsius, or at least 85 degrees Celsius.

The step of permeabilising the cell membranes may be performed for less than 5 seconds, less than 10 seconds, less than 30 seconds, less than 60 seconds, less than 2 minutes, less than 5 minutes, less than 10 minutes, less than 15 minutes, less than 30 minutes, less than 60 minutes, or less than 2 hours.

In the methods, the barcoded oligonucleotides, adapter oligonucleotides and/or multimeric barcoding reagents may be transferred into the cells by complexation with a transfection reagent or lipid carrier (followed by transfection, transfer, or release into the cells). This process may involve transfection, transfer or release of the reagents into the cell.

The transfection reagent may be a lipid transfection reagent e.g. a cationic lipid transfection reagent. Optionally, said cationic lipid transfection reagent comprises at least two alkyl chains. Optionally, said cationic lipid transfection reagent may be a commercially available cationic lipid transfection reagent such as Lipofectamine.

The barcoded oligonucleotides, adapter oligonucleotides and/or multimeric barcoding reagents may be transferred into the cells by complexation with a cationic polymer reagent (followed by transfection, transfer, or release into the cells). Optionally, said cationic polymer reagent may comprise a linear cationic polymer, such as spermine or poly-lysine. Optionally, said cationic polymer reagent may comprise a polyethyleneimine polymer. Optionally, said cationic polymer reagent may comprise a diethylaminoethyl (DEAE)-dextran polymer. Optionally, said cationic polymer reagent may comprise a branched cationic polymer.

The barcoded oligonucleotides, adapter oligonucleotides and/or multimeric barcoding reagents may be transferred into the cells by complexation with a dendrimer and/or an activated dendrimer (followed by transfection, transfer, or release into the cells). Optionally, said activated dendrimer is activated with one or more amino groups; optionally said amino groups are positively charged. Optionally, any such dendrimer and/or activated dendrimer comprises at least 2 generations, at least 3 generations, at least 5 generations, at least 10 generations, at least 20 generations, or at least 30 generations.

The barcoded oligonucleotides, adapter oligonucleotides and/or multimeric barcoding reagents may be transferred into the cells by complexation with a liposomal or micellar reagent (followed by transfection, transfer, or release into the cells). Optionally, the barcoded oligonucleotides, adapter oligonucleotides and/or multimeric barcoding reagents may be loaded into a preparation of liposomal or micellar reagents with a reagent loading step. Optionally, said liposomal or micellar reagents may comprise one or more amphiphiles. Optionally, said liposomal or micellar reagents may comprise one or more phospholipids. Optionally, said phospholipids may comprise one or more phosphatidylcholines. Optionally, said phospholipids may comprise one or more phophatidylethanolamine molecules. Optionally, said liposomal or micellar reagents may comprise copolymers. Optionally, said liposomal or micellar reagents may comprise block copolymers. Optionally, each liposomal or micellar reagent may on average be complexed with 1, or less than 1, or greater than 1, or any other number of multimeric barcoding reagent(s) within a preparation of such complexed multimeric barcoding reagent(s). Optionally, each liposomal or micellar reagent may on average be complexed with at least 2 barcoded oligonucleotides (and/or 2 adapter oligonucleotides).

The barcoded oligonucleotides, adapter oligonucleotides and/or multimeric barcoding reagents may be transferred into the cells by complexation within a solution of calcium chloride and phosphate to form a precipitate and then transfected into the cells.

The barcoded oligonucleotides, adapter oligonucleotides and/or multimeric barcoding reagents may be complexed to transfection reagents with a complexing incubation step. Optionally, this complexing incubation step may be at least 5 seconds, at least 10 seconds, at least 30 seconds, at least 60 seconds, at least 2 minutes, at least 5 minutes, at least 10 minutes, at least 30 minutes, at least 60 minutes, at least 2 hours in length, or at least 4 hours in length. Optionally, this complexing incubation step may take place at approximately 4 degrees Celsius, approximately 12 degrees Celsius, approximately 20 degrees Celsius, approximately 25 degrees Celsius, approximately 30 degrees Celsius, or approximately 37 degrees Celsius. Optionally, the complexed multimeric barcoding reagents may be further processed, and/or stored, prior to transfer into cells.

In the methods, after the barcoded oligonucleotides, adapter oligonucleotides and/or multimeric barcoding reagents are complexed to transfection reagents, a transfer incubation step may be performed. Optionally, this transfer incubation step may be at least 5 seconds, at least 10 seconds, at least 30 seconds, at least 60 seconds, at least 2 minutes, at least 5 minutes, at least 10 minutes, at least 30 minutes, at least 60 minutes, at least 2 hours in length, or at least 4 hours in length. Optionally, this transfer incubation step may take place at approximately 4 degrees Celsius, approximately 12 degrees Celsius, approximately 20 degrees Celsius, approximately 25 degrees Celsius, approximately 30 degrees Celsius, or approximately 37 degrees Celsius.

The barcoded oligonucleotides of the first multimeric barcoding reagent may be comprised within a first lipid carrier, and the barcoded oligonucleotides of the second multimeric barcoding reagent may be comprised within a second lipid carrier. Optionally, such barcoded oligonucleotides may be transferred into cells by a process involving merger of the liposome or micelle with the cell membrane. Optionally, this merger process may release the barcoded oligonucleotides into the cytoplasm of the cell. Optionally, the barcoded oligonucleotides may be loaded into a preparation of liposomal or micellar reagents with an oligonucleotide loading step. Optionally, said liposomes or micelles may comprise one or more amphiphiles. Optionally, said liposomes or micelles may comprise one or more phospholipids. Optionally, said phospholipids may comprise one or more phosphatidylcholines. Optionally, said phospholipids may comprise one or more phophatidylethanolamine molecules. Optionally, said liposomes or micelles may comprise copolymers. Optionally, said liposomes or micelles may comprise block copolymers. Optionally, each liposome or micelle may on average be complexed with, or loaded with, at least 2, at least 3, at least 5, at least 10, at least 50, at least 100, at least 500, at least 1000, at least 10,000, or at least 100,000 barcoded oligonucleotides, or any greater number of barcoded oligonucleotides.

In the methods, the barcoded oligonucleotides, adapter oligonucleotides and/or multimeric barcoding reagents may be transferred into the cells by a process comprising cell squeezing.

In the methods, the step of transferring may comprise mechanically deforming cells in the sample to produce transient membrane disruptions that enable the transfer of the barcoded oligonucleotides, adapter oligonucleotides and/or multimeric barcoding reagents into the cells. The sample may be contacted with a library of multimeric barcoding reagents (and/or adapter oligonucleotides for each multimeric barcoding reagent) before, during or after the step of mechanically deforming the cells.

Methods for cell squeezing are provided in Sharei et al, Cell Squeezing as a Robust, Microfluidic Intracellular Delivery Platform. J. Vis. Exp. (81, e50980, doi:10.3791/50980 (2013), and Sharei et al, Proc Natl Acad Sci USA. 2013 Feb. 5; 110(6):2082-7).

In methods of cell squeezing intact cells may be shunted through a mechanical conduit (e.g. a microfluidic channel within a microfluidic circuit) that is smaller (i.e. smaller in diameter) than a cell, and wherein, as a cell transits through this conduit or channel, the cell becomes 'squeezed' (that is, it encounters a mechanical stress and/or deformation or shear stress) and is at least partially deformed. As a function of this process, the cell membrane becomes partially disturbed, and this may allow molecules (including barcoded oligonucleotides, adapter oligonucleotides and/or multimeric barcoding reagents) to transit from the solution surrounding the cell, into the cell itself. Cell squeezing thus comprises a mechanical, non-chemical, non-biological means of transferring reagents into cells.

The methods may comprise mixing a library of multimeric barcoding reagents with a sample of cells and passing the resulting mixture through a cell squeezing apparatus. This process allows multimeric barcoding reagents from the library thereof to enter one or more cells in the sample of cells. The resulting cells may then be further processed; for example, they may be incubated for a period of time e.g. to allow the barcoding oligonucleotides to anneal to cognate nucleic acids within the cells into which they have been transferred.

In the methods, the barcoded oligonucleotides, adapter oligonucleotides and/or multimeric barcoding reagents may be transferred into the cells by a process comprising electroporation (or electropermeabilisation).

The sample may be contacted with a library of multimeric barcoding reagents (and/or adapter oligonucleotides for each multimeric barcoding reagent) before, during or after the process of electroporation process.

The electroporation may use a square electroporation waveform. The electroporation may use an exponential electroporation waveform.

During the electroporation process the peak voltage gradient may be at least 1.0 kilovolts per centimetre, at least 2.0 kilovolts per centimetre, at least 5.0 kilovolts per centimetre, at least 10.0 kilovolts per centimetre, at least 15.0 kilovolts per centimetre, or at least 20.0 kilovolts per centimetre.

During the electroporation process the electroporation pulses may be at least 100 microseconds in duration, at least 500 microseconds in duration, at least 1.0 millisecond in duration, at least 2.0 milliseconds in duration, at least 3.0 milliseconds in duration, at least 5.0 milliseconds in duration, or at least 10.0 milliseconds in duration.

These below methods describe particular techniques for use with any of the above methods wherein multimeric barcoding reagents are transferred (or internalized) into cells by any method. These methods describe alternative embodiments, as well as subsequent experimental steps, that could potentially be applicable to any of the above protocols.

In the methods, following a step of transferring multimeric barcoding reagent(s) or adapter oligonucleotides into cells, the cells may be incubated for a period of time to allow the target regions of the multimeric barcoding reagent(s) to anneal to sub-sequences of a target nucleic acid within the cell. The incubation period may be at least 1 minute, or at least 5 minutes, or at least 15 minutes, or at least 30 minutes, or at least 60 minutes. The incubation may take place within a solution containing a nucleic acid denaturant, such as DMSO or betaine. The incubation may take place at a temperature of at least 37 degrees Celsius, at least 45 degrees Celsius, at least 50 degrees Celsius, at least 55 degrees Celsius, at least 60 degrees Celsius, at least 65 degrees Celsius, or at least 70 degrees Celsius.

In the methods, following a step of introducing barcoded oligonucleotides and/or multimeric barcoding reagent(s) into cells, a reagent-division step may be performed in which multimeric barcoding reagents divide into two or more independently diffusible components thereof. Optionally, in embodiments wherein a multimeric barcoding reagent comprises barcoded oligonucleotides annealed to barcode molecules, this reagent-division step may comprise a step of denaturing one or more barcoded oligonucleotides from the barcode molecules to which they are annealed, such that said barcoded oligonucleotides are able to diffuse independently within the cell(s) into which they have been transferred. Optionally, such a denaturing step may be performed with a high-temperature incubation, wherein the barcoded oligonucleotides are denatured at a temperature of at least 37 degrees Celsius, at least 45 degrees Celsius, at least 50 degrees Celsius, at least 55 degrees Celsius, at least 60 degrees Celsius, at least 65 degrees Celsius, or at least 70 degrees Celsius. Optionally, this denaturation step takes place within a solution containing a nucleic acid denaturant, such as DMSO or betaine. Optionally, this denaturation step may take place prior to an incubation step as described above; or optionally this denaturation step may take place within the same step as an incubation step.

In the methods, following the transfer of barcoded oligonucleotides, adapter oligonucleotides and/or multimeric barcoding reagents into cells, and optionally following an incubation step, the cells may be contacted by a solution of oligonucleotides complementary to all or part of one or more target regions of the barcoded oligonucleotides within multimeric barcoding reagents.

In the methods, following introduction of the barcoded oligonucleotides, adapter oligonucleotides and/or multimeric barcoding reagents into the cell, and optionally following an incubation step, the cell(s) may be isolated from a reaction mixture by centrifugation.

In the methods, following the transfer of the barcoded oligonucleotides, adapter oligonucleotides and/or multimeric barcoding reagents into the cell, and optionally following an incubation step, the barcoded oligonucleotides and/or barcoded target nucleic acid molecules and/or multimeric barcoding reagent(s) may be isolated from the cell.

The multimeric barcoding reagents and/or barcoded oligonucleotides may comprise one or more biotin moieties.

In the methods, following the transfer of barcoded oligonucleotides, adapter oligonucleotides and/or multimeric barcoding reagents into the cell, and optionally following an incubation step, the barcoded oligonucleotides and/or barcoded target nucleic acid molecules and/or multimeric barcoding reagent(s) may be isolated by a process of: (a) dissolving and/or permeabilising the cell membranes, optionally using a chemical surfactant, by using a (molecular) solvent, or by incubation at high temperature; (b) contacting the resulting mixture with a solid support, optionally wherein the solid support comprises streptavidin moieties; and (c) capturing the barcoded oligonucleotides and/or barcoded target nucleic acid molecules and/or multimeric barcoding reagent(s) on the solid support, optionally through streptavidin-biotin interaction.

The solid support may be one or more magnetic beads, optionally wherein the one or more magnetic beads comprise streptavidin molecules on their surface. The magnetic bead(s) may isolated from a reaction mixture with a magnet.

In the methods, any step(s) of permeabilising cells and/or transferring multimeric barcoding reagents into cells and/or incubating cells may take place in a hypotonic solution. In the methods, any step(s) of permeabilising cells and/or transferring multimeric barcoding reagents into cells and/or incubating cells may take place in a hypertonic solution.

In the methods, a library of multimeric barcoding reagents may be provided in the same solution as a chemical surfactant, and/or in the same solution as a molecular solvent, and/or in the same solution as a denaturant.

The invention provides a method of preparing a nucleic acid sample for sequencing, wherein the sample comprises at least two cells, and wherein the method comprises the steps of: (a) contacting the sample with a library comprising at least two multimeric barcoding reagents, wherein each multimeric barcoding reagent comprises first and second barcode regions linked together, wherein each barcode region comprises a nucleic acid sequence and wherein the first and second barcode regions of a first multimeric barcoding reagent are different to the first and second barcode regions of a second multimeric barcoding reagent of the library; (b) lysing the cells or permeabilizing the cell membranes of the cells; and (c) appending barcode sequences to each of first and second sub-sequences of a target nucleic acid of the first cell to produce first and second barcoded target nucleic acid molecules for the first cell, wherein the first barcoded target nucleic acid molecule comprises the nucleic acid sequence of the first barcode region of the first multimeric barcoding reagent and the second barcoded target nucleic acid molecule comprises the nucleic acid sequence of the second barcode region of the first multimeric barcoding reagent, and appending barcode sequences to each of first and second sub-sequences of a target nucleic acid of the second cell to produce first and second barcoded target nucleic acid molecules for the second cell, wherein the first barcoded target nucleic acid molecule comprises the nucleic acid sequence of the first barcode region of the second multimeric barcoding reagent and the second barcoded target nucleic acid molecule comprises the nucleic acid sequence of the second barcode region of the second multimeric barcoding reagent.

The invention provides a method of preparing a nucleic acid sample for sequencing, wherein the sample comprises at least two cells, and wherein the method comprises (in order) the steps of:
  (a) contacting the sample with a library comprising at least two multimeric barcoding reagents, wherein each multimeric barcoding reagent comprises first and second barcoded oligonucleotides linked together, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library;
  (b) lysing the cells or permeabilizing the cell membranes of the cells; and
  (c) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules.

The method may comprise (in order) the steps of: (a) contacting the sample with a library comprising at least two multimeric barcoding reagents, wherein each multimeric barcoding reagent comprises first and second barcoded oligonucleotides linked together, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library; (b) lysing the cells or permeabilizing the cell membranes of the cells; and (c) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules.

The invention provides a method of preparing a nucleic acid sample for sequencing, wherein the sample comprises at least 10 cells, and wherein the method comprises in order the steps of: (a) contacting the sample with a library comprising at least two multimeric barcoding reagents, wherein each multimeric barcoding reagent comprises first and second barcoded oligonucleotides linked together and a cell-binding moiety, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library, wherein the cell-binding moiety of the first multimeric barcoding reagent binds to the cell membrane of a first cell prior to step (b), and wherein the cell-binding moiety of the second multimeric barcoding reagent binds to the cell membrane of a second cell prior to step (b); (b) lysing the cells or permeabilizing the cell membranes of the cells; and (c) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules. Preferably, the cells are comprised within a single contiguous aqueous volume during steps (a), (b) and/or (c).

In the methods, the step of annealing or ligating (step (c)) may comprise: (i) annealing the first and second barcoded oligonucleotides of the first multimeric barcoding reagent to first and second sub-sequences of a target nucleic acid of the first cell, and annealing the first and second barcoded oligonucleotides of the second multimeric barcoding reagent to first and second sub-sequences of a target nucleic acid of the second cell; and (ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the target nucleic acid as a template.

In the methods, the multimeric barcoding reagents may each comprise: (i) first and second hybridization molecules linked together, wherein each of the hybridization molecules comprises a nucleic acid sequence comprising a hybridization region; and (ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule.

The multimeric barcoding reagents may each comprise: (i) first and second barcode molecules linked together, wherein each of the barcode molecules comprises a nucleic acid sequence comprising a barcode region; and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule.

The invention provides a method of preparing a nucleic acid sample for sequencing, wherein the sample comprises at least two cells, and wherein the method comprises the steps of: (a) contacting the sample with a library comprising first and second multimeric barcoding reagents, wherein each multimeric barcoding reagent comprises: (i) first and second barcode molecules linked together, wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule and wherein the second barcoded oligonucleotide comprises a barcode region annealed to the barcode region of the second barcode molecule, and wherein the barcode regions of the first and second barcoded oligonucleotides of the first multimeric barcoding reagent are different to the barcode regions of the first and second barcoded oligonucleotides of the second multimeric barcoding reagent; wherein the sample is further contacted with first and second adapter oligonucleotides for each of the multimeric barcoding reagents, wherein the first and second adapter oligonucleotides each comprise an adapter region; (b) lysing the cells or permeabilizing the cell membranes of the cells; (c) annealing or ligating the first and second adapter oligonucleotides for the first multimeric barcoding reagent to sub-sequences of a target nucleic acid of the first cell, and annealing or ligating the first and second adapter oligonucleotides for the second multimeric barcoding reagent to sub-sequences of a target nucleic acid of the second cell; (d) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and (e) for each of the multimeric barcoding reagents, ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.

In the methods, the step of annealing or ligating (step (c)) may comprise annealing the first and second adapter oligonucleotides for the first multimeric barcoding reagent to sub-sequences of a target nucleic acid of the first cell, and annealing the first and second adapter oligonucleotides for the second multimeric barcoding reagent to sub-sequences of a target nucleic acid of the second cell, and wherein either: (i) for each of the multimeric barcoding reagents, step (e) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the target nucleic acid as a template, or (ii) for each of the multimeric barcoding reagents, before step (e), the method comprises extending the first and second adapter oligonucleotides to produce first and second different target nucleic acid molecules each of which comprises at least one nucleotide synthesised from the target nucleic acid as a template.

In the methods, following the step of lysing or permeabilising (step (b)), target nucleic acids from each cell within the sample may be able to diffuse out of the cell (i.e. out of the cytoplasmic space or cell volume). Optionally, the multimeric barcoding reagents are not able to enter the cell. Optionally, following step (b), the cell membrane is substantially or totally dissolved. Optionally, following step (b), the cell membrane remains partially intact but wherein messenger RNA molecules and/or other nucleic acid molecules are able to diffuse out of the cell (i.e. out of the cytoplasmic space or cell volume) through pores and/or other structural discontinuities within the cell membrane.

In the methods, step (b) may be performed by increasing the temperature of the sample. Optionally, a high temperature incubation step may be performed, for example the high temperature incubation step may be performed at a temperature of at least 37 degrees Celsius, at least 40 degrees Celsius, at least 50 degrees Celsius, at least 60 degrees Celsius, at least 70 degrees Celsius, at least 80 degrees Celsius, at least 90 degrees Celsius, or at least 95 degrees Celsius.

In the methods, step (b) may be performed in the presence of a chemical surfactant. The chemical surfactant may be a non-ionic surfactant. The chemical surfactant may be one or more of Triton X-100 ($C_{14}H_{22}O(C_2H_4O)n(n=9\text{-}10)$), Brij 35, Brij 58, Digitonin, IGEPAL CA-630, Saponin, TWEEN 20, TWEEN 40 and/or TWEEN 80.

In the methods, step (b) may be performed in the presence of a solvent or molecular solvent (capable of disturbing the lipid bilayer of the cell membrane). The solvent may be one or more of betaine, formamide, and/or dimethyl sulfoxide (DMSO).

In the methods, any step(s) may take place under hypotonic or hypertonic conditions. Optionally, step (b) may be performed under hypotonic or hypertonic conditions.

In the methods, the multimeric barcoding reagents and/or adapter oligonucleotides may each comprise a cell-binding moiety, optionally wherein the cell-binding moiety binds each multimeric barcoding reagent and/or adapter oligonucleotide to the cell membrane of a cell prior to step (b). Optionally, each of the barcoded oligonucleotides, multimeric hybridization molecules and/or multimeric barcode molecules comprise a cell-binding moiety. The cell-binding moiety of each barcoded oligonucleotide, multimeric hybridization molecule and/or multimeric barcode molecule may bind to the cell membrane of a cell prior to step (b).

In the methods, the step of annealing barcoded oligonucleotides to target nucleic acids may comprise an incubation step, wherein the sample is incubated for a period of time to allow the target regions of the barcoded oligonucleotides to anneal to target nucleic acids. Optionally, this incubation period is at least 1 minute, or at least 5 minutes, or at least 15 minutes, or at least 30 minutes, or at least 60 minutes. Optionally, this incubation takes place within a solution containing a nucleic acid denaturant, such as DMSO or betaine. Optionally, this incubation takes place at a temperature of at least 37 degrees Celsius, at least 45 degrees Celsius, at least 50 degrees Celsius, at least 55 degrees Celsius, at least 60 degrees Celsius, at least 65 degrees Celsius, or at least 70 degrees Celsius.

In the methods, during or prior to step (c), a reagent-division step may be performed in which multimeric barcoding reagents are divided into two or more independently diffusible components thereof. Optionally, wherein a multimeric barcoding reagent comprises barcoded oligonucleotides annealed to barcode molecules, this reagent-division step comprises a step of denaturing one or more barcoded oligonucleotides from the barcode molecules to which they are annealed, such that said barcoded oligonucleotides are able to diffuse independently within solution. Optionally, such a denaturing step may be performed with a high-temperature incubation, wherein the barcoded oligonucleotides are denatured at a temperature of at least 37 degrees Celsius, at least degrees Celsius, at least 50 degrees Celsius, at least 55 degrees Celsius, at least 60 degrees Celsius, at least 65 degrees Celsius, or at least 70 degrees Celsius. Optionally, this denaturation step takes place within a solution containing a nucleic acid denaturant, such as DMSO or betaine. Optionally, this reagent-division step and/or denaturation step may take place prior to an annealing step as described above; or optionally this reagent-division step and/or denaturation step may take place during the annealing step. Additionally, this reagent-division step and/or denaturation step may take place during the cell lysis step. For example, a single high-temperature thermal incubation step may have the effect of lysing cells through a thermal lysis process, and denaturing barcoded oligonucleotides from barcode molecules within multimeric barcoding reagents. Additionally, such a combined, high-temperature cell-lysis and reagent-division step may take place at the same temperature of and/or during the step of annealing the barcoded oligonucleotides to target nucleic acids.

The nucleic acid sample may have a concentration of cells for step (a) of less than 10 picomolar, less than 1 picomolar, less than 100 femtomolar, less than 10 femtomolar, less than 1 femtomolar, less than 100 attomolar, less than 10 attomolar, or less than 1 attomolar. Alternative higher or lower concentrations may also be used. Preferably, the cells will be at a concentration of less than 10 femtomolar.

The nucleic acid sample may have a concentration of cells for step (b) of less than 10 picomolar, less than 1 picomolar, less than 100 femtomolar, less than 10 femtomolar, less than 1 femtomolar, less than 100 attomolar, less than 10 attomolar, or less than 1 attomolar. Alternative higher or lower concentrations may also be used. Preferably, the cells will be at a concentration of less than 10 femtomolar.

The nucleic acid sample may have a concentration of cells for step (c) of less than 10 picomolar, less than 1 picomolar, less than 100 femtomolar, less than 10 femtomolar, less than 1 femtomolar, less than 100 attomolar, less than 10 attomolar, or less than 1 attomolar. Alternative higher or lower concentrations may also be used. Preferably, the cells will be at a concentration of less than 10 femtomolar.

In the methods, prior to step (b), the method may comprise diluting the nucleic acid sample. The step of diluting the sample may be performed after a step of binding cell-binding moieties (of adapter oligonucleotides, barcoded oligonucleotides and/or multimeric barcoding reagents) to cell membranes of cells in the sample. The nucleic acid sample may have a concentration of cells for step (a) and/or step (b) and/or step (c) of less than 10 picomolar, less than 1 picomolar, less than 100 femtomolar, less than 10 femtomolar, less than 1 femtomolar, less than 100 attomolar, less than 10 attomolar, or less than 1 attomolar. Alternative higher or lower concentrations may also be used. Preferably, the cells will be at a concentration of less than 10 femtomolar. Having a low concentration of cells in the nucleic acid sample during steps (b) and (c) may reduce the 'cross-barcoding' of two physically close cells by the same multimeric barcoding reagent.

In the methods, any of steps (a), (b) and/or (c) may be performed in a high-viscosity solution. Optionally, such a high-viscosity solution may be comprised of a poly (ethylene) glycol (PEG) solution, such as PEG 20,000. Optionally, such a solution may comprise at least 5% poly (ethylene) glycol, at least 10% poly (ethylene) glycol, at least 20% poly (ethylene) glycol, at least 25% poly (ethylene) glycol, at least 30% poly (ethylene) glycol, at least 40% poly (ethylene) glycol, or at least 50% poly (ethylene) glycol by weight or by volume. Optionally, such a high-viscosity solution may comprise a solidified or semi-solidified gel or hydrogel, such as an agarose gel, a polyacrylamide gel, a crosslinked gel such as a crosslinked PEG-acrylate/PEG-thiol hydrogel, or a block-copolymer gel. Optionally, such a high-viscosity solution may comprise the solution employed during any step of cell lysis and/or cell permeabilisation. Optionally, such a high-viscosity solution may comprise the solution employed during any step of annealing barcoded oligonucleotides to target nucleic acids. Optionally, such a high-viscosity solution may have a dynamic viscosity of at least 1.0 centipoise, at least 1.1 centipoise, at least 1.2 centipoise, at least 1.5 centipoise, at least 2.0 centipoise, at least 5.0 centipoise, at least 10.0 centipoise, at least 20.0 centipoise, at least 50.0 centipoise, at least 100.0 centipoise, or at least 200.0 centipoise (e.g. at 25 degrees Celsius at standard sea-level pressure). Preferably, such a high-viscosity solution will have a dynamic viscosity of at least 2.0 centipoise. The use of a high-viscosity solution may slow the diffusion of the barcoded oligonucleotides and their target nucleic acids away from each other—i.e. when a multimeric barcoding reagent has been bound to the membrane of a single particular cell, and then the membrane is lysed or permeabilised, a high viscosity solution will have the effect of keeping the barcoded oligonucleotides and target nucleic acids from the cells in the vicinity of the original cell for a longer period of time—thus keeping the effective 'concentration' of both higher for a longer period of time (since they will occupy a smaller overall volume for a longer period of time). This slowed diffusion may also have the further effect of slowing the diffusion of target nucleic acids from one cell into a volume occupied by target nucleic acids from another cell.

In the methods, after contacting a sample comprising cells with a library of at least 2 multimeric barcoding reagents, the barcoded oligonucleotides may be digested or partially digested with an exonuclease-digestion step. Optionally, this exonuclease-digestion step may be performed before, or may be performed after, a step of transferring multimeric barcoding reagents into cells. Optionally, this exonuclease-digestion step may be performed before, or may be performed after, a step of annealing barcoded oligonucleotides to target nucleic acids from cells. Optionally, this exonuclease-digestion step may be performed by E. coli Exonuclease I, or E. coli Lambda exonuclease.

In the methods, a sample comprising cells and/or a library of two or more multimeric barcoding reagents may be contacted with a solution of one or more blocking oligonucleotides, wherein said blocking oligonucleotides may be complementary to all or part of one or more barcoded oligonucleotides. Optionally, said blocking oligonucleotides may be complementary to all or part of the target region of one or more barcoded oligonucleotides.

In the methods, a sample comprising cells and/or a library of two or more multimeric barcoding reagents may be contacted with a solution of one or more blocking oligonucleotides, wherein the blocking oligonucleotides may be complementary to all or part of one or more target nucleic acids. Optionally, the blocking oligonucleotides may be complementary to one or more specific DNA or RNA sequences. Optionally, the blocking oligonucleotides may be complementary to one or more messenger RNA (mRNA) sequences. Optionally, the blocking oligonucleotides may be complementary to the poly(A) tail sequence of messenger RNA (mRNA) sequences. Optionally, the blocking oligonucleotides may comprise a poly(T) sequence of at least 2, at least 3, at least 5, at least 10, at least 20, at least 30, or at least 50 nucleotides that are complementary to the poly(A) tail sequence of messenger RNA (mRNA) sequences.

Optionally, any said blocking oligonucleotides may anneal to the respective sequences to which they are complementary or partially complementary. Optionally, the annealing temperature at which such blocking oligonucleotides hybridise to their respective complementary sequences may be lower than the temperature at which the target region of the barcoded oligonucleotides hybridise to the target region of their target cellular nucleic acids. Optionally, this blocking-oligonucleotide step may be performed before, or may be performed after, a step of contacting a sample of cells with a library of two or more multimeric barcoding reagents. Optionally, this blocking-oligonucleotide step may be performed before, or may be performed after, a step of transferring multimeric barcoding reagents into cells. Optionally, this blocking-oligonucleotide step may be performed before, or may be performed after, a step of binding multimeric barcoding reagents to the surface of cells, wherein said multimeric barcoding reagents comprise cell-binding moieties. Optionally, this blocking-oligonucleotide step may be performed before, or may be performed after, a step of lysing or permeabilising cells. Optionally, this blocking-oligonucleotide step may be performed before, or may be performed after, a step of annealing barcoded oligonucleotides to nucleic acids from cells. Optionally, this blocking-oligonucleotide step may be performed after a step of annealing barcoded oligonucleotides to nucleic acids from cells, wherein the blocking-oligonucleotide step comprises a process of lowering the temperature of the sample solution to a temperature at or below the temperature at which the blocking oligonucleotides anneal to their respective sequences. Optionally, this blocking oligonucleotide step may be performed upon a library of multimeric barcoding reagents, prior to contacting a sample of cells with said library. Optionally, the blocking oligonucleotides may comprise a blocking moiety at their 3' end which prevents extension of said 3' end by a polymerase. Any such blocking oligonucleotides may be present at a concentration of at least 1 nanomolar, at least 10 nanomolar, at least 100 nanomolar, or at least 1 micromolar.

One or more blocking oligonucleotides may be included together in the same solution as a chemical surfactant, and/or within the same solution as a molecular solvent, and/or within the same solution as a nucleic acid denaturant, and/or within the same solution as a library of multimeric barcoding reagents.

In the methods, after a step of annealing barcoded oligonucleotides to target nucleic acids, a blocking incubation may be performed to hybridise blocking oligonucleotides to complementary sequences within barcoded oligonucleotides. Optionally this blocking incubation may be performed at a temperature below the temperature at which barcoded oligonucleotides are annealed to nucleic acids from cells. Optionally this blocking incubation may be performed at a temperature below the temperature at which blocking oligonucleotides hybridise to complementary sequences within barcoded oligonucleotides.

In the methods, a nucleic acid size selection step may be performed after a step of annealing barcoded oligonucleotides to target nucleic acids. Optionally, this step may be performed by a gel-based size selection step. Optionally, this size selection step may be performed with a solid-phase reversible immobilisation process, such as a size selection step involving magnetic or superparamagnetic beads. Optionally, this size selection step may be performed with a column-based nucleic acid purification or size-selection step. Optionally, this size selection step may selectively or preferentially remove barcoded oligonucleotides that are not annealed or bound to nucleic acids from cells. Optionally, this size selection step may preferentially remove nucleic acid molecules less than 50 nucleotides in length, less than 100 nucleotides in length, less than 150 nucleotides in length, less than 200 nucleotides in length, less than 300 nucleotides in length, less than 400 nucleotides in length, less than 500 nucleotides in length, or less than 1000 nucleotides in length.

In the methods, the multimeric barcoding reagents, barcoded oligonucleotides and/or multimeric barcode molecules may comprise one or more biotin moieties.

In the methods, following a step of annealing barcoded oligonucleotides to target nucleic acid from a cell sample, the barcoded oligonucleotides and/or barcoded target nucleic acid molecules and/or multimeric barcoding reagent(s) may be isolated by a process of: (a) contacting the resulting mixture with a solid support, optionally wherein the solid support comprises streptavidin moieties; and (b) capturing the barcoded oligonucleotides and/or barcoded target nucleic acid molecules and/or multimeric barcoding reagent(s) on the solid support, optionally through streptavidin-biotin interaction.

The solid support may be one or more magnetic beads, optionally wherein the one or more magnetic beads comprise streptavidin molecules on their surface.

The magnetic bead(s) may be isolated from a reaction mixture with a magnet.

In the methods, the nucleic acid sample may comprise at least 2, at least 5, at least 10, at least 100, or at least $10^3$, at least $10^4$, at least $10^5$, at least $10^6$, at least $10^7$, at least $10^8$ or at least $10^9$ cells, wherein these cells are comprised within a single contiguous aqueous volume during any step of contacting the sample with a library of multimeric barcoding reagent (step (a)), and/or any step of lysing or permeabilising cells (step (b)), and/or any step of appending barcode sequences to target nucleic acids (steps (c), (d) and/or (e)). Preferably, in the methods, the nucleic acid sample comprises at least 10 cells, wherein these cells are comprised within a single contiguous aqueous volume during any step of contacting the sample with a library of multimeric barcoding reagent (step (a)), and any step of lysing or permeabilising cells (step (b)), and any step of appending barcode sequences to target nucleic acids (steps (c), (d) and/or (e))

Optionally, the nucleic acid sample may comprise at least 2, at least 5, at least 10, at least 100, or at least $10^3$, at least $10^4$, at least $10^5$, at least $10^6$, at least $10^7$, at least $10^8$ or at least $10^9$ cells, wherein these cells are partitioned within two or more contiguous aqueous volumes during any step of contacting the sample with a library of multimeric barcoding reagent (step (a)), and/or any step of lysing or permeabilising cells (step (b)), and/or any step of appending barcode sequences to target nucleic acids (steps (c), (d) and/or (e)).

In the methods, the nucleic acid sample may comprise at least 2, at least 5, at least 10, at least 100, or at least $10^3$, at least $10^4$, at least $10^5$, at least $10^6$, at least $10^7$, at least $10^8$ or at least $10^9$ cells, wherein these cells are not partitioned within two or more contiguous aqueous volumes during any step of contacting the sample with a library of multimeric barcoding reagent (step (a)), and/or any step of lysing or permeabilising cells (step (b)), and/or any step of appending barcode sequences to target nucleic acids (steps (c), (d) and/or (e)).

Optionally, barcoded target nucleic acid molecules are produced from target nucleic acids of at least 2, at least 5, at least 10, at least 100, or at least $10^3$, at least $10^4$, at least $10^5$, at least $10^6$, at least $10^7$, at least $10^8$ or at least $10^9$ cells.

Optionally the sequences of the barcoded target nucleic acid molecules produced for at least 10, at least 100, or at least $10^3$, at least $10^4$, at least $10^5$, at least $10^6$, at least $10^7$, at least $10^8$ or at least $10^9$ cells are determined.

In the methods, the library may comprise at least 100, or at least $10^3$, at least $10^4$, at least $10^5$, at least $10^6$, at least $10^7$, at least $10^8$ or at least $10^9$ multimeric barcoding reagents. In the methods, for each multimeric barcoding reagent, at least 2, at least 3, at least 5, at least 10, at least 25, at least 50, at least 100, at least 500, at least 1000, at least 5,000, at least 10,000, or at least 50,000 barcoded target nucleic acid molecules may be produced from the target nucleic acids of a single cell. Preferably, at least 2 barcoded target nucleic acid molecules may be produced from the target nucleic acids of a single cell for each multimeric barcoding reagent.

In the methods, each multimeric barcoding reagent may comprise at least 2, at least 3, at least 5, at least 10, at least 20, at least 50, at least 100, at least 200, at least 500, at least 1000, at least 5000, at least 10,000, at least 100,000, or at least 1,000,000 barcoded oligonucleotides. Optionally, different multimeric barcoding reagents within a library of multimeric barcoding reagents may comprise different numbers of barcoded oligonucleotides.

In the methods, on average, the barcoded oligonucleotides of a single multimeric barcoding reagent may anneal, cumulatively, to at least 1, at least 2, at least 3, at least 5, at least 10, at least 20, at least 50, at least 100, at least 200, at least 500, at least 1000, at least 5000, at least 10,000, or at least 100,000 target nucleic acids from cells.

In the methods, the group of target nucleic acid sequences complementary to the target regions of different barcoded oligonucleotides within a multimeric barcoding reagent or a library of multimeric barcoding reagents may comprise at least 2 different nucleic acid sequences, at least 3 different nucleic acid sequences, at least 4 different nucleic acid sequences, at least 5 different nucleic acid sequences, at least 10 different nucleic acid sequences, at least 20 different nucleic acid sequences, at least 50 different nucleic acid sequences, at least 100 different nucleic acid sequences, or at least 1000 different nucleic acid sequences.

In the methods, during any step(s), within a solution, volume, or reaction, cells may be present at particular concentrations within the solution volume, for example at concentrations of less than 10 picomolar, less than 1 picomolar, less than 100 femtomolar, less than 10 femtomolar, less than 1 femtomolar, less than 100 attomolar, less than 10 attomolar, or less than 1 attomolar.

In the methods, during any step(s), within a solution, volume, or reaction, multimeric barcoding reagents may be present at particular concentrations within the solution volume, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar.

In the methods, a sample comprising permeabilised, lysed, or intact cells, and/or comprising multimeric barcoding reagents, and/or comprising barcoded oligonucleotides, and/or comprising other oligonucleotide sequences, may be partitioned into two or more partition volumes. Optionally, said partition volumes may each comprise a different physical reaction vessel. Optionally, said partition volumes may each comprise a different droplet within an emulsion, such as different aqueous droplets within a water-in-oil emulsion. Such a partitioning event may take place before and/or during any one or more steps within any protocol. Following such a partitioning step, the reactions from two or more such partitions may be merged together to form a single reaction volume.

In the methods, the nucleic acid sample may comprise intact cells. The nucleic acid sample may comprise cells that have been partially degraded. The nucleic acid sample may comprise cells that have been partially permeabilised and/or fragmented. The nucleic acid sample may comprise cells that have been formalin crosslinked and paraffin embedded (ie, a FFPE sample). The nucleic acid sample may comprise cells that are contained within an intact tissue sample or section, or a partially intact tissue sample or section. The nucleic acid sample may comprise cells that have been processed through a tissue dissociation and/or tissue digestion process. Optionally, such a dissociation or digestion process may comprise digestion with a proteinase such as Proteinase K.

The nucleic acid sample may comprise cells that have been processed through a cell sorting process, such as a fluorescence activated cell sorting (FACS) process. The nucleic acid sample may comprise cells that are within a single cell suspension.

The nucleic acid sample may comprise lymphocytes, such as T cells, and/or B cells, and or a mixture of immune cells such as a sample of peripheral blood mononuclear cells (PBMCs). For example, a single multimeric barcoding reagent may be used to append barcode sequences to the sequences of a heavy chain immunoglobulin mRNA and a light chain immunoglobulin mRNA from the same single. Alternatively, a single multimeric barcoding reagent may be used to append barcode sequences to the sequences of an alpha chain mRNA and a beta chain mRNA of a T cell receptor.

The nucleic acid sample may comprise tumour cells. Optionally, the sample may comprise tumour-infiltrating lymphocytes (TILs). Optionally, the sample may comprise tumour samples comprising both tumour cells and tumour-infiltrating lymphocytes. Optionally, the sample may comprise circulating tumour cells (CTCs). The nucleic acid sample may be a human sample.

The target nucleic acid may be a (single) intact nucleic acid molecule of a cell, two or more fragments of a nucleic acid molecule of a cell (such fragments may be co-localised in the sample) or two or more nucleic acid molecules of a cell. Therefore, sub-sequences of a target nucleic acid of a cell may be sub-sequences of the same nucleic acid molecule, sub-sequences of different fragments of the same nucleic acid molecule, or sequences or sub-sequences of different nucleic acid molecules (for example, sequences of different messenger RNA molecules (or portions thereof) of a cell; e.g. first and second sub-sequences of a target nucleic acid of a cell may be first and second different messenger RNA molecules (or portions thereof) of a cell).

As used herein the term target nucleic acid refers to the nucleic acids present within cells and to copies or amplicons thereof. For example, where the target nucleic acid is genomic DNA, the term target nucleic acid means genomic DNA present in a cell and copies or amplicons thereof e.g. DNA molecules that may be prepared from the genomic DNA by a primer-extension reaction. As a further example, where the target nucleic acid is mRNA, the term target nucleic acid means mRNA present in the cell and copies or amplicons thereof e.g. cDNA synthesized from the mRNA by reverse transcription.

In any of the methods, the target nucleic acids may be DNA (e.g. genomic DNA) or RNA (e.g. mRNA). Such target nucleic acids may comprise DNA or RNA of any origin; for example they may comprise natural or unmodified genomic DNA or messenger RNA from an in vivo or in vitro sample of cells. Furthermore, they may comprise DNA or RNA of any sort of synthetic origin, such as DNA (and/or associated expressed RNA transcripts) from any sort of transfection or transduction method, such as linear or circular plasmids, viral transfection constructs, exogenously-administered DNA of any sort, exogenously-administered RNA of any sort (such as exogenously administered messenger RNA or short-interfering RNA or short-hairpin RNA), or CRISPR constructs and/or CRISPR expression constructs and/or derivatives thereof (e.g. a Cas9 nuclease and/or expressed version thereof, and/or a guide RNA and/or expressed version thereof). Furthermore, the target nucleic acids may comprise DNA and/or RNA sequences that comprise identifier or barcode sequences, wherein a sample of cells (e.g. an in vitro sample of cells or an in vivo population of cells) has been contacted and/or genetically modified with a pooled library of two or more different synthetic sequences, wherein each of said two or more synthetic sequences comprises an identifying sequence such as a barcode sequence (such as 'Guide Barcode' (GBC) sequences within expressed GBC transcripts within the Perturb-Seq protocol [Dixit et al., 2016, Cell 167, 1853-1866 and Adamson et al., 2016, Cell 167, 1867-1882], or identifying sequence barcodes from lentiviral expression libraries [e.g. the murine DECIPHER lentiviral shRNA libraries, CELLECTA, Inc]). In such approaches, said identifying sequences, upon being barcoded and sequenced by any method described herein, may be used to determine which one or more (if any) synthetic sequences that a given cell within the sample or population of cells was contacted and/or genetically modified with.

In any of the methods, the target nucleic acids may comprise exogenously-administered nucleic acid sequences comprising barcode sequences within a barcoded affinity probe, wherein a barcoded affinity probe comprises at least one affinity moiety linked to at least one barcode sequence.

Optionally, any affinity moiety may comprise one or more of: an antibody, an antibody fragment, a light chain antibody fragment, a single-chain variable fragment (scFv), a peptide, a cell penetrating peptide, an aptamer, a DNA adptamer, and/or an RNA aptamer. Optionally, any one or more affinity moiety may comprise a moiety capable of binding to, and/or comprising high and/or specific affinity for, a specific protein, glycoprotein, post-translationally modified protein, and/or other chemical or molecular species. Optionally, any one or more such affinity moiety may comprise a moiety capable of binding to, and/or comprising high and/or specific affinity for, a specific protein, glycoprotein, post-translationally modified protein, and/or other chemical or molecular species comprised on the surface of a cell, and/or comprised within the cell membrane of a cell, and/or comprised within the cytoplasm of a cell, and/or comprised within the nucleus of a cell, and/or any combination thereof.

Any barcoded affinity probe may comprise a probe-barcode oligonucleotide, wherein said probe-barcode oligonucleotide comprises a barcode sequence associated with and/or identifying of the affinity moiety to which it is linked. Optionally, any such barcode sequence may comprise a sequence at least 1, at least 2, at least 3, at least 5, at least 10, at least 20, or at least 30 nucleotides in length. Optionally, all probe-barcode oligonucleotides linked with the same particular affinity moiety (e.g., the same particular antibody species specific for the same protein target) may comprise the same sequence (e.g. the same identifying barcode sequence). Optionally, probe-barcode oligonucleotides linked with the same particular affinity moiety (e.g., the same particular antibody species specific for the same protein target) may comprise two or more different sequences (e.g. two or more different identifying barcode sequences). Optionally, any probe-barcode oligonucleotide may comprise an adapter and/or coupling sequence, wherein said sequence is at least 1, at least 2, at least 3, at least 5, at least 10, at least 20, or at least 30 nucleotides in length. Optionally, any adapter and/or coupling sequence within a probe-barcode oligonucleotide may comprise a sequence complementary to a target region of a barcoded oligonucleotide comprised within any multimeric barcoding reagent and/or library thereof. Optionally, any adapter and/or coupling sequence within a probe-barcode oligonucleotide may comprise a poly(A) sequence 2 or more nucleotides in length. Optionally, any adapter and/or coupling sequence within a probe-barcode oligonucleotide may be comprised within the 3' end, and/or within the 5' end, of said probe-barcode oligonucleotide.

Any probe-barcode oligonucleotide and affinity moiety comprised within a barcoded affinity probe may be linked by any means. Optionally, a probe-barcode oligonucleotide and affinity moiety may be linked by a covalent bond (for example, such as LighteningLink antibody labelling kits from Innova Biosciences). Optionally, a probe-barcode oligonucleotide and affinity moiety may be linked by a non-covalent bond (using for example wherein an affinity moiety comprises a streptavidin domain, and wherein a probe-barcode oligonucleotide comprises a biotin moiety to generate a non-covalent biotin/streptavidin link).

Any one or more barcoded affinity probes may be contacted and/or incubated with a sample of cells wherein said barcoded affinity probes are at any concentration, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, picomolar to 10 nanomolar, or 100 picomolar to 1 nanomolar.

Optionally, a pool of two or more different barcoded affinity probes may be used in the methods. The pool (or library) may comprise: a first barcoded affinity probe comprising a first affinity moiety and a first probe-barcode oligonucleotide, wherein the first affinity moiety is capable of binding to, and/or comprising high and/or specific affinity for, a first target (e.g. a specific protein, a glycoprotein, a post-translationally modified protein, and/or other chemical or molecular species); and a second barcoded affinity probe comprising a second affinity moiety and a second probe-barcode oligonucleotide, wherein the second affinity moiety is capable of binding to, and/or comprising high and/or specific affinity for, a second target (e.g. a specific protein, a glycoprotein, a post-translationally modified protein, and/or other chemical or molecular species). The pool (or library) of barcoded affinity probes may be provided within a single solution. The pool (or library) of barcoded affinity probes may be contacted and/or incubated with cells. Optionally, the pool (or library) may comprise at least 3, at least 5, at least 10, at least 20, or at least 30 different barcoded affinity probes (e.g. targeting at least 3, at least 5, at least 10, at least 20, or at least 30 different targets (e.g. specific proteins, glycoproteins, post-translationally modified proteins, and/or other chemical or molecular species)).

Optionally, the target nucleic acids may comprise probe-barcode oligonucleotide within barcoded affinity probes, wherein a sample of cells (e.g. an in vitro sample of cells or an in vivo population of cells) has been contacted and/or incubated with one or more such barcoded affinity probes. Optionally, a sample of cells may be chemically crosslinked (e.g. with formaldehyde) prior to any step of contacting and/or incubating cells with one or more barcoded affinity probes. Optionally, a sample of cells may be permeabilised (e.g. with a chemical surfactant) prior to any step of contacting and/or incubating cells with one or more barcoded affinity probes. Optionally, a sample of cells may be chemically crosslinked (e.g. with formaldehyde) and then permeabilised (e.g. with a chemical surfactant) prior to any step of contacting and/or incubating cells with one or more barcoded affinity probes.

Optionally, the target nucleic acids may comprise both nucleic acids comprised within a sample of cells and also probe-barcode oligonucleotide(s) within barcoded affinity probes, wherein the sample of cells (e.g. an in vitro sample of cells or an in vivo population of cells) has been contacted and/or incubated with one or more such barcoded affinity probes. Optionally, the target nucleic acids may comprise messenger RNA molecules comprised within a sample of cells and also probe-barcode oligonucleotide(s) within barcoded affinity probes, wherein the sample of cells (e.g. an in vitro sample of cells or an in vivo population of cells) has been contacted and/or incubated with one or more such barcoded affinity probes.

In the methods target nucleic acids from cells to which barcoded oligonucleotides anneal may comprise coupling sequences (e.g. synthetic nucleic acid sequences). Optionally, the target region of barcoded oligonucleotides within multimeric barcoding reagents may comprise sequences complementary to said coupling sequences to which they may anneal. Optionally, any said coupling sequences may comprise all or portions of synthetic oligonucleotides which have been transferred into cells within the nucleic acid sample. Optionally, such synthetic oligonucleotides may comprise a reagent-annealing region and a targeting region, wherein the reagent-annealing region is entirely or partially complementary to a target region within a barcoded oligonucleotide, and wherein the targeting region is entirely or partially complementary to a nucleic acid sequence found within the nucleic acid sample. Optionally, a targeting region may be entirely or partially complementary to a sequence within genomic DNA, or to a sequence within one or more messenger RNA (mRNA) molecules. Optionally, such synthetic oligonucleotides may comprise a linker region of at least 1 nucleotide between a reagent-annealing region and a targeting region. Optionally, the reagent-annealing region may be located within the 5' end of a synthetic oligonucleotide and a targeting region may be located within the 3' end of the synthetic oligonucleotide. Optionally, a solution of one or more synthetic oligonucleotides may be hybridised to one or more target nucleic acids within cells in a synthetic oligonucleotide annealing step. Optionally, such a synthetic oligonucleotide annealing step may be performed prior to contacting the sample of cells with a library of two or more multimeric barcoding reagents.

In the methods, the target nucleic acids from cells to which barcoded oligonucleotides anneal may be mRNA (messenger RNA) molecules. Optionally, the target region of barcoded oligonucleotides within multimeric barcoding reagents may comprise sequences complementary to sequences within one or more messenger RNA molecules to which they may anneal. Optionally, the target regions of barcoded oligonucleotides may be complementary to specific sequences within specific messenger RNA targets.

Optionally, the target regions of barcoded oligonucleotides may be complementary to poly(A) tail regions of messenger RNA molecules; in this case the target regions of barcoded oligonucleotides may comprise a poly(T) region of two or more contiguous nucleotides In the methods, each barcoded target nucleic acid molecule may be produced after isolation of the barcoded oligonucleotide annealed to a target mRNA molecule by extending the barcoded oligonucleotide using a reverse transcriptase and wherein the target mRNA molecule is employed as the template for a reverse transcription process by said reverse transcriptase.

In the methods, the mRNA molecules may be mRNA molecules corresponding to alpha and/or beta chains of a T-cell receptor sequence, optionally wherein the sequences of alpha and beta chains paired within an individual cell are determined.

In the methods, the mRNA molecules may be mRNA molecules corresponding to light and/or heavy chains of an immunoglobulin sequence, optionally wherein the sequences of light and heavy chains paired within an individual cell are determined.

Further details of the libraries of multimeric barcoding reagents and methods of the invention are provided below.

1. General Properties of Multimeric Barcoding Reagents

The invention provides multimeric barcoding reagents for labelling one or more target nucleic acids. A multimeric barcoding reagent comprises two or more barcode regions are linked together (directly or indirectly).

Each barcode region comprises a nucleic acid sequence. The nucleic acid sequence may be single-stranded DNA, double-stranded DNA, or single stranded DNA with one or more double-stranded regions.

Each barcode region may comprise a sequence that identifies the multimeric barcoding reagent. For example, this sequence may be a constant region shared by all barcode regions of a single multimeric barcoding reagent. Each barcode region may contain a unique sequence which is not present in other regions, and may thus serve to uniquely identify each barcode region. Each barcode region may comprise at least 5, at least 10, at least 15, at least 20, at least 25, at least 50 or at least 100 nucleotides. Preferably, each barcode region comprises at least 5 nucleotides. Preferably each barcode region comprises deoxyribonucleotides, optionally all of the nucleotides in a barcode region are deoxyribonucleotides. One or more of the deoxyribonucleotides may be a modified deoxyribonucleotide (e.g. a deoxyribonucleotide modified with a biotin moiety or a deoxyuracil nucleotide). The barcode regions may comprise one or more degenerate nucleotides or sequences. The barcode regions may not comprise any degenerate nucleotides or sequences.

The multimeric barcoding reagent may comprise at least 5, at least 10, at least 20, at least 25, at least 50, at least 75, at least 100, at least 200, at least 500, at least 1000, at least 5000, or at least 10,000 barcode regions. Preferably, the multimeric barcoding reagent comprises at least 5 barcode regions.

The multimeric barcoding reagent may comprise at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ unique or different barcode regions. Preferably, the multimeric barcoding reagent comprises at least 5 unique or different barcode regions.

A multimeric barcoding reagent may comprise: first and second barcode molecules linked together (i.e. a multimeric barcode molecule), wherein each of the barcode molecules comprises a nucleic acid sequence comprising a barcode region.

The barcode molecules of a multimeric barcode molecule may be linked on a nucleic acid molecule. The barcode molecules of a multimeric barcode molecule may be comprised within a (single) nucleic acid molecule. A multimeric barcode molecule may comprise a single, contiguous nucleic acid sequence comprising two or more barcode molecules. A multimeric barcode molecule may be a single-stranded nucleic acid molecule (e.g. single-stranded DNA), a double-stranded-stranded nucleic acid molecule or a single stranded molecule comprising one or more double-stranded regions. A multimeric barcode molecule may comprise one or more phosphorylated 5' ends capable of ligating to 3' ends of other nucleic acid molecules. Optionally, in a double-stranded region or between two different double-stranded regions, a multimeric barcode molecule may comprise one or more nicks, or one or more gaps, where the multimeric barcode molecule itself has been divided or separated. Any said gap may be at least one, at least 2, at least 5, at least 10, at least 20, at least 50, or at least 100 nucleotides in length. Said nicks and/or gaps may serve the purpose of increasing the molecular flexibility of the multimeric barcode molecule and/or multimeric barcoding reagent, for example to increase the accessibility of the molecule or reagent to interact with target nucleic acid molecules. Said nicks and/or gaps may also enable more efficient purification or removal of said molecules or reagents. A molecule and/or reagent comprising said nick(s) and/or gap(s) may retain links between different barcode molecules by having a complementary DNA strand which is jointly hybridised to regions of two or more divided parts of a multimeric barcode molecule.

The barcode molecules may be linked by a support e.g. a macromolecule, solid support or semi-solid support. The sequences of the barcode molecules linked to each support may be known. The barcode molecules may be linked to the support directly or indirectly (e.g. via a linker molecule). The barcode molecules may be linked by being bound to the support and/or by being bound or annealed to linker molecules that are bound to the support. The barcode molecules may be bound to the support (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The barcode molecules may be linked by a macromolecule by being bound to the macromolecule and/or by being annealed to the macromolecule.

The barcode molecules may be linked to the macromolecule directly or indirectly (e.g. via a linker molecule). The barcode molecules may be linked by being bound to the macromolecule and/or by being bound or annealed to linker molecules that are bound to the macromolecule. The barcode molecules may be bound to the macromolecule (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The macromolecule may be a synthetic polymer (e.g. a dendrimer) or a biopolymer such as a nucleic acid (e.g. a single-stranded nucleic acid such as single-stranded DNA), a peptide, a polypeptide or a protein (e.g. a multimeric protein).

The dendrimer may comprise at least 2, at least 3, at least 5, or at least 10 generations.

The macromolecule may be a nucleic acid comprising two or more nucleotides each capable of binding to a barcode molecule. Additionally or alternatively, the nucleic acid may comprise two or more regions each capable of hybridizing to a barcode molecule.

The nucleic acid may comprise a first modified nucleotide and a second modified nucleotide, wherein each modified nucleotide comprises a binding moiety (e.g. a biotin moiety, or an alkyne moiety which may be used for a click-chemical reaction) capable of binding to a barcode molecule. Optionally, the first and second modified nucleotides may be separated by an intervening nucleic acid sequence of at least one, at least two, at least 5 or at least 10 nucleotides.

The nucleic acid may comprise a first hybridisation region and a second hybridisation region, wherein each hybridisation region comprises a sequence complementary to and capable of hybridizing to a sequence of at least one nucleotide within a barcode molecule. The complementary sequence may be at least 5, at least 10, at least 15, at least 20, at least 25 or at least 50 contiguous nucleotides. Preferably, the complementary sequence is at least 10 contiguous nucleotides. Optionally, the first and second hybridisation regions may be separated by an intervening nucleic acid sequence of at least one, at least two, at least 5 or at least 10 nucleotides.

The macromolecule may be a protein such as a multimeric protein e.g. a homomeric protein or a heteromeric protein. For example, the protein may comprise streptavidin e.g. tetrameric streptavidin.

The support may be a solid support or a semi-solid support. The support may comprise a planar surface. The support may be a slide e.g. a glass slide. The slide may be a flow cell for sequencing. If the support is a slide, the first and second barcode molecules may be immobilized in a discrete region on the slide. Optionally, the barcode molecules of each multimeric barcoding reagent in a library are immobilized in a different discrete region on the slide to the barcode molecules of the other multimeric barcoding reagents in the library. The support may be a plate comprising wells, optionally wherein the first and second barcode molecules are immobilized in the same well. Optionally, the barcode molecules of each multimeric barcoding reagent in library are immobilized in a different well of the plate to the barcode molecules of the other multimeric barcoding reagents in the library.

Preferably, the support is a bead (e.g. a gel bead). The bead may be an agarose bead, a silica bead, a styrofoam bead, a gel bead (such as those available from 10× Genomics®), an antibody conjugated bead, an oligo-dT conjugated bead, a streptavidin bead or a magnetic bead (e.g. a superparamagnetic bead). The bead may be of any size and/or molecular structure. For example, the bead may be 10 nanometres to 100 microns in diameter, 100 nanometres to 10 microns in diameter, or 1 micron to 5 microns in diameter. Optionally, the bead is approximately nanometres in diameter, approximately 100 nanometres in diameter, approximately 1 micron in diameter, approximately 10 microns in diameter or approximately 100 microns in diameter. The bead may be solid, or alternatively the bead may be hollow or partially hollow or porous. Beads of certain sizes may be most preferable for certain barcoding methods. For example, beads less than 5.0 microns, or less than 1.0 micron, may be most useful for barcoding nucleic acid targets within individual cells. Preferably, the barcode molecules of each multimeric barcoding reagent in a library are linked together on a different bead to the barcode molecules of the other multimeric barcoding reagents in the library.

The support may be functionalised to enable attachment of two or more barcode molecules. This functionalisation may be enabled through the addition of chemical moieties (e.g. carboxylated groups, alkynes, azides, acrylate groups, amino groups, sulphate groups, or succinimide groups), and/or protein-based moieties (e.g. streptavidin, avidin, or protein G) to the support. The barcode molecules may be attached to the moieties directly or indirectly (e.g. via a linker molecule).

Functionalised supports (e.g. beads) may be brought into contact with a solution of barcode molecules under conditions which promote the attachment of two or more barcode molecules to each bead in the solution (generating multimeric barcoding reagents).

In a library of multimeric barcoding reagents, the barcode molecules of each multimeric barcoding reagent in a library may be linked together on a different support to the barcode molecules of the other multimeric barcoding reagents in the library.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 barcode molecules linked together, wherein each barcode molecule is as defined herein; and a barcoded oligonucleotide annealed to each barcode molecule, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ unique or different barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 unique or different barcode molecules linked together, wherein each barcode molecule is as defined herein; and a barcoded oligonucleotide annealed to each barcode molecule, wherein each barcoded oligonucleotide is as defined herein.

A multimeric barcoding reagent may comprise two or more barcoded oligonucleotides as defined herein, wherein the barcoded oligonucleotides each comprise a barcode region. A multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least 10,000, at least 100,000, or at least 1,000,000 unique or different barcoded oligonucleotides. Preferably, the multimeric barcoding reagent comprises at least 5 unique or different barcoded oligonucleotides.

The barcoded oligonucleotides of a multimeric barcoding reagent are linked together (directly or indirectly). The barcoded oligonucleotides of a multimeric barcoding reagent are linked together by a support e.g. a macromolecule, solid support or semi-solid support, as described herein. The multimeric barcoding reagent may comprise one or more polymers to which the barcoded oligonucleotides are annealed or attached. For example, the barcoded oligonucleotides of a multimeric barcoding reagent may be annealed to a multimeric hybridization molecule e.g. a multimeric barcode molecule. Alternatively, the barcoded oligonucleotides of a multimeric barcoding reagent may be linked together by a macromolecule (such as a synthetic polymer e.g. a dendrimer, or a biopolymer e.g. a protein) or a support (such as a solid support or a semi-solid support e.g. a gel bead). Additionally or alternatively, the barcoded oligonucleotides of a (single) multimeric barcoding reagent may linked together by being comprised within a (single) lipid carrier (e.g. a liposome or a micelle).

A multimeric barcoding reagent may comprise: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule.

The hybridization molecules comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The hybridization molecules may comprise one or more degenerate nucleotides or sequences. The hybridization molecules may not comprise any degenerate nucleotides or sequences.

The hybridization molecules of a multimeric hybridization molecule may be linked on a nucleic acid molecule. Such a nucleic acid molecule may provide the backbone to which single-stranded barcoded oligonucleotides may be annealed. The hybridization molecules of a multimeric hybridization molecule may be comprised within a (single) nucleic acid molecule. A multimeric hybridization molecule may comprise a single, contiguous nucleic acid sequence comprising two or more hybridization molecules. A multimeric hybridization molecule may be a single-stranded nucleic acid molecule (e.g. single-stranded DNA) comprising two or more hybridization molecules. A multimeric hybridization molecule may comprise one or more double-stranded regions. Optionally, in a double-stranded region or between two different double-stranded regions, a multimeric hybridization molecule may comprise one or more nicks, or one or more gaps, where the multimeric hybridization molecule itself has been divided or separated. Any said gap may be at least one, at least 2, at least 5, at least 10, at least 20, at least 50, or at least 100 nucleotides in length. Said nicks and/or gaps may serve the purpose of increasing the molecular flexibility of the multimeric hybridization molecule and/or multimeric barcoding reagent, for example to increase the accessibility of the molecule or reagent to interact with target nucleic acid molecules. Said nicks and/or gaps may also enable more efficient purification or removal of said molecules or reagents. A molecule and/or reagent comprising said nick(s) and/or gap(s) may retain links between different hybridization molecules by having a complementary DNA strand which is jointly hybridised to regions of two or more divided parts of a multimeric hybridization molecule.

The hybridization molecules may be linked by a macromolecule by being bound to the macromolecule and/or by being annealed to the macromolecule.

The hybridization molecules may be linked to the macromolecule directly or indirectly (e.g. via a linker molecule). The hybridization molecules may be linked by being bound to the macromolecule and/or by being bound or annealed to linker molecules that are bound to the macromolecule. The hybridization molecules may be bound to the macromolecule (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The macromolecule may be a synthetic polymer (e.g. a dendrimer) or a biopolymer such as a nucleic acid (e.g. a single-stranded nucleic acid such as single-stranded DNA), a peptide, a polypeptide or a protein (e.g. a multimeric protein).

The dendrimer may comprise at least 2, at least 3, at least 5, or at least 10 generations.

The macromolecule may be a nucleic acid comprising two or more nucleotides each capable of binding to a hybridization molecule. Additionally or alternatively, the nucleic acid may comprise two or more regions each capable of hybridizing to a hybridization molecule.

The nucleic acid may comprise a first modified nucleotide and a second modified nucleotide, wherein each modified nucleotide comprises a binding moiety (e.g. a biotin moiety, or an alkyne moiety which may be used for a click-chemical reaction) capable of binding to a hybridization molecule. Optionally, the first and second modified nucleotides may be separated by an intervening nucleic acid sequence of at least one, at least two, at least 5 or at least 10 nucleotides.

The nucleic acid may comprise a first hybridisation region and a second hybridisation region, wherein each hybridisation region comprises a sequence complementary to and capable of hybridizing to a sequence of at least one nucleotide within a hybridization molecule. The complementary sequence may be at least 5, at least 10, at least 15, at least 20, at least 25 or at least 50 contiguous nucleotides. Optionally, the first and second hybridisation regions may be separated by an intervening nucleic acid sequence of at least one, at least two, at least 5 or at least 10 nucleotides.

The macromolecule may be a protein such as a multimeric protein e.g. a homomeric protein or a heteromeric protein. For example, the protein may comprise streptavidin e.g. tetrameric streptavidin.

The hybridization molecules may be linked by a support. The hybridization molecules may be linked to the support directly or indirectly (e.g. via a linker molecule). The hybridization molecules may be linked by being bound to the support and/or by being bound or annealed to linker molecules that are bound to the support. The hybridization molecules may be bound to the support (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The support may be a solid support or a semi-solid support. The support may comprise a planar surface. The support may be a slide e.g. a glass slide. The slide may be a flow cell for sequencing. If the support is a slide, the first and second hybridization molecules may be immobilized in a discrete region on the slide. Optionally, the hybridization molecules of each multimeric barcoding reagent in a library are immobilized in a different discrete region on the slide to the hybridization molecules of the other multimeric barcoding reagents in the library. The support may be a plate comprising wells, optionally wherein the first and second hybridization molecules are immobilized in the same well. Optionally, the hybridization molecules of each multimeric barcoding reagent in library are immobilized in a different well of the plate to the hybridization molecules of the other multimeric barcoding reagents in the library.

Preferably, the support is a bead (e.g. a gel bead). The bead may be an agarose bead, a silica bead, a styrofoam bead, a gel bead (such as those available from 10× Genomics®), an antibody conjugated bead, an oligo-dT conjugated bead, a streptavidin bead or a magnetic bead (e.g. a superparamagnetic bead). The bead may be of any size and/or molecular structure. For example, the bead may be 10 nanometres to 100 microns in diameter, 100 nanometres to 10 microns in diameter, or 1 micron to 5 microns in diameter. Optionally, the bead is approximately nanometres in diameter, approximately 100 nanometres in diameter, approximately 1 micron in diameter, approximately 10 microns in diameter or approximately 100 microns in diameter. The bead may be solid, or alternatively the bead may be hollow or partially hollow or porous. Beads of certain sizes may be most preferable for certain barcoding methods. For example, beads less than 5.0 microns, or less than 1.0 micron, may be most useful for barcoding nucleic acid targets within individual cells. Preferably, the hybridization molecules of each multimeric barcoding reagent in a library are linked together on a different bead to hybridization molecules of the other multimeric barcoding reagents in the library.

The support may be functionalised to enable attachment of two or more hybridization molecules. This functionalisation may be enabled through the addition of chemical moieties (e.g. carboxylated groups, alkynes, azides, acrylate groups, amino groups, sulphate groups, or succinimide groups), and/or protein-based moieties (e.g. streptavidin, avidin, or protein G) to the support. The hybridization molecules may be attached to the moieties directly or indirectly (e.g. via a linker molecule).

Functionalised supports (e.g. beads) may be brought into contact with a solution of hybridization molecules under conditions which promote the attachment of two or more hybridization molecules to each bead in the solution (generating multimeric barcoding reagents).

In a library of multimeric barcoding reagents, the hybridization molecules of each multimeric barcoding reagent in a library may be linked together on a different support to the hybridization molecules of the other multimeric barcoding reagents in the library.

Optionally, the hybridization molecules are attached to the beads by covalent linkage, non-covalent linkage (e.g. a streptavidin-biotin bond) or nucleic acid hybridization.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, or at least 10,000 hybridization molecules linked together, wherein each hybridization molecule is as defined herein; and a barcoded oligonucleotide annealed to each hybridization molecule, wherein each barcoded oligonucleotide is as defined herein. Preferably, the multimeric barcoding reagent comprises at least 5 hybridization molecules linked together, wherein each hybridization molecule is as defined herein; and a barcoded oligonucleotide annealed to each hybridization molecule, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, or at least 10,000 unique or different hybridization molecules linked together, wherein each hybridization molecule is as defined herein; and a barcoded oligonucleotide annealed to each hybridization molecule, wherein each barcoded oligonucleotide is as defined herein. Preferably, the multimeric barcoding reagent comprises at least 5 unique or different hybridization molecules linked together, wherein each hybridization molecule is as defined herein; and a barcoded oligonucleotide annealed to each hybridization molecule, wherein each barcoded oligonucleotide is as defined herein.

The multimeric hybridization molecule may be a multimeric barcode molecule, wherein the first hybridization molecule is a first barcode molecule and the second hybridization molecule is a second barcode molecule. A multimeric barcoding reagent may comprise: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide is annealed to the barcode region of the first barcode molecule, and wherein the second barcoded oligonucleotide is annealed to the barcode region of the second barcode molecule.

The barcoded oligonucleotides of a multimeric barcoding reagent may comprise: a first barcoded oligonucleotide comprising, optionally in the 5' to 3' direction, a barcode region, and a target region capable of annealing or ligating to a first sub-sequence of the target nucleic acid; and a second barcoded oligonucleotide comprising, optionally in the 5' to 3' direction, a barcode region, and a target region capable of annealing or ligating to a second sub-sequence of the target nucleic acid.

The barcoded oligonucleotides of a multimeric barcoding reagent may comprise: a first barcoded oligonucleotide comprising a barcode region, and a target region capable of ligating to a first sub-sequence of the target nucleic acid; and a second barcoded oligonucleotide comprising a barcode region, and a target region capable of ligating to a second sub-sequence of the target nucleic acid.

The barcoded oligonucleotides of a multimeric barcoding reagent may comprise: a first barcoded oligonucleotide comprising, in the 5' to 3' direction, a barcode region, and a target region capable of annealing to a first sub-sequence of the target nucleic acid; and a second barcoded oligonucleotide comprising, in the 5' to 3' direction, a barcode region, and a target region capable of annealing to a second sub-sequence of the target nucleic acid.

2. General Properties of Barcoded Oligonucleotides

A barcoded oligonucleotide comprises a barcode region. The barcoded oligonucleotides may comprise, optionally in the 5' to 3' direction, a barcode region and a target region. The target region is capable of annealing or ligating to a sub-sequence of the target nucleic acid. Alternatively, a barcoded oligonucleotide may consist essentially of or consist of a barcode region.

The 5' end of a barcoded oligonucleotide may be phosphorylated. This may enable the 5' end of the barcoded oligonucleotide to be ligated to the 3' end of a target nucleic acid. Alternatively, the 5' end of a barcoded oligonucleotide may not be phosphorylated.

A barcoded oligonucleotide may be a single-stranded nucleic acid molecule (e.g. single-stranded DNA). A barcoded oligonucleotide may comprise one or more double-stranded regions. A barcoded oligonucleotide may be a double-stranded nucleic acid molecule (e.g. double-stranded DNA).

The barcoded oligonucleotides may comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The barcoded oligonucleotides may comprise one or more degenerate nucleotides or sequences. The barcoded oligonucleotides may not comprise any degenerate nucleotides or sequences.

The barcode regions of each barcoded oligonucleotide may comprise different sequences. Each barcode region may comprise a sequence that identifies the multimeric barcoding reagent. For example, this sequence may be a constant region shared by all barcode regions of a single multimeric barcoding reagent. The barcode region of each barcoded oligonucleotide may contain a unique sequence which is not present in other barcoded oligonucleotides, and may thus serve to uniquely identify each barcoded oligonucleotide. Each barcode region may comprise at least 5, at least 10, at least 15, at least 20, at least 25, at least 50 or at least 100 nucleotides. Preferably, each barcode region comprises at least 5 nucleotides. Preferably each barcode region comprises deoxyribonucleotides, optionally all of the nucleotides in a barcode region are deoxyribonucleotides. One or more of the deoxyribonucleotides may be a modified deoxyribonucleotide (e.g. a deoxyribonucleotide modified with a biotin moiety or a deoxyuracil nucleotide). The barcode regions may comprise one or more degenerate nucleotides or sequences. The barcode regions may not comprise any degenerate nucleotides or sequences.

The target regions of each barcoded oligonucleotide may comprise different sequences. Each target region may comprise a sequence capable of annealing to only a single sub-sequence of a target nucleic acid within a sample of nucleic acids (i.e. a target specific sequence). Each target region may comprise one or more random, or one or more degenerate, sequences to enable the target region to anneal to more than one sub-sequence of a target nucleic acid. Each target region may comprise at least 5, at least 10, at least 15, at least 20, at least 25, at least 50 or at least 100 nucleotides. Preferably, each target region comprises at least 5 nucleotides. Each target region may comprise 5 to 100 nucleotides, 5 to 10 nucleotides, 10 to 20 nucleotides, 20 to nucleotides, 30 to 50 nucleotides, 50 to 100 nucleotides, 10 to 90 nucleotides, 20 to 80 nucleotides, 30 to 70 nucleotides or 50 to 60 nucleotides. Preferably, each target region comprises 30 to 70 nucleotides. Preferably each target region comprises deoxyribonucleotides, optionally all of the nucleotides in a target region are deoxyribonucleotides. One or more of the deoxyribonucleotides may be a modified deoxyribonucleotide (e.g. a deoxyribonucleotide modified with a biotin moiety or a deoxyuracil nucleotide). Each target region may comprise one or more universal bases (e.g. inosine), one or modified nucleotides and/or one or more nucleotide analogues.

The target regions may be used to anneal the barcoded oligonucleotides to sub-sequences of target nucleic acids, and then may be used as primers for a primer-extension reaction or an amplification reaction e.g. a polymerase chain reaction. Alternatively, the target regions may be used to ligate the barcoded oligonucleotides to sub-sequences of target nucleic acids. The target region may be at the 5' end of a barcoded oligonucleotide. Such a target region may be phosphorylated. This may enable the 5' end of the target region to be ligated to the 3' end of a sub-sequence of a target nucleic acid.

The barcoded oligonucleotides may further comprise one or more adapter region(s). An adapter region may be between the barcode region and the target region. A barcoded oligonucleotide may, for example, comprise an adapter region 5' of a barcode region (a 5' adapter region) and/or an adapter region 3' of the barcode region (a 3' adapter region). Optionally, the barcoded oligonucleotides comprise, in the 5' to 3' direction, a barcode region, an adapter region and a target region.

The adapter region(s) of the barcoded oligonucleotides may comprise a sequence complementary to an adapter region of a multimeric barcode molecule or a sequence complementary to a hybridization region of a multimeric hybridization molecule. The adapter region(s) of the barcoded oligonucleotides may enable the barcoded oligonucleotides to be linked to a macromolecule or support (e.g. a bead). The adapter region(s) may be used for manipulating, purifying, retrieving, amplifying, or detecting barcoded oligonucleotides and/or target nucleic acids to which they may anneal or ligate.

The adapter region of each barcoded oligonucleotide may comprise a constant region. Optionally, all adapter regions of barcoded oligonucleotides of each multimeric barcoding reagent are substantially identical. The adapter region may comprise at least 1, at least 2, at least 3, at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

The barcoded oligonucleotides may be synthesized by a chemical oligonucleotide synthesis process. The barcoded oligonucleotides synthesis process may include one or more step of an enzymatic production process, an enzymatic amplification process, or an enzymatic modification procedure, such as an in vitro transcription process, a reverse transcription process, a primer-extension process, or a polymerase chain reaction process.

These general properties of barcoded oligonucleotides are applicable to any of the multimeric barcoding reagents described herein.

3. General Properties of Libraries of Multimeric Barcoding Reagents

The invention provides a library of multimeric barcoding reagents comprising first and second multimeric barcoding reagents as defined herein, wherein the barcode regions of the first multimeric barcoding reagent are different to the barcode regions of the second multimeric barcoding reagent.

The library of multimeric barcoding reagents may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the library comprises at least 10 multimeric barcoding reagents as defined herein. Preferably, the first and second barcode regions of each multimeric barcoding reagent are different to the barcode regions of at least 9 other multimeric barcoding reagents in the library.

The first and second barcode regions of each multimeric barcoding reagent may be different to the barcode regions of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The first and second barcode regions of each multimeric barcoding reagent may be different to the barcode regions of all of the other multimeric barcoding reagents in the library. Preferably, the first and second barcode regions of each multimeric barcoding reagent are different to the barcode regions of at least 9 other multimeric barcoding reagents in the library.

The barcode regions of each multimeric barcoding reagent may be different to the barcode regions of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The barcode regions of each multimeric barcoding reagent may be different to the barcode regions of all of the other multimeric barcoding reagents in the library. Preferably, the barcode regions of each multimeric barcoding reagent are different to the barcode regions of at least 9 other multimeric barcoding reagents in the library.

The invention provides a library of multimeric barcoding reagents comprising first and second multimeric barcoding reagents as defined herein, wherein the barcode regions of the barcoded oligonucleotides of the first multimeric barcoding reagent are different to the barcode regions of the barcoded oligonucleotides of the second multimeric barcoding reagent.

Different multimeric barcoding reagents within a library of multimeric barcoding reagents may comprise different numbers of barcoded oligonucleotides.

The library of multimeric barcoding reagents may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the library comprises at least 10 multimeric barcoding reagents as defined herein. Preferably, the barcode regions of the first and second barcoded oligonucleotides of each multimeric barcoding reagent are different to the barcode regions of the barcoded oligonucleotides of at least 9 other multimeric barcoding reagents in the library.

The barcode regions of the first and second barcoded oligonucleotides of each multimeric barcoding reagent may be different to the barcode regions of the barcoded oligonucleotides of at least 4, at least 9, at least 19, at least 24, at least 49, at least 74, at least 99, at least 249, at least 499, at least 999 (i.e. $10^3$-1), at least $10^4$-1, at least $10^6$-1, at least $10^6$-1, at least $10^7$-1, at least $10^8$-1 or at least $10^6$-1 other multimeric barcoding reagents in the library. The barcode regions of the first and second barcoded oligonucleotides of each multimeric barcoding reagent may be different to the barcode regions of the barcoded oligonucleotides of all of the other multimeric barcoding reagents in the library. Preferably, the barcode regions of the first and second barcoded oligonucleotides of each multimeric barcoding reagent are different to the barcode regions of the barcoded oligonucleotides of at least 9 other multimeric barcoding reagents in the library.

The barcode regions of the barcoded oligonucleotides of each multimeric barcoding reagent may be different to the barcode regions of the barcoded oligonucleotides of at least 4, at least 9, at least 19, at least 24, at least 49, at least 74, at least 99, at least 249, at least 499, at least 999 (i.e. $10^3$-1), at least $10^4$-1, at least $10^6$-1, at least $10^6$-1, at least $10^7$-1, at least $10^8$-1 or at least $10^6$-1 other multimeric barcoding reagents in the library. The barcode regions of the barcoded oligonucleotides of each multimeric barcoding reagent may be different to the barcode regions of the barcoded oligonucleotides of all of the other multimeric barcoding reagents in the library. Preferably, the barcode regions of the barcoded oligonucleotides of each multimeric barcoding reagent are different to the barcode regions of the barcoded oligonucleotides of at least 9 other multimeric barcoding reagents in the library.

These general properties of libraries of multimeric barcoding reagents are applicable to any of the multimeric barcoding reagents described herein.

4. Multimeric Barcoding Reagents Comprising Barcoded Oligonucleotides Annealed to a Multimeric Barcode Molecule The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises, optionally in the 5' to 3' direction, a barcode region annealed to the barcode region of the first barcode molecule and a target region capable of annealing or ligating to a first sub-sequence of the target nucleic acid, and wherein the second barcoded oligonucleotide comprises, optionally in the 5' to 3' direction, a barcode region annealed to the barcode region of the second barcode molecule and a target region capable of annealing or ligating to a second sub-sequence of the target nucleic acid.

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises a barcode region annealed to the barcode region of the first barcode molecule and a target region capable of ligating to a first sub-sequence of the target nucleic acid, and wherein the second barcoded oligonucleotide comprises a barcode region annealed to the barcode region of the second barcode molecule and a target region capable of ligating to a second sub-sequence of the target nucleic acid.

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises in the 5' to 3' direction a barcode region annealed to the barcode region of the first barcode molecule and a target region capable of annealing to a first sub-sequence of the target nucleic acid, and wherein the second barcoded oligonucleotide comprises in the 5' to 3' direction a barcode region annealed to the barcode region of the second barcode molecule and a target region capable of annealing to a second sub-sequence of the target nucleic acid.

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises a barcode region annealed to the barcode region of the first barcode molecule and capable of ligating to a first sub-sequence of the target nucleic acid, and wherein the second barcoded oligonucleotide comprises a barcode region annealed to the barcode region of the second barcode molecule and capable of ligating to a second sub-sequence of the target nucleic acid.

Each barcoded oligonucleotide may consist essentially of or consist of a barcode region.

Preferably, the barcode molecules comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The barcode molecules may comprise one or more degenerate nucleotides or sequences. The barcode molecules may not comprise any degenerate nucleotides or sequences.

The barcode regions may uniquely identify each of the barcode molecules. Each barcode region may comprise a sequence that identifies the multimeric barcoding reagent. For example, this sequence may be a constant region shared by all barcode regions of a single multimeric barcoding reagent. Each barcode region may comprise at least 5, at least 10, at least 15, at least 20, at least 25, at least 50 or at least 100 nucleotides. Preferably, each barcode region comprises at least 5 nucleotides. Preferably each barcode region comprises deoxyribonucleotides, optionally all of the nucleotides in a barcode region are deoxyribonucleotides. One or more of the deoxyribonucleotides may be a modified deoxyribonucleotide (e.g. a deoxyribonucleotide modified with a biotin moiety or a deoxyuracil nucleotide). The barcode regions may comprise one or more degenerate nucleotides or sequences. The barcode regions may not comprise any degenerate nucleotides or sequences.

Preferably, the barcode region of the first barcoded oligonucleotide comprises a sequence that is complementary and annealed to the barcode region of the first barcode molecule and the barcode region of the second barcoded oligonucleotide comprises a sequence that is complementary and annealed to the barcode region of the second barcode molecule. The complementary sequence of each barcoded oligonucleotide may be at least 5, at least 10, at least 15, at least 20, at least 25, at least 50 or at least 100 contiguous nucleotides.

The target regions of the barcoded oligonucleotides (which are not annealed to the multimeric barcode molecule (s)) may be non-complementary to the multimeric barcode molecule(s).

The barcoded oligonucleotides may comprise a linker region between the barcode region and the target region. The linker region may comprise one or more contiguous nucleotides that are not annealed to the multimeric barcode molecule and are non-complementary to the subsequences of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

Barcode molecules may further comprise one or more nucleic acid sequences that are not complementary to barcode regions of barcoded oligonucleotides. For example, barcode molecules may comprise one or more adapter regions. A barcode molecule, may, for example, comprise an adapter region 5' of a barcode region (a 5' adapter region) and/or an adapter region 3' of the barcode region (a 3' adapter region). The adapter region(s) (and/or one or more portions of an adapter region) may be complementary to and anneal to oligonucleotides e.g. the adapter regions of barcoded oligonucleotides. Alternatively, the adapter region(s) (and/or one or more portions of an adapter region) of barcode molecule may not be complementary to sequences of barcoded oligonucleotides. The adapter region(s) may be used for manipulating, purifying, retrieving, amplifying, and/or detecting barcode molecules.

The multimeric barcoding reagent may be configured such that: each of the barcode molecules comprises a nucleic acid sequence comprising in the 5' to 3' direction an adapter region and a barcode region; the first barcoded oligonucleotide comprises, optionally in the 5' to 3' direction, a barcode region annealed to the barcode region of the first barcode molecule, an adapter region annealed to the adapter region of the first barcode molecule and a target region capable of annealing to a first sub-sequence of the target nucleic acid; and the second barcoded oligonucleotide comprises, optionally in the 5' to 3' direction, a barcode region annealed to the barcode region of the second barcode molecule, an adapter region annealed to the adapter region of the second barcode molecule and a target region capable of annealing to a second sub-sequence of the target nucleic acid.

The adapter region of each barcode molecule may comprise a constant region. Optionally, all adapter regions of a multimeric barcoding reagent are substantially identical. The adapter region may comprise at least 1, at least 2, at least 3, at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

The barcoded oligonucleotides may comprise a linker region between the adapter region and the target region. The linker region may comprise one or more contiguous nucleotides that are not annealed to the multimeric barcode molecule and are non-complementary to the subsequences of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

The barcode molecules of a multimeric barcode molecule may be linked on a nucleic acid molecule. Such a nucleic acid molecule may provide the backbone to which single-stranded barcoded oligonucleotides may be annealed. Alternatively, the barcode molecules of a multimeric barcode molecule may be linked together by any of the other means described herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, or at least 10,000 barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 barcode molecules linked together, wherein each barcode molecule is as defined herein; and a barcoded oligonucleotide annealed to each barcode molecule, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ unique or different barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 unique or different barcode molecules linked together, wherein each barcode molecule is as defined herein; and a barcoded oligonucleotide annealed to each barcode molecule, wherein each barcoded oligonucleotide is as defined herein.

The multimeric barcoding reagent may comprise: at least 5, at least 10, at least 20, at least 25, at least 50, at least 75, at least 100, at least 200, at least 500, at least 1000, at least 5000, or at least 10,000 barcode regions, wherein each barcode region is as defined herein; and a barcoded oligonucleotide annealed to each barcode region, wherein each barcoded oligonucleotide is as defined herein. Preferably, the multimeric barcoding reagent comprises at least 5 barcode regions, wherein each barcode region is as defined herein; and a barcoded oligonucleotide annealed to each barcode region, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ unique or different barcode regions, wherein each barcode region is as defined herein; and a barcoded oligonucleotide annealed to each barcode region, wherein each barcoded oligonucleotide is as defined herein.

Preferably, the multimeric barcoding reagent comprises at least 5 unique or different barcode regions, wherein each barcode region is as defined herein; and a barcoded oligonucleotide annealed to each barcode region, wherein each barcoded oligonucleotide is as defined herein.

FIG. 1 shows a multimeric barcoding reagent, including first (D1, E1, and F1) and second (D2, E2, and F2) barcode molecules, which each include a nucleic acid sequence comprising a barcode region (E1 and E2). These first and second barcode molecules are linked together, for example by a connecting nucleic acid sequence (S). The multimeric barcoding reagent also comprises first (A1, B1, C1, and G1) and second (A2, B2, C2, and G2) barcoded oligonucleotides.

These barcoded oligonucleotides each comprise a barcode region (B1 and B2) and a target region (G1 and G2).

The barcode regions within the barcoded oligonucleotides may each contain a unique sequence which is not present in other barcoded oligonucleotides, and may thus serve to uniquely identify each such barcode molecule. The target regions may be used to anneal the barcoded oligonucleotides to sub-sequences of target nucleic acids, and then may be used as primers for a primer-extension reaction or an amplification reaction e.g. a polymerase chain reaction.

Each barcode molecule may optionally also include a 5' adapter region (F1 and F2). The barcoded oligonucleotides may then also include a 3' adapter region (C1 and C2) that is complementary to the 5' adapter region of the barcode molecules.

Each barcode molecule may optionally also include a 3' region (D1 and D2), which may be comprised of identical sequences within each barcode molecule. The barcoded oligonucleotides may then also include a 5' region (A1 and A2) which is complementary to the 3' region of the barcode molecules. These 3' regions may be useful for manipulation or amplification of nucleic acid sequences, for example sequences that are generated by labeling a nucleic acid target with a barcoded oligonucleotide. The 3' region may comprise at least 4, at least 5, at least 6, at least 8, at least 10, at least 15, at least 20, at least 25, at least 50, at least 100, or at least 250 nucleotides. Preferably, the 3' region comprises at least 4 nucleotides. Preferably each 3' region comprises deoxyribonucleotides, optionally all of the nucleotides in an 3' region are deoxyribonucleotides. One or more of the deoxyribonucleotides may be a modified deoxyribonucleotide (e.g. a deoxyribonucleotide modified with a biotin moiety or a deoxyuracil nucleotide). Each 3' region may comprise one or more universal bases (e.g. inosine), one or modified nucleotides and/or one or more nucleotide analogues.

The invention provides a library of multimeric barcoding reagents comprising at least 10 multimeric barcoding reagents for labelling a target nucleic acid for sequencing, wherein each multimeric barcoding reagent comprises: first and second barcode molecules comprised within a (single) nucleic acid molecule, wherein each of the barcode molecules comprises a nucleic acid sequence comprising a barcode region; and first and second barcoded oligonucleotides, wherein the first barcoded oligonucleotide comprises, optionally in the 5' to 3' direction, a barcode region complementary and annealed to the barcode region of the first barcode molecule and a target region capable of annealing or ligating to a first sub-sequence of the target nucleic acid, and wherein the second barcoded oligonucleotide comprises, optionally in the 5' to 3' direction, a barcode region complementary and annealed to the barcode region of the second barcode molecule and a target region capable of annealing or ligating to a second sub-sequence of the target nucleic acid. Preferably, the barcode regions of the first and second barcoded oligonucleotides of each multimeric barcoding reagent are different to the barcode regions of the barcoded oligonucleotides of at least 9 other multimeric barcoding reagents in the library.

5. Multimeric Barcoding Reagents Comprising Barcoded Oligonucleotides Annealed to a Multimeric Hybridization Molecule The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide comprises, optionally in the 5' to 3' direction, an adapter region annealed to the hybridization region of the first hybridization molecule, a barcode region, and a target region capable of annealing or ligating to a first sub-sequence of the target nucleic acid, and wherein the second barcoded oligonucleotide comprises, optionally in the 5' to 3' direction, an adapter region annealed to the hybridization region of the second hybridization molecule, a barcode region, and a target region capable of annealing or ligating to a second sub-sequence of the target nucleic acid.

Optionally, the first and second barcoded oligonucleotides each comprise an adapter region and a target region in a single contiguous sequence that is complementary and annealed to a hybridization region of a hybridization molecule, and also capable of annealing or ligating to a sub-sequence of a target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide comprises, optionally in the 5' to 3' direction, a barcode region, an adapter region annealed to the hybridization region of the first hybridization molecule and a target region capable of annealing or ligating to a first sub-sequence of the target nucleic acid, and wherein the second barcoded oligonucleotide comprises, optionally in the 5' to 3' direction, a barcode region, an adapter region annealed to the hybridization region of the second hybridization molecule and a target region capable of annealing or ligating to a second sub-sequence of the target nucleic acid.

Optionally, the first and second barcoded oligonucleotides each comprise an adapter region and a target region in a single contiguous sequence that is complementary and annealed to a hybridization region of a hybridization molecule, and also capable of annealing or ligating to a sub-sequence of a target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide comprises (in the 5'-3' or 3'-5' direction) an adapter region annealed to the hybridization region of the first hybridization molecule, a barcode region and a target region capable of ligating to a first sub-sequence of the target nucleic acid, and wherein the second barcoded oligonucleotide comprises (in the 5'-3' or 3'-5' direction) an adapter region annealed to the hybridization region of the second hybridization molecule, a barcode region and a target region capable of ligating to a second sub-sequence of the target nucleic acid.

Optionally, the first and second barcoded oligonucleotides each comprise an adapter region and a target region in a single contiguous sequence that is complementary and annealed to a hybridization region of a hybridization molecule, and also capable of ligating to a sub-sequence of a target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide comprises (in the 5'-3' or 3'-5' direction) a barcode region, an adapter region annealed to the hybridization region of the first hybridization molecule and a target region capable of ligating to a first sub-sequence of the target nucleic acid, and wherein the second barcoded oligonucleotide comprises (in the 5'-3' or 3'-5' direction) a barcode region, an adapter region annealed to the hybridization region of the second hybridization molecule and a target region capable of ligating to a second sub-sequence of the target nucleic acid.

Optionally, the first and second barcoded oligonucleotides each comprise an adapter region and a target region in a single contiguous sequence that is complementary and annealed to a hybridization region of a hybridization molecule, and also capable of ligating to a sub-sequence of a target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a barcode region; and first and second barcoded oligonucleotides, wherein the first barcoded oligonucleotide comprises in the 5' to 3' direction an adapter region annealed to the hybridization region of the first hybridization molecule, a barcode region and a target region capable of annealing to a first sub-sequence of the target nucleic acid, and wherein the second barcoded oligonucleotide comprises in the 5' to 3' direction an adapter region annealed to the hybridization region of the second hybridization molecule, a barcode region and a target region capable of annealing to a second sub-sequence of the target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a barcode region; and first and second barcoded oligonucleotides, wherein the first barcoded oligonucleotide comprises in the 5' to 3' direction a barcode region, an adapter region annealed to the hybridization region of the first hybridization molecule and a target region capable of annealing to a first sub-sequence of the target nucleic acid, and wherein the second barcoded oligonucleotide comprises in the 5' to 3' direction a barcode region, an adapter region annealed to the hybridization region of the second hybridization molecule and a target region capable of annealing to a second sub-sequence of the target nucleic acid.

Optionally, the first and second barcoded oligonucleotides each comprise an adapter region and a target region in a single contiguous sequence that is complementary and annealed to a hybridization region of a hybridization molecule, and also capable of annealing to a sub-sequence of a target nucleic acid.

Preferably, the adapter region of the first barcoded oligonucleotide comprises a sequence that is complementary and annealed to the hybridization region of the first hybridization molecule and the adapter region of the second barcoded oligonucleotide comprises a sequence that is complementary and annealed to the hybridization region of the second hybridization molecule. The complementary sequence of each barcoded oligonucleotide may be at least 5, at least 10, at least 15, at least 20, at least 25, at least 50 or at least 100 contiguous nucleotides.

The hybridization region of each hybridization molecule may comprise a constant region. Preferably, all hybridization regions of a multimeric barcoding reagent are substantially identical. Optionally, all hybridization regions of a library of multimeric barcoding reagents are substantially identical. The hybridization region may comprise at least 1, at least 2, at least 3, at least 4, at least 5, at least 6, at least 8, at least 10, at least 15, at least 20, at least 25, at least 50, at least 100, or at least 250 nucleotides. Preferably, the hybridization region comprises at least 4 nucleotides. Preferably each hybridization region comprises deoxyribonucleotides, optionally all of the nucleotides in a hybridization region are deoxyribonucleotides. One or more of the deoxyribonucleotides may be a modified deoxyribonucleotide (e.g. a deoxyribonucleotide modified with a biotin moiety or a deoxyuracil nucleotide). Each hybridization region may comprise one or more universal bases (e.g. inosine), one or modified nucleotides and/or one or more nucleotide analogues.

The target regions of the barcoded oligonucleotides may not be annealed to the multimeric hybridization molecule(s). The target regions of the barcoded oligonucleotides may be non-complementary to the multimeric hybridization molecule(s).

The barcoded oligonucleotides may comprise a linker region between the adapter region and the target region. The linker region may comprise one or more contiguous nucleotides that are not annealed to the multimeric hybridization molecule and are non-complementary to the subsequences of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

Hybridization molecules may further comprise one or more nucleic acid sequences that are not complementary to barcoded oligonucleotides. For example, hybridization molecules may comprise one or more adapter regions. A hybridization molecule, may, for example, comprise an adapter region 5' of a hybridization region (a 5' adapter region) and/or an adapter region 3' of the hybridization region (a 3' adapter region). The adapter region(s) may be used for manipulating, purifying, retrieving, amplifying, and/or detecting hybridization molecules.

The adapter region of each hybridization molecule may comprise a constant region. Optionally, all adapter regions of a multimeric hybridization reagent are substantially identical. The adapter region may comprise at least 1, at least 2, at least 3, at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

The barcoded oligonucleotides may comprise a linker region between the adapter region and the target region. The linker region may comprise one or more contiguous nucleotides that are not annealed to the multimeric hybridization molecule and are non-complementary to the subsequences of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

The invention provides a library of multimeric barcoding reagents comprising at least 10 multimeric barcoding reagents for labelling a target nucleic acid for sequencing, wherein each multimeric barcoding reagent comprises: first and second hybridization molecules comprised within a (single) nucleic acid molecule, wherein each of the hybridization molecules comprises a nucleic acid sequence comprising a hybridization region; and first and second barcoded oligonucleotides, wherein the first barcoded oligonucleotide comprises, optionally in the 5' to 3' direction, an adapter region complementary and annealed to the hybridization region of the first hybridization molecule, a barcode region and a target region capable of annealing or ligating to a first sub-sequence of the target nucleic acid, and wherein the second barcoded oligonucleotide comprises, optionally in the 5' to 3' direction, an adapter region complementary and annealed to the hybridization region of the second hybridization molecule, a barcode region and a target region capable of annealing or ligating to a second sub-sequence of the target nucleic acid.

Preferably, the barcode regions of the first and second barcoded oligonucleotides of each multimeric barcoding reagent are different to the barcode regions of the barcoded oligonucleotides of at least 9 other multimeric barcoding reagents in the library.

The invention provides a library of multimeric barcoding reagents comprising at least 10 multimeric barcoding reagents for labelling a target nucleic acid for sequencing, wherein each multimeric barcoding reagent comprises: first and second hybridization molecules comprised within a (single) nucleic acid molecule, wherein each of the hybridization molecules comprises a nucleic acid sequence comprising a hybridization region; and first and second barcoded oligonucleotides, wherein the first barcoded oligonucleotide comprises, optionally in the 5' to 3' direction, a barcode region, an adapter region complementary and annealed to the hybridization region of the first hybridization molecule and a target region capable of annealing or ligating to a first sub-sequence of the target nucleic acid, and wherein the second barcoded oligonucleotide comprises, optionally in the 5' to 3' direction, a barcode region, an adapter region complementary and annealed to the hybridization region of the second hybridization molecule and a target region capable of annealing or ligating to a second sub-sequence of the target nucleic acid. Preferably, the barcode regions of the first and second barcoded oligonucleotides of each multimeric barcoding reagent are different to the barcode regions of the barcoded oligonucleotides of at least 9 other multimeric barcoding reagents in the library.

6. Multimeric Barcoding Reagents Comprising Barcoded Oligonucleotides Linked by a Macromolecule The invention provides a multimeric barcoding reagent for labelling a target nucleic acid, wherein the reagent comprises first and second barcoded oligonucleotides linked together by a macromolecule, and wherein the barcoded oligonucleotides each comprise a barcode region.

The first barcoded oligonucleotide may further comprise a target region capable of annealing or ligating to a first sub-sequence of the target nucleic acid, and the second barcoded oligonucleotide may further comprise a target region capable of annealing or ligating to a second sub-sequence of the target nucleic acid.

The first barcoded oligonucleotide may comprise in the 5'-3' direction a barcode region and a target region capable of annealing to a first sub-sequence of the target nucleic acid, and the second barcoded oligonucleotide may comprise in the 5'-3' direction a barcode region and a target region capable of annealing to a second sub-sequence of the target nucleic acid.

The barcoded oligonucleotides may further comprise any of the features described herein.

The barcoded oligonucleotides may be linked by a macromolecule by being bound to the macromolecule and/or by being annealed to the macromolecule.

The barcoded oligonucleotides may be linked to the macromolecule directly or indirectly (e.g. via a linker molecule). The barcoded oligonucleotides may be linked by being bound to the macromolecule and/or by being bound or annealed to linker molecules that are bound to the macromolecule. The barcoded oligonucleotides may be bound to the macromolecule (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The macromolecule may be a synthetic polymer (e.g. a dendrimer) or a biopolymer such as a nucleic acid (e.g. a single-stranded nucleic acid such as single-stranded DNA), a peptide, a polypeptide or a protein (e.g. a multimeric protein).

The dendrimer may comprise at least 2, at least 3, at least 5, or at least 10 generations.

The macromolecule may be a nucleic acid comprising two or more nucleotides each capable of binding to a barcoded oligonucleotide. Additionally or alternatively, the nucleic acid may comprise two or more regions each capable of hybridizing to a barcoded oligonucleotide.

The nucleic acid may comprise a first modified nucleotide and a second modified nucleotide, wherein each modified nucleotide comprises a binding moiety (e.g. a biotin moiety, or an alkyne moiety which may be used for a click-chemical reaction) capable of binding to a barcoded oligonucleotide. Optionally, the first and second modified nucleotides may be separated by an intervening nucleic acid sequence of at least one, at least two, at least 5 or at least 10 nucleotides.

The nucleic acid may comprise a first hybridisation region and a second hybridisation region, wherein each hybridisation region comprises a sequence complementary to and capable of hybridizing to a sequence of at least one nucleotide within a barcoded oligonucleotide. The complementary sequence may be at least 5, at least 10, at least 15, at least 20, at least 25 or at least 50 contiguous nucleotides. Optionally, the first and second hybridisation regions may be separated by an intervening nucleic acid sequence of at least one, at least two, at least 5 or at least 10 nucleotides.

The macromolecule may be a protein such as a multimeric protein e.g. a homomeric protein or a heteromeric protein. For example, the protein may comprise streptavidin e.g. tetrameric streptavidin.

Libraries of multimeric barcoding reagents comprising barcoded oligonucleotides linked by a macromolecule are also provided. Such libraries may be based on the general properties of libraries of multimeric barcoding reagents described herein. In the libraries, each multimeric barcoding reagent may comprise a different macromolecule.

7. Multimeric Barcoding Reagents Comprising Barcoded Oligonucleotides Linked by a Solid Support or a Semi-Solid Support The invention provides a multimeric barcoding reagent for labelling a target nucleic acid, wherein the reagent comprises first and second barcoded oligonucleotides linked together by a solid support or a semi-solid support, and wherein the barcoded oligonucleotides each comprise a barcode region.

The first barcoded oligonucleotide may further comprise a target region capable of annealing or ligating to a first sub-sequence of the target nucleic acid, and the second barcoded oligonucleotide may further comprise a target region capable of annealing or ligating to a second sub-sequence of the target nucleic acid.

The first barcoded oligonucleotide may comprise in the 5'-3' direction a barcode region and a target region capable of annealing to a first sub-sequence of the target nucleic acid, and the second barcoded oligonucleotide may comprise in the 5'-3' direction a barcode region and a target region capable of annealing to a second sub-sequence of the target nucleic acid.

The barcoded oligonucleotides may further comprise any of the features described herein.

The barcoded oligonucleotides may be linked by a solid support or a semi-solid support. The barcoded oligonucleotides may be linked to the support directly or indirectly (e.g. via a linker molecule). The barcoded oligonucleotides may be linked by being bound to the support and/or by being bound or annealed to linker molecules that are bound to the support. The barcoded oligonucleotides may be bound to the support (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The support may comprise a planar surface. The support may be a slide e.g. a glass slide. The slide may be a flow cell for sequencing. If the support is a slide, the first and second barcoded oligonucleotides may be immobilized in a discrete region on the slide. Optionally, the barcoded oligonucleotides of each multimeric barcoding reagent in a library are immobilized in a different discrete region on the slide to the barcoded oligonucleotides of the other multimeric barcoding reagents in the library. The support may be a plate comprising wells, optionally wherein the first and second barcoded oligonucleotides are immobilized in the same well. Optionally, the barcoded oligonucleotides of each multimeric barcoding reagent in library are immobilized in a different well of the plate to the barcoded oligonucleotides of the other multimeric barcoding reagents in the library.

Preferably, the support is a bead (e.g. a gel bead). The bead may be an agarose bead, a silica bead, a styrofoam bead, a gel bead (such as those available from 10× Genomics®), an antibody conjugated bead, an oligo-dT conjugated bead, a streptavidin bead or a magnetic bead (e.g. a superparamagnetic bead). The bead may be of any size and/or molecular structure. For example, the bead may be 10 nanometres to 100 microns in diameter, 100 nanometres to 10 microns in diameter, or 1 micron to 5 microns in diameter. Optionally, the bead is approximately nanometres in diameter, approximately 100 nanometres in diameter, approximately 1 micron in diameter, approximately 10 microns in diameter or approximately 100 microns in diameter. The bead may be solid, or alternatively the bead may be hollow or partially hollow or porous. Beads of certain sizes may be most preferable for certain barcoding methods. For example, beads less than 5.0 microns, or less than 1.0 micron, may be most useful for barcoding nucleic acid targets within individual cells. Preferably, the barcoded oligonucleotides of each multimeric barcoding reagent in a library are linked together on a different bead to the barcoded oligonucleotides of the other multimeric barcoding reagents in the library.

The support may be functionalised to enable attachment of two or more barcoded oligonucleotides. This functionalisation may be enabled through the addition of chemical moieties (e.g. carboxylated groups, alkynes, azides, acrylate groups, amino groups, sulphate groups, or succinimide groups), and/or protein-based moieties (e.g. streptavidin, avidin, or protein G) to the support. The barcoded oligonucleotides may be attached to the moieties directly or indirectly (e.g. via a linker molecule).

Functionalised supports (e.g. beads) may be brought into contact with a solution of barcoded oligonucleotides under conditions which promote the attachment of two or more barcoded oligonucleotides to each bead in the solution (generating multimeric barcoding reagents).

Libraries of multimeric barcoding reagents comprising barcoded oligonucleotides linked by a support are also provided. Such libraries may be based on the general properties of libraries of multimeric barcoding reagents described herein. In the libraries, each multimeric barcoding reagent may comprise a different support (e.g. a differently labelled bead). In a library of multimeric barcoding reagents, the barcoded oligonucleotides of each multimeric barcoding reagent in a library may be linked together on a different support to the barcoded oligonucleotides of the other multimeric barcoding reagents in the library.

8. Multimeric Barcoding Reagents Comprising Barcoded Oligonucleotides Linked Together by being Comprised within a Lipid Carrier The invention provides a multimeric barcoding reagent for labelling a target nucleic acid, wherein the reagent comprises first and second barcoded oligonucleotides and a lipid carrier, wherein the first and second barcoded oligonucleotides are linked together by being comprised within the lipid carrier, and wherein the barcoded oligonucleotides each comprise a barcode region.

The first barcoded oligonucleotide may further comprise a target region capable of annealing or ligating to a first sub-sequence of the target nucleic acid, and the second barcoded oligonucleotide may further comprise a target region capable of annealing or ligating to a second sub-sequence of the target nucleic acid.

The first barcoded oligonucleotide may comprise in the 5'-3' direction a barcode region and a target region capable of annealing to a first sub-sequence of the target nucleic acid, and the second barcoded oligonucleotide may comprise in the 5'-3' direction a barcode region and a target region capable of annealing to a second sub-sequence of the target nucleic acid.

The barcoded oligonucleotides may further comprise any of the features described herein.

The invention provides a library of multimeric barcoding reagents comprising first and second multimeric barcoding reagents as defined herein, wherein the barcoded oligonucleotides of the first multimeric barcoding reagent are comprised within a first lipid carrier, and wherein the barcoded oligonucleotides of the second multimeric barcoding reagent are comprised with a second lipid carrier, and wherein the barcode regions of the barcoded oligonucleotides of the first multimeric barcoding reagent are different to the barcode regions of the barcoded oligonucleotides of the second multimeric barcoding reagent.

The library of multimeric barcoding reagents may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the library comprises at least 10 multimeric barcoding reagents as defined herein. Preferably, the barcode regions of the first and second barcoded oligonucleotides of each multimeric barcoding reagent are different to the barcode regions of the barcoded oligonucleotides of at least 9 other multimeric barcoding reagents in the library.

The barcoded oligonucleotides of each multimeric barcoding reagent are comprised within a different lipid carrier.

The lipid carrier may be a liposome or a micelle. The lipid carrier may be a phospholipid carrier. The lipid carrier may comprise one or more amphiphilic molecules. The lipid carrier may comprise one or more phospholipids. The phospholipid may be phosphatidylcholine. The lipid carrier may comprise one or more of the following constituents: phophatidylethanolamine, phosphatidylserine, cholesterol, cardiolipin, dicetylphosphate, stearylamine, phosphatidylglycerol, dipalmitoylphosphatidylcholine, distearylphosphatidylcholine, and/or any related and/or derivative molecules thereof. Optionally, the lipid carrier may comprise any combination of two or more constituents described above, with or without further constituents.

The lipid carrier (e.g. a liposome or a micelle) may be unilamellar or multilamellar. A library of multimeric barcoding reagents may comprise both unilamellar and multilamellar lipid carriers. The lipid carrier may comprise a copolymer e.g. a block copolymer.

The lipid carrier may comprise at least 2, at least 3, at least 5, at least 10, at least 50, at least 100, at least 500, at least 1000, at least 10,000, or at least 100,000 barcoded oligonucleotides, or any greater number of barcoded oligonucleotides.

Any lipid carrier (e.g. liposome or micelle, and/or liposomal or micellar reagent) may on average be complexed with 1, or less than 1, or greater than 1 multimeric barcoding reagent(s) to form a library of such multimeric barcoding reagent(s).

The invention provides a library of multimeric barcoding reagents comprising at least 10 multimeric barcoding reagents as defined herein, wherein each multimeric barcoding reagent comprises first and second barcoded oligonucleotides comprised within a different lipid carrier, and wherein the barcode regions of the first and second barcoded oligonucleotides of each multimeric barcoding reagent are different to the barcode regions of the barcoded oligonucleotides of at least 9 other multimeric barcoding reagents in the library.

A method for preparing multimeric barcoding reagents comprises loading barcoded oligonucleotides and/or multimeric barcoding reagent(s) into lipid carriers (e.g. liposomes or micelles). The method may comprise a step of passive, active, and/or remote loading. Pre-formed lipid carriers (e.g. liposomes and/or micelles) may be loaded by contacting them with a solution of barcoded oligonucleotides and/or multimeric barcoding reagent(s). Lipid carriers (e.g. liposomes and/or micelles) may be loaded by contacting them with a solution of barcoded oligonucleotides and/or multimeric barcoding reagent(s) prior to and/or during the formation or synthesis of the lipid carriers. The method may comprise passive encapsulation and/or trapping of barcoded oligonucleotides and/or multimeric barcoding reagent(s) in lipid carriers.

Lipid carriers (e.g. liposomes and/or micelles) may be prepared by a method based on sonication, a French press-based method, a reverse phase method, a solvent evaporation method, an extrusion-based method, a mechanical mixing-based method, a freeze/thaw-based method, a dehydrate/rehydrate-based method, and/or any combination hereof.

Lipid carriers (e.g. liposomes and/or micelles) may be stabilized and/or stored prior to use using known methods.

Any of the multimeric barcoding reagents or kits described herein may be comprised with a lipid carrier.

9. Kits Comprising Multimeric Barcoding Reagents and Adapter Oligonucleotides

The invention further provides kits comprising one or more of the components defined herein. The invention also provides kits specifically adapted for performing any of the methods defined herein.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (b) first and second adapter oligonucleotides, wherein the first adapter oligonucleotide comprises, optionally in the 5' to 3' direction, an adapter region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adapter region capable of annealing to the adapter region of the second barcode molecule and a target region capable of annealing or ligating to a second sub-sequence of the target nucleic acid.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising an adapter region and a barcode region, and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (b) first and second adapter oligonucleotides, wherein the first adapter oligonucleotide comprises an adapter region capable of annealing to the adapter region of the first barcode molecule and a target region capable of ligating to a first sub-sequence of the target nucleic acid, and wherein the second adapter oligonucleotide comprises an adapter region capable of annealing to the adapter region of the second barcode molecule and a target region capable of ligating to a second sub-sequence of the target nucleic acid.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising in the 5' to 3' direction an adapter region and a barcode region, and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (b) first and second adapter oligonucleotides, wherein the first adapter oligonucleotide comprises in the 5' to 3' direction an adapter region capable of annealing to the adapter region of the first barcode molecule and a target region capable of annealing to a first sub-sequence of the target nucleic acid, and wherein the second adapter oligonucleotide comprises in the 5' to 3' direction an adapter region capable of annealing to the adapter region of the second barcode molecule and a target region capable of annealing to a second sub-sequence of the target nucleic acid.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (b) first and second adapter oligonucleotides, wherein the first adapter oligonucleotide comprises an adapter region capable of annealing to the adapter region of the first barcode molecule and capable of ligating to a first sub-sequence of the target nucleic acid, and wherein the second adapter oligonucleotide comprises an adapter region capable of annealing to the adapter region of the second barcode molecule and capable of ligating to a second sub-sequence of the target nucleic acid.

Each adapter oligonucleotide may consist essentially of or consist of an adapter region. Each adapter oligonucleotide may not comprise a target region.

Preferably, the adapter region of the first adapter oligonucleotide comprises a sequence that is complementary to and capable of annealing to the adapter region of the first barcode molecule and the adapter region of the second adapter oligonucleotide comprises a sequence that is complementary to and capable of annealing to the adapter region of the second barcode molecule. The complementary sequence of each adapter oligonucleotide may be at least 5, at least 10, at least 15, at least 20, at least 25, at least 50 or at least 100 contiguous nucleotides.

The target regions of the adapter oligonucleotides may not be capable of annealing to the multimeric barcode molecule (s)). The target regions of the adapter oligonucleotides may be non-complementary to the multimeric barcode molecule (s).

The target regions of each adapter oligonucleotide may comprise different sequences. Each target region may comprise a sequence capable of annealing to only a single sub-sequence of a target nucleic acid within a sample of nucleic acids. Each target region may comprise one or more random, or one or more degenerate, sequences to enable the target region to anneal to more than one sub-sequence of a target nucleic acid. Each target region may comprise at least 5, at least 10, at least 15, at least 20, at least 25, at least 50 or at least 100 nucleotides. Preferably, each target region comprises at least 5 nucleotides. Each target region may comprise to 100 nucleotides, 5 to 10 nucleotides, 10 to 20 nucleotides, 20 to 30 nucleotides, 30 to 50 nucleotides, 50 to 100 nucleotides, 10 to 90 nucleotides, 20 to 80 nucleotides, 30 to 70 nucleotides or 50 to 60 nucleotides. Preferably, each target region comprises 30 to 70 nucleotides. Preferably each target region comprises deoxyribonucleotides, optionally all of the nucleotides in a target region are deoxyribonucleotides. One or more of the deoxyribonucleotides may be a modified deoxyribonucleotide (e.g. a deoxyribonucleotide modified with a biotin moiety or a deoxyuracil nucleotide). Each target region may comprise one or more universal bases (e.g. inosine), one or modified nucleotides and/or one or more nucleotide analogues.

The target regions may be used to anneal the adapter oligonucleotides to sub-sequences of target nucleic acids, and then may be used as primers for a primer-extension reaction or an amplification reaction e.g. a polymerase chain reaction. Alternatively, the target regions may be used to ligate the adapter oligonucleotides to sub-sequences of target nucleic acids. The target region may be at the 5' end of an adapter oligonucleotide. Such a target region may be phosphorylated. This may enable the 5' end of the target region to be ligated to the 3' end of a sub-sequence of a target nucleic acid.

The adapter oligonucleotides may comprise a linker region between the adapter region and the target region. The linker region may comprise one or more contiguous nucleotides that are not annealed to the first and second barcode molecules (i.e. the multimeric barcode molecule) and are non-complementary to the subsequences of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the kits described herein.

Each of the components of the kit may take any of the forms defined herein.

The multimeric barcoding reagent(s) and adapter oligonucleotides may be provided in the kit as physically separated components.

The kit may comprise: (a) a multimeric barcoding reagent comprising at least 5, at least 10, at least 20, at least 25, at least 50, at least 75 or at least 100 barcode molecules linked together, wherein each barcode molecule is as defined herein; and (b) an adapter oligonucleotide capable of annealing to each barcode molecule, wherein each adapter oligonucleotide is as defined herein.

FIG. 2 shows a kit comprising a multimeric barcoding reagent and adapter oligonucleotides for labelling a target nucleic acid. In more detail, the kit comprises first (D1, E1, and F1) and second (D2, E2, and F2) barcode molecules, with each incorporating a barcode region (E1 and E2) and also a 5' adapter region (F1 and F2). These first and second barcode molecules are linked together, in this embodiment by a connecting nucleic acid sequence (S).

The kit further comprises first (A1 and B1) and second (A2 and B2) barcoded oligonucleotides, which each comprise a barcode region (B1 and B2), as well as 5' regions (A1 and A2). The 5' region of each barcoded oligonucleotide is complementary to, and thus may be annealed to, the 3' regions of the barcode molecules (D1 and D2). The barcode regions (B1 and B2) are complementary to, and thus may be annealed to, the barcode regions (E1 and E2) of the barcode molecules.

The kit further comprises first (C1 and G1) and second (C2 and G2) adapter oligonucleotides, wherein each adapter oligonucleotide comprises an adapter region (C1 and C2) that is complementary to, and thus able to anneal to, the 5' adapter region of a barcode molecule (F1 and F2). These adapter oligonucleotides may be synthesised to include a 5'-terminal phosphate group. Each adapter oligonucleotide also comprises a target region (G1 and G2), which may be used to anneal the barcoded-adapter oligonucleotides (A1, B1, C1 and G1, and A2, B2, C2 and G2) to target nucleic acids, and then may be used as primers for a primer-extension reaction or a polymerase chain reaction.

The kit may comprise a library of two or more multimeric barcoding reagents, wherein each multimeric barcoding reagent is as defined herein, and adapter oligonucleotides for each of the multimeric barcoding reagents, wherein each adapter oligonucleotide is as defined herein. The barcode regions of the first and second barcoded oligonucleotides of the first multimeric barcoding reagent are different to the barcode regions of the first and second barcoded oligonucleotides of the second multimeric barcoding reagent.

The kit may comprise a library comprising at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the kit comprises a library comprising at least 10 multimeric barcoding reagents as defined herein. The kit may further comprise adapter oligonucleotides for each of the multimeric barcoding reagents, wherein each adapter oligonucleotide may take the form of any of the adapter oligonucleotides defined herein. Preferably, the barcode regions of the first and second barcoded oligonucleotides of each multimeric barcoding reagent are different to the barcode regions of the barcoded oligonucleotides of at least 9 other multimeric barcoding reagents in the library.

The barcode regions of the first and second barcoded oligonucleotides of each multimeric barcoding reagent may be different to the barcode regions of the barcoded oligonucleotides of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The barcode regions of the first and second barcoded oligonucleotides of each multimeric barcoding reagent may be different to the barcode regions of the barcoded oligonucleotides of all of the other multimeric barcoding reagents in the library. Preferably, the barcode regions of the first and second barcoded oligonucleotides of each multimeric barcoding reagent are different to the barcode regions of the barcoded oligonucleotides of at least 9 other multimeric barcoding reagents in the library.

The barcode regions of the barcoded oligonucleotides of each multimeric barcoding reagent may be different to the barcode regions of the barcoded oligonucleotides of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The barcode regions of the barcoded oligonucleotides of each multimeric barcoding reagent may be different to the barcode regions of the barcoded oligonucleotides of all of the other multimeric barcoding reagents in the library. Preferably, the barcode regions of the barcoded oligonucleotides of each multimeric barcoding reagent are different to the barcode regions of the barcoded oligonucleotides of at least 9 other multimeric barcoding reagents in the library The invention provides a kit for labelling a target nucleic acid for sequencing, wherein the kit comprises: (a) a library of multimeric barcoding reagents comprising at least 10 multimeric barcoding reagents, wherein each multimeric barcoding reagent comprised: (i) first and second barcode molecules comprised within a (single) nucleic acid molecule, wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region complementary and annealed to the barcode region of the first barcode molecule, and wherein the second barcoded oligonucleotide comprises a barcode region complementary and annealed to the barcode region of the second barcode molecule; and (b) first and second adapter oligonucleotides for each of the multimeric barcoding reagents, wherein the first adapter oligonucleotide comprises, optionally in the 5' to 3' direction, an adapter region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adapter region capable of annealing to the adapter region of the second barcode molecule and a target region capable of annealing or ligating to a second sub-sequence of the target nucleic acid.

10. Kits Comprising Multimeric Barcoding Reagents, Adapter Oligonucleotides and Extension Primers The invention further provides a kit for labelling a target nucleic acid for sequencing, wherein the kit comprises: (a) a multimeric barcode molecule comprising first and second barcode molecules linked together, wherein each of the barcode molecules comprises a nucleic acid sequence comprising, optionally in the 5' to 3' direction, an adapter region, a barcode region, and a priming region; (b) first and second extension primers for the multimeric barcode molecule, wherein the first extension primer comprises a sequence capable of annealing to the priming region of the first barcode molecule, and wherein the second extension primer comprises a sequence capable of annealing to the priming region of the second barcode molecule; and (c) first and second adapter oligonucleotides for the multimeric barcode molecule, wherein the first adapter oligonucleotide comprises, optionally in the 5' to 3' direction, an adapter region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adapter region capable of annealing to the adapter region of the second barcode molecule and a target region capable of annealing or ligating to a second sub-sequence of the target nucleic acid.

The invention further provides a kit for labelling a target nucleic acid for sequencing, wherein the kit comprises: (a) a multimeric barcode molecule comprising first and second barcode molecules linked together, wherein each of the barcode molecules comprises a nucleic acid sequence comprising, optionally in the 5' to 3' direction, an adapter region, a barcode region, and a priming region; (b) first and second extension primers for the multimeric barcode molecule, wherein the first extension primer comprises a sequence capable of annealing to the priming region of the first barcode molecule, and wherein the second extension primer comprises a sequence capable of annealing to the priming region of the second barcode molecule; and (c) first and second adapter oligonucleotides for the multimeric barcode molecule, wherein the first adapter oligonucleotide comprises an adapter region capable of annealing to the adapter region of the first barcode molecule and capable of ligating to a first sub-sequence of the target nucleic acid, and wherein the second adapter oligonucleotide comprises an adapter region capable of annealing to the adapter region of the second barcode molecule and capable of ligating to a second sub-sequence of the target nucleic acid.

Each adapter oligonucleotide may consist essentially of or consist of an adapter region.

The components of the kit may take any of the forms described herein.

Preferably, the first extension primer comprises a sequence that is complementary to and capable of annealing to the priming region of the first barcode molecule and the second extension primer comprises a sequence that is complementary to and capable of annealing to the priming region of the second barcode molecule. The complementary sequence of each extension primer may be at least 5, at least 10, at least 15, at least 20, at least 25, at least 50 or at least 100 contiguous nucleotides.

The first and second extension primers may be capable of being extended using the barcode regions of the first and second barcode molecules as templates to produce first and second barcoded oligonucleotides, wherein the first barcoded oligonucleotide comprises a sequence complementary to the barcode region of the first barcode molecule and the second barcoded oligonucleotide comprises a sequence complementary to the barcode region of the second barcode molecule.

The first and second extension primers may be identical in sequence. Alternatively, the first and second extension primers may be different in sequence.

The first and/or second extension primers may further comprise one or more regions with nucleic acid sequences that are not complementary to the first barcode molecule and second barcode molecule, respectively. Optionally, such a non-complementary region may include a binding site for one or more amplification primers. Optionally, such a non-complementary region may be positioned within the 5' region of the molecule. Optionally, the first and second extension primers may comprise a terminal 5' phosphate group capable of ligating to a 3' end of a nucleic acid molecule.

The first and/or second extension primers may further comprise one or more secondary barcode regions. Optionally, a secondary barcode region may be comprised within a region of the extension primer that is non-complementary to a barcode molecule. Optionally, a secondary barcode region may be comprised within a region of the extension primer that is between a 3' region of the extension primer that is complementary to a barcode molecule and a 5' region of the extension primer that comprises a binding site for an amplification primer.

A secondary barcode region may comprise a sequence of one or more nucleotides, wherein sequences of the secondary barcode regions of the first extension primer and the second extension primer are different. Optionally, said one or more nucleotides may comprise random or degenerate nucleotides. Optionally, said one or more nucleotides may comprise different but non-random nucleotides. Any secondary barcode region may comprise at least 2, at least 3, at least 5, at least 10, at least 15, at least 20, or at least 30 nucleotides. Any secondary barcode region may comprise a contiguous sequence of barcode oligonucleotides, or may comprise two or more different segments separated by at least one non-barcode or invariant nucleotide. Optionally, any secondary barcode region may comprise a unique molecular identifier (UMI).

The kit may comprise a library of two or more multimeric barcode molecules, wherein each multimeric barcode molecule is as defined herein, and first and second extension primers, and first and second adapter oligonucleotides, for each of the multimeric barcode molecule. The extension primers and adapter oligonucleotides may take any of the forms described herein. The barcode regions of the first and second barcode molecules of the first multimeric barcode molecule are different to the barcode regions of the first and second barcode molecules of the second multimeric barcode molecule.

The kit may comprise a library comprising at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcode molecules as defined herein. Preferably, the kit comprises a library comprising at least 10 multimeric barcode molecules as defined herein. The kit may further comprise extension primers and/or adapter oligonucleotides for each of the multimeric barcode molecules. The extension primers and adapter oligonucleotides may take any of the forms described herein. Preferably, the barcode regions of the first and second barcode molecules of each multimeric barcode molecule are different to the barcode regions of the barcode molecules of at least 9 other multimeric barcode molecules in the library.

The barcode regions of the first and second barcode molecules of each multimeric barcode molecule may be different to the barcode regions of the barcoded molecules of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^3$-1 other multimeric barcode molecules in the library. The barcode regions of the first and second barcode molecules of each multimeric barcode molecule may be different to the barcode regions of the barcode molecules of all of the other multimeric barcode molecules in the library. Preferably, the barcode regions of the first and second barcode molecules of each multimeric barcode molecule are different to the barcode regions of the barcode molecules of at least 9 other multimeric barcode molecules in the library.

The barcode regions of the barcode molecules of each multimeric barcode molecule may be different to the barcode regions of the barcode molecules of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^3$-1 other multimeric barcode molecules in the library. The barcode regions of the barcode molecules of each multimeric barcode molecules may be different to the barcode regions of the barcode molecules of all of the other multimeric barcode molecules in the library. Preferably, the barcode regions of the barcode molecules of each multimeric barcode molecule are different to the barcode regions of the barcode molecules of at least 9 other multimeric barcode molecules in the library.

The invention further provides a kit for labelling a target nucleic acid for sequencing, wherein the kit comprises: (a) a library of multimeric barcode molecules comprising at least 10 multimeric barcode molecules, each multimeric barcode molecule comprising first and second barcode molecules comprised within a (single) nucleic acid molecule, wherein each of the barcode molecules comprises a nucleic acid sequence comprising, optionally in the 5' to 3' direction, an adapter region, a barcode region, and a priming region, and wherein the barcode regions of the first and second barcode molecules of each multimeric barcode molecule are different to the barcode regions of at least 9 other multimeric barcode molecules in the library; (b) first and second extension primers for each of the multimeric barcode molecules, wherein the first extension primer comprises a sequence capable of annealing to the priming region of the first barcode molecule, and wherein the second extension primer comprises a sequence capable of annealing to the priming region of the second barcode molecule; and (c) first and second adapter oligonucleotides for each of the multimeric barcode molecules, wherein the first adapter oligonucleotide comprises, optionally in the 5' to 3' direction, an adapter region capable of annealing to the adapter region of the first barcode molecule and a target region capable of annealing or ligating to a first sub-sequence of the target nucleic acid, and wherein the second adapter oligonucleotide comprises, optionally in the 5' to 3' direction, an adapter region capable of annealing to the adapter region of the second barcode molecule and a target region capable of annealing or ligating to a second sub-sequence of the target nucleic acid.

11. Methods of Preparing a Nucleic Acid Sample for Sequencing

The methods of preparing a nucleic acid sample for sequencing may comprise (i) contacting the nucleic acid sample with a multimeric barcoding reagent comprising first and second barcode regions linked together, wherein each barcode region comprises a nucleic acid sequence, and (ii) appending barcode sequences to first and second sub-sequences of a target nucleic acid to produce first and second different barcoded target nucleic acid molecules, wherein the first barcoded target nucleic acid molecule comprises the nucleic acid sequence of the first barcode region and the second barcoded target nucleic acid molecule comprises the nucleic acid sequence of the second barcode region.

In methods in which the multimeric barcoding reagent comprises first and second barcoded oligonucleotides linked together, the barcode sequences may be appended to first and second sub-sequences of the target nucleic acid by any of the methods described herein.

The first and second barcoded oligonucleotides may be ligated to the first and second sub-sequences of the target nucleic acid to produce the first and second different barcoded target nucleic acid molecules. Optionally, prior to the ligation step, the method comprises appending first and second coupling sequences to the target nucleic acid, wherein the first and second coupling sequences are the first and second sub-sequences of the target nucleic acid to which the first and second barcoded oligonucleotides are ligated.

The first and second barcoded oligonucleotides may be annealed to the first and second sub-sequences of the target nucleic acid extended to produce the first and second different barcoded target nucleic acid molecules. Optionally, prior to the annealing step, the method comprises appending first and second coupling sequences to the target nucleic acid, wherein the first and second coupling sequences are the first and second sub-sequences of the target nucleic acid to which the first and second barcoded oligonucleotides are annealed.

The first and second barcoded oligonucleotides may be annealed at their 5' ends to the first and second sub-sequences of the target nucleic acid and first and second target primers may be annealed to third and fourth sub-sequences of the target nucleic acid, respectively, wherein the third subsequence is 3' of the first subsequence and wherein the fourth sub-sequence is 3' of the second subsequence. The method further comprises extending the first target primer using the target nucleic acid as template until it reaches the first sub-sequence to produce a first extended target primer, and extending the second target primer using the target nucleic acid as template until it reaches the second sub-sequence to produce a second extended target primer, and ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different and each comprises at least one nucleotide synthesised from the target nucleic acid as a template. Optionally, prior to either or both annealing step(s), the method comprises appending first and second, and/or third and fourth, coupling sequences to the target nucleic acid, wherein the first and second coupling sequences are the first and second sub-sequences of the target nucleic acid to which the first and second barcoded oligonucleotides are annealed, and/or wherein the third and fourth coupling sequences are the third and fourth sub-sequences of the target nucleic acid to which the first and second target primers are annealed.

As described herein, prior to annealing or ligating a multimeric hybridization molecule, multimeric barcode molecule, barcoded oligonucleotide, adapter oligonucleotide or target primer to a target nucleic acid, a coupling sequence may be appended to the target nucleic acid. The multimeric hybridization molecule, multimeric barcode molecule, barcoded oligonucleotide, adapter oligonucleotide or target primer may then be annealed or ligated to the coupling sequence.

A coupling sequence may be added to the 5' end or 3' end of two or more target nucleic acids of the nucleic acid sample (e.g. a FFPE DNA sample). In this method, the target regions (of the barcoded oligonucleotides) may comprise a sequence that is complementary to the coupling sequence.

A coupling sequence may be comprised within a double-stranded coupling oligonucleotide or within a single-stranded coupling oligonucleotide. A coupling oligonucleotide may be appended to the target nucleic acid by a double-stranded ligation reaction or a single-stranded ligation reaction. A coupling oligonucleotide may comprise a single-stranded 5' or 3' region capable of ligating to a target nucleic acid and the coupling sequence may be appended to the target nucleic acid by a single-stranded ligation reaction.

A coupling oligonucleotide may comprise a blunt, recessed, or overhanging 5' or 3' region capable of ligating to a target nucleic acid and the coupling sequence may be appended to the target nucleic acid a double-stranded ligation reaction.

The end(s) of a target nucleic acid may be converted into blunt double-stranded end(s) in a blunting reaction, and the coupling oligonucleotide may comprise a blunt double-stranded end, and wherein the coupling oligonucleotide may be ligated to the target nucleic acid in a blunt-end ligation reaction.

The end(s) of a target nucleic acid may be converted into blunt double-stranded end(s) in a blunting reaction, and then converted into a form with (a) single 3' adenosine overhang(s), and wherein the coupling oligonucleotide may comprise a double-stranded end with a single 3' thymine overhang capable of annealing to the single 3' adenosine overhang of the target nucleic acid, and wherein the coupling oligonucleotide is ligated to the target nucleic acid in a double-stranded A/T ligation reaction The target nucleic acid may be contacted with a restriction enzyme, wherein the restriction enzyme digests the target nucleic acid at restriction sites to create (a) ligation junction(s) at the restriction site(s), and wherein the coupling oligonucleotide comprises an end compatible with the ligation junction, and wherein the coupling oligonucleotide is then ligated to the target nucleic acid in a double-stranded ligation reaction.

A coupling oligonucleotide may be appended via a primer-extension or polymerase chain reaction step.

A coupling oligonucleotide may be appended via a primer-extension or polymerase chain reaction step, using one or more oligonucleotide(s) that comprise a priming segment including one or more degenerate bases.

A coupling oligonucleotide may be appended via a primer-extension or polymerase chain reaction step, using one or more oligonucleotide(s) that further comprise a priming or hybridisation segment specific for a particular target nucleic acid sequence.

A coupling sequence may be added by a polynucleotide tailing reaction. A coupling sequence may be added by a terminal transferase enzyme (e.g. a terminal deoxynucleotidyl transferase enzyme). A coupling sequence may be appended via a polynucleotide tailing reaction performed with a terminal deoxynucleotidyl transferase enzyme, and wherein the coupling sequence comprises at least two contiguous nucleotides of a homopolymeric sequence.

A coupling sequence may comprise a homopolymeric 3' tail (e.g. a poly(A) tail). Optionally, in such methods, the target regions (of the barcoded oligonucleotides) comprise a complementary homopolymeric 3' tail (e.g. a poly(T) tail).

A coupling sequence may be comprised within a synthetic transposome, and may be appended via an in vitro transposition reaction.

A coupling sequence may be appended to a target nucleic acid, and wherein a barcode oligonucleotide is appended to the target nucleic acid by at least one primer-extension step or polymerase chain reaction step, and wherein said barcode oligonucleotide comprises a region of at least one nucleotide in length that is complementary to said coupling sequence. Optionally, this region of complementarity is at the 3' end of the barcode oligonucleotide. Optionally, this region of complementarity is at least 2 nucleotides in length, at least 5 nucleotides in length, at least 10 nucleotides in length, at least 20 nucleotides in length, or at least 50 nucleotides in length.

In methods in which an adapter oligonucleotide is appended (e.g. ligated or annealed) to a target nucleic acid, the adapter region of the adapter oligonucleotide provides a coupling sequence capable of hybridizing to the adapter region of a multimeric hybridization molecule or a multimeric barcode molecule.

The invention provides a method of preparing a nucleic acid sample for sequencing comprising the steps of: (a) appending a coupling sequence to first and second sub-sequences of a target nucleic acid; (b) contacting the nucleic acid sample with a multimeric barcoding reagent comprising first and second barcode molecules linked together, wherein each of the barcode molecules comprises a nucleic acid sequence comprising (in the 5' to 3' or 3' to 5' direction), a barcode region and an adapter region; (c) annealing the coupling sequence of the first sub-sequence to the adapter region of the first barcode molecule, and annealing the coupling sequence of the second sub-sequence to the adapter region of the second barcode molecule; and (d) appending barcode sequences to each of the at least two sub-sequences of the target nucleic acid to produce first and second different barcoded target nucleic acid molecules, wherein the first barcoded target nucleic acid molecule comprises the nucleic acid sequence of the barcode region of the first barcode molecule and the second barcoded target nucleic acid molecule comprises the nucleic acid sequence of the barcode region of the second barcode molecule.

In the method, each of the barcode molecules may comprise a nucleic acid sequence comprising, in the 5' to 3' direction, a barcode region and an adapter region, and step (d) may comprise extending the coupling sequence of the first sub-sequence of the target nucleic acid using the barcode region of the first barcode molecule as a template to produce a first barcoded target nucleic acid molecule, and extending the coupling sequence of the second sub-sequence of the target nucleic acid using the barcode region of the second barcode molecule as a template to produce a second barcoded target nucleic acid molecule, wherein the first barcoded target nucleic acid molecule comprises a sequence complementary to the barcode region of the first barcode molecule and the second barcoded target nucleic acid molecule comprises a sequence complementary to the barcode region of the second barcode molecule.

In the method, each of the barcode molecules may comprise a nucleic acid sequence comprising, in the 5' to 3' direction, an adapter region and a barcode region, and step (d) may comprise (i) annealing and extending a first extension primer using the barcode region of the first barcode molecule as a template to produce a first barcoded oligonucleotide, and annealing and extending a second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule, (ii) ligating the 3' end of the first barcoded oligonucleotide to the 5' end of the coupling sequence of the first sub-sequence of the target nucleic acid to produce a first barcoded target nucleic acid molecule and ligating the 3' end of the second barcoded oligonucleotide to the 5' end of the coupling sequence of the second sub-sequence of the target nucleic acid to produce a second barcoded target nucleic acid molecule.

In the method, each of the barcode molecules may comprise a nucleic acid sequence comprising, in the 5' to 3' direction, an adapter region, a barcode region and a priming region wherein step (d) comprises (i) annealing a first extension primer to the priming region of the first barcode molecule and extending the first extension primer using the barcode region of the first barcode molecule as a template to produce a first barcoded oligonucleotide, and annealing a second extension primer to the priming region of the second barcode molecule and extending the second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule, (ii) ligating the 3' end of the first barcoded oligonucleotide to the 5' end of the coupling sequence of the first sub-sequence of the target nucleic acid to produce a first barcoded target nucleic acid molecule and ligating the 3' end of the second barcoded oligonucleotide to the 5' end of the coupling sequence of the second sub-sequence of the target nucleic acid to produce a second barcoded target nucleic acid molecule.

The methods for preparing a nucleic acid sample for sequencing may be used to prepare a range of different nucleic acid samples for sequencing. The target nucleic acids may be DNA molecules (e.g. genomic DNA molecules) or RNA molecules (e.g. mRNA molecules). The target nucleic acids may be from any sample. For example, an individual cell (or cells), a tissue, a bodily fluid (e.g. blood, plasma and/or serum), a biopsy or a formalin-fixed paraffin-embedded (FFPE) sample.

The sample may comprise at least 10, at least 100, or at least $10^3$, at least $10^4$, at least $10^5$, at least $10^6$, at least $10^7$, at least $10^8$ or at least $10^9$ target nucleic acids The target nucleic acid may be a (single) intact nucleic acid molecule of a cell or two or more co-localised fragments of a nucleic acid molecule of a cell. As used herein the term target nucleic acid refers to the nucleic acids present within cells and to copies or amplicons thereof. For example, where the target nucleic acid is genomic DNA, the term target nucleic acid means genomic DNA present in a cell and copies or amplicons thereof e.g. DNA molecules that may be prepared from the genomic DNA by a primer-extension reaction. As a further example, where the target nucleic acid is mRNA, the term target nucleic acid means mRNA present in the cell and copies or amplicons thereof e.g. cDNA synthesized from the mRNA by reverse transcription.

The method may comprise producing at least 2, at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ different barcoded target nucleic acid molecules. Preferably, the method comprises producing at least 5 different barcoded target nucleic acid molecules.

Each barcoded target nucleic acid molecule may comprise at least 1, at least 5, at least 10, at least 25, at least 50, at least 100, at least 250, at least 500, at least 1000, at least 2000, at least 5000, or at least 10,000 nucleotides synthesised from the target nucleic acid as template. Preferably, each barcoded target nucleic acid molecule comprises at least 20 nucleotides synthesised from the target nucleic acid as template.

Alternatively, each barcoded target nucleic acid molecule may comprise at least 5, at least 10, at least 25, at least 50, at least 100, at least 250, at least 500, at least 1000, at least 2000, at least 5000, or at least 10,000 nucleotides of the target nucleic acid. Preferably, each barcoded target nucleic acid molecule comprises at least 5 nucleotides of the target nucleic acid.

A universal priming sequence may be added to the barcoded target nucleic acid molecules. This sequence may enable the subsequent amplification of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different barcoded target nucleic acid molecules using one forward primer and one reverse primer.

The method may comprise preparing two or more independent nucleic acid samples for sequencing, wherein each nucleic acid sample is prepared using a different library of multimeric barcoding reagents (or a different library of multimeric barcode molecules), and wherein the barcode regions of each library of multimeric barcoding reagents (or multimeric barcode molecules) comprise a sequence that is different to the barcode regions of the other libraries of multimeric barcoding reagents (or multimeric barcode molecules). Following the separate preparation of each of the samples for sequencing, the barcoded target nucleic acid molecules prepared from the different samples may be pooled and sequenced together. The sequence read generated for each barcoded target nucleic acid molecule may be used to identify the library of multimeric barcoding reagents (or multimeric barcode molecules) that was used in its preparation and thereby to identify the nucleic acid sample from which it was prepared.

In any method of preparing a nucleic acid sample for sequencing, the target nucleic acid molecules may be present at particular concentrations within the nucleic acid sample, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, 10 picomolar to 10 nanomolar, or 100 picomolar to 1 nanomolar. Preferably, the concentrations are 10 picomolar to 1 nanomolar.

In any method of preparing a nucleic acid sample for sequencing, the multimeric barcoding reagents may be present at particular concentrations within the nucleic acid sample, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, picomolar to 10 nanomolar, or 100 picomolar to 1 nanomolar. Preferably, the concentrations are 1 picomolar to 100 picomolar.

In any method of preparing a nucleic acid sample for sequencing, the multimeric barcode molecules may be present at particular concentrations within the nucleic acid sample, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, picomolar to 10 nanomolar, or 100 picomolar to 1 nanomolar. Preferably, the concentrations are 1 picomolar to 100 picomolar.

In any method of preparing a nucleic acid sample for sequencing, the barcoded oligonucleotides may be present at particular concentrations within the nucleic acid sample, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, picomolar to 10 nanomolar, or 100 picomolar to 1 nanomolar. Preferably, the concentrations are 100 picomolar to 100 nanomolar.

12. Methods of Preparing a Nucleic Acid Sample for Sequencing Using Multimeric Barcoding Reagents The invention provides a method of preparing a nucleic acid sample for sequencing, wherein the method comprises the steps of: contacting the nucleic acid sample with a multimeric barcoding reagent as defined herein; annealing the target region of the first barcoded oligonucleotide to a first sub-sequence of a target nucleic acid, and annealing the target region of the second barcoded oligonucleotide to a second sub-sequence of the target nucleic acid; and extending the first and second barcoded oligonucleotides to produce first and second different barcoded target nucleic acid molecules, wherein each of the barcoded target nucleic acid molecules comprises at least one nucleotide synthesised from the target nucleic acid as a template.

In any method of preparing a nucleic acid sample for sequencing, either the nucleic acid molecules within the nucleic acid sample, and/or the multimeric barcoding reagents, may be present at particular concentrations within the solution volume, for example at concentrations of at least 100 nanomolar, at least 10 nanomolar, at least 1 nanomolar, at least 100 picomolar, at least picomolar, or at least 1 picomolar. The concentrations may be 1 picomolar to 100 nanomolar, picomolar to 10 nanomolar, or 100 picomolar to 1 nanomolar. Alternative higher or lower concentrations may also be used.

The method of preparing a nucleic acid sample for sequencing may comprise contacting the nucleic acid sample with a library of multimeric barcoding reagents as defined herein, and wherein: the barcoded oligonucleotides of the first multimeric barcoding reagent anneal to sub-sequences of a first target nucleic acid and first and second different barcoded target nucleic acid molecules are produced, wherein each barcoded target nucleic acid molecule comprises at least one nucleotide synthesised from the first target nucleic acid as a template; and the barcoded oligonucleotides of the second multimeric barcoding reagent anneal to sub-sequences of a second target nucleic acid and first and second different barcoded target nucleic acid molecules are produced, wherein each barcoded target nucleic acid molecule comprises at least one nucleotide synthesised from the second target nucleic acid as a template.

In the method the barcoded oligonucleotides may be isolated from the nucleic acid sample after annealing to the sub-sequences of the target nucleic acid and before the barcoded target nucleic acid molecules are produced. Optionally, the barcoded oligonucleotides are isolated by capture on a solid support through a streptavidin-biotin interaction.

Additionally or alternatively, the barcoded target nucleic acid molecules may be isolated from the nucleic acid sample. Optionally, the barcoded target nucleic acid molecules are isolated by capture on a solid support through a streptavidin-biotin interaction.

The step of extending the barcoded oligonucleotides may be performed while the barcoded oligonucleotides are annealed to the barcode molecules.

FIG. 3 shows a method of preparing a nucleic acid sample for sequencing, in which a multimeric barcoding reagent defined herein (for example, as illustrated in FIG. 1) is used to label and extend two or more nucleic acid sub-sequences in a nucleic acid sample. In this method, a multimeric barcoding reagent is synthesised which incorporates at least a first (A1, B1, C1, and G1) and a second (A2, B2, C2, and G2) barcoded oligonucleotide, which each comprise both a barcode region (B1 and B2) and a target region (G1 and G2 respectively).

A nucleic acid sample comprising a target nucleic acid is contacted or mixed with the multimeric barcoding reagent, and the target regions (G1 and G2) of two or more barcoded oligonucleotides are allowed to anneal to two or more corresponding sub-sequences within the target nucleic acid (H1 and H2). Following the annealing step, the first and second barcoded oligonucleotides are extended (e.g. with the target regions serving as primers for a polymerase) into the sequence of the target nucleic acid, such that at least one nucleotide of a sub-sequence is incorporated into the extended 3' end of each of the barcoded oligonucleotides. This method creates barcoded target nucleic acid molecules, wherein two or more sub-sequences from the target nucleic acid are labeled by a barcoded oligonucleotide.

Alternatively, the method may further comprise the step of dissociating the barcoded oligonucleotides from the barcode molecules before annealing the target regions of the barcoded oligonucleotides to sub-sequences of the target nucleic acid.

FIG. 4 shows a method of preparing a nucleic acid sample for sequencing, in which a multimeric barcoding reagent described herein (for example, as illustrated in FIG. 1) is used to label and extend two or more nucleic acid sub-sequences in a nucleic acid sample, but wherein the barcoded oligonucleotides from the multimeric barcoding reagent are dissociated from the barcode molecules prior to annealing to (and extension of) target nucleic acid sequences. In this method, a multimeric barcoding reagent is synthesised which incorporates at least a first (A1, B1, C1, and G1) and a second (A2, B2, C2, and G2) barcoded oligonucleotide, which each comprise a barcode region (B1 and B2) and a target region (G1 and G2).

A nucleic acid sample comprising a target nucleic acid is contacted with the multimeric barcoding reagent, and then the barcoded oligonucleotides are dissociated from the barcode molecules. This step may be achieved, for example, through exposing the reagent to an elevated temperature (e.g. a temperature of at least 35° C., at least 40° C., at least 45° C., at least 50° C., at least 55° C., at least 60° C., at least 65° C., at least 70° C., at least 75° C., at least 80° C., at least 85° C., or at least 90° C.) or through a chemical denaturant, or a combination thereof. This step may also denature double-stranded nucleic acids within the sample itself. The barcoded oligonucleotides may then be allowed to for diffuse for a certain amount of time (e.g. at least 5 seconds, at least 15 seconds, at least 30 seconds, at least 60 seconds, at least 2 minutes, at least 5 minutes, at least 15 minutes, at least 30 minutes, or at least 60 minutes) (and correspondingly, to diffuse a certain physical distance within the sample).

The conditions of the reagent-sample mixture may then be changed to allow the target regions (G1 and G2) of two or more barcoded oligonucleotides to anneal to two or more corresponding sub-sequences within the target nucleic acid (H1 and H2). This could comprise, for example, lowering the temperature of the solution to allow annealing (for example, lowering the temperature to less than 90° C., less than 85° C., less than 70° C., less than 65° C., less than 60° C., less than 55° C., less than 50° C., less than 45° C., less than 40° C., less than 35° C., less than 30° C., less than 25° C., or less than 20° C.). Following this annealing step (or for example, following a purification/preparation step), the first and second barcoded oligonucleotides are extended (e.g. with the target regions serving as primers for a polymerase) into the sequence of the target nucleic acid, such that at least one nucleotide of a sub-sequence is incorporated into the extended 3' end of each of the barcoded oligonucleotides.

This method creates barcoded target nucleic acid molecules wherein two or more sub-sequences from the nucleic acid sample are labeled by a barcoded oligonucleotide. In addition, the step of dissociating the barcoded oligonucleotides and allowing them to diffuse through the sample holds advantages for particular types of samples. For example, cross-linked nucleic acid samples (e.g. formalin-fixed, paraffin-embedded (FFPE) samples) may be amenable to the diffusion of relatively small, individual barcoded oligonucleotides. This method may allow labeling of nucleic acid samples with poor accessibility (e.g. FFPE samples) or other biophysical properties e.g. where target nucleic acid sub-sequences are physically far away from each other.

A universal priming sequence may be added to the barcoded target nucleic acid molecules. This sequence may enable the subsequent amplification of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different barcoded target nucleic acid molecules using one forward primer and one reverse primer.

Prior to contacting the nucleic acid sample with a multimeric barcoding reagent, or library of multimeric barcoding reagents, as defined herein, a coupling sequence may be added to the 5' end or 3' end of two or more target nucleic acids of the nucleic acid sample (e.g. a FFPE DNA sample). In this method, the target regions may comprise a sequence that is complementary to the coupling sequence. The coupling sequence may comprise a homopolymeric 3' tail (e.g. a poly(A) tail). The coupling sequence may be added by a terminal transferase enzyme. In the method in which the coupling sequence comprises a poly(A) tail, the target regions may comprise a poly(T) sequence. Such coupling sequences may be added following a high-temperature incubation of the nucleic acid sample, to denature the nucleic acids contained therein prior to adding a coupling sequence.

Alternatively, a coupling sequence could be added by digestion of a target nucleic acid sample (e.g. an FFPE DNA sample) with a restriction enzyme, in which case a coupling sequence may be comprised of one or more nucleotides of a restriction enzyme recognition sequence. In this case, a coupling sequence may be at least partially double-stranded, and may comprise a blunt-ended double-stranded DNA sequence, or a sequence with a 5' overhang region of 1 or more nucleotides, or a sequence with a 3' overhang region of 1 or more nucleotides. In these cases, target regions in multimeric barcoding reagents may then comprise sequences that are either double-stranded and blunt-ended (and thus able to ligate to blunt-ended restriction digestion products), or the target regions may contain 5' or 3' overhang sequences of 1 or more nucleotides, which make them cohesive (and thus able to anneal with and ligate to) against said restriction digestion products.

The method may comprise preparing two or more independent nucleic acid samples for sequencing, wherein each nucleic acid sample is prepared using a different library of multimeric barcoding reagents (or a different library of multimeric barcode molecules), and wherein the barcode regions of each library of multimeric barcoding reagents (or multimeric barcode molecules) comprise a sequence that is different to the barcode regions of the other libraries of multimeric barcoding reagents (or multimeric barcode molecules). Following the separate preparation of each of the samples for sequencing, the barcoded target nucleic acid molecules prepared from the different samples may be pooled and sequenced together. The sequence read generated for each barcoded target nucleic acid molecule may be used to identify the library of multimeric barcoding reagents (or multimeric barcode molecules) that was used in its preparation and thereby to identify the nucleic acid sample from which it was prepared.

The invention provides a method of preparing a nucleic acid sample for sequencing, wherein the method comprises the steps of: (a) contacting the nucleic acid sample with a multimeric barcoding reagent, wherein each barcoded oligonucleotide comprises in the 5' to 3' direction a target region and a barcode region, and first and second target primers; (b) annealing the target region of the first barcoded oligonucleotide to a first sub-sequence of a target nucleic acid and annealing the target region of the second barcoded oligonucleotide to a second sub-sequence of the target nucleic acid; (c) annealing the first target primer to a third sub-sequence of the target nucleic acid, wherein the third sub-sequence is 3' of the first sub-sequence, and annealing the second target primer to a fourth sub-sequence of the target nucleic acid, wherein the fourth sub-sequence is 3' of the second sub-sequence; (d) extending the first target primer using the target nucleic acid as template until it reaches the first sub-sequence to produce a first extended target primer, and extending the second target primer using the target nucleic acid as template until it reaches the second sub-sequence to produce a second extended target primer; and (e) ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different, and wherein each of the barcoded target nucleic acid molecules comprises at least one nucleotide synthesised from the target nucleic acid as a template.

In the method, steps (b) and (c) may be performed at the same time.

13. Methods of Preparing a Nucleic Acid Sample for Sequencing Using Multimeric Barcoding Reagents and Adapter Oligonucleotides The methods provided below may be performed with any of the kits defined herein.

The invention further provides a method of preparing a nucleic acid sample for sequencing, wherein the method comprises the steps of: (a) contacting the nucleic acid sample with a first and second adapter oligonucleotide as defined herein; (b) annealing or ligating the first adapter oligonucleotide to a first sub-sequence of a target nucleic acid, and annealing or ligating the second adapter oligonucleotide to a second sub-sequence of the target nucleic acid; (c) contacting the nucleic acid sample with a multimeric barcoding reagent as defined herein; (d) annealing the adapter region of the first adapter oligonucleotide to the adapter region of the first barcode molecule, and annealing the adapter region of the second adapter oligonucleotide to the adapter region of the second barcode molecule; and (e) ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide.

The invention further provides a method of preparing a nucleic acid sample for sequencing, wherein the method comprises the steps of: (a) contacting the nucleic acid sample with a first and second adapter oligonucleotide as defined herein; (b) the first adapter oligonucleotide to a first sub-sequence of a target nucleic acid, and ligating the second adapter oligonucleotide to a second sub-sequence of the target nucleic acid; (c) contacting the nucleic acid sample with a multimeric barcoding reagent as defined herein; (d) annealing the adapter region of the first adapter oligonucleotide to the adapter region of the first barcode molecule, and annealing the adapter region of the second adapter oligonucleotide to the adapter region of the second barcode molecule; and (e) extending the first adapter oligonucleotide using the barcode region of the first barcode molecule as a template to produce a first barcoded target nucleic acid molecule, and extending the second adapter oligonucleotide using the barcode region of the second barcode molecule as a template to produce a second barcoded target nucleic acid molecule, wherein the first barcoded target nucleic acid molecule comprises a sequence complementary to the barcode region of the first barcode molecule and the second barcoded target nucleic acid molecule comprises a sequence complementary to the barcode region of the second barcode molecule.

The invention further provides a method of preparing a nucleic acid sample for sequencing, wherein the method comprises the steps of: (a) contacting the nucleic acid sample with a first and second adapter oligonucleotide as defined herein; (b) annealing the target region of the first adapter oligonucleotide to a first sub-sequence of a target nucleic acid, and annealing the target region of the second adapter oligonucleotide to a second sub-sequence of the target nucleic acid; (c) contacting the nucleic acid sample with a multimeric barcoding reagent as defined herein; (d) annealing the adapter region of the first adapter oligonucleotide to the adapter region of the first barcode molecule, and annealing the adapter region of the second adapter oligonucleotide to the adapter region of the second barcode molecule; and (e) ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide.

In the method the first and second barcoded-adapter oligonucleotides may be extended to produce first and second different barcoded target nucleic acid molecules each of which comprises at least one nucleotide synthesised from the target nucleic acid as a template.

Alternatively, the first and second adapter oligonucleotides may be extended to produce first and second different target nucleic acid molecules each of which comprises at least one nucleotide synthesised from the target nucleic acid as a template. In this method, step (f) produces a first barcoded target nucleic acid molecule (i.e. the first barcoded oligonucleotide ligated to the extended first adapter oligonucleotide) and a second barcoded target nucleic acid molecule (i.e. the second barcoded oligonucleotide ligated to the extended second adapter oligonucleotide).

The step of extending the adapter oligonucleotides may be performed before step (c), before step (d) and/or before step (e), and the first and second adapter oligonucleotides may remain annealed to the first and second barcode molecules until after step (e).

The method may be performed using a library of multimeric barcoding reagents as defined herein and an adapter oligonucleotide as defined herein for each of the multimeric barcoding reagents. Preferably, the barcoded-adapter oligonucleotides of the first multimeric barcoding reagent anneal to sub-sequences of a first target nucleic acid and first and second different barcoded target nucleic acid molecules are produced, wherein each barcoded target nucleic acid molecule comprises at least one nucleotide synthesised from the first target nucleic acid as a template; and the barcoded-adapter oligonucleotides of the second multimeric barcoding reagent anneal to sub-sequences of a second target nucleic acid and first and second different barcoded target nucleic acid molecules are produced, wherein each barcoded target nucleic acid molecule comprises at least one nucleotide synthesised from the second target nucleic acid as a template.

The method may be performed using a library of multimeric barcoding reagents as defined herein and an adapter oligonucleotide as defined herein for each of the multimeric barcoding reagents. Preferably, the adapter oligonucleotides of the first multimeric barcoding reagent anneal to sub-sequences of a first target nucleic acid and first and second different target nucleic acid molecules are produced, wherein each target nucleic acid molecule comprises at least one nucleotide synthesised from the first target nucleic acid as a template; and the adapter oligonucleotides of the second multimeric barcoding reagent anneal to sub-sequences of a second target nucleic acid and first and second different target nucleic acid molecules are produced, wherein each target nucleic acid molecule comprises at least one nucleotide synthesised from the second target nucleic acid as a template.

The barcoded-adapter oligonucleotides may be isolated from the nucleic acid sample after annealing to the sub-sequences of the target nucleic acid and before the barcoded target nucleic acid molecules are produced. Optionally, the barcoded-adapter oligonucleotides are isolated by capture on a solid support through a streptavidin-biotin interaction.

The barcoded target nucleic acid molecules may be isolated from the nucleic acid sample. Optionally, the barcoded target nucleic acid molecules are isolated by capture on a solid support through a streptavidin-biotin interaction.

FIG. 5 shows a method of preparing a nucleic acid sample for sequencing using a multimeric barcoding reagent. In the method first (C1 and G1) and second (C2 and G2) adapter oligonucleotides are annealed to a target nucleic acid in the nucleic acid sample, and then used in a primer extension reaction. Each adapter oligonucleotide is comprised of an adapter region (C1 and C2) that is complementary to, and thus able to anneal to, the 5' adapter region of a barcode molecule (F1 and F2). Each adapter oligonucleotide is also comprised of a target region (G1 and G2), which may be used to anneal the barcoded oligonucleotides to target nucleic acids, and then may be used as primers for a primer-extension reaction or a polymerase chain reaction. These adapter oligonucleotides may be synthesised to include a 5'-terminal phosphate group.

The adapter oligonucleotides, each of which has been extended to include sequence from the target nucleic acid, are then contacted with a multimeric barcoding reagent which comprises a first (D1, E1, and F1) and second (D2, E2, and F2) barcode molecule, as well as first (A1 and B1) and second (A2 and B2) barcoded oligonucleotides, which each comprise a barcode region (B1 and B2), as well as 5' regions (A1 and A2). The first and second barcode molecules each comprise a barcode region (E1 and E2), an adapter region (F1 and F2), and a 3' region (D1 and D2), and are linked together, in this embodiment by a connecting nucleic acid sequence (S).

After contacting the primer-extended nucleic acid sample with a multimeric barcoding reagent, the 5' adapter regions (C1 and C2) of each adapter oligonucleotides are able to anneal to a 'ligation junction' adjacent to the 3' end of each barcoded oligonucleotide (J1 and J2). The 5' end of the extended adapter oligonucleotides are then ligated to the 3' end of the barcoded oligonucleotides within the multimeric barcoding reagent, creating a ligated base pair (K1 and K2) where the ligation junction was formerly located. The solution may subsequently be processed further or amplified, and used in a sequencing reaction.

This method, like the methods illustrated in FIGS. 3 and 4, creates barcoded target nucleic acid molecules, wherein two or more sub-sequences from the nucleic acid sample are labeled by a barcoded oligonucleotide. In this method a multimeric barcoding reagent does not need to be present for the step of annealing target regions to sub-sequences of the target nucleic acid, or the step of extending the annealed target regions using a polymerase. This feature may hold advantages in certain applications, for example wherein a large number of target sequences are of interest, and the target regions are able to hybridise more rapidly to target nucleic acids when they are not constrained molecularly by a multimeric barcoding reagent.

14. Methods of Preparing a Nucleic Acid Sample for Sequencing Using Multimeric Barcoding Reagents, Adapter Oligonucleotides and Extension Primers The invention further provides a method of preparing a nucleic acid sample for sequencing, wherein the method comprises the steps of: (a) contacting the nucleic acid sample with first and second adapter oligonucleotides as defined herein; (b) annealing the target region of the first adapter oligonucleotide to a first sub-sequence of a target nucleic acid, and annealing the target region of the second adapter oligonucleotide to a second sub-sequence of the target oligonucleotide; (c) contacting the nucleic acid sample with a library of multimeric barcode molecules as defined herein and first and second extension primers as defined herein; (d) annealing the adapter region of the first adapter oligonucleotide to the adapter region of the first barcode molecule, and annealing the adapter region of the second adapter oligonucleotide to the adapter region of the second barcode molecule; (e) extending the first extension primer using the barcode region of the first barcode molecule as a template to produce a first barcoded oligonucleotide, and extending the second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule; and (f) ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide.

In the method the first and second barcoded-adapter oligonucleotides may be extended to produce first and second different barcoded target nucleic acid molecules each of which comprises at least one nucleotide synthesised from the target nucleic acid as a template.

Alternatively, the first and second adapter oligonucleotides may be extended to produce first and second different target nucleic acid molecules each of which comprises at least one nucleotide synthesised from the target nucleic acid as a template. In this method, step (f) produces a first barcoded target nucleic acid molecule (i.e. the first barcoded oligonucleotide ligated to the extended first adapter oligonucleotide) and a second barcoded target nucleic acid molecule (i.e. the second barcoded oligonucleotide ligated to the extended second adapter oligonucleotide).

The step of extending the adapter oligonucleotides may be performed before step (c), before step (d), before step (e) and/or before step (f), and the first and second adapter oligonucleotides may remain annealed to the first and second barcode molecules until after step (f).

The extension primers may be annealed to the multimeric barcode molecules prior to step (c). Alternatively, the nucleic acid sample may be contacted with a library of multimeric barcode molecules as defined herein and separate extension primers as defined herein. The extension primers may then be annealed to the multimeric barcode molecules in the nucleic acid sample. The extension primers may be annealed to the multimeric barcode molecules during step (d).

The methods may use a library of first and second extension primers e.g. the library may comprise first and second extension primers for each multimeric barcode molecule. Optionally, each extension primer in the library of extension primers may comprise a secondary barcode region, wherein said secondary barcode region is different to the secondary barcode regions within the other extension primers within the library. Optionally, such a library may comprise at least 2, at least 3, at least 4, at least 5, at least 10, at least 20, at least 50, at least 100, at least 500, at least 1000, at least 5,000, or at least 10,000 different extension primers.

15. Methods of Preparing a Nucleic Acid Sample for Sequencing Using Multimeric Barcoding Reagents, Adapter Oligonucleotides and Target Primers The invention further provides a method of preparing a nucleic acid sample for sequencing, wherein the method comprises the steps of: (a) contacting the nucleic acid sample with first and second adapter oligonucleotides, wherein each adapter oligonucleotide comprises in the 5' to 3' direction a target region and an adapter region, and first and second target primers; (b) annealing the target region of the first adapter oligonucleotide to a first sub-sequence of a target nucleic acid, and annealing the target region of the second adapter oligonucleotide to a second sub-sequence of the target nucleic acid; (c) annealing the first target primer to a third sub-sequence of the target nucleic acid, wherein the third sub-sequence is 3' of the first sub-sequence, and annealing the second target primer to a fourth sub-sequence of the target nucleic acid, wherein the fourth sub-sequence is 3' of the second sub-sequence; (d) extending the first target primer using the target nucleic acid as template until it reaches the first sub-sequence to produce a first extended target primer, and extending the second target primer using the target nucleic acid as template until it reaches the second sub-sequence to produce a second extended target primer; (e) ligating the 3' end of the first extended target primer to the 5' end of the first adapter oligonucleotide, and ligating the 3' end of the second extended target primer to the 5' end of the second adapter oligonucleotide; (f) contacting the nucleic acid sample with a library of multimeric barcode molecules as defined herein; (g) annealing the adapter region of the first adapter oligonucleotide to the adapter region of the first barcode molecule, and annealing the adapter region of the second adapter oligonucleotide to the adapter region of the second barcode molecule; and (h) extending the first adapter oligonucleotide using the barcode region of the first barcode molecule as a template to produce a first barcoded oligonucleotide, and extending the second adapter oligonucleotide using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule.

In the method, steps (b) and (c) may be performed at the same time.

In the method, steps (f)-(h) may be performed before steps (d) and (e). In this method, first and second different barcoded target nucleic acid molecules, each of which comprises at least one nucleotide synthesised from the target nucleic acid as a template, are produced by the completion of step (e).

In the method, steps (f)-(h) may be performed after steps (d) and (e). In this method, first and second different barcoded target nucleic acid molecules, each of which comprises at least one nucleotide synthesised from the target nucleic acid as a template, are produced by the completion of step (h).

FIG. 6 illustrates one way in which this method may be performed. In this method, the target nucleic acid is genomic DNA. It will be appreciated that the target nucleic acid may be another type of nucleic acid e.g. an RNA molecule such as an mRNA molecule.

16. Methods of Preparing a Nucleic Acid Sample for Sequencing Using Multimeric Barcoding Reagents and Target Primers The invention further provides a method of preparing a nucleic acid sample for sequencing, wherein the method comprises the steps of: (a) contacting the nucleic acid sample with first and second barcoded oligonucleotides linked together, wherein each barcoded oligonucleotide comprises in the 5' to 3' direction a target region and a barcode region, and first and second target primers; (b) annealing the target region of the first barcoded oligonucleotide to a first sub-sequence of a target nucleic acid, and annealing the target region of the second barcoded oligonucleotide to a second sub-sequence of the target nucleic acid; (c) annealing the first target primer to a third sub-sequence of the target nucleic acid, wherein the third sub-sequence is 3' of the first sub-sequence, and annealing the second target primer to a fourth sub-sequence of the target nucleic acid, wherein the fourth sub-sequence is 3' of the second sub-sequence; (d) extending the first target primer using the target nucleic acid as template until it reaches the first sub-sequence to produce a first extended target primer, and extending the second target primer using the target nucleic acid as template until it reaches the second sub-sequence to produce a second extended target primer; (e) ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different and each comprises at least one nucleotide synthesised from the target nucleic acid as a template.

17. Methods of Assembling Multimeric Barcode Molecules by Rolling Circle Amplification The invention further provides a method of assembling a library of multimeric barcode molecules from a library of nucleic acid barcode molecules, wherein said nucleic acid barcode molecules are amplified by one or more rolling circle amplification (RCA) processes. In this method, nucleic acid barcode molecules may each comprise, optionally in the 5' to 3' direction, a barcode region and an adapter region. Optionally, the nucleic acid barcode molecules may comprise a phosphorylated 5' end capable of ligating to a 3' end of a nucleic acid molecule.

In this method, nucleic acid barcode molecules within the library are converted into a circular form, such that the barcode region and the adapter region from a barcode molecule are comprised within a contiguous circular nucleic acid molecule. Optionally, such a step of converting nucleic acid barcode molecules into circular form may be performed by an intramolecular single-stranded ligation reaction. For example, nucleic acid barcode molecules comprising a phosphorylated 5' end may be circularised by incubation with a single-stranded nucleic acid ligase, such as T4 RNA Ligase 1, or by incubation with a thermostable single-stranded nucleic acid ligase, such as the CircLigase thermostable single-stranded nucleic acid ligase (from Epicentre Bio). Optionally, an exonuclease step may be performed to deplete or degrade uncircularised and/or unligated molecules; optionally wherein the exonuclease step is performed by *E. coli* exonuclease I, or by *E. coli* lambda exonuclease.

Optionally, a step of converting nucleic acid barcode molecules into circular form may be performed using a circularisation primer. In this embodiment, nucleic acid barcode molecules comprise a phosphorylated 5' end. Furthermore, in this embodiment, a circularisation primer comprising a 5' region complementary to the 3' region of a barcode molecule, and a 3' region complementary to the 5' region of a barcode molecule, is annealed to a barcode molecule, such that the 5' end and the 3' end of the barcode molecule are immediately adjacent to each other whilst annealed along the circularisation primer. Following the annealing step, the annealed barcode molecules are ligated with a ligase enzyme, such as T4 DNA ligase, which ligates the 3' end of the barcode molecule to the 5' end of the barcode molecule. Optionally, an exonuclease step may be performed to deplete or degrade uncircularised and/or unligated molecules; optionally wherein the exonuclease step is performed by *E. coli* exonuclease I, or by *E. coli* lambda exonuclease.

Following a circularisation step, circularised barcode molecules may be amplified with a rolling circle amplification step. In this process, a primer is annealed to a circularised nucleic acid strand comprising a barcode molecule, and the 3' end of said primer is extended with a polymerase exhibiting strand displacement behaviour. For each original circularised barcode molecule, this process may form a linear (non-circular) multimeric barcode molecule comprising copies of the original circularised barcode molecule, as illustrated in FIG. 7. In one embodiment, a circularisation primer that has been annealed to a barcode molecule may serve as the primer for a rolling circle amplification step. Optionally, following circularisation, a separate amplification primer which is at least partially complementary to the circularised barcode molecule, may be annealed to the circularised barcode molecule to prime a rolling circle amplification step.

During said rolling circle amplification step, the primer may be extended by the polymerase, wherein the polymerase extends along the circularised template until it encounters the 5' end of the amplification primer and/or circularisation primer, whereupon it continues amplification along the circularised template whilst displacing the 5' end of the primer, and then displacing the previously amplified strand, in a process of rolling circle amplification. Following any such amplification step, a purification and/or cleanup step may be performed to isolate products of such rolling circle amplification. Optionally, a purification and/or cleanup step may comprise a size-selection process, such as a gel-based size selection process, or a solid-phase reversible immobilisation size-selection process, such as a magnetic bead-based solid-phase reversible immobilisation size-selection process. Optionally, amplification products at least 100 nucleotides in length, at least 500 nucleotides in length, at least 1000 nucleotides in length, at least 2000 nucleotides in length, at least 5000 nucleotides in length, at least 10,000 nucleotides in length, at least 20,000 nucleotides in length, at least 50,000 nucleotides in length, or at least 100,000 nucleotides in length may be purified. Optionally, before and/or during any rolling circle amplification step, a single-stranded DNA binding protein (such as T4 Gene 32 Protein) may be included in a reaction mixture, such as to prevent the formation of secondary structures by circularised templates and/or amplification products. During or after any such rolling circle amplification step, said single-stranded DNA binding protein may be removed and/or inactivated, such as by a heat-inactivation step.

Optionally, such a process of rolling circle amplification may be performed by phi29 DNA polymerase. Optionally, such a process of rolling circle amplification may be performed by a Bst or Bsm DNA polymerase. Optionally, such a process of rolling circle amplification may be performed such that at least one full copy of the circularised template is produced by the polymerase. Optionally, such a process of rolling circle amplification may be performed such that at least 2, at least 3, at least 5, at least 10, at least 50, at least 100, at least 200, at least 500, at least 1000, at least 2000, at least 5000, or at least 10,000 full copies of the circularised template are produced by the polymerase.

An example of this method is provided in FIG. 7. In the figure, a barcode molecule comprising an adapter region and a barcode region is circularised (e.g. using a single-stranded ligation reaction). A primer is then annealed to the resulting circularised product, and said primer is then extended using a strand-displacing polymerase (such as phi29 DNA polymerase). Whilst synthesising the extension product, the polymerase then processes one circumference around the circularised product, and then displaces the original primer in a strand-displacement reaction. The rolling-circle amplification process may then proceed to create a long contiguous nucleic acid molecule comprising many tandem copies of the circularised sequence—i.e. many tandem copies of a barcode and adapter sequence (and/or sequences complementary to a barcode and adapter sequence) of a barcode molecule.

Multimeric barcode molecules may also be amplified by rolling circle amplification.

18. Methods of Amplifying Multimeric Barcode Molecules by Rolling Circle Amplification A) Properties of Multimeric Barcode Molecules The invention further provides a method of amplifying multimeric barcode molecules from a library of multimeric barcode molecules, wherein said multimeric barcode molecules are amplified by one or more rolling circle amplification (RCA) processes. In this method, a multimeric barcode molecule comprises at least two barcode molecules linked together within a (single) nucleic acid molecule. Optionally, each barcode region of a barcode molecule may be adjacent to one or more adapter regions; optionally, such an adapter region may be at the 5' end of the associated barcode region, or may be at the 3' end of the associated barcode region. Optionally, each barcode region is associated with both a 3' adapter region and a 5' adapter region; optionally the 3' adapter region and a 5' adapter region may comprise different adapter sequences. Optionally, one or more adapter regions may comprise a sequence complementary to or identical to an adapter region of an adapter oligonucleotide. Optionally, one or more adapter regions may comprise a sequence complementary to or identical to all or part of an extension primer. A multimeric barcode molecule may take any of the forms described herein.

Each multimeric barcode molecule may further comprise, optionally within the 5' end of the multimeric barcode molecule, a forward reagent amplification sequence, which may comprise a sequence complementary to or identical to a forward reagent amplification primer. Each multimeric barcode molecule may further comprise, optionally within the 3' end of the multimeric barcode molecule, a reverse reagent amplification sequence, which may comprise a sequence complementary to or identical to a reverse reagent amplification primer.

A multimeric barcoding molecule may comprise at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ different barcode molecules. Any library of multimeric barcode molecules may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different multimeric barcode molecules.

B) Methods of Circularising Multimeric Barcode Molecules and/or Libraries Thereof In a method of amplifying multimeric barcode molecules, multimeric barcode molecules (and/or a library thereof) are converted into a circular form, such that the 2 or more barcode regions (and, optionally, 2 or more adapter regions) from a multimeric barcode molecule are comprised within a contiguous circular nucleic acid molecule. Optionally, a step of converting multimeric barcode molecules into circular form may be performed by an intramolecular double-stranded ligation reaction. For example, multimeric barcode molecules comprising double-stranded sequences and phosphorylated 5' ends may comprise blunt ends, or optionally may have their ends converted into a blunt form with a blunting reaction. Such multimeric barcode molecules may then be converted into circular form by an intramolecular double-stranded ligation reaction with a T4 DNA Ligase enzyme, such that one end of a multimeric barcode molecule is ligated on one or both stranded to the other end of the same multimeric barcode molecule.

In an alternative embodiment, a step of converting multimeric barcode molecules into circular form may be performed by an intramolecular double-stranded ligation reaction wherein the ends of multimeric barcode molecules comprise ends generated by a restriction digestion step. In one such embodiment, multimeric barcode molecules comprising double-stranded sequences comprise recognition sites for one or more restriction endonuclease enzymes within their 5' and 3' regions. In a digestion reaction, said multimeric barcode molecules are digested with such one or more restriction endonuclease enzymes to create digested multimeric barcode molecules comprising ends with the restriction digestion products. These digested multimeric barcode molecules may optionally then be purified, for example with a gel-based or bead-based size selection step. The digested multimeric barcode molecules may then be converted into circular form by an intramolecular double-stranded ligation reaction with a T4 DNA Ligase enzyme, such that the restriction-digested site on one end of a multimeric barcode molecule is ligated to the restriction-digested site on the other end of the same multimeric barcode molecule. Optionally, the ends produced by the restriction enzyme(s) may be blunt, or may comprise a 3' overhang of 1 or more nucleotides, or may comprise a 5' overhang of 1 or more nucleotides.

During any step of assembling, amplifying, ligating, and/or circularising barcode molecules and/or multimeric barcode molecules, and/or libraries or constituents thereof, the concentration of such molecules within solution may be retained within certain ranges. For example, the concentration of barcode molecules and/or multimeric barcode molecules may be less than 100 nanomolar, less than 10 nanomolar, less than 1 nanomolar, less than 100 picomolar, less than 10 picomolar, less than 1 picomolar, less than 100 femtomolar, less than 10 femtomolar, or less than 1 femtomolar. Optionally, during any step of assembling, amplifying, ligating, and/or circularising barcode molecules and/or multimeric barcode molecules, and/or libraries or constituents thereof, the concentration of such molecules within solution may allow two or more different barcode molecules and/or multimeric barcode molecules to become appended, concatenated, or ligated to each other within solution, optionally wherein such appended, concatenated, or ligated products are then further amplified during an amplification step.

C) Methods of Amplifying Circularised Multimeric Barcode Molecules with Rolling Circle Amplification Following a circularisation step, circularised multimeric barcode molecules are amplified with a rolling circle amplification step. In this process, a primer is annealed to a circularised nucleic acid strand comprising a multimeric barcode molecule, and the 3' end of said primer is extended with a polymerase exhibiting strand displacement behaviour. In one embodiment, a circularisation primer that has been annealed to a multimeric barcode molecule may serve as the primer for a rolling circle amplification step. Optionally, following circularisation, one or more separate amplification primer(s) which are at least partially complementary to a circularised multimeric barcode molecule, may be annealed to the circularised barcode molecule to prime a rolling circle amplification step. Optionally, oligonucleotides at least partially complementary to one or more adapter regions comprised within a multimeric barcode molecule may be employed as amplification primers. Optionally, following any step of annealing one or more amplification primers to circularised multimeric barcode molecules, a cleanup step may be performed to deplete non-annealed primers from the solution and/or to isolate primer-annealed multimeric barcode molecules. Optionally, such a cleanup step may comprise a size-selection step, such as a gel-based size-selection step or bead-based size selection step, such as a solid-phase reversible immobilisation step. Optionally, before and/or during any rolling circle amplification step, a single-stranded DNA binding protein (such as T4 Gene 32 Protein) may be included in a reaction mixture, such as to prevent the formation of secondary structures by circularised templates and/or amplification products. During or after any such rolling circle amplification step, said single-stranded DNA binding protein may be removed and/or inactivated, such as by a heat-inactivation step.

During said rolling circle amplification step, each primer may be extended by the polymerase, wherein the polymerase extends along the circularised template until it encounters the 5' end of an amplification primer and/or a circularisation primer, whereupon it continues amplification along the circularised template whilst displacing the 5' end of the primer, and then displacing the previously amplified strand, in a process of rolling circle amplification. Following any such amplification step, a purification and/or cleanup step may be performed to isolate products of such rolling circle amplification. Optionally, a purification step and/or cleanup step may comprise a size-selection process, such as a gel-based size selection process, or a solid-phase reversible immobilisation size-selection process, such as a magnetic bead-based solid-phase reversible immobilisation size-selection process. Optionally, amplification products at least 100 nucleotides in length, at least 500 nucleotides in length, at least 1000 nucleotides in length, at least 2000 nucleotides in length, at least 5000 nucleotides in length, at least 10,000 nucleotides in length, at least 20,000 nucleotides in length, at least 50,000 nucleotides in length, or at least 100,000 nucleotides in length may be purified.

Optionally, such a process of rolling circle amplification may be performed by phi29 DNA polymerase. Optionally, such a process of rolling circle amplification may be performed by a Bst or Bsm DNA polymerase. Optionally, such a process of rolling circle amplification may be performed such that at least one full copy of the circularised template is produced by the polymerase. Optionally, such a process of rolling circle amplification may be performed such that at least 2, at least 3, at least 5, at least 10, at least 50, at least 100, at least 200, at least 500, at least 1000, at least 2000, at least 5000, or at least 10,000 full copies of the circularised multimeric barcode molecule template are produced by the polymerase from each primer that has been annealed to the circularised multimeric barcode molecule.

Optionally, at least 2, at least 3, at least 5, at least 10, at least 20, at least 50, at least 100, or at least 500 primers may be annealed to a circularised multimeric barcode molecule and used to prime rolling circle amplification reactions along the multimeric barcode molecule to which they are annealed. Parts of the extension products produced from these primers may remain annealed to the circularised multimeric barcode molecule to which they were originally annealed, thus producing a macromolecular nucleic acid complex comprising a circularised multimeric barcode molecule, and two or more rolling circle amplification products at least partially annealed thereto.

The sequences within a multimeric barcode molecule may be configured such that the rolling circle amplification products comprise one or more adapter regions and/or adapter sequences, such that said adapter regions and/or adapter sequences are able to hybridise to complementary sequences, for example complementary sequences comprised within coupling oligonucleotides, adapter oligonucleotides, and/or extension primers. Part or all of any such rolling circle amplification product(s) and/or macromolecular nucleic acid complex may be used to synthesise a multimeric barcoding reagent, for example by serving as barcode molecules to synthesise barcoded oligonucleotides. Part or all of any such rolling circle amplification product(s) and/or macromolecular nucleic acid complex may serve as barcode molecules to be used to barcode nucleic acid molecules within a nucleic acid sample.

D) Methods of Processing Rolling-Circle-Amplified Multimeric Barcode Molecules With A Primer Extension Process Following any process of rolling circle amplification of a multimeric barcode molecule and/or library thereof, one or more primer extension steps may be performed on the resulting products. The resulting primer-extension products may comprise single stranded nucleic acid molecules comprising all or part of multimeric barcode molecules, and or parts of two or more multimeric barcode molecules. In some embodiments, such primer-extension products may comprise a library of single stranded nucleic acid molecules, wherein each single nucleic acid strand comprises a multimeric barcode molecule. In other embodiments, such primer-extension products may be annealed or partially annealed to the template molecules from which they are synthesised. Optionally, any multimeric barcode molecules resulting from any such primer-extension process may be used to create a multimeric barcoding reagent and/or library thereof. Optionally, any multimeric barcode molecules resulting from any such primer-extension process may be used to barcode nucleic acid molecules within a nucleic acid sample; optionally the barcode sequences comprising said multimeric barcode molecules may be appended to nucleic acid molecules within a nucleic acid sample.

In one such embodiment of a primer-extension process, a primer complementary to, or identical in sequence to, all or part of a forward reagent amplification sequence and/or all or part of a reverse reagent amplification sequence may be used. In one such embodiment, a primer at least partially complementary to a reagent amplification sequence(s) comprised within the polymerase-extension products of the rolling circle amplification reaction may be used to perform one or more primer-extension reactions and/or cycles. In one embodiment of a primer-extension process, a library of random primers are used for said primer-extension process, for example random hexamer primers, random octamer primers, or random decamer primers. Optionally, any primer used in a primer-extension process may comprise one or more modifications, such as phosphorothioate bonds, and specifically such as phosphorothioate bonds within the 3' most one or two nucleotide bonds within the primer. Such 3' phosphorothioate bonds may prevent degradation of said primers by polymerases which exhibit exonuclease behaviour.

Optionally, such a primer-extension step may be performed by a polymerase that exhibits 5'-3' exonuclease behaviour (such as DNA Polymerase I from *E. coli*) and/or flap endonuclease behaviour (such as Taq polymerase from *Thermus aquaticus*), such that nucleic acid sequences annealed immediately downstream of a processing polymerase are degraded or partially degraded during the process of primer-extension by said polymerase.

Optionally, such a primer-extension step may be performed by a polymerase that exhibits strand displacement behaviour, such as phi29 DNA polymerase, Vent polymerase, Deep Vent polymerase, or exonuclease-deficient derivatives thereof (e.g. from New England Bioloabs), or Bst or Bsm DNA polymerase, such that nucleic acid sequences annealed immediately downstream of a processing polymerase are displaced during the process of primer-extension by said polymerase. Optionally, said displaced nucleic acid sequences may comprise other primer-extension products produced during the primer-extension process. Optionally, such a primer-extension step may be performed by phi29 DNA polymerase, wherein the primers used for said primer-extension step comprise random primers.

Any such primer-extension step performed by a polymerase that exhibits strand displacement behaviour may have the effect of displacing regions of multimeric barcode molecules (and/or nucleic acid strands comprising sequences from multimeric barcode molecules, e.g. those that are produced by such a primer extension process) comprising one or more adapter regions and/or adapter sequences, such that said adapter regions and/or adapter sequences are converted into a single-stranded form, such that the resulting single-stranded adapter regions are able to hybridise to complementary sequences, for example complementary sequences comprised within coupling oligonucleotides, adapter oligonucleotides, and/or extension primers. Parts of such strand-displaced molecules may remain annealed to the template molecules from which they were synthesised. Part or all of any given strand-displaced nucleic acid molecule synthesised by such a primer-extension process may be used to synthesise a multimeric barcoding reagent. Part or all of any given strand-displaced nucleic acid molecule synthesised by such a primer-extension process may be used to barcode nucleic acid molecules within a nucleic acid sample.

Optionally, such a primer-extension step may be performed by a polymerase that does not exhibit 5'-3' exonuclease, or flap endonuclease behaviour, or strand-displacement behaviour (such as Pfu and/or Phusion polymerases or derivatives thereof (New England Biolabs), or T4 DNA Polymerase), such that nucleic acid sequences annealed immediately downstream of a processing polymerase halt the extension of the polymerase when it encounters them thereat.

Optionally, any such primer-extension step may comprise at least 1, at least 5, at least 10, at least 15, at least 20, at least 30, at least 50, or at least 100 cycles of primer-extension. Optionally, such primer-extension cycles may be performed within repeating cycles of primer extension, template denaturating, and primer annealing. Optionally, any such primer-extension step may be performed in a buffer comprising one or more macromolecular crowding agents, such as polyethylene glycol (PEG) reagents, for example PEG 8000.

Optionally, primer-extension products at least 100 nucleotides in length, at least 500 nucleotides in length, at least 1000 nucleotides in length, at least 2000 nucleotides in length, at least 5000 nucleotides in length, at least 10,000 nucleotides in length, at least 20,000 nucleotides in length, at least 50,000 nucleotides in length, or at least 100,000 nucleotides in length may be produced by any above primer extension process. Optionally, such a process of primer-extension may be performed such that at least one full copy of the circularised template is produced by the polymerase. Optionally, such a process of primer-extension may be performed such that at least 2, at least 3, at least 5, at least 10, at least 50, at least 100, at least 200, at least 500, at least 1000, at least 2000, at least 5000, or at least 10,000 copies of the multimeric barcode molecule template are produced by the polymerase during each primer extension step. Optionally, the length in time (eg seconds, or minutes) of a primer-extension reaction may be configured such that each primer-extension product is approximately the same length as a single multimeric barcode reagent within the library. For example, if a polymerase used for primer extension processes at a rate of 1000 nucleotides per minute, and the mean length of a multimeric barcode reagent within a library of multimeric barcode reagents is 1000 nucleotides, then the primer-extension cycle may be configured to be 1 minute in length.

Optionally, following one or more primer-extension steps, the resulting primer-extension products may be isolated or purified by a cleanup reaction. Optionally, such a cleanup reaction may comprise a size-selection step, such as a gel-based size-selection step or bead-based size selection step, such as a solid-phase reversible immobilisation step. Optionally, primer-extension products at least 100 nucleotides in length, at least 500 nucleotides in length, at least 1000 nucleotides in length, at least 2000 nucleotides in length, at least 5000 nucleotides in length, at least 10,000 nucleotides in length, at least 20,000 nucleotides in length, at least 50,000 nucleotides in length, or at least 100,000 nucleotides in length may be purified.

E) Methods of Processing Rolling-Circle-Amplified and/or Primer-Extended Multimeric Barcode Molecules with a Denaturation Process Prior to or following any purification step and/or size selection step, and/or prior to use for synthesising multimeric barcoding reagents, and/or prior to use for barcoding nucleic acids within a sample of nucleic acids, any rolling circle amplification products or primer-extension products produced as above may be denatured with a denaturing step. Such a denaturing step may be a thermal denaturing step, wherein the products are incubated at a high temperature to melt annealed sequences and/or secondary structure. Such a denaturing step may be performed at a temperature of at least 60 degrees Celsius, at least 70 degrees Celsius, at least 80 degrees Celsius, at least 90 degrees Celsius, or at least 95 degrees Celsius. Such a denaturing step may have the effect of denaturing regions of multimeric barcode molecules comprising one or more adapter regions and/or adapter sequences into single-stranded form, such that the resulting single-stranded adapter regions are able to hybridise to complementary sequences, for example complementary sequences comprised within coupling oligonucleotides, adapter oligonucleotides, and/or extension primers.

In alternative embodiments, no such denaturing step may be performed prior to or following any purification step and/or size selection step, and/or prior to use for synthesising multimeric barcoding reagents, and/or prior to use for barcoding nucleic acids within a sample of nucleic acids. For example, nucleic acid strands comprising primer-extension products produced during a primer-extension step may remain annealed or partially annealed to the template molecules from which they were synthesised. The resulting nucleic acid macromolecules may comprise a total of at least 2 individual nucleic acid strands, at least 3 individual nucleic acid strands, at least 5 individual nucleic acid strands, at least 10 individual nucleic acid strands, at least 50 individual nucleic acid strands, at least 100 individual nucleic acid strands, at least 500 individual nucleic acid strands, at least 1000 individual nucleic acid strands, at least 5000 individual nucleic acid strands, or at least 10,000 individual nucleic acid strands. Optionally, individual nucleic acid strands may comprise all or parts of one or more multimeric barcoding molecules. Such nucleic acid macromolecules and/or libraries thereof may be used for synthesising multimeric barcoding reagents, and/or for barcoding nucleic acids within a sample of nucleic acids.

19. Methods of Synthesising a Multimeric Barcoding Reagent

The invention further provides a method of synthesising a multimeric barcoding reagent for labelling a target nucleic acid comprising: (a) contacting first and second barcode molecules with first and second extension primers, wherein each of the barcode molecules comprises a single-stranded nucleic acid comprising in the 5' to 3' direction an adapter region, a barcode region and a priming region; (b) annealing the first extension primer to the priming region of the first barcode molecule and annealing the second extension primer to the priming region of the second barcode molecule; and (c) synthesising a first barcoded extension product by extending the first extension primer and synthesising a second barcoded extension product by extending the second extension primer, wherein the first barcoded extension product comprises a sequence complementary to the barcode region of the first barcode molecule and the second barcoded extension product comprises a sequence complementary to the barcode region of the second barcode molecule, and wherein the first barcoded extension product does not comprise a sequence complementary to the adapter region of the first barcode molecule and the second barcoded extension product does not comprise a sequence complementary to the adapter region of the second barcode molecule; and wherein the first and second barcode molecules are linked together.

The method may further comprise the following steps before the step of synthesising the first and second barcoded extension products: (a) contacting first and second barcode molecules with first and second blocking primers; and (b) annealing the first blocking primer to the adapter region of the first barcode molecule and annealing the second blocking primer to the adapter region of the second barcode molecule; and wherein the method further comprises the step of dissociating the blocking primers from the barcode molecules after the step of synthesising the barcoded extension products.

In the method, the extension step, or a second extension step performed after the synthesis of an extension product, may be performed, in which one or more of the four canonical deoxyribonucleotides is excluded from the extension reaction, such that the second extension step terminates at a position before the adapter region sequence, wherein the position comprises a nucleotide complementary to the excluded deoxyribonucleotide. This extension step may be performed with a polymerase lacking 3' to 5' exonuclease activity.

The barcode molecules may be provided by a single-stranded multimeric barcode molecule as defined herein.

The barcode molecules may be synthesised by any of the methods defined herein. The barcode regions may uniquely identify each of the barcode molecules. The barcode molecules may be linked on a nucleic acid molecule. The barcode molecules may be linked together in a ligation reaction. The barcode molecules may be linked together by a further step comprising attaching the barcode molecules to a solid support.

The first and second barcode molecules may be assembled as a double-stranded multimeric barcode molecule by any of the methods defined herein prior to step (a) defined above (i.e. contacting first and second barcode molecules with first and second extension primers). The double-stranded multimeric barcode molecule may be dissociated to produce single-stranded multimeric barcode molecules for use in step (a) defined above (i.e. contacting first and second barcode molecules with first and second extension primers).

The method may further comprise the steps of: (a) annealing an adapter region of a first adapter oligonucleotide to the adapter region of the first barcode molecule and annealing an adapter region of a second adapter oligonucleotide to the adapter region of the second barcode molecule, wherein the first adapter oligonucleotide further comprises a target region capable of annealing to a first sub-sequence of the target nucleic acid and the second adapter oligonucleotide further comprises a target region capable of annealing to a second sub-sequence of the target nucleic acid; and (b) ligating the 3' end of the first barcoded extension product to the 5' end of the first adapter oligonucleotide to produce a first barcoded oligonucleotide and ligating the 3' end of the second barcoded extension product to the 5' end of the second adapter oligonucleotide to produce a second barcoded oligonucleotide. Optionally, the annealing step (a) may be performed before the step of synthesising the first and second barcoded extension products and wherein the step of synthesising the first and second barcoded extension products is conducted in the presence of a ligase enzyme that performs the ligation step (b). The ligase may be a thermostable ligase. The extension and ligation reaction may proceed at over 37 degrees Celsius, over 45 degrees Celsius, or over 50 degrees Celsius.

The target regions may comprise different sequences. Each target region may comprise a sequence capable of annealing to only a single sub-sequence of a target nucleic acid within a sample of nucleic acids. Each target region may comprise one or more random, or one or more degenerate, sequences to enable the target region to anneal to more than one sub-sequence of a target nucleic acid. Each target region may comprise at least 5, at least 10, at least 15, at least 20, at least 25, at least 50 or at least 100 nucleotides. Preferably, each target region comprises at least 5 nucleotides. Each target region may comprise 5 to 100 nucleotides, 5 to 10 nucleotides, 10 to 20 nucleotides, 20 to 30 nucleotides, 30 to 50 nucleotides, 50 to 100 nucleotides, 10 to 90 nucleotides, 20 to 80 nucleotides, 30 to 70 nucleotides or 50 to 60 nucleotides. Preferably, each target region comprises 30 to 70 nucleotides. Preferably each target region comprises deoxyribonucleotides, optionally all of the nucleotides in a target region are deoxyribonucleotides. One or more of the deoxyribonucleotides may be a modified deoxyribonucleotide (e.g. a deoxyribonucleotide modified with a biotin moiety or a deoxyuracil nucleotide). Each target region may comprise one or more universal bases (e.g. inosine), one or modified nucleotides and/or one or more nucleotide analogues.

The adapter region of each adapter oligonucleotide may comprise a constant region. Optionally, all adapter regions of adapter oligonucleotides that anneal to a single multimeric barcoding reagent are substantially identical. The adapter region may comprise at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

For any of the methods involving adapter oligonucleotides, the 3' end of the adapter oligonucleotide may include a reversible terminator moiety or a reversible terminator nucleotide (for example, a 3'-O-blocked nucleotide), for example at the 3' terminal nucleotide of the target region. When used in an extension and/or extension and ligation reaction, the 3' ends of these adapter oligonucleotides may be prevented from priming any extension events. This may minimize mis-priming or other spurious extension events during the production of barcoded oligonucleotides. Prior to using the assembled multimeric barcoding reagents, the terminator moiety of the reversible terminator may be removed by chemical or other means, thus allowing the target region to be extended along a target nucleic acid template to which it is annealed.

Similarly, for any of the methods involving adapter oligonucleotides, one or more blocking oligonucleotides complementary to one or more sequences within the target region(s) may be employed during extension and/or extension and ligation reactions. The blocking oligonucleotides may comprise a terminator and/or other moiety on their 3' and/or 5' ends such that they are not able to be extended by polymerases. The blocking oligonucleotides may be designed such that they anneal to sequences fully or partially complementary to one or more target regions, and are annealed to said target regions prior to an extension and/or extension and ligation reaction. The use of blocking primers may prevent target regions from annealing to, and potentially mis-priming along, sequences within the solution for which such annealing is not desired (for example, sequence features within barcode molecules themselves). The blocking oligonucleotides may be designed to achieve particular annealing and/or melting temperatures. Prior to using the assembled multimeric barcoding reagents, the blocking oligonucleotide(s) may then be removed by, for example, heat-denaturation and then size-selective cleanup, or other means. The removal of the blocking oligonucleotide(s) may allow the target region to be extended along a target nucleic acid template to which it is annealed.

The method may comprise synthesising a multimeric barcoding reagent comprising at least 5, at least 10, at least 20, at least 25, at least 50, at least 75 or at least 100 barcode molecules, and wherein: (a) each barcode molecule is as defined herein; and (b) a barcoded extension product is synthesised from each barcode molecule according to any method defined herein; and, optionally, (c) an adapter oligonucleotide is ligated to each of the barcoded extension products to produce barcoded oligonucleotides according to any of the methods defined herein.

The invention further provides a method of synthesising a library of multimeric barcoding reagents, wherein the method comprises repeating the steps of any of the methods defined herein to synthesise two or more multimeric barcoding reagents. Optionally, the method comprises synthesising a library of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, at least $10^9$ or at least 1010 multimeric barcoding reagents as defined herein. Preferably, the library comprises at least 5 multimeric barcoding reagents as defined herein. Preferably, the barcode regions of each of the multimeric barcoding reagents may be different to the barcode regions of the other multimeric barcoding reagents.

FIG. 8 illustrates a method of synthesizing a multimeric barcoding reagent for labeling a target nucleic acid. In this method, first (D1, E1, and F1) and second (D2, E2, and F2) barcode molecules, which each include a nucleic acid sequence comprising a barcode region (E1 and E2), and which are linked by a connecting nucleic acid sequence (S), are denatured into single-stranded form. To these single-stranded barcode molecules, a first and second extension primer (A1 and A2) is annealed to the 3' region of the first and second barcode molecules (D1 and D2), and a first and second blocking primer (R1 and R2) is annealed to the 5' adapter region (F1 and F2) of the first and second barcode molecules. These blocking primers (R1 and R2) may be modified on the 3' end such that they cannot serve as a priming site for a polymerase.

A polymerase is then used to perform a primer extension reaction, in which the extension primers are extended to make a copy (B1 and B2) of the barcode region of the barcode molecules (E1 and E2). This primer extension reaction is performed such that the extension product terminates immediately adjacent to the blocking primer sequence, for example through use of a polymerase which lacks strand displacement or 5'-3' exonuclease activity. The blocking primers (R1 and R2) are then removed, for example through high-temperature denaturation.

This method thus creates a multimeric barcoding reagent containing a first and second ligation junction (J1 and J2) adjacent to a single-stranded adapter region (F1 and F2). This multimeric barcoding reagent may be used in the method illustrated in FIG. 5.

The method may further comprise the step of ligating the 3' end of the first and second barcoded oligonucleotides created by the primer-extension step (the 3' end of B1 and B2) to first (C1 and G1) and second (C2 and G2) adapter oligonucleotides, wherein each adapter oligonucleotide comprises an adapter region (C1 and C2) which is complementary to, and thus able to anneal to, the adapter region of a barcode molecule (F1 and F2). The adapter oligonucleotides may be synthesised to include a 5'-terminal phosphate group.

Each adapter oligonucleotide may also comprise a target region (G1 and G2), which may be used to anneal the barcoded oligonucleotides to target nucleic acids, and may separately or subsequently be used as primers for a primer-extension reaction or a polymerase chain reaction. The step of ligating the first and second barcoded oligonucleotides to the adapter oligonucleotides produces a multimeric barcoding reagent as illustrated in FIG. 1 that may be used in the methods illustrated in FIG. 3 and/or FIG. 4.

FIG. 9 shows a method of synthesizing multimeric barcoding reagents (as illustrated in FIG. 1) for labeling a target nucleic acid. In this method, first (D1, E1, and F1) and second (D2, E2, and F2) barcode molecules, which each include a nucleic acid sequence comprising a barcode region (E1 and E2), and which are linked by a connecting nucleic acid sequence (S), are denatured into single-stranded form. To these single-stranded barcode molecules, a first and second extension primer (A1 and A2) is annealed to the 3' region of the first and second barcode molecules (D1 and D2), and the adapter regions (C1 and C2) of first (C1 and G1) and second (C2 and G2) adapter oligonucleotides are annealed to the 5' adapter regions (F1 and F2) of the first and second barcode molecules. These adapter oligonucleotides may be synthesised to include a 5'-terminal phosphate group.

A polymerase is then used to perform a primer extension reaction, in which the extension primers are extended to make a copy (B1 and B2) of the barcode region of the barcode molecules (E1 and E2). This primer extension reaction is performed such that the extension product terminates immediately adjacent to the adapter region (C1 and C2) sequence, for example through use of a polymerase which lacks strand displacement or 5'-3' exonuclease activity.

A ligase enzyme is then used to ligate the 5' end of the adapter oligonucleotides to the adjacent 3' end of the corresponding extension product. In an alternative embodiment, a ligase enzyme may be included with the polymerase enzyme in one reaction which simultaneously effects both primer-extension and ligation of the resulting product to the adapter oligonucleotide. Through this method, the resulting barcoded oligonucleotides may subsequently be used as primers for a primer-extension reaction or a polymerase chain reaction, for example as in the method shown in FIG. 3 and/or FIG. 4.

The invention further provides a method of synthesising a multimeric barcoding reagent comprising appending one or more (donor) multimeric barcoding reagents to a support. Multimeric hybridization molecules (e.g. multimeric barcode molecules) may be appended to a support. Additionally or alternatively, barcoded oligonucleotides, which may have been synthesised from a multimeric barcode molecule, may be appended to a support. The support may be any support described herein e.g. a macromolecule, solid support or semi-solid support.

The support may be selected based on the desired structural and/or functional properties of the multimeric barcoding reagent. For example: barcoded oligonucleotides may be appended to magnetic beads. This may allow a laboratory scientist to easily manipulate the barcoded oligonucleotides, for example to perform washing steps, or purification steps. Furthermore, the functional properties of the bead may enable a scientist to isolate or purify nucleic acids from a nucleic acid sample that may be hybridised to and/or barcoded with the barcoded oligonucleotides. Furthermore, appending barcoded oligonucleotides to a support may change the overall structural nature of the barcoded oligonucleotides. For example, appending barcoded oligonucleotides to a streptavidin tetramer may change the three-dimensional structure of the barcoded oligonucleotides such that cross-hybridisation between the target regions of different barcoded oligonucleotides is reduced, thereby reducing the amount of potential mis-priming between barcoded oligonucleotides, and/or enhancing the accessibility of the target regions to potential target nucleic acids within a sample.

20. Methods of Sequencing and/or Processing Sequencing Data

The invention further provides a method of sequencing a sample, wherein the sample has been prepared by any one of the methods of preparing a nucleic acid sample for sequencing as defined herein. The method of sequencing the sample comprises the steps of: isolating the barcoded target nucleic acid molecules, and producing a sequence read from each barcoded target nucleic acid molecule that comprises the barcode region, the target region and at least one additional nucleotide from the target nucleic acid. Each sequence read may comprise at least 5, at least 10, at least 25, at least 50, at least 100, at least 250, at least 500, at least 1000, at least 2000, at least 5000, or at least 10,000 nucleotides from the target nucleic acid. Preferably, each sequence read comprises at least 5 nucleotides from the target nucleic acid.

The methods may produce a sequence read from one or more barcoded target nucleic acid molecule produced from at least at least 10, at least 100, or at least $10^3$, at least $10^4$, at least $10^5$, at least $10^6$, at least $10^7$, at least $10^8$ or at least $10^9$ different target nucleic acids.

Sequencing may be performed by any method known in the art. For example, by chain-termination or Sanger sequencing. Preferably, sequencing is performed by a next-generation sequencing method such as sequencing by synthesis, sequencing by synthesis using reversible terminators (e.g. Illumina sequencing), pyrosequencing (e.g. 454 sequencing), sequencing by ligation (e.g. SOLiD sequencing), single-molecule sequencing (e.g. Single Molecule, Real-Time (SMRT) sequencing, Pacific Biosciences), or by nanopore sequencing (e.g. on the Minion or Promethion platforms, Oxford Nanopore Technologies).

The invention further provides a method for processing sequencing data obtained by any of the methods defined herein. The method for processing sequence data comprises the steps of: (a) identifying for each sequence read the sequence of the barcode region and the sequence from the target nucleic acid; and (b) using the information from step (a) to determine a group of sequences from the target nucleic acid that were labelled with barcode regions from the same multimeric barcoding reagent.

The method may further comprise the step of determining a sequence of a target nucleic acid by analysing the group of sequences to identify contiguous sequences, wherein the sequence of the target nucleic acid comprises nucleotides from at least two sequence reads.

The target nucleic acid may be an intact nucleic acid molecule, co-localised fragments of a nucleic acid molecule, or nucleic acid molecules from a single cell. Preferably, the target nucleic acid is a single intact nucleic acid molecule, two or more co-localised fragments of a single nucleic acid molecule, or two or more nucleic acid molecules from a single cell.

The invention further provides an algorithm for processing (or analysing) sequencing data obtained by any of the methods defined herein. The algorithm may be configured to perform any of the methods for processing sequencing data defined herein. The algorithm may be used to detect the sequence of a barcode region within each sequence read, and also to detect the sequence within a sequence read that is derived from a target nucleic acid, and to separate these into two associated data sets.

The invention further provides a method of generating a synthetic long read from a target nucleic acid comprising the steps of: (a) preparing a nucleic acid sample for sequencing according to any of the methods defined herein; (b) sequencing the sample, optionally wherein the sample is sequenced by any of the methods defined herein; and (c) processing the sequence data obtained by step (b), optionally wherein the sequence data is processed according to any of the methods defined herein; wherein step (c) generates a synthetic long read comprising at least one nucleotide from each of the at least two sequence reads.

The method may enable the phasing of a target sequence of a target nucleic acid molecule i.e. it may enable the determination of which copy of a chromosome (i.e. paternal or maternal) the sequence is located. The target sequence may comprise a specific target mutation, translocation, deletion or amplification and the method may be used to assign the mutation, translocation, deletion or amplification to a specific chromosome. The phasing two or more target sequences may also enable the detection of aneuploidy.

The synthetic long read may comprise at least 50, at least 100, at least 250, at least 500, at least 750, at least 1000, at least 2000, at least $10^4$, at least $10^5$, at least $10^6$, at least $10^7$ or at least $10^8$ nucleotides. Preferably, the synthetic long read comprises at least 50 nucleotides.

The invention further provides a method of sequencing two or more co-localised target nucleic acids comprising the steps of: (a) preparing a nucleic acid sample for sequencing according to any of the methods defined herein; (b) sequencing the sample, optionally wherein the sample is sequenced by any of the methods defined herein; and (c) processing the sequence data obtained by step (b), optionally wherein the sequence data is processed according to any of the methods defined herein; wherein step (c) identifies at least two sequence reads comprising nucleotides from at least two target nucleic acids co-localised in the sample.

The invention further provides a method of sequencing target nucleic acids from an individual cell comprising the steps of: (a) preparing a nucleic acid sample for sequencing according any of the methods defined herein, wherein the multimeric barcoding reagent(s), or multimeric barcode molecule(s), and/or adapter oligonucleotides are introduced into the cell; (b) sequencing the sample, optionally wherein the sample is sequenced by any of the methods defined herein; and (c) processing the sequence data obtained by step (b), optionally wherein the sequence data is processed according to any of the methods defined herein; wherein step (c) identifies at least two sequence reads comprising nucleotides from at least two target nucleic acids from the cell.

The multimeric barcoding reagent(s) and/or adapter oligonucleotides may be introduced into the cell by chemical complexation with a lipid transfection reagent and then transfection into the cell.

The multimeric barcoding reagent(s) and/or adapter oligonucleotides may be introduced into the cell through the steps of: (a) permeabilising the cell membrane by contacting it with a chemical surfactant; and then (b) contacting the cell with the multimeric barcoding reagent(s) and/or adapter oligonucleotides. The chemical surfactant may be a non-ionic surfactant. The chemical surfactant may be Triton X-100 ($C_{14}H_{22}O(C_2H_4O)n(n=9-10)$). The chemical surfactant may be in solution at a concentration of less than 200 micromolar, or less than 500 micromolar, or less than 1 milimolar.

In the method, following the step of introducing the multimeric barcoding reagent(s) and/or adapter oligonucleotides into the cell, the cell may be incubated for a period of time to allow the target regions of the multimeric barcoding reagent(s) or adapter oligonucleotide(s) to anneal to sub-sequences of the target nucleic acids within the cell. The incubation period may be at least 1 minute, or at least 5 minutes, or at least 15 minutes, or at least 30 minutes, or at least 60 minutes. Preferably, the incubation period is at least 1 minute. The incubation may take place within a solution containing a nucleic acid denaturant e.g. dimethyl sulfoxide (DMSO) or betaine. The incubation may take place at a temperature of at least 20 degrees Celsius, at least 37 degrees Celsius, at least 45 degrees Celsius, or at least 50 degrees Celsius. Preferably, the incubation takes place at a temperature of at least 20 degrees Celsius.

In methods involving the use of multimeric barcoding reagents, the incubation step may substantially dissociate the barcoded oligonucleotides from the barcode molecules (or multimeric barcode molecule). This may enable the barcoded oligonucleotides to diffuse more readily throughout the cell improving the efficiency with which the target regions of the barcoded oligonucleotides are able to anneal to sub-sequences of the target nucleic acids.

In the method, following introduction of the multimeric barcoding reagent(s) and/or adapter oligonucleotides into the cell, and optionally following the incubation step, the cell may be contacted by a solution of oligonucleotides complementary to the target regions of the multimeric barcoding reagents.

In the method, following introduction of the multimeric barcoding reagent(s) and/or adapter oligonucleotides into the cell, and optionally following the incubation step, the cell may be isolated from a reaction mixture e.g. by centrifugation.

In the method, following introduction of the multimeric barcoding reagent(s) and/or adapter oligonucleotides into the cell, and optionally following the incubation step, the barcoded oligonucleotides and/or barcoded target nucleic acid molecules and/or multimeric barcoding reagent(s) may be isolated from the cell.

The multimeric barcoding reagents, barcoded oligonucleotides and/or adapter oligonucleotides may comprise one or more biotin moieties.

In the method, following introduction of the multimeric barcoding reagent(s) and/or adapter oligonucleotides into the cell, and optionally following the incubation step, the barcoded oligonucleotides and/or barcoded target nucleic acid molecules and/or multimeric barcoding reagent(s) may be isolated by a process of: (a) optionally dissolving the cell membranes e.g. using a chemical surfactant or by incubation at high temperature; (b) contacting the resulting mixture with a solid support, optionally wherein the solid support comprises streptavidin moieties; and (c) capturing the barcoded oligonucleotides and/or barcoded target nucleic acid molecules and/or multimeric barcoding reagent(s) on the solid support, optionally through streptavidin-biotin interaction. The solid support may be one or more magnetic beads, optionally wherein the one or more magnetic beads comprise streptavidin molecules on their surface. The magnetic bead(s) may be isolated from a reaction mixture with a magnet.

The target nucleic acids may be DNA molecules (e.g. genomic DNA molecules) or RNA molecules (e.g. mRNA molecules).

Preferably, each barcoded target nucleic acid molecule is produced after isolation of the barcoded oligonucleotide annealed to a target mRNA molecule by extending the barcoded oligonucleotide using a reverse transcriptase and the target mRNA molecule as the template.

The mRNA molecules may be mRNA molecules corresponding to alpha and/or beta chains of a T-cell receptor sequence, optionally wherein the sequences of alpha and beta chains paired within an individual cell are determined.

The mRNA molecules may be mRNA molecules corresponding to light and/or heavy chains of an immunoglobulin sequence, optionally wherein the sequences of light and heavy chains paired within an individual cell are determined.

The method may be used to sequence target nucleic acids in at least 10, at least 100, or at least $10^3$, at least $10^4$, at least $10^5$, at least $10^6$, at least $10^7$, at least $10^8$ or at least $10^9$ cells. Preferably, the method may be used to sequence target nucleic acids in at least 10 cells. Preferably the cells are T-cells and/or B-cells.

Any method of analysing barcoded nucleic acid molecules by sequencing (e.g. to generate synthetic long reads, or to analyse nucleic acid sequences from single cells) may comprise a redundant sequencing reaction, wherein target nucleic acid molecules that have been barcoded in a barcoding reaction are sequenced two or more times within a sequencing reaction. Optionally, each such barcoded molecule from a sample may be sequenced, on average, at least twice, at least 3 times, at least 5 times, at least 10 times, at least 20 times, at least 50 times, or at least 100 times.

In any method of analysing barcoded nucleic acid molecules by sequencing (e.g. to generate synthetic long reads, or to analyse nucleic acid sequences from single cells), an error correction process may be employed. This process may comprise the steps of: (i) determining two or more sequence reads from a sequencing dataset comprising the same barcode sequence, and (ii) aligning the sequences from said two or more sequence reads to each other. Optionally, this error correction process may further comprise a step of (iii) determining a majority and/or most common and/or most likely nucleotide at each position within the sequence read and/or at each position within the sequence of the target nucleic acid molecule. This step may optionally comprise establishing a consensus sequence of each target nucleic acid sequence by any process of error correction, error removal, error detection, error counting, or statistical error removal. This step may further comprise the step of collapsing multiple sequence reads comprising the same barcode sequence into a representation comprising a single, error-corrected read. Optionally, any step of determining two or more sequence reads from a sequencing dataset comprising the same barcode sequence, may comprise determining sequence reads comprising barcode sequences with at least a certain extent of identical nucleotides and/or sequence similarity, for example at least 70%, at least 80%, at least 90%, or at least 95% sequence similarity (for example, allowing for mismatches and/or insertions or deletions at any point between to barcode sequences).

In any method of analysing barcoded nucleic acid molecules by sequencing (e.g. to generate synthetic long reads, or to analyse nucleic acid sequences from single cells), an alternative error correction process may be employed, comprising the steps of: (i) determining two or more sequence reads from a sequencing dataset that comprise the same target nucleic acid sequence, wherein said two or more sequence reads further comprise two or more different barcode sequences, wherein the barcode sequences are from the same multimeric barcode molecule and/or multimeric barcoding reagent, and (ii) aligning the sequences from said two or more sequence reads to each other. Optionally, this error correction process may further comprise a step of (iii) determining a majority and/or most common and/or most likely nucleotide at each position within the sequence of the target nucleic acid molecule. This step may optionally comprise establishing a consensus sequence of the target nucleic acid molecule by any process of error correction, error removal, error detection, error counting, or statistical error removal. This step may further comprise the step of collapsing multiple sequence reads comprising the same target nucleic acid molecule into a representation comprising a single, error-corrected read. The target nucleic acid molecule may comprise, for example, a genomic DNA sequence; alternatively, the target nucleic acid molecule may comprise all or part of a messenger RNA sequence such as an expressed gene or an expressed adaptive immune receptor chain. Optionally, any step of comparing two barcode sequences, and/or comparing a sequenced barcode sequence and a reference barcode sequence, may comprise determining sequences comprising at least a certain extent of identical nucleotides and/or sequence similarity, for example at least 70%, at least 80%, at least 90%, or at least 95% sequence similarity (for example, allowing for mismatches and/or insertions or deletions at any point between to barcode sequences).

In any method of analysing barcoded nucleic acid molecules by sequencing, the number of barcode sequences appended to specific nucleic acid targets by any given multimeric barcoding reagent, and/or across a group of two or more different multimeric barcoding reagents, may be quantitated. For example, the number of different barcode sequences from a multimeric barcoding reagent appended to a particular messenger RNA transcript (or any other specific nucleic acid targets) from a single cell may be determined. Any type of specific nucleic acid target may be quantitated, such as any transcript, any genomic DNA sequence, any synthetic barcode sequence, any adaptive immune receptor chain and/or immune receptor sequence, or any specific mutation sequence. Any such process of quantitation may be repeated for any number of specific nucleic acid targets and/or groups thereof.

21. Uses of a Multimeric Barcoding Reagent, Library or Kit

The invention further provides the use of a multimeric barcoding reagent as defined herein, a library of multimeric barcoding reagents as defined herein, or a kit as defined herein, to produce two or more sequence reads from a target nucleic acid, wherein two or more sequence reads can be identified as derived from the same target nucleic acid and combined to produce a synthetic long read.

The invention further provides the use of a multimeric barcoding reagent as defined herein, a library of multimeric barcoding reagents as defined herein, or a kit as defined herein, to label a formalin-fixed paraffin-embedded (FFPE) nucleic acid sample, wherein the multimeric barcoding reagent or the components of the kit is/are introduced into the sample and used to label a set of two or more co-localised target nucleic acids for sequencing.

The multimeric barcoding reagents for use in labelling a FFPE nucleic acid sample may be less than 10 kb, less than 5 kb, less than 2 kb, less than 1 kb in length or less than 500 bp. Preferably, the multimeric barcoding reagents are less than 1 kb in length.

The invention further provides the use of a multimeric barcoding reagent as defined herein, a library of multimeric barcoding reagents as defined herein, or a kit as defined herein, to label target nucleic acids in an individual cell, wherein the multimeric barcoding reagent or the components of the kit is/are introduced into a cell and used to label a set of two or more target nucleic acids in the cell for sequencing.

The invention further provides the use of a multimeric barcoding reagent as defined herein, a library of multimeric barcoding reagents as defined herein, or a kit as defined herein, to label target nucleic acids in a sample of human plasma or serum, wherein the multimeric barcoding reagent or the components of the kit is/are used to label a set of two or more target nucleic acids in the plasma or serum for sequencing.

The invention is further defined in the following set of numbered clauses:

1. A library of multimeric barcoding reagents comprising at least 2 multimeric barcoding reagents for labelling target nucleic acids for sequencing, wherein each multimeric barcoding reagent comprises:
   (a) first and second hybridization molecules linked together, wherein each of the hybridization molecules comprises a nucleic acid sequence comprising a hybridization region;
   (b) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule, wherein the barcoded oligonucleotides each comprise a barcode region; and
   (c) a cell-binding moiety;
   wherein the barcode regions of the first and second barcoded oligonucleotides of a first multimeric barcoding reagent of the library are different to the barcode regions of the first and second barcoded oligonucleotides of a second multimeric barcoding reagent of the library.

2. The method of clause 1, wherein a cell-binding moiety is attached to each of the hybridization molecules.
3. The library of clause 1, wherein the library comprises at least two multimeric barcoding reagents, wherein each multimeric barcoding reagent comprises:
   (a) first and second barcode molecules linked together, wherein each of the barcode molecules comprises a nucleic acid sequence comprising a barcode region;
   (b) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and
   (c) a cell-binding moiety;
   wherein the barcode regions of the first and second barcoded oligonucleotides of a first multimeric barcoding reagent of the library are different to the barcode regions of the first and second barcoded oligonucleotides of a second multimeric barcoding reagent of the library.
4. The library of clause 3, wherein a cell-binding moiety is attached to each of the barcode molecules.
5. The library of any one of clauses 1-4, wherein a cell-binding moiety is attached to each of the barcoded oligonucleotides.
6. A kit for labelling target nucleic acids for sequencing, wherein the kit comprises:
   (a) a library of multimeric barcoding reagents comprising at least two multimeric barcoding reagents, wherein each multimeric barcoding reagent comprises
      (i) first and second barcode molecules linked together, wherein each of the barcode molecules comprises a nucleic acid sequence comprising, optionally in the 5' to 3' direction, an adapter region and a barcode region,
      (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule;
      wherein the barcode regions of the first and second barcoded oligonucleotides of a first multimeric barcoding reagent of the library are different to the barcode regions of the first and second barcoded oligonucleotides of a second multimeric barcoding reagent of the library; and
   (b) first and second adapter oligonucleotides for each of the multimeric barcoding reagents, wherein the first adapter oligonucleotide comprises an adapter region capable of annealing to the adapter region of the first barcode molecule and wherein the second adapter oligonucleotide comprises an adapter region capable of annealing to the adapter region of the second barcode molecule, and wherein a cell-binding moiety is attached to each of the adapter oligonucleotides.
7. The kit of clause 6, wherein the multimeric barcoding reagents each comprise a cell-binding moiety.
8. The kit of clause 7, wherein a cell-binding moiety is attached to each of the barcode molecules.
9. The kit of clause 7 or clause 8, wherein a cell-binding moiety is attached to each of the barcoded oligonucleotides.
10. The library of any one of clauses 1-5, wherein the first multimeric barcoding reagent is comprised within a first lipid carrier and the second multimeric barcoding reagent is comprised within a second lipid carrier.
11. The kit of any one of clauses 6-9, wherein the first and second adapter oligonucleotides for the first multimeric barcoding reagent are comprised within a first lipid carrier and the first and second adapter oligonucleotides for the second multimeric barcoding reagent are comprised within a second lipid carrier.
12. The kit of clause 11, wherein the first lipid carrier further comprises the first multimeric barcoding reagent and wherein the second lipid carrier further comprises the second multimeric barcoding reagent.
13. The library or kit of any one of clauses 10-12, wherein the lipid carrier is a liposome or a micelle.
14. The library or kit of any one of clauses 1-13, wherein the multimeric barcoding reagents each comprise a solid support or semi-solid support, and wherein a cell-binding moiety is attached to the solid support.
15. The library or kit of any one of clauses 1-14, wherein a cell-binding moiety is attached to each barcoded oligonucleotide, hybridization molecule, barcode molecule and/or adapter oligonucleotide by a linker molecule.
16. The library of kit of any one of clauses 1-15, wherein the cell-binding moiety is capable of initiating endocytosis on binding to a cell membrane.
17. The library or kit of any one of clauses 1-16, wherein the cell-binding moiety comprises one or more moieties selected from: a peptide, a cell penetrating peptide, an aptamer, a DNA adptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a cationic lipid, a cationic polymer, poly(ethylene) glycol, spermine, a spermine derivatives or analogue, a poly-lysine, a poly-lysine derivative or analogue, polyethyleneimine, diethylaminoethyl (DEAE)-dextran, cholesterol, a sterol moiety, a cationic molecule, a hydrophobic molecule and an amphiphilic molecule.
18. A method of preparing a nucleic acid sample for sequencing, wherein the sample comprises at least two cells, and wherein the method comprises the steps of:
   (a) contacting the sample with a library comprising at least two multimeric barcoding reagents, wherein each multimeric barcoding reagent comprises first and second barcode regions linked together and a cell-binding moiety, wherein each barcode region comprises a nucleic acid sequence and wherein the first and second barcode regions of a first multimeric barcoding reagent are different to the first and second barcode regions of a second multimeric barcoding reagent of the library, wherein the cell-binding moiety of the first multimeric barcoding reagent from the library binds to the cell membrane of a first cell of the sample and the first and second barcode regions of the first multimeric barcoding reagent are internalized into the first cell, and wherein the cell-binding moiety of the second multimeric barcoding reagent from the library binds to the cell membrane of a second cell of the sample and the first and second barcode regions of the second multimeric barcoding reagent are internalized into the second cell; and (b) appending barcode sequences to each of first and second sub-sequences of a target nucleic acid of the first cell to produce first and second barcoded target nucleic acid molecules for the first cell, wherein the first barcoded target nucleic acid molecule comprises the nucleic acid sequence of the first barcode region of the first multimeric barcoding reagent and the second barcoded target nucleic acid molecule comprises the nucleic acid sequence of the second barcode region of the first multimeric barcoding reagent, and appending barcode sequences to each of first and second sub-sequences of a target nucleic acid of the second cell to produce first and second barcoded target nucleic acid molecules for the second cell, wherein the first barcoded target nucleic acid molecule comprises the nucleic acid sequence of the first barcode region of the second multimeric barcoding reagent and the second barcoded target nucleic acid molecule comprises the nucleic acid sequence of the second barcode region of the second multimeric barcoding reagent.

19. The method of clause 18, wherein the method comprises the steps of:
(a) contacting the sample with a library comprising at least two multimeric barcoding reagents, wherein each multimeric barcoding reagent comprises first and second barcoded oligonucleotides linked together and a cell-binding moiety, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library, wherein the cell-binding moiety of a first multimeric barcoding reagent from the library binds to the cell membrane of a first cell of the sample and the first and second barcoded oligonucleotides of the first multimeric barcoding reagent are internalized into the first cell, and wherein the cell-binding moiety of a second multimeric barcoding reagent from the library binds to the cell membrane of a second cell of the sample and the first and second barcoded oligonucleotides of the second multimeric barcoding reagent are internalized into the second cell; and
(b) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules.

20. The method of clause 18, wherein step (b) comprises:
(i) annealing the first and second barcoded oligonucleotides of the first multimeric barcoding reagent to first and second sub-sequences of a target nucleic acid of the first cell, and annealing the first and second barcoded oligonucleotides of the second multimeric barcoding reagent to first and second sub-sequences of a target nucleic acid of the second cell; and
(ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the target nucleic acid as a template.

21. The method of any one of clauses 18-20, wherein a cell-binding moiety is attached to each of the barcoded oligonucleotides.

22. The method of any one of clauses 18-21, wherein the multimeric barcoding reagents each comprise:
(i) first and second hybridization molecules linked together, wherein each of the hybridization molecules comprises a nucleic acid sequence comprising a hybridization region; and
(ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule;
optionally wherein the first multimeric barcoding reagent is internalized into the first cell and the second multimeric barcoding reagent is internalized into the second cell.

23. The method of clause 22, wherein a cell-binding moiety is attached to each of the hybridization molecules.

24. The method of clause 22, wherein the multimeric barcoding reagents each comprise:
(i) first and second barcode molecules linked together, wherein each of the barcode molecules comprises a nucleic acid sequence comprising a barcode region; and
(ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule;
optionally wherein the first multimeric barcoding reagent is internalized into the first cell and the second multimeric barcoding reagent is internalized into the second cell.

25. The method of clause 24, wherein a cell-binding moiety is attached to each of the barcode molecules.

26. A method of preparing a nucleic acid sample for sequencing, wherein the sample comprises at least two cells, and wherein the method comprises the steps of:
(a) contacting the sample with a library comprising first and second multimeric barcoding reagents, wherein each multimeric barcoding reagent comprises:
(i) first and second barcode molecules linked together, wherein each of the barcode molecules comprises a nucleic acid sequence comprising, optionally in the 5' to 3' direction, an adapter region and a barcode region, and
(ii) first and second barcoded oligonucleotides, wherein the first barcoded oligonucleotide comprises a barcode region annealed to the barcode region of the first barcode molecule and wherein the second barcoded oligonucleotide comprises a barcode region annealed to the barcode region of the second barcode molecule, and wherein the barcode regions of the first and second barcoded oligonucleotides of the first multimeric barcoding reagent of the library are different to the barcode regions of the first and second barcoded oligonucleotides of the second multimeric barcoding reagent of the library;

wherein the sample is further contacted with first and second adapter oligonucleotides for each of the multimeric barcoding reagents, wherein the first and second adapter oligonucleotides each comprise an adapter region, wherein a cell-binding moiety is attached to each of the adapter oligonucleotides, and wherein the cell-binding moieties of the first and second adapter oligonucleotides for the first multimeric barcoding reagent bind to the cell membrane of a first cell of the sample and the first and second adapter oligonucleotides for the first multimeric barcoding reagent are internalized into the first cell, and wherein the cell-binding moieties of the first and second adapter oligonucleotides for the second multimeric barcoding reagent bind to the cell membrane of a second cell of the sample and the first and second adapter oligonucleotides for the second multimeric barcoding reagent are internalized into the second cell;

(b) annealing or ligating the first and second adapter oligonucleotides for the first multimeric barcoding reagent to sub-sequences of a target nucleic acid of the first cell, and annealing or ligating the first and second adapter oligonucleotides for the second multimeric barcoding reagent to sub-sequences of a target nucleic acid of the second cell;

(c) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and (d) for each of the multimeric barcoding reagents, ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.

27. The method of clause 26, wherein step (b) comprises annealing the first and second adapter oligonucleotides for the first multimeric barcoding reagent to sub-sequences of a target nucleic acid of the first cell, and annealing the first and second adapter oligonucleotides for the second multimeric barcoding reagent to sub-sequences of a target nucleic acid of the second cell, and wherein either:

(i) for each of the multimeric barcoding reagents, step (d) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the target nucleic acid as a template, or (ii) for each of the multimeric barcoding reagents, before step (d), the method comprises extending the first and second adapter oligonucleotides to produce first and second different target nucleic acid molecules each of which comprises at least one nucleotide synthesised from the target nucleic acid as a template.

28. The method of clause 27, wherein the multimeric barcoding reagents each comprise a cell-binding moiety, optionally wherein:

(i) the cell-binding moiety of the first multimeric barcoding reagent binds to the cell membrane of the first cell of the sample and the multimeric barcoding reagent is internalized into the first cell and (ii) the cell-binding moiety of the second multimeric barcoding reagent binds to the cell membrane of the second cell of the sample and the second multimeric barcoding reagent is internalized into the second cell.

29. The method of clause 28, wherein a cell-binding moiety is attached to each of the barcode molecules.

30. The method of clause 28 or clause 29, wherein a cell-binding moiety is attached to each of the barcoded oligonucleotides.

31. The method of any one of clauses 18-25, wherein the first multimeric barcoding reagent is comprised within a first lipid carrier and the second multimeric barcoding reagent is comprised within a second lipid carrier, optionally wherein in step (a) the first lipid carrier merges with the cell membrane of the first cell and the first and second barcoded oligonucleotides of the first multimeric barcoding reagent are internalized into the first cell, and the second lipid carrier merges with the cell membrane of the second cell and the first and second barcoded oligonucleotides of the first multimeric barcoding reagent are internalized into the second cell.

32. The method of any one of clauses 26-30, wherein the first and second adapter oligonucleotides for the first multimeric barcoding reagent are comprised within a first lipid carrier and the first and second adapter oligonucleotides for the second multimeric barcoding reagent are comprised within a second lipid carrier, optionally wherein in step (a) the first lipid carrier merges with the cell membrane of the first cell and the first and second adapter oligonucleotides for the first multimeric barcoding reagent are internalized into the first cell, and the second lipid carrier merges with the cell membrane of the second cell and the first and second adapter oligonucleotides for the second multimeric barcoding reagent are internalized into the second cell.

33. The method of clause 32, wherein the first lipid carrier further comprises the first multimeric barcoding reagent and wherein the second lipid carrier further comprises the second multimeric barcoding reagent.

34. The method of any one of clauses 31-33, wherein the lipid carrier is a liposome or micelle.

35. The method of any one of clauses 18-34, wherein the multimeric barcoding reagents each comprise a solid support or semi-solid support, and wherein a cell-binding moiety is attached to the solid support.

36. The method of any one of clauses 18-35, wherein a cell-binding moiety is attached to each barcoded oligonucleotide, hybridization molecule, barcode molecule and/or adapter oligonucleotide by a linker molecule.

37. The method of any one of clauses 18-36, wherein the multimeric barcoding reagents and/or adapter oligonucleotides are internalized by endocytosis.

38. The method of any one of clauses 18-37, wherein the cell-binding moiety comprises one or more moieties selected from: a peptide, a cell penetrating peptide, an aptamer, a DNA adptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a cationic lipid, a cationic polymer, poly(ethylene) glycol, spermine, a spermine derivatives or analogue, a poly-lysine, a poly-lysine derivative or analogue, polyethyleneimine, diethylaminoethyl (DEAE)-dextran, cholesterol, a sterol moiety, a cationic molecule, a hydrophobic molecule and an amphiphilic molecule.

39. A method of preparing a nucleic acid sample for sequencing, wherein the sample comprises at least two cells, and wherein the method comprises the steps of:
   (a) contacting the sample with a library comprising at least two multimeric barcoding reagents, wherein each multimeric barcoding reagent comprises first and second barcode regions linked together, wherein each barcode region comprises a nucleic acid sequence and wherein the first and second barcode regions of a first multimeric barcoding reagent are different to the first and second barcode regions of a second multimeric barcoding reagent of the library;
   (b) transferring the first and second barcode regions of the first multimeric barcoding reagent from the library into a first cell of the sample and transferring the first and second barcode regions of the second multimeric barcoding reagent from the library into a second cell of the sample; and
   (c) appending barcode sequences to each of first and second sub-sequences of a target nucleic acid of the first cell to produce first and second barcoded target nucleic acid molecules for the first cell, wherein the first barcoded target nucleic acid molecule comprises the nucleic acid sequence of the first barcode region of the first multimeric barcoding reagent and the second barcoded target nucleic acid molecule comprises the nucleic acid sequence of the second barcode region of the first multimeric barcoding reagent, and appending barcode sequences to each of first and second sub-sequences of a target nucleic acid of the second cell to produce first and second barcoded target nucleic acid molecules for the second cell, wherein the first barcoded target nucleic acid molecule comprises the nucleic acid sequence of the first barcode region of the second multimeric barcoding reagent and the second barcoded target nucleic acid molecule comprises the nucleic acid sequence of the second barcode region of the second multimeric barcoding reagent.

40. The method of clause 39, wherein the method comprises the steps of:
   (a) contacting the sample with a library comprising at least two multimeric barcoding reagents, wherein each multimeric barcoding reagent comprises first and second barcoded oligonucleotides linked together, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library;
   (b) transferring the first and second barcoded oligonucleotides of the first multimeric barcoding reagent from the library into a first cell of the sample and transferring the first and second barcoded oligonucleotides of the second multimeric barcoding reagent from the library into a second cell of the sample; and
   (c) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules.

41. The method of clause 40, wherein step (c) comprises:
   (i) annealing the first and second barcoded oligonucleotides of the first multimeric barcoding reagent to first and second sub-sequences of a target nucleic acid of the first cell, and annealing the first and second barcoded oligonucleotides of the second multimeric barcoding reagent to first and second sub-sequences of a target nucleic acid of the second cell; and
   (ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the target nucleic acid as a template.

42. The method of any one of clauses 39-41, wherein the multimeric barcoding reagents each comprise:
   (i) first and second hybridization molecules linked together, wherein each of the hybridization molecules comprises a nucleic acid sequence comprising a hybridization region; and
   (ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule;
   optionally wherein step (b) comprises transferring the first multimeric barcoding reagent into the first cell and transferring the second multimeric barcoding reagent into the second cell.

43. The method of clause 42, wherein the multimeric barcoding reagents each comprise:
   (i) first and second barcode molecules linked together, wherein each of the barcode molecules comprises a nucleic acid sequence comprising a barcode region; and
   (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule;

optionally wherein step (b) comprises transferring the first multimeric barcoding reagent into the first cell and transferring the second multimeric barcoding reagent into the second cell.

44. A method of preparing a nucleic acid sample for sequencing, wherein the sample comprises at least two cells, and wherein the method comprises the steps of:
   (a) contacting the sample with a library comprising first and second multimeric barcoding reagents, wherein each multimeric barcoding reagent comprises:
      (i) first and second barcode molecules linked together, wherein each of the barcode molecules comprises a nucleic acid sequence comprising, optionally in the 5' to 3' direction, an adapter region and a barcode region, and
      (ii) first and second barcoded oligonucleotides, wherein the first barcoded oligonucleotide comprises a barcode region annealed to the barcode region of the first barcode molecule, wherein the second barcoded oligonucleotide comprises a barcode region annealed to the barcode region of the second barcode molecule, and wherein the barcode regions of the first and second barcoded oligonucleotides of the first multimeric barcoding reagent of the library are different to the barcode regions of the first and second barcoded oligonucleotides of the second multimeric barcoding reagent of the library;
   wherein the sample is further contacted with first and second adapter oligonucleotides for each of the multimeric barcoding reagents, wherein the first and second adapter oligonucleotides each comprise an adapter region;
   (b) transferring the first and second adapter oligonucleotides for the first multimeric barcoding reagent into the first cell and transferring the first and second adapter oligonucleotides for the second multimeric barcoding reagent into the second cell, optionally wherein the step further comprises transferring the first multimeric barcoding reagent into the first cell and transferring the second multimeric barcoding reagent into the second cell;
   (c) annealing or ligating the first and second adapter oligonucleotides for the first multimeric barcoding reagent to sub-sequences of a target nucleic acid of the first cell, and annealing or ligating the first and second adapter oligonucleotides for the second multimeric barcoding reagent to sub-sequences of a target nucleic acid of the second cell;
   (d) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and
   (e) for each of the multimeric barcoding reagents, ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.

45. The method of clause 44, wherein step (c) comprises annealing the first and second adapter oligonucleotides for the first multimeric barcoding reagent to sub-sequences of a target nucleic acid of the first cell, and annealing the first and second adapter oligonucleotides for the second multimeric barcoding reagent to sub-sequences of a target nucleic acid of the second cell, and wherein either:
   (i) for each of the multimeric barcoding reagents, step (e) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the target nucleic acid as a template, or
   (ii) for each of the multimeric barcoding reagents, before step (e), the method comprises extending the first and second adapter oligonucleotides to produce first and second different target nucleic acid molecules each of which comprises at least one nucleotide synthesised from the target nucleic acid as a template.

46. The method of any one of clauses 39-45, wherein prior to step (b), the cell membrane of the cells are permeabilised by contact with a chemical surfactant.

47. The method of any one of clauses 39-46, wherein prior to step (b), the cell membrane of the cells are permeabilised by contact with a solvent.

48. The method of any one of clauses 39-47, wherein the barcoded oligonucleotides, adapter oligonucleotides and/or multimeric barcoding reagents are transferred into the cells by complexation with a transfection reagent or lipid carrier.

49. The method of any one of clauses 39-48, wherein the barcoded oligonucleotides of the first multimeric barcoding reagent are comprised within a first lipid carrier, and wherein the barcoded oligonucleotides of the second multimeric barcoding reagent are comprised within a second lipid carrier.

50. The method of any one of clauses 39-49, wherein the barcoded oligonucleotides, adapter oligonucleotides and/or multimeric barcoding reagents are transferred into the cells by a process comprising cell squeezing.

51. The method of any one of clauses 39-50, wherein the barcoded oligonucleotides, adapter oligonucleotides and/or multimeric barcoding reagents are transferred into the cells by a process comprising electroporation.

52. A method of preparing a nucleic acid sample for sequencing, wherein the sample comprises at least two cells, and wherein the method comprises the steps of:
   (a) contacting the sample with a library comprising at least two multimeric barcoding reagents, wherein each multimeric barcoding reagent comprises first and second barcode regions linked together, wherein each barcode region comprises a nucleic acid sequence and wherein the first and second barcode regions of a first multimeric barcoding reagent are different to the first and second barcode regions of a second multimeric barcoding reagent of the library;
   (b) lysing the cells or permeabilizing the cell membranes of the cells; and (c) appending barcode sequences to each of first and second sub-sequences of a target nucleic acid of the first cell to produce first and second barcoded target nucleic acid molecules for the first cell, wherein the first barcoded target nucleic acid molecule comprises the nucleic acid sequence of the first barcode region of the first multimeric barcoding reagent and the second barcoded target nucleic acid molecule comprises the nucleic acid sequence of the second barcode region of the first multimeric barcoding reagent, and appending barcode sequences to each of first and second sub-sequences of a target nucleic acid of the second cell to produce first and second barcoded target nucleic acid molecules for the second cell, wherein the first barcoded target nucleic acid molecule comprises the nucleic acid sequence of the first barcode region of the second multimeric barcoding reagent and the second barcoded target nucleic acid molecule comprises the nucleic acid sequence of the second barcode region of the second multimeric barcoding reagent.

53. The method of clause 52, wherein the method comprises the steps of:
   (a) contacting the sample with a library comprising at least two multimeric barcoding reagents, wherein each multimeric barcoding reagent comprises first and second barcoded oligonucleotides linked together, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library;
   (b) lysing the cells or permeabilizing the cell membranes of the cells; and
   (c) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules.

54. The method of clause 52, wherein step (c) comprises:
   (i) annealing the first and second barcoded oligonucleotides of the first multimeric barcoding reagent to first and second sub-sequences of a target nucleic acid of the first cell, and annealing the first and second barcoded oligonucleotides of the second multimeric barcoding reagent to first and second sub-sequences of a target nucleic acid of the second cell; and
   (ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the target nucleic acid as a template.

55. The method of any one of clauses 52-54, wherein the multimeric barcoding reagents each comprise:
   (i) first and second hybridization molecules linked together, wherein each of the hybridization molecules comprises a nucleic acid sequence comprising a hybridization region; and
   (ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule.

56. The method of clause 55, wherein the multimeric barcoding reagents each comprise:
   (i) first and second barcode molecules linked together, wherein each of the barcode molecules comprises a nucleic acid sequence comprising a barcode region; and
   (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule.

57. A method of preparing a nucleic acid sample for sequencing, wherein the sample comprises at least two cells, and wherein the method comprises the steps of:
   (a) contacting the sample with a library comprising first and second multimeric barcoding reagents, wherein each multimeric barcoding reagent comprises:
     (i) first and second barcode molecules linked together, wherein each of the barcode molecules comprises a nucleic acid sequence comprising, optionally in the 5' to 3' direction, an adapter region and a barcode region, and
     (ii) first and second barcoded oligonucleotides, wherein the first barcoded oligonucleotide comprises a barcode region annealed to the barcode region of the first barcode molecule and wherein the second barcoded oligonucleotide comprises a barcode region annealed to the barcode region of the second barcode molecule, and wherein the barcode regions of the first and second barcoded oligonucleotides of the first multimeric barcoding reagent are different to the barcode regions of the first and second barcoded oligonucleotides of the second multimeric barcoding reagent;
   wherein the sample is further contacted with first and second adapter oligonucleotides for each of the multimeric barcoding reagents, wherein the first and second adapter oligonucleotides each comprise an adapter region;
   (b) lysing the cells or permeabilizing the cell membranes of the cells;
   (c) annealing or ligating the first and second adapter oligonucleotides for the first multimeric barcoding reagent to sub-sequences of a target nucleic acid of the first cell, and annealing or ligating the first and second adapter oligonucleotides for the second multimeric barcoding reagent to sub-sequences of a target nucleic acid of the second cell;
   (d) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and (e) for each of the multimeric barcoding reagents, ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.

58. The method of clause 57, wherein step (c) comprises annealing the first and second adapter oligonucleotides for the first multimeric barcoding reagent to sub-sequences of a target nucleic acid of the first cell, and annealing the first and second adapter oligonucleotides for the second multimeric barcoding reagent to sub-sequences of a target nucleic acid of the second cell, and wherein either:

(i) for each of the multimeric barcoding reagents, step (e) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the target nucleic acid as a template, or (ii) for each of the multimeric barcoding reagents, before step (e), the method comprises extending the first and second adapter oligonucleotides to produce first and second different target nucleic acid molecules each of which comprises at least one nucleotide synthesised from the target nucleic acid as a template.

59. The method of any one of clauses 52-58, wherein following step (b) target nucleic acids from each cell within the sample are able to diffuse out of the cell.

60. The method of any one of clauses 52-59, wherein step (b) is performed by increasing the temperature of the sample.

61. The method of any one of clauses 52-60, wherein step (b) is performed in the presence of a chemical surfactant.

62. The method of any one of clauses 52-61, wherein step (b) is performed in the presence of a solvent.

63. The method of any one of clauses 52-62, wherein step (b) is performed under hypotonic or hypertonic conditions.

64. The method of any one of clauses 52-63, wherein the multimeric barcoding reagents and/or adapter oligonucleotides each comprise a cell-binding moiety, optionally wherein the cell-binding moiety binds each multimeric barcoding reagent and/or adapter oligonucleotide to the cell membrane of the cells prior to step (b).

65. The method of any one of clauses 18-64, wherein the target nucleic acids are mRNA.

BRIEF DESCRIPTION OF THE DRAWINGS

The invention, together with further objects and advantages thereof, may best be understood by making reference to the description taken together with the accompanying drawings, in which:

FIG. 15 is a table showing the results of barcoding genomic DNA loci of three human genes (BRCA1, HLA-A and DQB1) with multimeric barcoding reagents containing barcoded oligonucleotides.

FIG. 18 illustrates examples of multimeric barcoding reagents comprising cell-binding moieties.

FIG. 19A-19B illustrates a method of transferring multimeric barcoding reagents into cells via cell-binding moieties.

FIG. 20A-20B illustrates a method of transferring multimeric barcoding reagents into cells via liposomal delivery.

FIG. 21A-21B illustrates a method of transferring multimeric barcoding reagents into cells via transfection.

FIG. 22A-22B illustrates a method of transferring multimeric barcoding reagents into cells via a permeabilisation process.

FIG. 24A-24B illustrates a method of barcoding cellular nucleic acids with a membrane-permeabilisation and barcoded oligonucleotide-release step.

FIG. 18 illustrates examples of multimeric barcoding reagents comprising cell-binding moieties.

Figure 1:
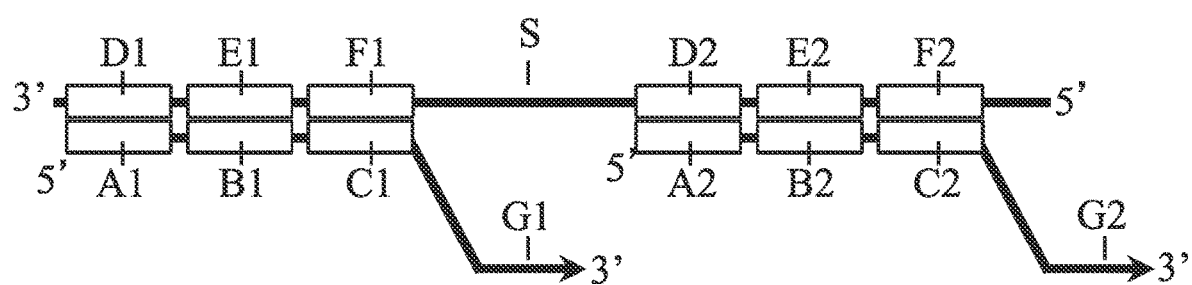
FIG. 1 illustrates a multimeric barcoding reagent that may be used in the method illustrated in FIG. 3 or FIG. 4.
Figure 2:
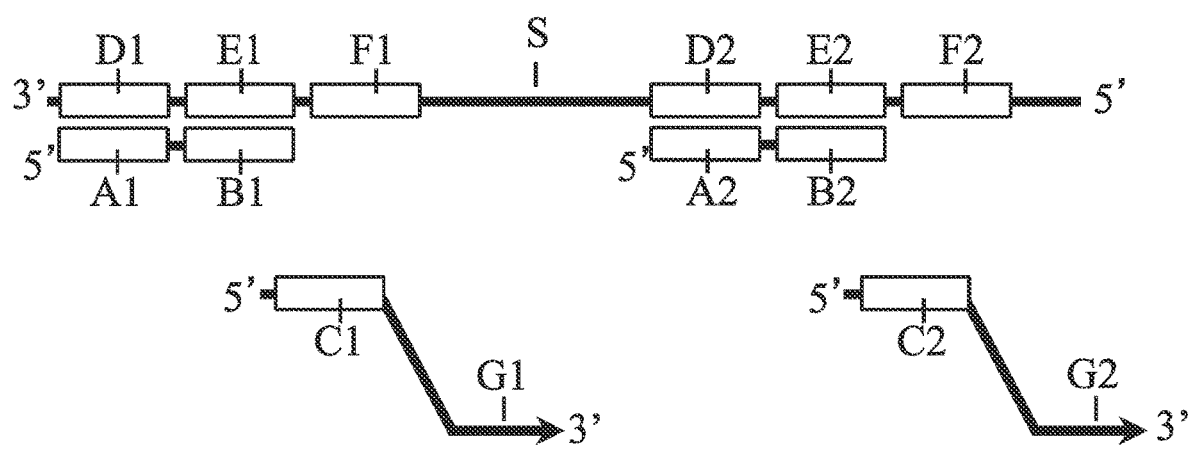
FIG. 2 illustrates a kit comprising a multimeric barcoding reagent and adapter oligonucleotides for labelling a target nucleic acid.
Figure 3:
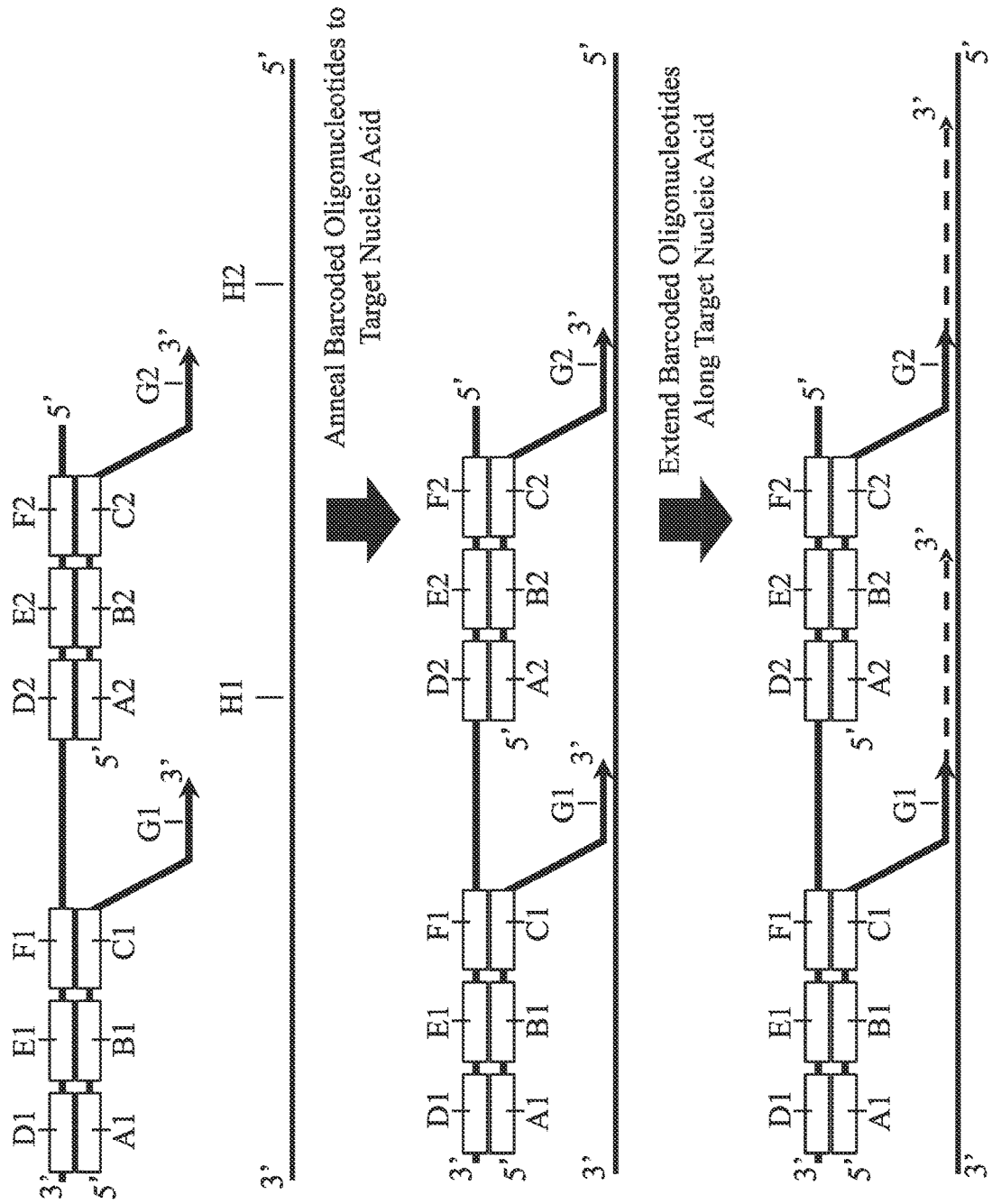
FIG. 3 illustrates a first method of preparing a nucleic acid sample for sequencing using a multimeric barcoding reagent.
Figure 4:
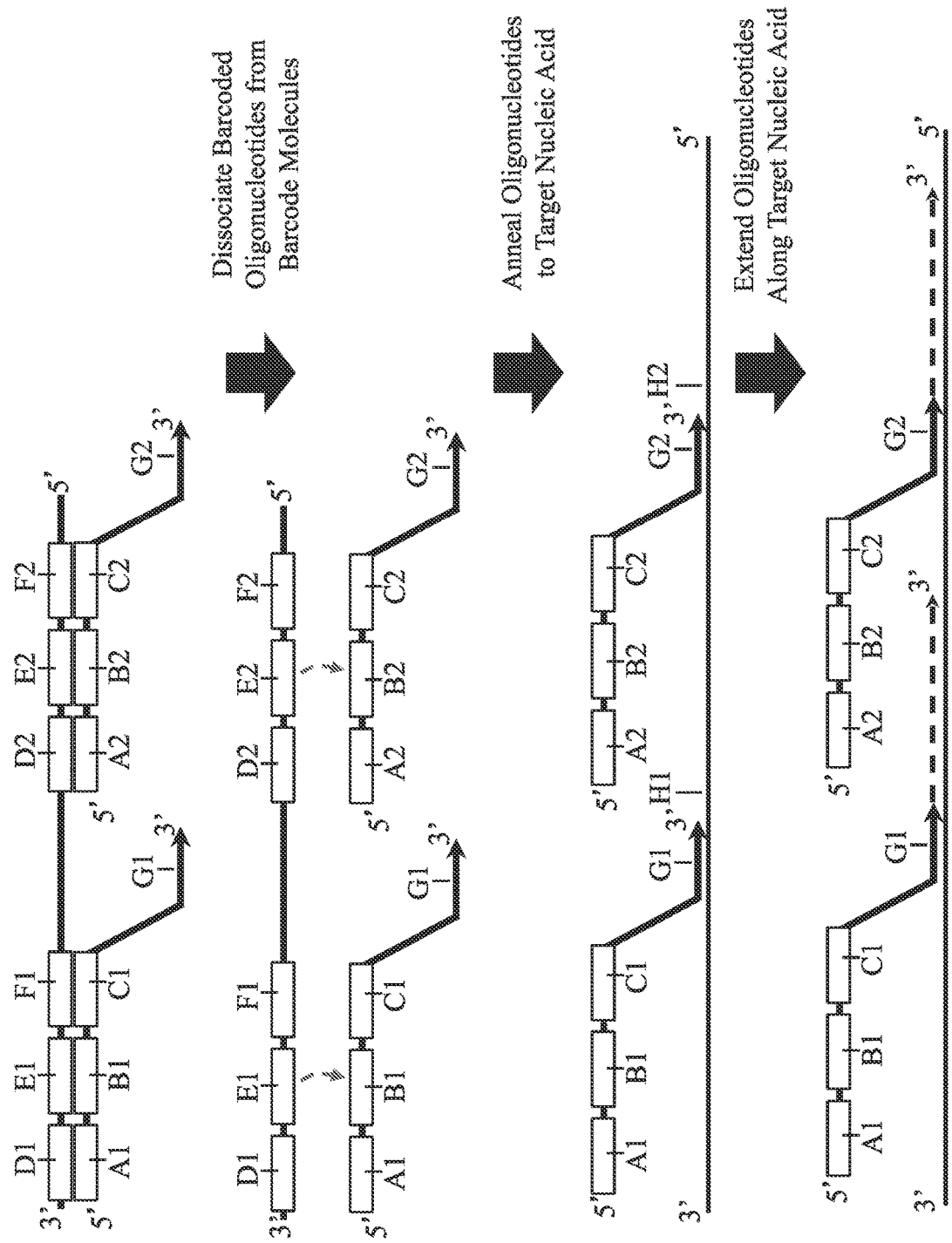
FIG. 4 illustrates a second method of preparing a nucleic acid sample for sequencing using a multimeric barcoding reagent.
Figure 5:
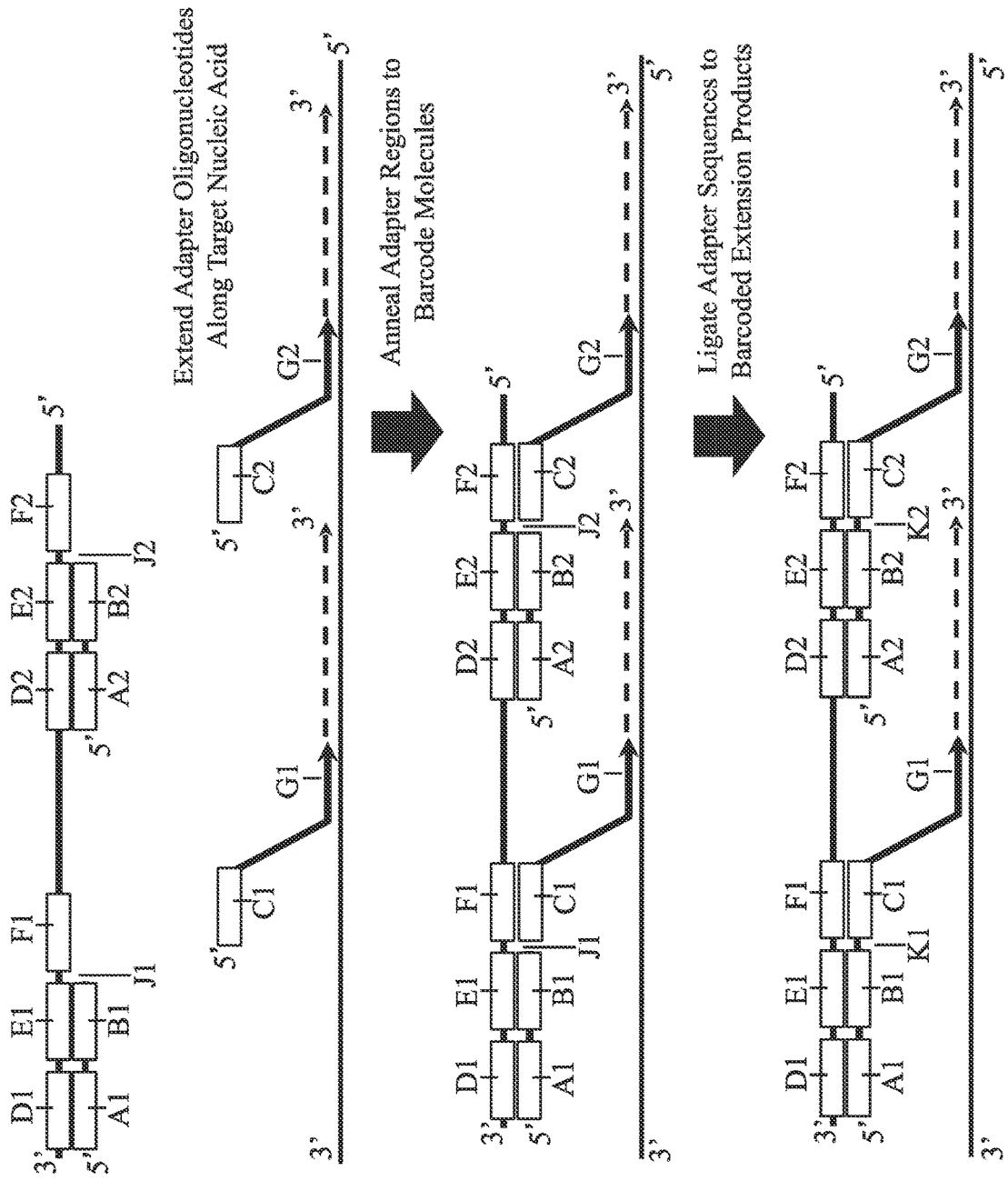
FIG. 5 illustrates a method of preparing a nucleic acid sample for sequencing using a multimeric barcoding reagent and adapter oligonucleotides.
Figure 6:
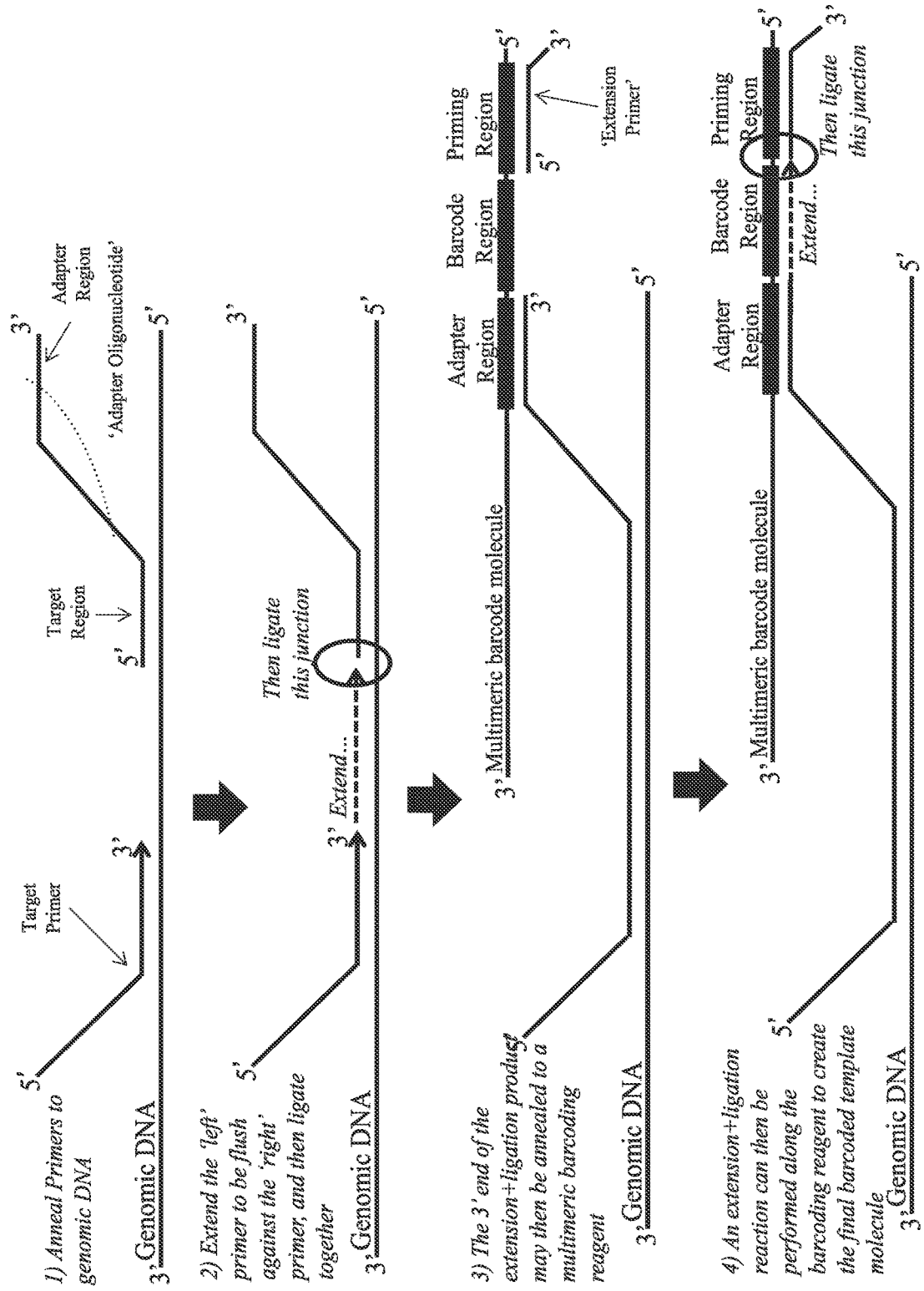
FIG. 6 illustrates a method of preparing a nucleic acid sample for sequencing using a multimeric barcoding reagent, adapter oligonucleotides and target oligonucleotides.
Figure 7:
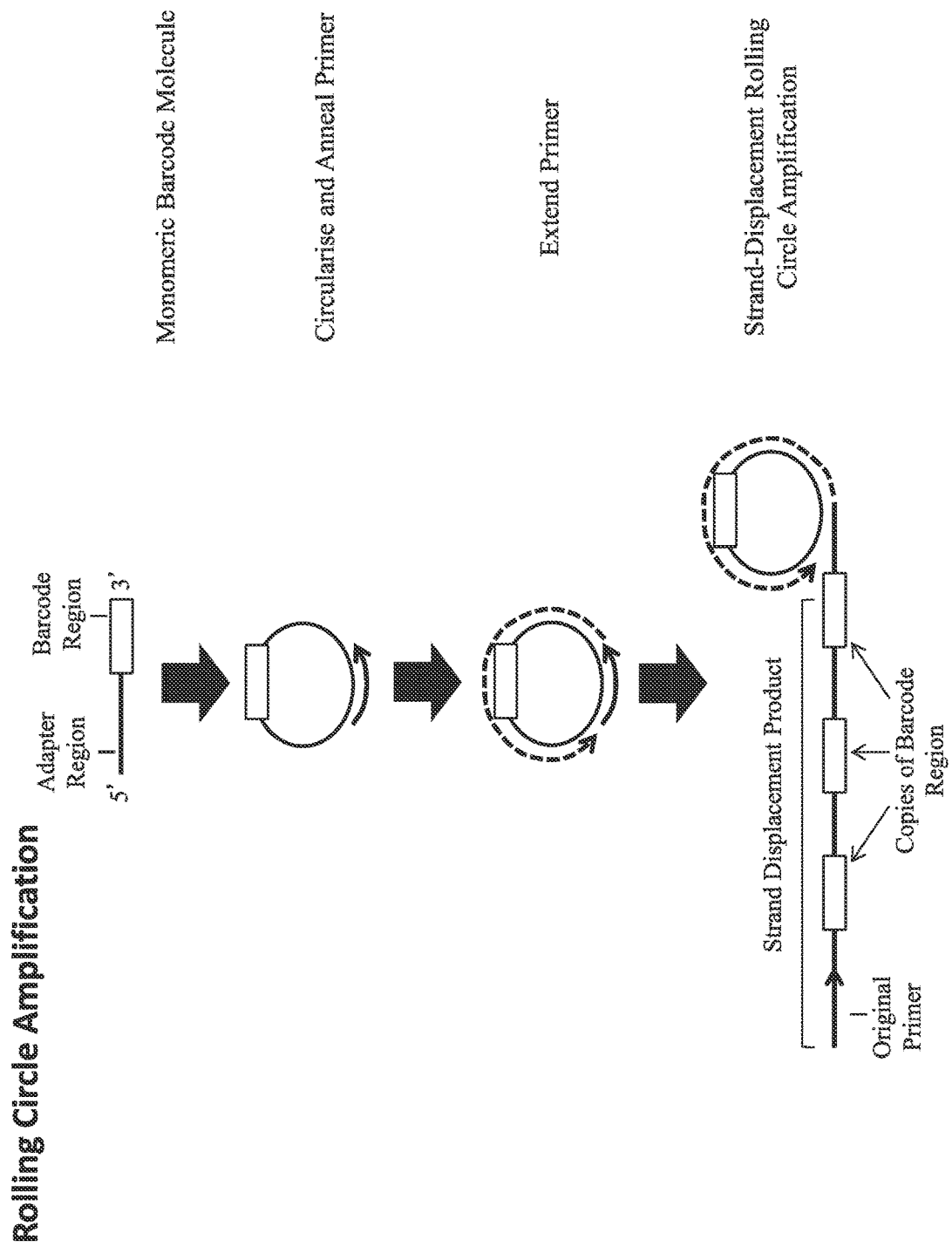
FIG. 7 illustrates a method of assembling a multimeric barcode molecule using a rolling circle amplification process.
Figure 8:
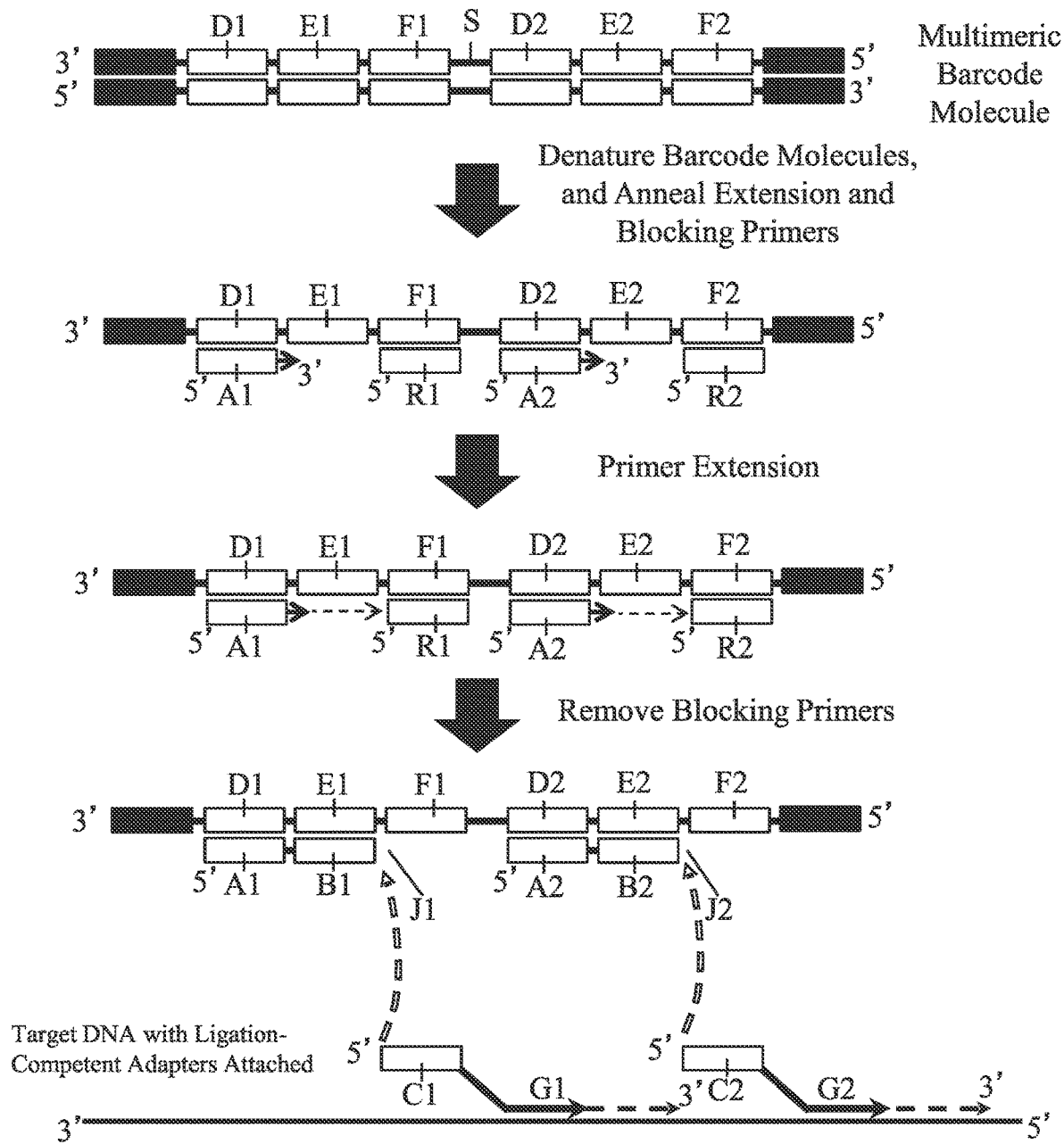
FIG. 8 illustrates a method of synthesizing multimeric barcoding reagents for labeling a target nucleic acid that may be used in the methods illustrated in FIG. 3, FIG. 4 and/or FIG. 5.
Figure 9:
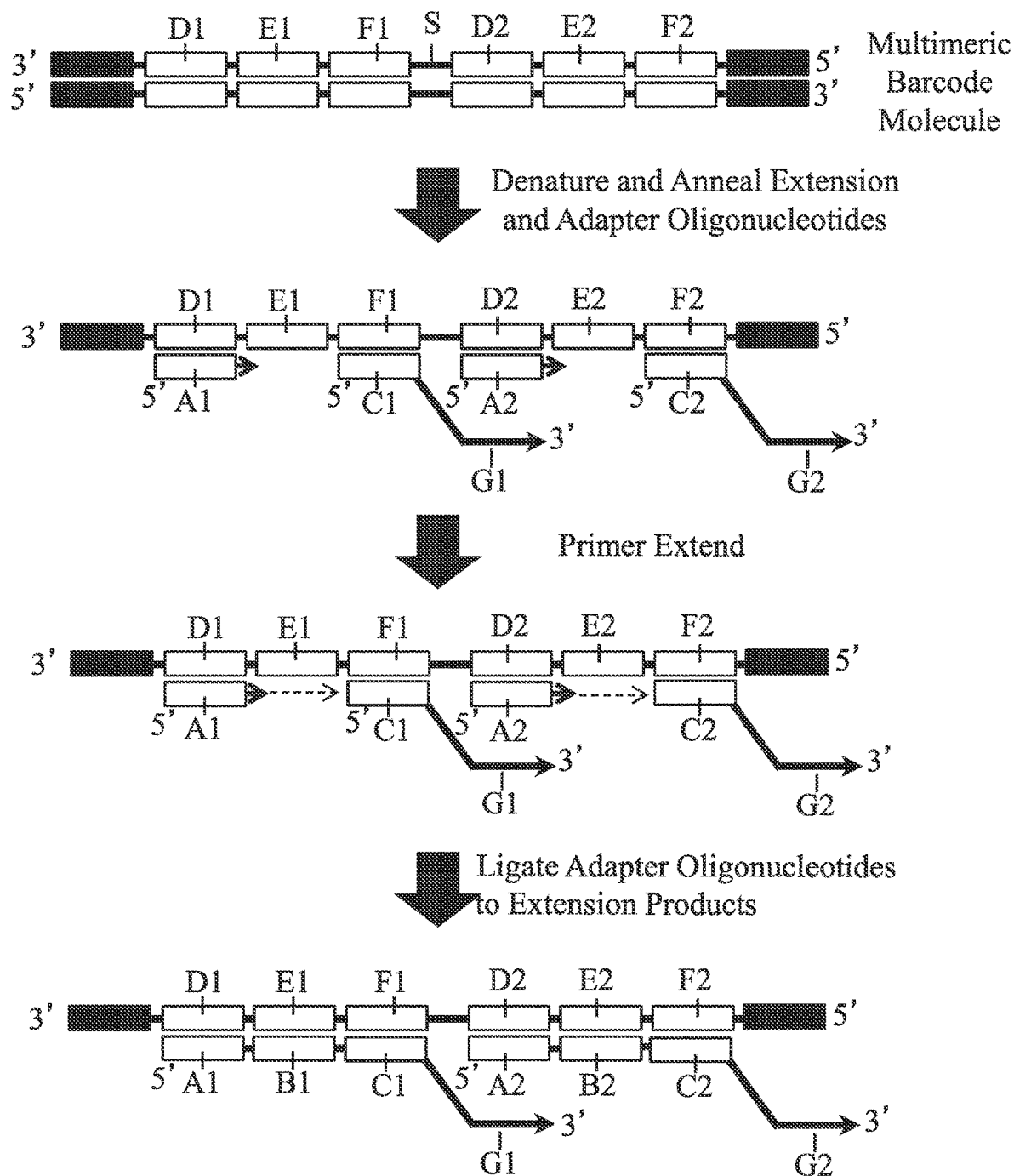
FIG. 9 illustrates an alternative method of synthesizing multimeric barcoding reagents (as illustrated in FIG. 1) for labeling a target nucleic acid that may be used in the method illustrated in FIG. 3 and/or FIG. 4.

The figure shows two different schematic variants of a multimeric barcoding reagent comprising cell-binding moieties. In a first such embodiment (left), a number of cell-binding moieties are attached to a support (such as a bead, or a nucleic acid molecule), and a number of barcoded oligonucleotides are likewise attached to the support. The cell-binding moieties may comprise any sort of molecule or compound able to preferentially interact with cell surfaces, such as antibodies or aptamers which have affinity for specific proteins on the surface of cells, or charge molecules such as poly-lysine moieties which have electrostatic affinity for the charged cell membrane. The attachment of such cell-binding moieties and barcoded oligonucleotides to the support may be direct (e.g. through direct covalent chemical complexation), may be non-covalent (e.g. through protein-protein interactions), and/or may be indirect, such as involving secondary attachment molecules.

In a second embodiment (on right), a number of cell-binding moieties are appended to a support, as are a number of linker molecules comprising a nucleic acid sequence. These linker molecules may be attached directly to the support (e.g. through chemical complexation), or through any other indirect and/or non-covalent binding. A barcoded oligonucleotide is annealed to the nucleic acid sequence of each linker molecule, thus forming an indirect attachment of each barcoded oligonucleotide to the support within the overall multimeric barcoding reagent. The hybridisation region formed between the linker molecules and the barcoded oligonucleotides may further allow for manipulation of the interaction between the barcoded oligonucleotides and the support; for example, a high temperature incubation process may be used to denature the hybridisation region and thus allow barcoded oligonucleotides to diffuse away in solution from the support itself.

FIG. 19A-19B illustrates an example of a method of transferring multimeric barcoding reagents into cells via cell-binding moieties. In the method, multimeric barcoding reagents are transferred into cells by a transfer process involving cell-binding moieties. These cell-binding moieties may comprise any sort of molecular, macromolecular, and/or solid moiety that is capable of preferentially interacting with a cell. For example, this may comprise an antibody capable of binding to a specific protein on the cell surface; alternatively, for example, this may comprise a cationic macromolecule such as a poly-lysine moiety that preferentially interacts with the cell surface by electrostatic attraction.

In a first step, a library of two or more multimeric barcoding reagents each comprising one or more cell-binding moieties are incubated with a sample of cells for a period of time, during which time the multimeric barcoding reagents migrate to come into contact with a cell membrane, and become bound to said cell membrane via one or more associated cell-binding moieties.

In a second step following this cell-binding step, the sample of cells bound to multimeric barcoding reagents is incubated for a period of time, during which time multimeric barcoding reagents are transferred into cells. This transfer process may be effected by any one or more known process of cells internalising constituents bound to or within their cell membrane, such as endocytosis, pinocytosis, and/or phagocytosis. In this illustration, a first multimeric barcoding reagent-lipid complex is transferred into a first cell, and a second multimeric barcoding reagent-lipid complex is transferred into a second cell; in actual embodiments a large library of multimeric barcoding reagents may be transferred into a large sample of cells.

Following this transfer step, an incubation step is performed, during which time messenger RNA molecules complementary to the target regions of barcoded oligonucleotides comprised within the transferred multimeric barcoding reagents are allowed to anneal to said target regions. This incubation may be performed at a temperature conducive to such an annealing process, and/or may be performed in the presence of a modified annealing buffer which may be conducive to such an annealing process (such as a buffer containing a nucleic acid denaturant, such as betaine or DMSO).

Following the annealing step, messenger RNA molecules from individual cells are thus annealed to barcoded oligonucleotides from the multimeric barcoding reagent which was transferred into that cell. In subsequent processing steps (for example, after a step of isolating the annealed messenger RNA molecules and barcoded oligonucleotides), the messenger RNA may be reverse-transcribed with a reverse transcriptase, and then optionally amplified such as with a PCR process, prior to performing a sequencing reaction. The reverse transcription may include either and/or both first-strand reverse transcription (e.g. first-strand cDNA synthesis) and also second-strand synthesis. Furthermore, any step of reverse transcription and/or cDNA synthesis may include any further standard step of cDNA processing, such as fragmentation (e.g. acoustic fragmentation such as Covaris sonication, or e.g. enzymatic fragmentation such as with a fragmentase enzyme, a restriction enzyme, and/or an in vitro transposase enzyme) and adapter (e.g. PCR adapter and/or sequencing adapter) ligation and/or adapter in vitro transposition at any stage(s) prior to and/or after reverse transcription and/or second strand synthesis and/or PCR.

Figure 20B:
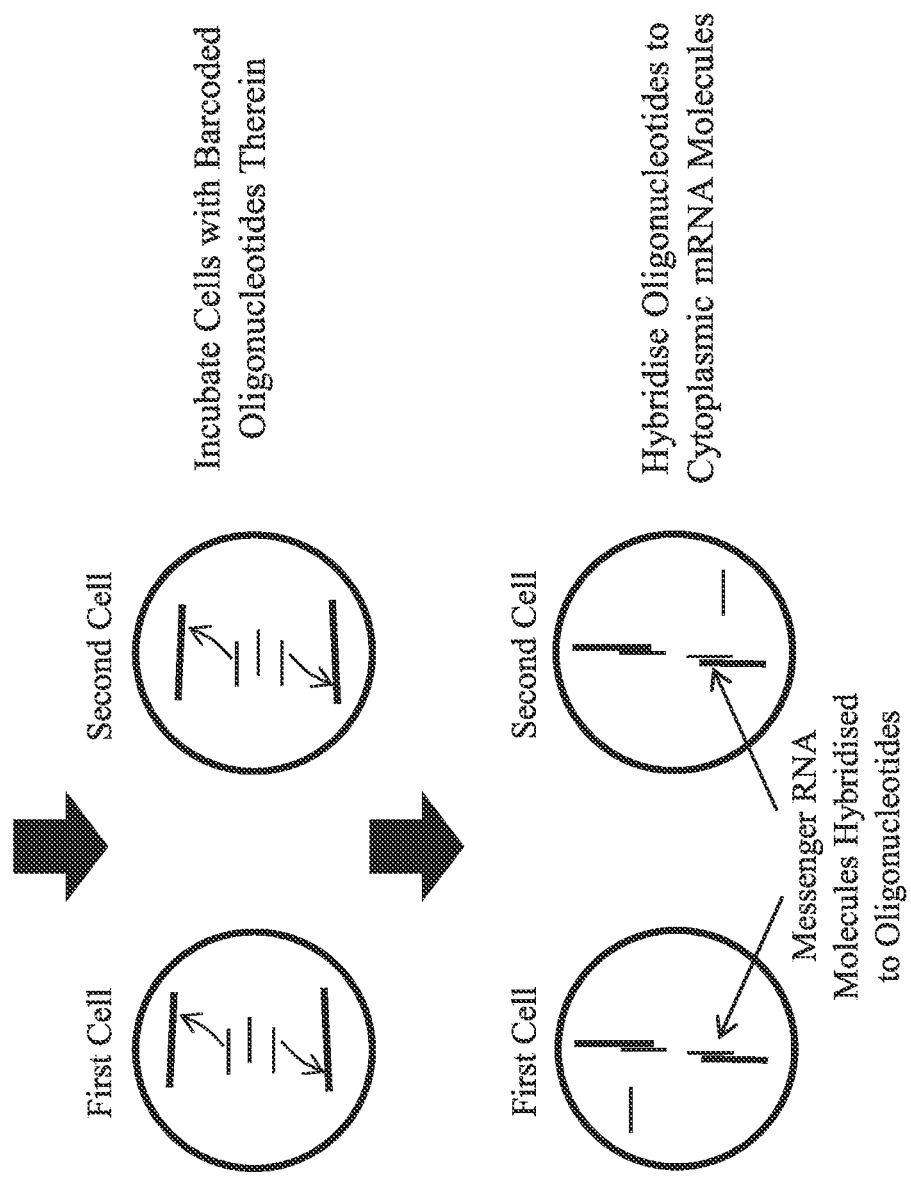

FIG. 20A-20B illustrates a method of transferring multimeric barcoding reagents into cells via liposomal delivery. In the method, multimeric barcoding reagents are transferred into cells by a transfer process involving barcoded oligonucleotides being comprised within liposomal compounds, and then transferring said barcoded oligonucleotides by liposomal delivery. In this embodiment, barcoded oligonucleotides are encapsulated within liposomes. These barcoded oligonucleotides may optionally be associated with other molecular moieties.

In a first step, the library of liposomes is incubated with a sample of two or more cells, and the liposomes are allowed to interact with the cell membranes of cells within the sample. As with standard liposomal delivery methods, the liposome may then fuse with the cell membrane, and/or be internalised into the cell, and release its constituent barcoded oligonucleotides into the cytoplasm, thus achieving liposomal delivery of barcoded oligonucleotides into cells of the sample.

Following this liposomal-delivery step, an incubation step is performed, during which time messenger RNA molecules complementary to the target regions of barcoded oligonucleotides delivered by the liposomes are allowed to anneal to said target regions. This incubation may be performed at a temperature conducive to such an annealing process, and/or may be performed in the presence of a modified annealing buffer which may be conducive to such an annealing process (such as a buffer containing a nucleic acid denaturant, such as betaine or DMSO).

Following the annealing step, messenger RNA molecules from individual cells are thus annealed to barcoded oligonucleotides that have been delivered by a liposome. In subsequent processing steps (for example, after a step of isolating the annealed messenger RNA molecules and barcoded oligonucleotides), the messenger RNA may be reverse-transcribed with a reverse transcriptase, and then optionally amplified such as with a PCR process, prior to performing a sequencing reaction.

FIG. 21A-21B illustrates an example of a method of transferring multimeric barcoding reagents into cells via transfection. In the method, multimeric barcoding reagents are transferred into cells by a transfection process. In a first step, multimeric barcoding reagents (e.g., barcoded oligonucleotides annealed along a multimeric barcode molecule) are complexed with a lipid transfection reagent. These complexes, analogous to lipid-complexed plasmids, will have biophysical and electrostatic character conducive to interaction with a cell membrane and then transfection into cells.

The resulting multimeric barcoding reagent-lipid complexes are then incubated with a sample of cells for a period of time, during which time the complexes migrate to come into contact with a cell membrane, and are transfected into cells. In this illustration, a first multimeric barcoding reagent-lipid complex is transfected into a first cell, and a second multimeric barcoding reagent-lipid complex is transfected into a second cell; in actual embodiments a large library of multimeric barcoding reagents may be transfected into a large sample of cells.

Following this transfection step, an incubation step is performed, during which time messenger RNA molecules complementary to the target regions of barcoded oligonucleotides comprised within the transfected multimeric barcoding reagents are allowed to anneal to said target regions. This incubation may be performed at a temperature conducive to such an annealing process, and/or may be performed in the presence of a modified annealing buffer which may be conducive to such an annealing process (such as a buffer containing a nucleic acid denaturant, such as betaine or DMSO).

Following the annealing step, messenger RNA molecules from individual cells are thus annealed to barcoded oligonucleotides from the multimeric barcoding reagent which was transferred into that cell. In subsequent processing steps (for example, after a step of isolating the annealed messenger RNA molecules and barcoded oligonucleotides), the messenger RNA may be reverse-transcribed with a reverse transcriptase, and then optionally amplified such as with a PCR process, prior to performing a sequencing reaction FIG. 22A-22B illustrates an example of a method of transferring multimeric barcoding reagents into cells via a permeabilisation process. In the method, multimeric barcoding reagents are transferred into cells by a permeabilisation process. In a first step, the membranes of cells are permeabilised with a permeabilisation process. This may, in one embodiment, be performed by exposure to a chemical surfactant such as a non-ionic detergent. Following this permeabilisation process, the membrane of each cell will have biophysical character conducive to diffusion of macromolecular species such as multimeric barcoding reagents therethrough.

The resulting permeabilised cells are then incubated with a library of two or more multimeric barcoding reagents for a period of time, during which time the multimeric barcoding reagents migrate to come into contact with a cell membrane, and are transferred into cells by a diffusion process. In this illustration, a first multimeric barcoding reagent diffuses into a first cell, and a second multimeric barcoding reagent diffuses into a second cell; in actual embodiments a large library of multimeric barcoding reagents may be transferred into a large sample of cells by this method.

Following this diffusion step, an incubation step is performed, during which time messenger RNA molecules complementary to the target regions of barcoded oligonucleotides comprised within the transferred multimeric barcoding reagents are allowed to anneal to said target regions. This incubation may be performed at a temperature conducive to such an annealing process, and/or may be performed in the presence of a modified annealing buffer which may be conducive to such an annealing process (such as a buffer containing a nucleic acid denaturant, such as betaine or DMSO).

Following the annealing step, messenger RNA molecules from individual cells are thus annealed to barcoded oligonucleotides from the multimeric barcoding reagent which was transferred into that cell. In subsequent processing steps (for example, after a step of isolating the annealed messenger RNA molecules and barcoded oligonucleotides), the messenger RNA may be reverse-transcribed with a reverse transcriptase, and then optionally amplified such as with a PCR process, prior to performing a sequencing reaction.

Figure 23A:
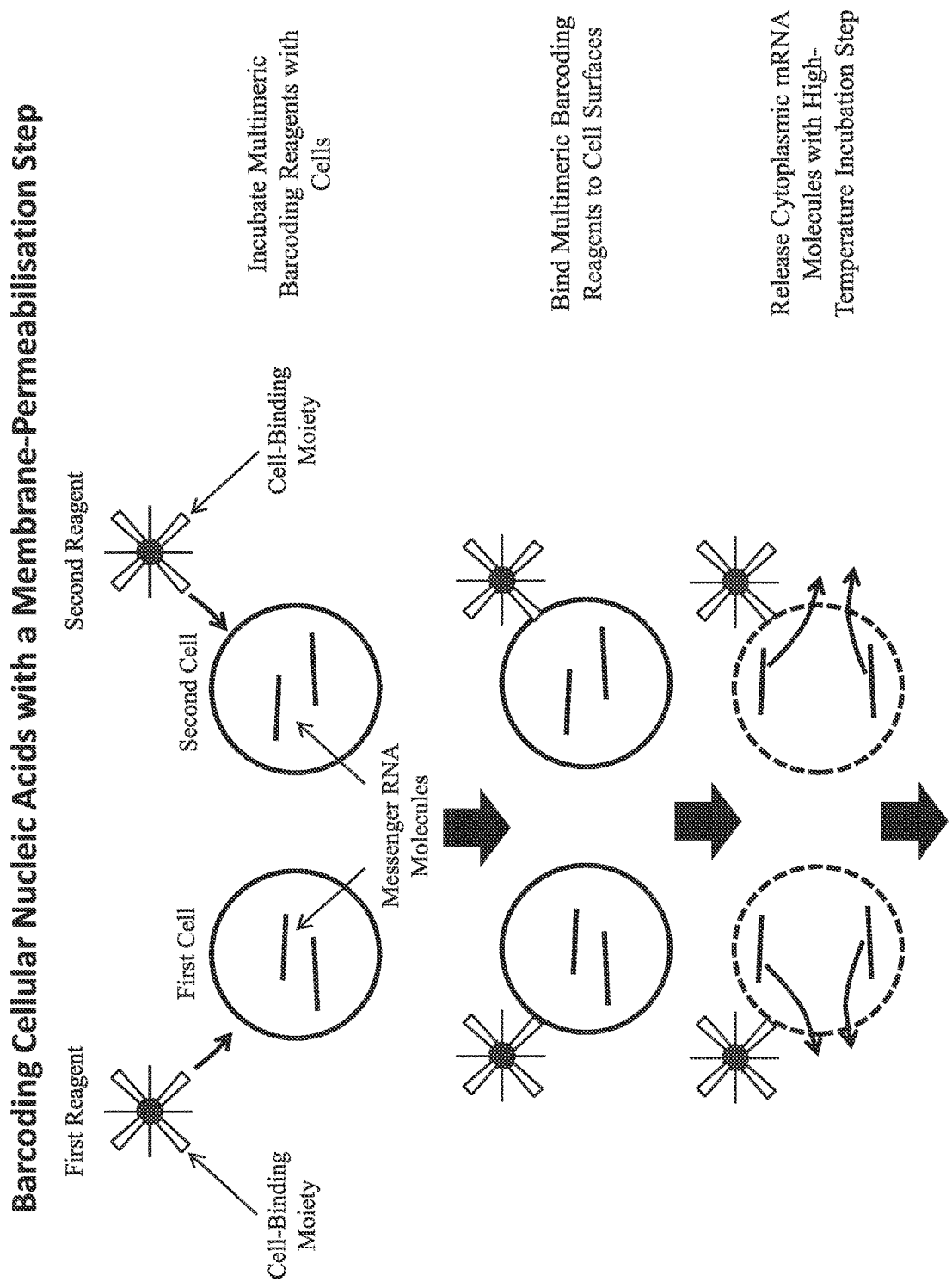
FIG. 23A-23B illustrates a method of barcoding cellular nucleic acids with a membrane-permeabilisation step.
Figure 23B:
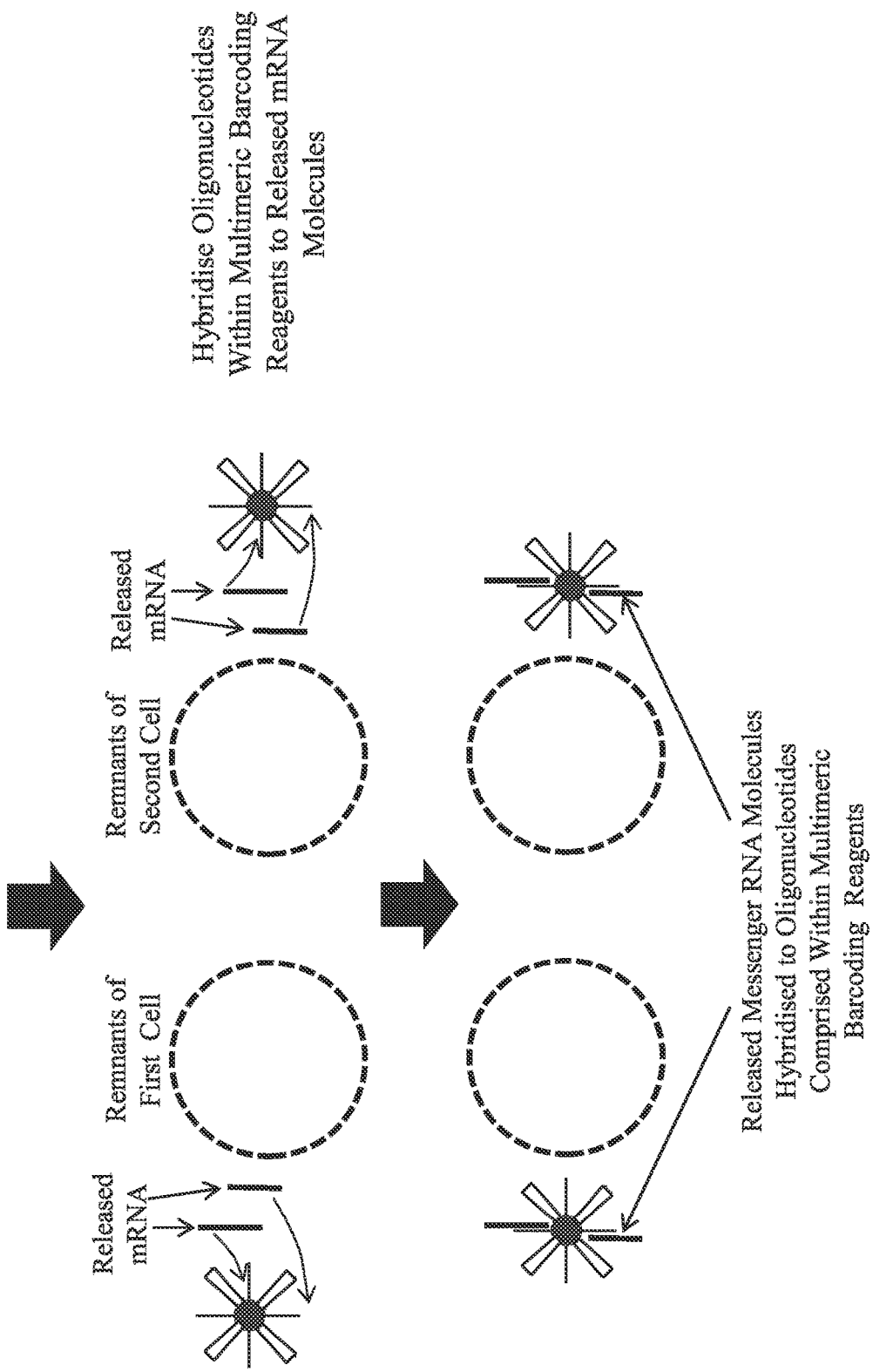

FIG. 23A-23B illustrates an examples of a method of barcoding cellular nucleic acids with a membrane-permeabilisation step. In the method, messenger RNA molecules are released from cells, whereupon they are barcoded by barcoded oligonucleotides that are within spatial proximity of the cell itself. In a first step, a library of two or more multimeric barcoding reagents are mixed with a sample of two or more cells. Optionally, as shown, said multimeric barcoding reagents may comprise cell-binding moieties which drive them to preferentially interact with the membranes of cells within the samples; an incubation step is performed to allow the multimeric barcoding reagents to bind to the cell surfaces.

In a second step, a membrane-permeabilisation and/or cell lysis process is performed, in which the cell membrane is made permeable to macromolecules such that messenger RNA molecules and/or oligonucleotides may diffuse through the membrane space. This step may be performed by a number of means, such as by a high-temperature incubation step as illustrated here. This permeabilisation and/or lysis step enables molecular interaction between barcoded oligonucleotides and their target nucleic acids.

Following this membrane-permeabilisation and/or lysis step, an incubation step is performed, during which time messenger RNA molecules complementary to the target regions of barcoded oligonucleotides comprised within the multimeric barcoding reagents are allowed to anneal to said target regions. This incubation may be performed at a temperature conducive to such an annealing process, and/or may be performed in the presence of a modified annealing buffer which may be conducive to such an annealing process (such as a buffer containing a nucleic acid denaturant, such as betaine or DMSO). This incubation may further be performed in the presence of a thickening agent, such as poly(ethylene) glycol (PEG), to retard the diffusion of barcoded oligonucleotides and/or target nucleic acid molecules within solution.

Following the annealing step, messenger RNA molecules from individual cells are thus annealed to barcoded oligonucleotides from the multimeric barcoding reagent which was within spatial proximity to that cell. In subsequent processing steps (for example, after a step of isolating the annealed messenger RNA molecules and barcoded oligonucleotides), the messenger RNA may be reverse-transcribed with a reverse transcriptase, and then optionally amplified such as with a PCR process, prior to performing a sequencing reaction.

FIG. 24A-24B illustrates a method of barcoding cellular nucleic acids with a membrane-permeabilisation and barcoded oligonucleotide-release step. In the method, messenger RNA molecules may be released from cells, whereupon they are barcoded by barcoded oligonucleotides that are released from multimeric barcoding reagents that were within spatial proximity to the cell said itself. In a first step, a library of two or more multimeric barcoding reagents are mixed with a sample of two or more cells. Optionally, as shown, said multimeric barcoding reagents may comprise cell-binding moieties which drive them to preferentially interact with the membranes of cells within the samples; an incubation step is performed to allow the multimeric barcoding reagents to bind to the cell surfaces.

In a second step, a membrane-permeabilisation and/or cell lysis process is performed, in which the cell membrane is made permeable to macromolecules such that messenger RNA molecules and/or oligonucleotides may diffuse through the membrane space. This step may be performed by a number of means, such as by a high-temperature incubation step as illustrated here. This permeabilisation and/or lysis step enables molecular interaction between barcoded oligonucleotides and their nucleic acid targets.

In this embodiment, this high-temperature incubation step further dissociates barcoded oligonucleotides from their respective multimeric barcoding reagents—specifically in this embodiment, said barcoded oligonucleotides are annealed to linker molecules which themselves are appended to the solid/molecular support of each multimeric barcoding reagent. This high-temperature incubation step is performed at a temperature above the melting temperature of the barcoded oligonucleotide-linker hybridisation region, and thus the barcoded oligonucleotides become free to diffuse in solution.

Following this membrane-permeabilisation and/or lysis step, an incubation step is performed, during which time messenger RNA molecules complementary to the target regions of barcoded oligonucleotides released from the multimeric barcoding reagents are allowed to anneal to said target regions. This incubation may be performed at a temperature conducive to such an annealing process, and/or may be performed in the presence of a modified annealing buffer which may be conducive to such an annealing process (such as a buffer containing a nucleic acid denaturant, such as betaine or DMSO). This incubation may further be performed in the presence of a thickening agent, such as poly(ethylene) glycol (PEG), to retard the diffusion of barcoded oligonucleotides and/or target nucleic acid molecules within solution.

Following the annealing step, messenger RNA molecules from individual cells are thus annealed to barcoded oligonucleotides released from the multimeric barcoding reagent which was within spatial proximity to that cell. In subsequent processing steps (for example, after a step of isolating the annealed messenger RNA molecules and barcoded oligonucleotides), the messenger RNA may be reverse-transcribed with a reverse transcriptase, and then optionally amplified such as with a PCR process, prior to performing a sequencing reaction.

EXAMPLES

Materials and Methods
Method 1—Synthesis of a Library of Nucleic Acid Barcode Molecules
Synthesis of Double-Stranded Sub-Barcode Molecule Library
In a PCR tube, 10 microliters of 10 micromolar BC_MX3 (an equimolar mixture of all sequences in SEQ ID NO: 18 to 269) were added to 10 microliters of 10 micromolar BC_ADD_TP1 (SEQ ID NO: 1), plus 10 microliters of 10× CutSmart Buffer (New England Biolabs) plus 1.0 microliter of 10 millimolar deoxynucleotide triphosphate nucleotide mix (Invitrogen) plus 68 microliters $H_2O$, to final volume of 99 microliters. The PCR tube was placed on a thermal cycler and incubated at 75° C. for 5 minutes, then slowly annealed to 4° C., then held 4° C., then placed on ice. 1.0 microliter of Klenow polymerase fragment (New England Biolabs; at 5 U/uL) was added to the solution and mixed. The PCR tube was again placed on a thermal cycler and incubated at 25° C. for 15 minutes, then held at 4° C. The solution was then purified with a purification column (Nucleotide Removal Kit; Qiagen), eluted in 50 microliters $H_2O$, and quantitated spectrophotometrically.

Synthesis of Double-Stranded Downstream Adapter Molecule
In a PCR tube, 0.5 microliters of 100 micromolar BC_ANC_TP1 (SEQ ID NO: 2) were added to 0.5 microliters of 100 micromolar BC_ANC_BT1 (SEQ ID NO: 3), plus 20 microliters of 10× CutSmart Buffer (New England Biolabs) plus 178 microliters $H_2O$, to final volume of 200 microliters. The PCR tube was placed on a thermal cycler and incubated at 95° C. for 5 minutes, then slowly annealed to 4° C., then held 4° C., then placed on ice, then stored at −20° C.

Ligation of Double-Stranded Sub-Barcode Molecule Library to Double-Stranded Downstream Adapter Molecule
In a 1.5 milliliter Eppendorf tube, 1.0 microliter of Double-Stranded Downstream Adapter Molecule solution was added to 2.5 microliters of Double-Stranded Sub-Barcode Molecule Library, plus 2.0 microliters of 10× T4 DNA Ligase buffer, and 13.5 microliters $H_2O$ to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters $H_2O$.

PCR Amplification of Ligated Library
In a PCR tube, 2.0 microliters of Ligated Library were added to 2.0 microliters of 50 micromolar BC_FWD_PR1

(SEQ ID NO: 4), plus 2.0 microliters of 50 micromolar BC_REV_PR1 (SEQ ID NO: 5), plus 10 microliters of 10× Taq PCR Buffer (Qiagen) plus 2.0 microliter of 10 millimolar deoxynucleotide triphosphate nucleotide mix (Invitrogen) plus 81.5 microliters $H_2O$, plus 0.5 microliters Qiagen Taq Polymerase (at 5 U/uL) to final volume of 100 microliters. The PCR tube was placed on a thermal cycler and amplified for 15 cycles of: 95° C. for 30 seconds, then 59° C. for seconds, then 72° C. for 30 seconds; then held at 4° C. The solution was then purified with 1.8× volume (180 microliters) Ampure XP Beads (Agencourt; as per manufacturer's instructions), and eluted in 50 microliters $H_2O$.

Uracil Glycosylase Enzyme Digestion

To an eppendorf tube 15 microliters of the eluted PCR amplification, 1.0 microliters $H_2O$, plus 2.0 microliters 10× CutSmart Buffer (New England Biolabs), plus 2.0 microliter of USER enzyme solution (New England Biolabs) was added and mixed. The tube was incubated at 37° C. for 60 minutes, then the solution was purified with 1.8× volume (34 microliters) Ampure XP Beads (Agencourt; as per manufacturer's instructions), and eluted in 34 microliters $H_2O$.

MlyI Restriction Enzyme Cleavage

To the eluate from the previous (glycosylase digestion) step, 4.0 microliters 10× CutSmart Buffer (New England Biolabs), plus 2.0 microliter of MlyI enzyme (New England Biolabs, at 5 U/uL) was added and mixed. The tube was incubated at 37° C. for 60 minutes, then the solution was purified with 1.8× volume (72 microliters) Ampure XP Beads (Agencourt; as per manufacturer's instructions), and eluted in 40 microliters $H_2O$.

Ligation of Sub-Barcode Library to MlyI-Cleaved Solution

In a 1.5 milliliter Eppendorf tube, 10 microliter of MlyI-Cleaved Solution solution was added to 2.5 microliters of Double-Stranded Sub-Barcode Molecule Library, plus 2.0 microliters of 10× T4 DNA Ligase buffer, and 4.5 microliters $H_2O$ to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters $H_2O$.

Repeating Cycles of Sub-Barcode Addition

The experimental steps of: 1) Ligation of Sub-Barcode Library to MlyI-Cleaved Solution, 2) PCR Amplification of Ligated Library, 3) Uracil Glycosylase Enzyme Digestion, and 4) MlyI Restriction Enzyme Cleavage were repeated, in sequence, for a total of five cycles.

Synthesis of Double-Stranded Upstream Adapter Molecule

In a PCR tube, 1.0 microliters of 100 micromolar BC_USO_TP1 (SEQ ID NO: 6) were added to 1.0 microliters of 100 micromolar BC_USO_BT1 (SEQ ID NO: 7), plus 20 microliters of 10× CutSmart Buffer (New England Biolabs) plus 178 microliters $H_2O$, to final volume of 200 microliters. The PCR tube was placed on a thermal cycler and incubated at 95° C. for 60 seconds, then slowly annealed to 4° C., then held 4° C., then placed on ice, then stored at −20° C.

Ligation of Double-Stranded Upstream Adapter Molecule

In a 1.5 milliliter Eppendorf tube, 3.0 microliters of Upstream Adapter solution were added to 10.0 microliters of final (after the fifth cycle) MlyI-Cleaved solution, plus 2.0 microliters of 10× T4 DNA Ligase buffer, and 5.0 microliters $H_2O$ to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters $H_2O$.

PCR Amplification of Upstream Adapter-Ligated Library

In a PCR tube, 6.0 microliters of Upstream Adapter-Ligated Library were added to 1.0 microliters of 100 micromolar BC_CS_PCR_FWD1 (SEQ ID NO: 8), plus 1.0 microliters of 100 micromolar BC_CS_PCR_REV1 (SEQ ID NO: 9), plus 10 microliters of 10× Taq PCR Buffer (Qiagen) plus 2.0 microliter of 10 millimolar deoxynucleotide triphosphate nucleotide mix (Invitrogen) plus 73.5 microliters $H_2O$, plus 0.5 microliters Qiagen Taq Polymerase (at 5 U/uL) to final volume of 100 microliters. The PCR tube was placed on a thermal cycler and amplified for 15 cycles of: 95° C. for seconds, then 61° C. for 30 seconds, then 72° C. for 30 seconds; then held at 4° C. The solution, containing a library of amplified nucleic acid barcode molecules, was then purified with 1.8× volume (180 microliters) Ampure XP Beads (Agencourt; as per manufacturer's instructions). The library of amplified nucleic acid barcode molecules was then eluted in 40 microliters $H_2O$.

The library of amplified nucleic acid barcode molecules sythesised by the method described above was then used to assemble a library of multimeric barcode molecules as described below.

Method 2—Assembly of a Library of Multimeric Barcode Molecules

A library of multimeric barcode molecules was assembled using the library of nucleic acid barcode molecules synthesised according to the methods of Method 1.

Primer-Extension with Forward Termination Primer and Forward Splinting Primer

In a PCR tube, 5.0 microliters of the library of amplified nucleic acid barcode molecules were added to 1.0 microliters of 100 micromolar CS_SPLT_FWD1 (SEQ ID NO: 10), plus 1.0 microliters of 5 micromolar CS_TERM_FWD1 (SEQ ID NO: 11), plus 10 microliters of 10× Thermopol Buffer (NEB) plus 2.0 microliter of 10 millimolar deoxynucleotide triphosphate nucleotide mix (Invitrogen) plus 80.0 microliters $H_2O$, plus 1.0 microliters Vent Exo-Minus Polymerase (New England Biolabs, at 2 U/uL) to final volume of 100 microliters. The PCR tube was placed on a thermal cycler and amplified for 1 cycle of: 95° C. for 30 seconds, then 53° C. for 30 seconds, then 72° C. for 60 seconds, then 1 cycle of: 95° C. for 30 seconds, then 50° C. for 30 seconds, then 72° C. for 60 seconds, then held at 4° C. The solution was then purified a PCR purification column (Qiagen), and eluted in 85.0 microliters $H_2O$.

Primer-Extension with Reverse Termination Primer and Reverse Splinting Primer

In a PCR tube, the 85.0 microliters of forward-extension primer-extension products were added to 1.0 microliters of 100 micromolar CS_SPLT_REV1 (SEQ ID NO: 12), plus 1.0 microliters of 5 micromolar CS_TERM_REV1 (SEQ ID NO: 13), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 100 microliters. The PCR tube was placed on a thermal cycler and amplified for 1 cycle of: 95° C. for 30 seconds, then 53° C. for 30 seconds, then 72° C. for 60 seconds, then 1 cycle of: 95° C. for 30 seconds, then 50° C. for 30 seconds, then 72° C. for 60 seconds, then held at 4° C. The solution was then purified a PCR purification column (Qiagen), and eluted in 43.0 microliters $H_2O$.

Linking Primer-Extension Products with Overlap-Extension PCR

In a PCR tube were added the 43.0 microliters of reverse-extension primer-extension products, plus 5.0 microliters of 10× Thermopol Buffer (NEB) plus 1.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 50 microliters. The PCR tube was placed on a thermal cycler and amplified for 5 cycles of: 95° C. for 30 seconds, then 60° C. for 60 seconds, then 72° C. for 2 minutes; then 5 cycles of: 95° C. for 30 seconds, then 60° C. for 60 seconds, then 72° C. for 5 minutes; then 5 cycles of: 95° C. for 30 seconds, then 60° C. for 60 seconds, then 72° C. for 10 minutes; then held at 4° C. The solution was then purified with 0.8× volume (80 microliters) Ampure XP Beads (Agencourt; as per manufacturer's instructions), and eluted in 40 microliters $H_2O$.

Amplification of Overlap-Extension Products

In a PCR tube were added 2.0 microliters of Overlap-Extension PCR solution, plus 1.0 microliters of 100 micromolar CS_PCR_FWD1 (SEQ ID NO: 14), plus 1.0 microliters of 100 micromolar CS_PCR_REV1 (SEQ ID NO: 15), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL), plus 83.0 microliters $H_2O$ to final volume of 100 microliters. The PCR tube was placed on a thermal cycler and amplified for 15 cycles of: 95° C. for 30 seconds, then 58° C. for 30 seconds, then 72° C. for 10 minutes; then held at 4° C. The solution was then purified with 0.8× volume (80 microliters) Ampure XP Beads (Agencourt; as per manufacturer's instructions), and eluted in 50 microliters $H_2O$, and quantitated spectrophotometrically.

Gel-Based Size Selection of Amplified Overlap-Extension Products

Approximately 250 nanograms of Amplified Overlap-Extension Products were loaded and run on a 0.9% agarose gel, and then stained and visualised with ethidium bromide. A band corresponding to 1000 nucleotide size (plus and minus 100 nucleotides) was excised and purified with a gel extraction column (Gel Extraction Kit, Qiagen) and eluted in 50 microliters $H_2O$.

Amplification of Overlap-Extension Products

In a PCR tube were added 10.0 microliters of Gel-Size-Selected solution, plus 1.0 microliters of 100 micromolar CS_PCR_FWD1 (SEQ ID NO: 14), plus 1.0 microliters of 100 micromolar CS_PCR_REV1 (SEQ ID NO: 15), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 75.0 microliters $H_2O$ to final volume of 100 microliters. The PCR tube was placed on a thermal cycler and amplified for 15 cycles of: 95° C. for 30 seconds, then 58° C. for 30 seconds, then 72° C. for 4 minutes; then held at 4° C. The solution was then purified with 0.8× volume (80 microliters) Ampure XP Beads (Agencourt; as per manufacturer's instructions), and eluted in 50 microliters $H_2O$, and quantitated spectrophotometrically.

Selection and Amplification of Quantitatively Known Number of Multimeric Barcode Molecules Amplified gel-extracted solution was diluted to a concentration of 1 picogram per microliter, and then to a PCR tube was added 2.0 microliters of this diluted solution (approximately 2 million individual molecules), plus 0.1 microliters of 100 micromolar CS_PCR_FWD1 (SEQ ID NO: 14), plus 0.1 microliters of 100 micromolar CS_PCR_REV1 (SEQ ID NO: 15), plus 1.0 microliter 10× Thermopol Buffer (NEB) plus 0.2 microliter of 10 millimolar deoxynucleotide triphosphate nucleotide mix (Invitrogen), plus 0.1 microliters Vent Exo-Minus Polymerase (New England Biolabs, at 2 U/uL) plus 6.5 microliters $H_2O$ to final volume of 10 microliters. The PCR tube was placed on a thermal cycler and amplified for 11 cycles of: 95° C. for 30 seconds, then 57° C. for 30 seconds, then 72° C. for 4 minutes; then held at 4° C.

To the PCR tube was added 1.0 microliters of 100 micromolar CS_PCR_FWD1 (SEQ ID NO: 14), plus 1.0 microliters of 100 micromolar CS_PCR_REV1 (SEQ ID NO: 15), plus 9.0 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 76.0 microliters $H_2O$ to final volume of 100 microliters. The PCR tube was placed on a thermal cycler and amplified for 10 cycles of: 95° C. for 30 seconds, then 57° C. for 30 seconds, then 72° C. for 4 minutes; then held at 4° C. The solution was then purified with 0.8× volume (80 microliters) Ampure XP Beads (Agencourt; as per manufacturer's instructions), and eluted in 50 microliters $H_2O$, and quantitated spectrophotometrically.

Method 3: Production of Single-Stranded Multimeric Barcode Molecules by In Vitro Transcription and cDNA Synthesis This method describes a series of steps to produce single-stranded DNA strands, to which oligonucleotides may be annealed and then barcoded along. This method begins with four identical reactions performed in parallel, in which a promoter site for the T7 RNA Polymerase is appended to the 5' end of a library of multimeric barcode molecules using an overlap-extension PCR amplification reaction. Four identical reactions are performed in parallel and then merged to increase the quantitative amount and concentration of this product available. In each of four identical PCR tubes, approximately 500 picograms of size-selected and PCR-amplified multimeric barcode molecules (as produced in the 'Selection and Amplification of Quantitatively Known Number of Multimeric Barcode Molecules' step of Method 2) were mixed with 2.0 microliters of 100 micromolar CS_PCR_FWD1J7 (SEQ ID NO. 270) and 2.0 microliters of 100 micromolar CS_PCR_REV4 (SEQ ID NO. 271), plus 20.0 microliters of 10× Thermopol PCR buffer, plus 4.0 microliters of 10 millimolar deoxynucleotide triphosphate nucleotide mix, and 2.0 microliters Vent Exo Minus polymerase (at 5 units per microliter) plus water to a total volume of 200 microliters. The PCR tube was placed on a thermal cycler and amplified for 22 cycles of: 95° C. for 60 seconds, then 60° C. for 30 seconds, then 72° C. for 3 minutes; then held at 4° C. The solution from all four reactions was then purified with a gel extraction column (Gel Extraction Kit, Qiagen) and eluted in 52 microliters $H_2O$.

Fifty (50) microliters of the eluate was mixed with 10 microliters 10× NEBuffer 2 (NEB), plus 0.5 microliters of 10 millimolar deoxynucleotide triphosphate nucleotide mix, and 1.0 microliters Vent Exo Minus polymerase (at 5 units per microliter) plus water to a total volume of 100 microliters. The reaction was incubated for 15 minutes at room temperature, then purified with 0.8× volume (80 microliters) Ampure XP Beads (Agencourt; as per manufacturer's instructions), and eluted in 40 microliters $H_2O$, and quantitated spectrophotometrically.

A transcription step is then performed, in which the library of PCR-amplified templates containing T7 RNA Polymerase promoter site (as produced in the preceding step) is used as a template for T7 RNA polymerase. This comprises an amplification step to produce a large amount of RNA-based nucleic acid corresponding to the library of multimeric barcode molecules (since each input PCR molecule can serve as a template to produce a large number of cognate RNA molecules). In the subsequent step, these RNA molecules are then reverse transcribed to create the desired, single-stranded multimeric barcode molecules. Ten (10) microliters of the eluate was mixed with microliters 5× Transcription Buffer (Promega), plus 2.0 microliters of 10 millimolar deoxynucleotide triphosphate nucleotide mix, plus 10 microliters of 0.1 milimolar DTT, plus 4.0 microliters SuperAseIn (Ambion), and 4.0 microliters Promega T7 RNA Polymerase (at 20 units per microliter) plus water to a total volume of 100 microliters. The reaction was incubated 4 hours at 3TC, then purified with an RNEasy Mini Kit (Qiagen), and eluted in 50 micoliters $H_2O$, and added to 6.0 microliters SuperAseIn (Ambion).

The RNA solution produced in the preceding in vitro transcription step is then reverse transcribed (using a primer specific to the 3' ends of the RNA molecules) and then digested with RNAse H to create single-stranded DNA molecules corresponding to multimeric barcode molecules, to which oligonucleotides maybe be annealed and then barcoded along. In two identical replicate tubes, 23.5 microliters of the eluate was mixed with 5.0 microliters of 10 millimolar deoxynucleotide triphosphate nucleotide mix, plus 3.0 microliters SuperAseIn (Ambion), and 10.0 microliters of 2.0 micromolar CS_PCR_REV1 (SEQ ID NO. 272) plus water to final volume of 73.5 microliters. The reaction was incubated on a thermal cycler at 65° C. for 5 minutes, then 50° C. for 60 seconds; then held at 4° C. To the tube was added 20 microliters 5× Reverse Transcription buffer (Invitrogen), plus 5.0 microliters of 0.1 milimolar DTT, and 1.75 microliters Superscript III Reverse Transcriptase (Invitrogen). The reaction was incubated at 55° C. for 45 minutes, then 60° C. for 5 minutes; then 70° C. for 15 minutes, then held at 4° C., then purified with a PCR Cleanup column (Qiagen) and eluted in 40 microliters $H_2O$.

Sixty (60) microliters of the eluate was mixed with 7.0 microliters 10× RNAse H Buffer (Promega), plus 4.0 microliters RNAse H (Promega. The reaction was incubated 12 hours at 3TC, then 95° C. for 10 minutes, then held at 4° C., then purified with 0.7× volume (49 microliters) Ampure XP Beads (Agencourt; as per manufacturer's instructions), and eluted in 30 microliters $H_2O$, and quantitated spectrophotometrically.

Method 4: Production of Multimeric Barcoding Reagents Containing Barcoded Oligonucleotides This method describes steps to produce multimeric barcoding reagents from single-stranded multimeric barcode molecules (as produced in Method 3) and appropriate extension primers and adapter oligonucleotides.

In a PCR tube, approximately 45 nanograms of single-stranded RNAse H-digested multimeric barcode molecules (as produced in the last step of Method 3) were mixed with 0.25 microliters of micromolar DS_ST_05 (SEQ ID NO. 273, an adapter oligonucleotide) and 0.25 microliters of micromolar US_PCR_Prm_Only_03 (SEQ ID NO. 274, an extension primer), plus 5.0 microliters of 5× Isothermal extension/ligation buffer, plus water to final volume of 19.7 microliters. In order to anneal the adapter oligonucleotides and extension primers to the multimeric barcode molecules, in a thermal cycler, the tube was incubated at 98° C. for 60 seconds, then slowly annealed to 55° C., then held at 55° C. for 60 seconds, then slowly annealed to 50° C. then held at 50° C. for 60 seconds, then slowly annealed to 20° C. at 0.1° C./sec, then held at 4° C. To the tube was added 0.3 microliters (0.625 U) Phusion Polymerase (NEB; 2 U/uL) 2.5 microliters (100 U) Taq DNA Ligase (NEB; 40 U/uL); and 2.5 microliters 100 milimolar DTT. In order to extend the extension primer(s) across the adjacent barcode region(s) of each multimeric barcode molecule, and then to ligate this extension product to the phosphorylated 5' end of the adapter oligonucleotide annealed to the downstream thereof, the tube was then incubated at 50° C. for 3 minutes, then held at 4° C. The reaction was then purified with a PCR Cleanup column (Qiagen) and eluted in 30 microliters $H_2O$, and quantitated spectrophotometrically.

Method 5: Production of Synthetic DNA Templates of Known Sequence

This method describes a technique to produce synthetic DNA templates with a large number of tandemly-repeated, co-linear molecular sequence identifiers, by circularizing and then tandemly amplifying (with a processive, strand-displacing polymerase) oligonucleotides containing said molecular sequence identifiers. This reagent may then be used to evaluate and measure the multimeric barcoding reagents described herein.

In a PCR was added 0.4 microliters of 1.0 micromolar Syn_Temp_01 (SEQ ID NO. 275) and 0.4 microliters of 1.0 micromolar ST_Splint_02 (SEQ ID NO. 276) and 10.0 microliters of 10× NEB CutSmart buffer. On a thermal cycler, the tube was incubated at 95° C. for 60 seconds, then held at 75° C. for 5 minutes, then slowly annealed to 20° C. then held at 20° C. for 60 seconds, then held at 4° C. To circularize the molecules through an intramolecular ligation reaction, the tube was then added 10.0 microliters ribo-ATP and 5.0 microliters T4 DNA Ligase (NEB; High Concentration). The tube was then incubated at room temperature for 30 minutes, then at 65° C. for 10 minutes, then slowly annealed to 20° C. then held at 20° C. for 60 seconds, then held at 4° C. To each tube was then added 10× NEB CutSmart buffer, 4.0 microliters of 10 millimolar deoxynucleotide triphosphate nucleotide mix, and 1.5 microliters of diluted phi29 DNA Polymerase (NEB; Diluted 1:20 in 1× CutSmart buffer) plus water to a total volume of 200 microliters. The reaction was incubated at 30° C. for 5 minutes, then held at 4° C., then purified with 0.7× volume (140 microliters) Ampure XP Beads (Agencourt; as per manufacturer's instructions), and eluted in 30 microliters $H_2O$, and quantitated spectrophotometrically.

Method 6: Barcoding Synthetic DNA Templates of Known Sequence with Multimeric Barcoding Reagents Containing Barcoded Oligonucleotides In a PCR tube were added 10.0 microliters 5× Phusion HF buffer (NEB), plus 1.0 microliters 10 millimolar deoxynucleotide triphosphate nucleotide mix, plus 2.0 microliters (10 nanograms) 5.0 nanogram/microliters Synthetic DNA Templates of Known Sequence (as produced by Method 5), plus water to final volume of 42.5 microliters. The tube was then incubated at 98° C. for 60 seconds, then held at 20° C. To the tube was added 5.0 microliters of 5.0 picogram/microliter Multimeric Barcoding Reagents Containing Barcoded Oligonucleotides (as produced by Method 4). The reaction was then incubated at 70° C. for 60 seconds, then slowly annealed to 60° C., then 60° C. for five minutes, then slowly annealed to 55° C., then 55° C. for five minutes, then slowly annealed to 50° C., then 50° C. for five minutes, then held at 4° C. To the reaction was added 0.5 microliters of Phusion Polymerase (NEB), plus 2.0 microliters 10 uM SynTemp_PE2_B1_Short1 (SEQ ID NO. 277, a primer that is complementary to part of the extension products produced by annealing and extending the multimeric barcoding reagents created by Method 4 along the synthetic DNA templates created by Method 5, serves as a primer for the primer-extension and then PCR reactions described in this method). Of this reaction, a volume of 5.0 microliters was added to a new PCR tube, which was then incubated for 30 seconds at 55° C., 30 seconds 60° C., and 30 seconds 72° C., then followed by 10 cycles of: 98° C. then 65° C. then 72° C. for 30 seconds each, then held at 4° C. To each tube was then added 9.0 microliters 5× Phusion buffer, plus 1.0 microliters 10 millimolar deoxynucleotide triphosphate nucleotide mix, plus 1.75 microliters 10 uM SynTemp_PE2_B1_Short1 (SEQ ID NO. 277), plus 1.75 microliters 10 uM US_PCR_Prm_Only_02 (SEQ ID NO. 278, a primer partially complementary to the extension primer employed to generate the multimeric barcoding reagents as per Method 4, and serving as the 'forward' primer in this PCR amplification reaction), plus 0.5 microliters Phusion Polymerase (NEB), plus water to final volume of 50 microliters. The PCR tube was placed on a thermal cycler and amplified for 24 cycles of: 98° C. for 30 seconds, then 72° C. for 30 seconds; then held at 4° C., then purified with 1.2× volume (60 microliters) Ampure XP Beads (Agencourt; as per manufacturer's instructions), and eluted in 30 microliters H$_2$O, and quantitated spectrophotometrically.

The resulting library was then barcoded for sample identification by a PCR-based method, amplified, and sequenced by standard methods using a 150-cycle, mid-output NextSeq flowcell (Illumina), and demultiplexed informatically for further analysis.

Method 7: Barcoding Synthetic DNA Templates of Known Sequence with Multimeric Barcoding Reagents and Separate Adapter Oligonucleotides To anneal and extend adapter oligonucleotides along the synthetic DNA templates, in a PCR tube were added 10.0 microliters 5× Phusion HF buffer (NEB), plus 1.0 microliters 10 millimolar deoxynucleotide triphosphate nucleotide mix, plus 5.0 microliters (25 nanograms) 5.0 nanogram/microliters Synthetic DNA Templates of Known Sequence (as produced by Method 5), plus 0.25 microliters of 10 micromolar DS_ST_05 (SEQ ID NO. 273, an adapter oligonucleotide), plus water to final volume of 49.7 microliters. On a thermal cycler, the tube was incubated at 98° C. for 2 minutes, then 63° C. for 1 minute, then slowly annealed to 60° C. then held at 60° C. for 1 minute, then slowly annealed to 5TC then held at 5TC for 1 minute, then slowly annealed to 54° C. then held at 54° C. for 1 minute, then slowly annealed to 50° C. then held at 50° C. for 1 minute, then slowly annealed to 45° C. then held at 45° C. for 1 minute, then slowly annealed to 40° C. then held at 40° C. for 1 minute, then held at 4° C. To the tube was added 0.3 microliters Phusion Polymerase (NEB), and the reaction was incubated at 45° C. for 20 seconds, then 50° C. for 20 seconds, then 55° C. for 20 seconds, 60° C. for 20 seconds, then 72° C. for 20 seconds, then held at 4° C.; the reaction was then purified with 0.8× volume (40 microliters) Ampure XP Beads (Agencourt; as per manufacturer's instructions), and eluted in 30 microliters H$_2$O, and quantitated spectrophotometrically.

In order to anneal adapter oligonucleotides (annealed and extended along the synthetic DNA templates as in the previous step) to multimeric barcode molecules, and then to anneal and then extend extension primer(s) across the adjacent barcode region(s) of each multimeric barcode molecule, and then to ligate this extension product to the phosphorylated 5' end of the adapter oligonucleotide annealed to the downstream thereof, to a PCR tube was added 10 microliters of the eluate from the previous step (containing the synthetic DNA templates along which the adapter oligonucleotides have been annealed and extended), plus 3.0 microliters of a 50.0 nanomolar solution of RNAse H-digested multimeric barcode molecules (as produced in the last step of Method 3), plus 6.0 microliters of 5× Isothermal extension/ligation buffer, plus water to final volume of 26.6 microliters. On a thermal cycler, the tube was incubated at 70° C. for 60 seconds, then slowly annealed to 60° C., then held at 60° C. for 5 minutes, then slowly annealed to 55° C. then held at 55° C. for 5 minutes, then slowly annealed to 50° C. at 0.1° C./sec then held at 50° C. for 30 minutes, then held at 4° C. To the tube was added 0.6 microliters 10 uM US_PCR_Prm_Only_02 (SEQ ID NO: 278, an extension primer), and the reaction was incubated at 50° C. for 10 minutes, then held at 4° C. To the tube was added 0.3 microliters (0.625 U) Phusion Polymerase (NEB; 2 U/uL) 2.5 microliters (100 U) Taq DNA Ligase (NEB; 40 U/uL); and 2.5 microliters 100 milimolar DTT. The tube was then incubated at 50° C. for 5 minutes, then held at 4° C. The reaction was then purified with 0.7× volume (21 microliters) Ampure XP Beads (Agencourt; as per manufacturer's instructions), and eluted in 30 microliters H$_2$O, and quantitated spectrophotometrically.

To a new PCR tube was add 25.0 microliters of the eluate, plus 10.0 microliters 5× Phusion HF buffer (NEB), plus 1.0 microliters 10 millimolar deoxynucleotide triphosphate nucleotide mix, plus 2.0 microliters 10 uM SynTemp_PE2_B1_Short1 (SEQ ID NO: 277; a primer that is complementary to part of the extension products produced by the above steps; serves as a primer for the primer-extension and then PCR reactions described here), plus 0.5 uL Phusion Polymerase (NEB), plus water to final volume of 49.7 microliters. Of this reaction, a volume of 5.0 microliters was added to a new PCR tube, which was then incubated for 30 seconds at 55° C., 30 seconds 60° C., and 30 seconds 72° C., then followed by 10 cycles of: 98° C. then 65° C. then 72° C. for seconds each, then held at 4° C. To each tube was then added 9.0 microliters 5× Phusion buffer, plus 1.0 microliters 10 millimolar deoxynucleotide triphosphate nucleotide mix, plus 1.75 microliters 10 uM SynTemp_PE2_B1_Short1 (SEQ ID NO: 277), plus 1.75 microliters 10 uM US_PCR_Prm_Only_02 (SEQ ID NO: 278), plus 0.5 microliters Phusion Polymerase (NEB), plus water to final volume of 50 microliters. The PCR tube was placed on a thermal cycler and amplified for 24 cycles of: 98° C. for 30 seconds, then 72° C. for 30 seconds; then held at 4° C., then purified with 1.2× volume (60 microliters) Ampure XP Beads (Agencourt; as per manufacturer's instructions), and eluted in 30 microliters H$_2$O, and quantitated spectrophotometrically.

The resulting library was then barcoded for sample identification by a PCR-based method, amplified, and sequenced by standard methods using a 150-cycle, mid-output NextSeq flowcell (Illumina), and demultiplexed informatically for further analysis.

Method 9: Barcoding Genomic DNA Loci with Multimeric Barcoding Reagents Containing Barcoded Oligonucleotides This method describes a framework for barcoding targets within specific genomic loci (e.g. barcoding a number of exons within a specific gene) using multimeric barcoding reagents that contain barcoded oligonucleotides. First, a solution of Multimeric Barcode Molecules was produced by In Vitro Transcription and cDNA Synthesis (as described in Method 3). Then, solutions of multimeric barcoding reagents containing barcoded oligonucleotides was produced as described in Method 4, with a modification made such that instead of using an adapter oligonucleotide targeting a synthetic DNA template (i.e. DS_ST_05, SEQ ID NO: 273, as used in Method 4), adapter oligonucleotides targeting the specific genomic loci were included at that step. Specifically, a solution of multimeric barcoding reagents containing appropriate barcoded oligonucleotides was produced individually for each of three different human genes: BRCA1 (containing 7 adapter oligonucleotides, SEQ ID NOs 279-285), HLA-A (containing 3 adapter oligonucleotides, SEQ ID NOs 286-288), and DQB1 (containing 2 adapter oligonucleotides, SEQ ID NOs 289-290). The process of Method 4 was conducted for each of these three solutions as described above. These three solutions were then merged together, in equal volume, and diluted to a final, total concentration all barcoded oligonucleotides of approximately 50 nanomolar.

In a PCR tube were plus 2.0 microliters 5× Phusion HF buffer (NEB), plus 1.0 microliter of 100 nanogram/microliter human genomic DNA (NA12878 from Coriell Institute) to final volume of 9.0 microliters. In certain variant versions of this protocol, the multimeric barcoding reagents (containing barcoded oligonucleotides) were also added at this step, prior to the high-temperature 98° C. incubation. The reaction was incubated at 98° C. for 120 seconds, then held at 4° C. To the tube was added 1.0 microliters of the above 50 nanomolar solution of multimeric barcode reagents, and then the reaction was incubated for 1 hour at 55° C., then 1 hour at 50° C., then 1 hour at 45° C., then held at 4° C. (Note that for certain samples, this last annealing process was extended to occur overnight, for a total of approximately 4 hours per temperature step).

In order to add a reverse universal priming sequence to each amplicon sequence (and thus to enable subsequent amplification of the entire library at once, using just one forward and one reverse amplification primer), the reaction was diluted 1:100, and 1.0 microliter of the resulting solution was added in a new PCR tube to 20.0 microliters 5× Phusion HF buffer (NEB), plus 2.0 microliters 10 millimolar deoxynucleotide triphosphate nucleotide mix, plus 1.0 microliters a reverse-primer mixture (equimolar concentration of SEQ ID Nos 291-303, each primer at 5 micromolar concentration), plus 1.0 uL Phusion Polymerase (NEB), plus water to final volume of 100 microliters. The reaction was incubated at 53° C. for 30 seconds, 72° C. for 45 seconds, 98° C. for 90 seconds, then 68° C. for 30 seconds, then 64° C. for 30 seconds, then 72° C. for 30 seconds; then held at 4° C. The reaction was then purified with 0.8× volume (80 microliters) Ampure XP Beads (Agencourt; as per manufacturer's instructions), and eluted in 30 microliters $H_2O$, and quantitated spectrophotometrically.

The resulting library was then barcoded for sample identification by a PCR-based method, amplified, and sequenced by standard methods using a 150-cycle, mid-output NextSeq flowcell (Illumina), and demultiplexed informatically for further analysis.

Method 10—Sequencing the Library of Multimeric Barcode Molecules

Preparing Amplified Selected Molecules for Assessment with High-Throughput Sequencing To a PCR tube was added 1.0 microliters of the amplified selected molecule solution, plus 1.0 microliters of 100 micromolar CS_SQ_AMP_REV1 (SEQ ID NO: 16), plus 1.0 microliters of 100 micromolar US_PCR_Prm_Only_02 (SEQ ID NO: 17), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 84.0 microliters $H_2O$ to final volume of 100 microliters. The PCR tube was placed on a thermal cycler and amplified for 3 cycles of: 95° C. for 30 seconds, then 56° C. for 30 seconds, then 72° C. for 3 minutes; then held at 4° C. The solution was then purified with 0.8× volume (80 microliters) Ampure XP Beads (Agencourt; as per manufacturer's instructions), and eluted in 85 microliters $H_2O$.

This solution was then added to a new PCR tube, plus 1.0 microliters of 100 micromolar Illumina_PE1, plus 1.0 microliters of 100 micromolar Illumina_PE2, plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 100 microliters. The PCR tube was placed on a thermal cycler and amplified for 4 cycles of: 95° C. for 30 seconds, then 64° C. for 30 seconds, then 72° C. for 3 minutes; then 18 cycles of: 95° C. for 30 seconds, then 67° C. for 30 seconds, then 72° C. for 3 minutes; then held at 4° C. The solution was then purified with 0.8× volume (80 microliters) Ampure XP Beads (Agencourt; as per manufacturer's instructions), and eluted in 40 microliters $H_2O$.

High-throughput Illumina sequencing was then performed on this sample using a MiSeq sequencer with paired-end, 250-cycle V2 sequencing chemistry.

Figure 17:
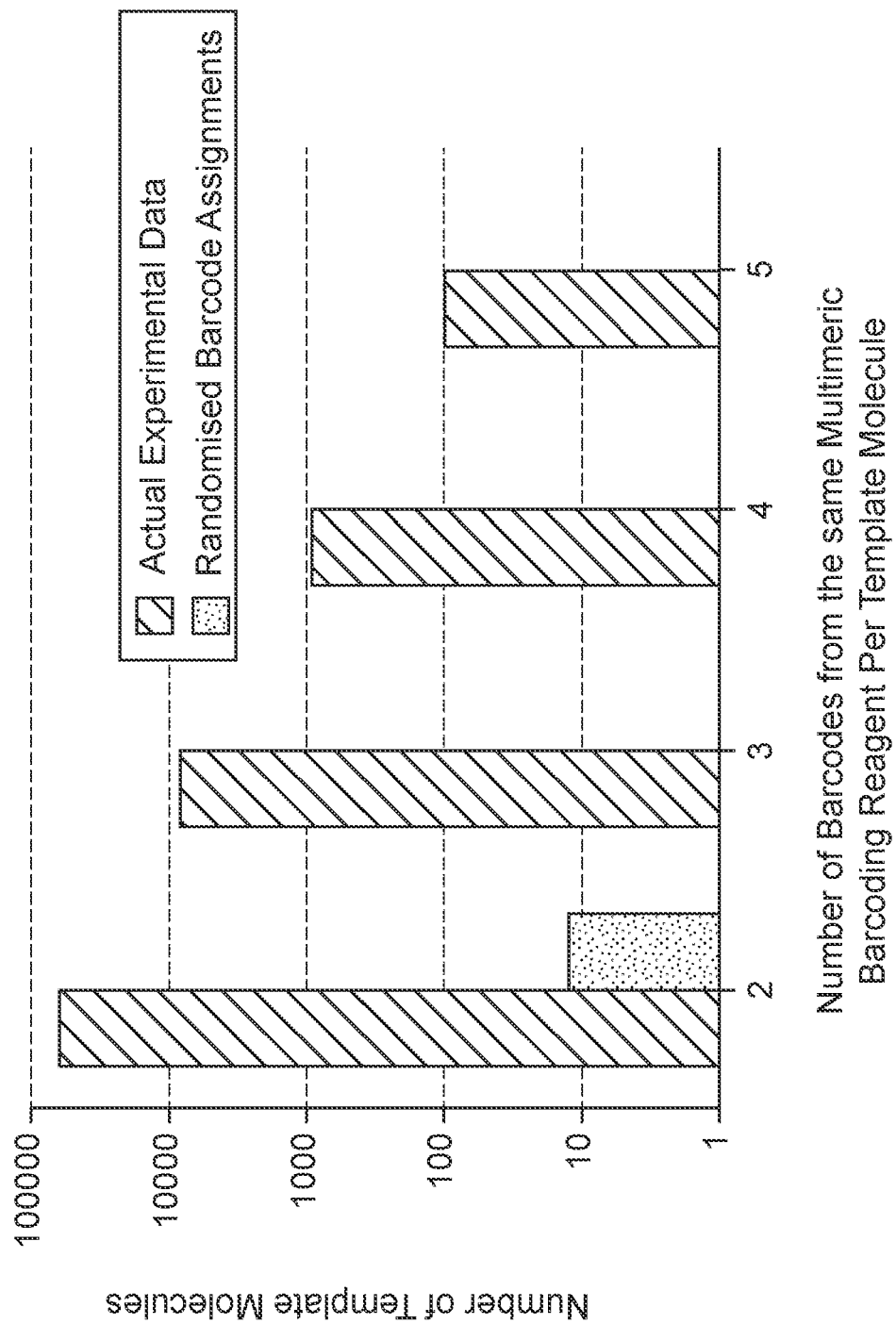
FIG. 17 is a graph showing the number of barcodes from the same multimeric barcoding reagent that labelled sequences on the same synthetic template molecule against the number of synthetic template molecules.

Method 11—Assessment of Multimeric Nature of Barcodes Annealed and Extended Along Single Synthetic Template DNA Molecules A library of barcoded synthetic DNA templates was created using a solution of multimeric barcoding reagents produced according to a protocol as described generally in Method 3 and Method 4, and using a solution of synthetic DNA templates as described in Method 5, and using a laboratory protocol as described in Method 6; the resulting library was then barcoded for sample identification by a PCR-based method, amplified, and sequenced by standard methods using a 150-cycle, mid-output NextSeq flowcell (Illumina), and demultiplexed informatically for further analysis. The DNA sequencing results from this method were then compared informatically with data produced from Method 10 to assess the degree of overlap between the multimeric barcoding of synthetic DNA templates and the arrangement of said barcodes on individual multimeric barcoding reagents (the results are shown in FIG. 17).

Results

Structure and Expected Sequence Content of Each Sequence Multimeric Barcoding Reagent Molecule The library of multimeric barcode molecules synthesised as described in Methods 1 to 3 was prepared for high-throughput sequencing, wherein each molecule sequenced includes a contiguous span of a specific multimeric barcode molecule (including one or more barcode sequences, and one or more associate upstream adapter sequences and/or downstream adapter sequences), all co-linear within the sequenced molecule. This library was then sequenced with paired-end 250 nucleotide reads on a MiSeq sequencer (Illumina) as described. This yielded approximately 13.5 million total molecules sequenced from the library, sequenced once from each end, for a total of approximately 27 million sequence reads.

Each forward read is expected to start with a six nucleotide sequence, corresponding to the 3' end of the upstream adapter: TGACCT This forward read is followed by the first barcode sequence within the molecule (expected to be nt long).

This barcode is then followed by an 'intra-barcode sequence' (in this case being sequenced in the 'forward' direction (which is 82 nucleotides including both the downstream adapter sequence and upstream adapter sequence in series): ATACCTGACTGCTCGTCAGTTGAGCGAATTCCGTATGGTGGTACACACCTACACTACTCGGACGCTCTTCCGATCTTGACCT (SEQ ID NO: 304)

Within the 250 nucleotide forward read, this will then be followed by a second barcode, another intra-barcode sequence, and then a third barcode, and then a fraction of another intra-barcode sequence.

Each reverse read is expected to start with a sequence corresponding to the downstream adapter sequence: GCTCAACTGACGAGCAGTCAGGTAT (SEQ ID NO: 305)

This reverse read is then followed by the first barcode coming in from the opposite end of the molecule (also 20 nucleotides long, but sequenced from the opposite strand of the molecule and thus of the inverse orientation to those sequenced by the forward read) This barcode is then followed by the 'intra-barcode sequence' but in the inverse orientation (as it is on the opposite strand):

AGGTCAAGATCG-GAAGAGCGTCCGAGTAGTGTAGGTGTGTACCAC-CATACGGAATTCGCTC
AACTGACGAGCAGTCAGGTAT (SEQ ID NO: 306)

Likewise this 250 nucleotide reverse read will then be followed by a second barcode, another intra-barcode sequence, and then a third barcode, and then a fraction of another intra-barcode sequence.

Sequence Extraction and Analysis

With scripting in Python, each associated pair of barcode and flanking upstream-adapter and downstream-adapter sequence were isolated, with each individual barcode sequence of each barcode molecule then isolated, and each barcode sequence that was sequenced within the same molecule being annotated as belonging to the same multimeric barcode molecule in the library of multimeric barcode molecules. A simple analysis script (Networkx; Python) was employed to determine overall multimeric barcode molecule barcode groups, by examining overlap of barcode-barcode pairs across different sequenced molecules. Several metrics of this data were made, including barcode length, sequence content, and the size and complexity of the multimeric barcode molecules across the library of multimeric barcode molecules.

Number of Nucleotides within Each Barcode Sequence

Figure 10:
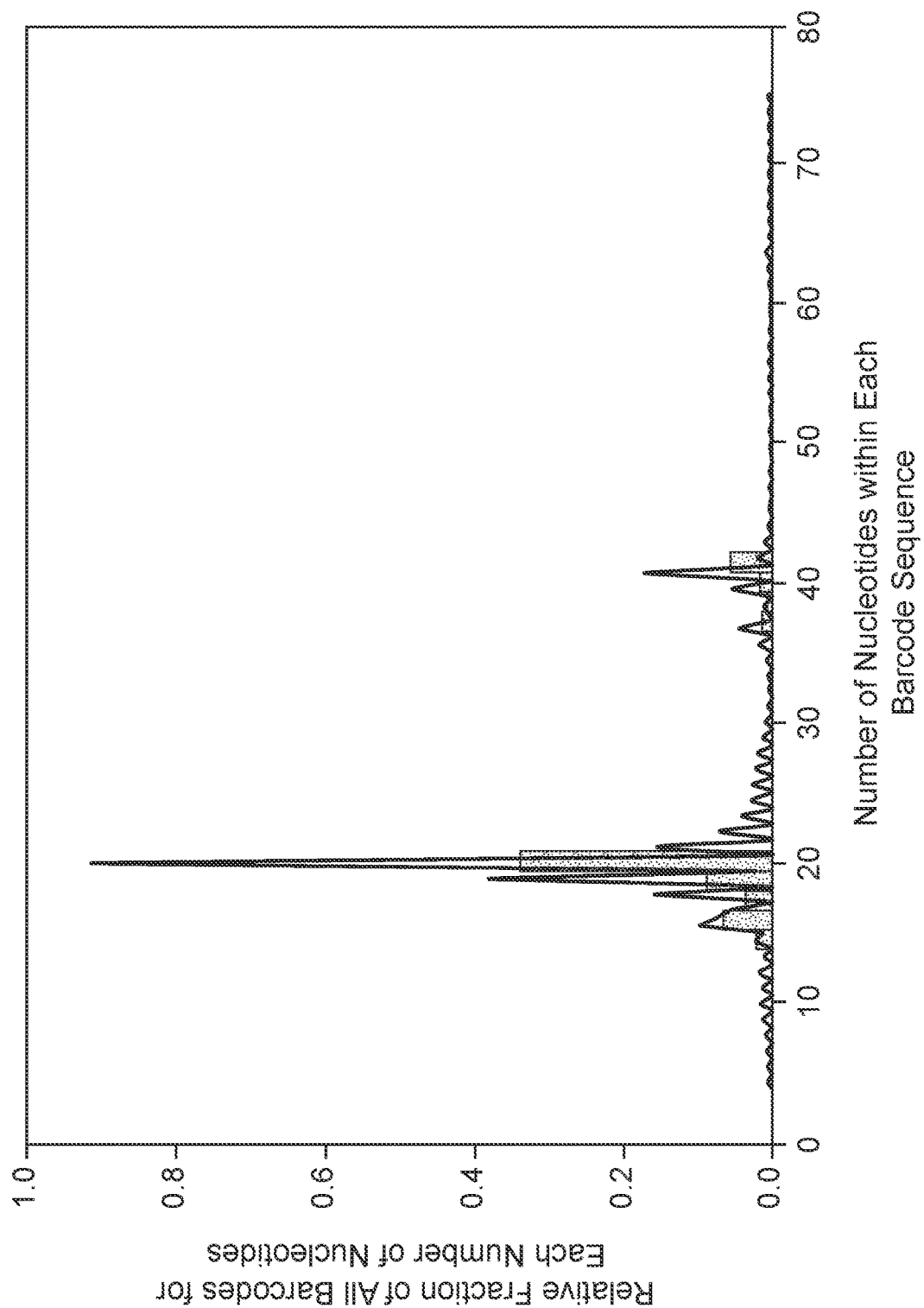
FIG. 10 is a graph showing the total number of nucleotides within each barcode sequence.

Each individual barcode sequence from each barcode molecule, contained within each Illumina-sequenced molecule was isolated, and the total length of each such barcode was determined by counting the number of nucleotides between the upstream adapter molecule sequence, and the downstream adapter molecule sequence. The results are shown in FIG. 10.

The overwhelming majority of barcodes are 20 nucleotides long, which corresponds to five additions of our four-nucleotide-long sub-barcode molecules from our double-stranded sub-barcode library. This is thus the expected and desired result, and indicates that each 'cycle' of: Ligation of Sub-Barcode Library to MlyI-Cleaved Solution, PCR Amplification of the Ligated Library, Uracil Glycosylase Enzyme Digestion, and MlyI Restriction Enzyme Cleavage, was successful and able to efficiently add new four-nucleotide sub-barcode molecules at each cycle, and then was successfully able to amplify and carry these molecules forward through the protocol for continued further processing, including through the five total cycles of sub-barcode addition, to make the final, upstream-adapter-ligated libraries.

We also used this sequence analysis method to quantitate the total number of unique barcodes in total, across all sequenced multimeric barcode molecules: this amounted to 19,953,626 total unique barcodes, which is essentially identical to the 20 million barcodes that would be expected, given that we synthesised 2 million multimeric barcode molecules, each with approximately 10 individual barcode molecules.

Together, this data and analysis thus shows that the methods of creating complex, combinatoric barcodes from sub-barcode sequences is effective and useful for the purpose of synthesising multimeric barcode molecules.

Total Number of Unique Barcode Molecules in Each Multimeric Barcode Molecule

Figure 11:
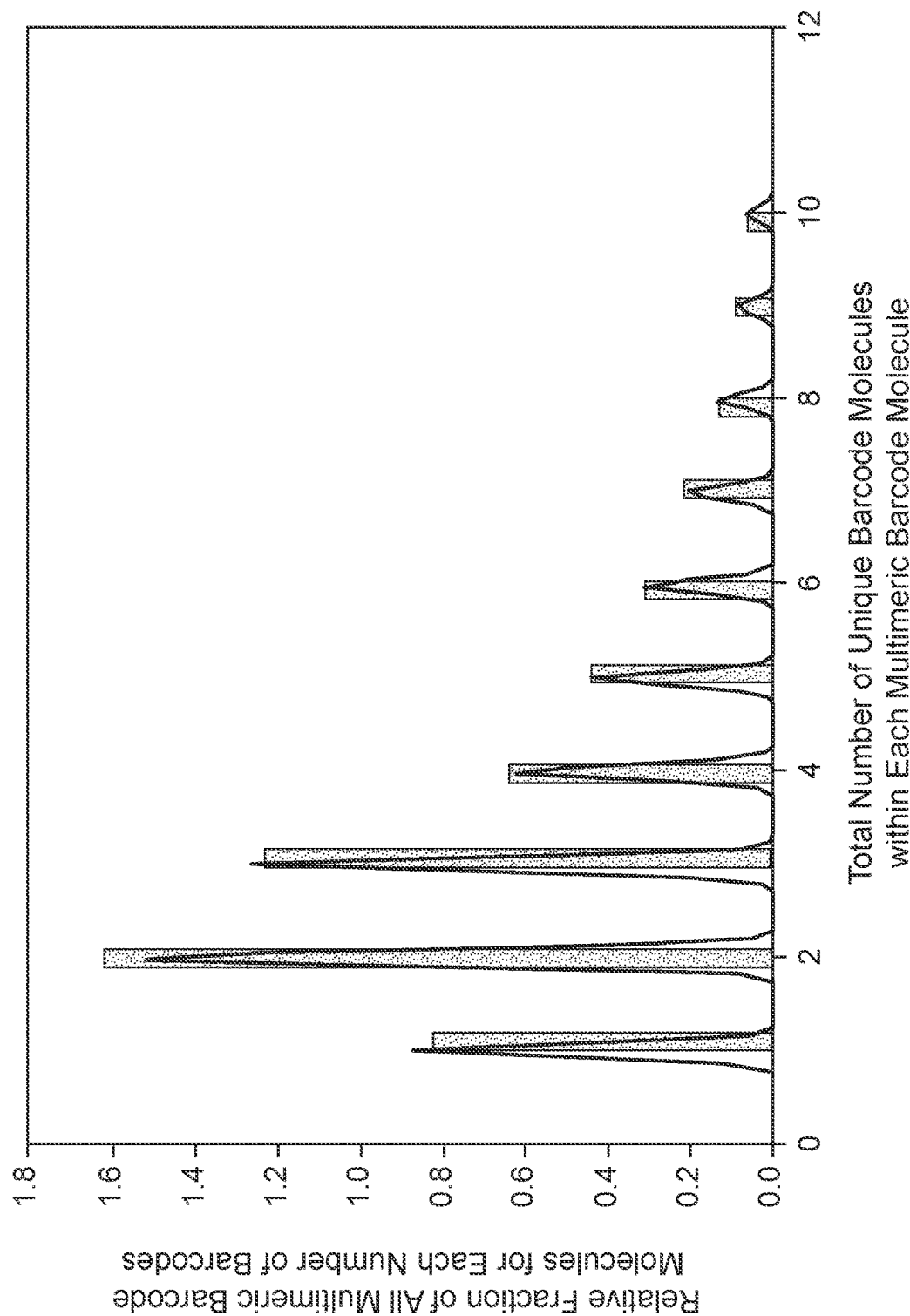
FIG. 11 is a graph showing the total number of unique barcode molecules in each sequenced multimeric barcode molecule.

FIG. 11 shows the results of the quantification of the total number of unique barcode molecules (as determined by their respective barcode sequences) in each sequenced multimeric barcode molecule. As described above, to do this we examined, in the first case, barcode sequences which were present and detected within the same individual molecules sequenced on the sequencer. We then employed an additional step of clustering barcode sequences further, wherein we employed a simple network analysis script (Networkx) which can determine links between individual barcode sequences based both upon explicit knowledge of links (wherein the barcodes are found within the same, contiguous sequenced molecule), and can also determine 'implicit' links, wherein two or more barcodes, which are not sequenced within the same sequenced molecule, instead both share a direct link to a common, third barcode sequence (this shared, common link thus dictating that the two first barcode sequences are in fact located on the same multimeric barcode molecule).

This figure shows that the majority of multimeric barcode molecules sequenced within our reaction have two or more unique barcodes contained therein, thus showing that, through our Overlap-Extension PCR linking process, we are able to link together multiple barcode molecules into multimeric barcode molecules. Whilst we would expect to see more multimeric barcode molecules exhibiting closer to the expected number of barcode molecules (10), we expect that this observed effect is due to insufficiently high sequencing depth, and that with a greater number of sequenced molecules, we would be able to observe a greater fraction of the true links between individual barcode molecules. This data nonetheless suggest that the fundamental synthesis procedure we describe here is efficacious for the intended purpose.

Representative Multimeric Barcode Molecules

Figure 12:
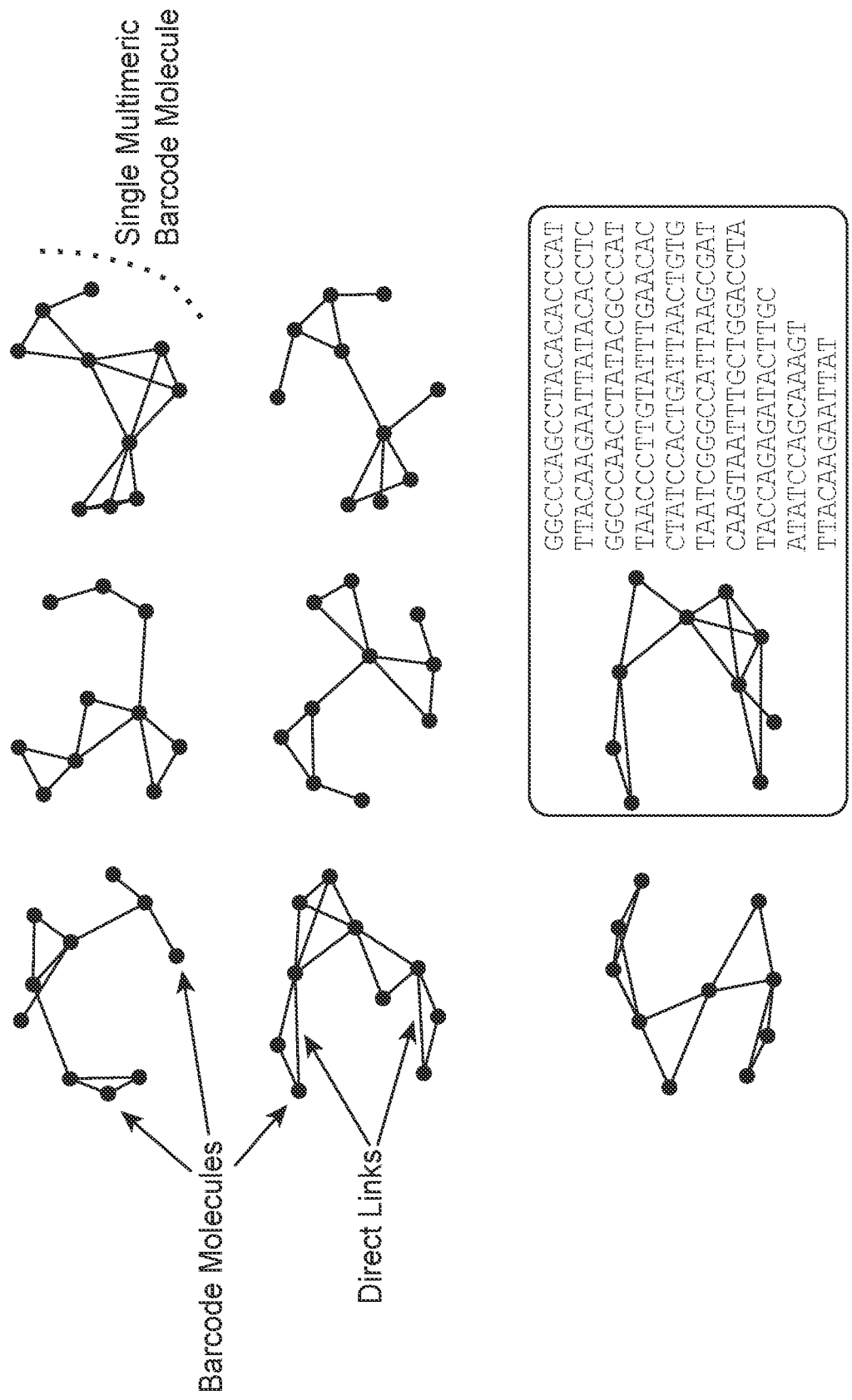
FIG. 12 shows representative multimeric barcode molecules that were detected by the analysis script: GGCCCAGCCTACACACCCAT (SEQ ID NO: 307); TTACAAGAATTATACACCTC (SEQ ID NO: 308); GGCCCAACCTATACGCCCAT (SEQ ID NO: 309); TAACCCTTGTATTTGAACAC (SEQ ID NO: 310); CTATCCACTGATTAACTGTG (SEQ ID NO: 311); TAATCGGGCCATTAAGCGAT (SEQ ID NO: 312); CAAGTAATTTGCTGGACCTA (SEQ ID NO: 313); TACCAGAGATACTTGC (SEQ ID NO: 314); ATATCCAGCAAAGT (SEQ ID NO: 315); and TTACAAGAATTAT (SEQ ID NO: 316).

FIG. 12 shows representative multimeric barcode molecules that have been detected by our analysis script. In this figure, each 'node' is a single barcode molecule (from its associated barcode sequence), each line is a 'direct link' between two barcode molecules that have been sequenced at least once in the same sequenced molecule, and each cluster of nodes is an individual multimeric barcode molecule, containing both barcodes with direct links and those within implicit, indirect links as determined by our analysis script. The inset figure includes a single multimeric barcode molecule, and the sequences of its constituent barcode molecules contained therein.

This figure illustrates the multimeric barcode molecule synthesis procedure: that we are able to construct barcode molecules from sub-barcode molecule libraries, that we are able to link multiple barcode molecules with an overlap-extension PCR reaction, that we are able to isolate a quantitatively known number of individual multimeric barcode molecules, and that we are able to amplify these and subject them to downstream analysis and use.

Barcoding Synthetic DNA Templates of Known Sequence with (i) Multimeric Barcoding Reagents Containing Barcoded Oligonucleotides, and (ii) Multimeric Barcoding Reagents and Separate Adapter Oligonucleotides Sequence Extraction and Analysis With scripting in Python and implemented in an Amazon Web Services (AWS) framework, for each sequence read following sample-demultiplexing, each barcode region from the given multimeric barcode reagent was isolated from its flanking upstream-adapter and downstream-adapter sequence. Likewise, each molecular sequence identifier region from the given synthetic DNA template molecule was isolated from its flanking upstream and downstream sequences. This process was repeated for each molecule in the sample library; a single filtering step was performed in which individual barcodes and molecular sequence identifiers that were present in only a single read (thus likely to represent either sequencing error or error from the enzymatic sample-preparation process) were censored from the data. For each molecular sequence identifier, the total number of unique (ie with different sequences) barcode regions found associated therewith within single sequence reads was quantitated. A histogram plot was then created to visualize the distribution of this number across all molecular sequence identifiers found in the library.

Discussion

Figure 13:
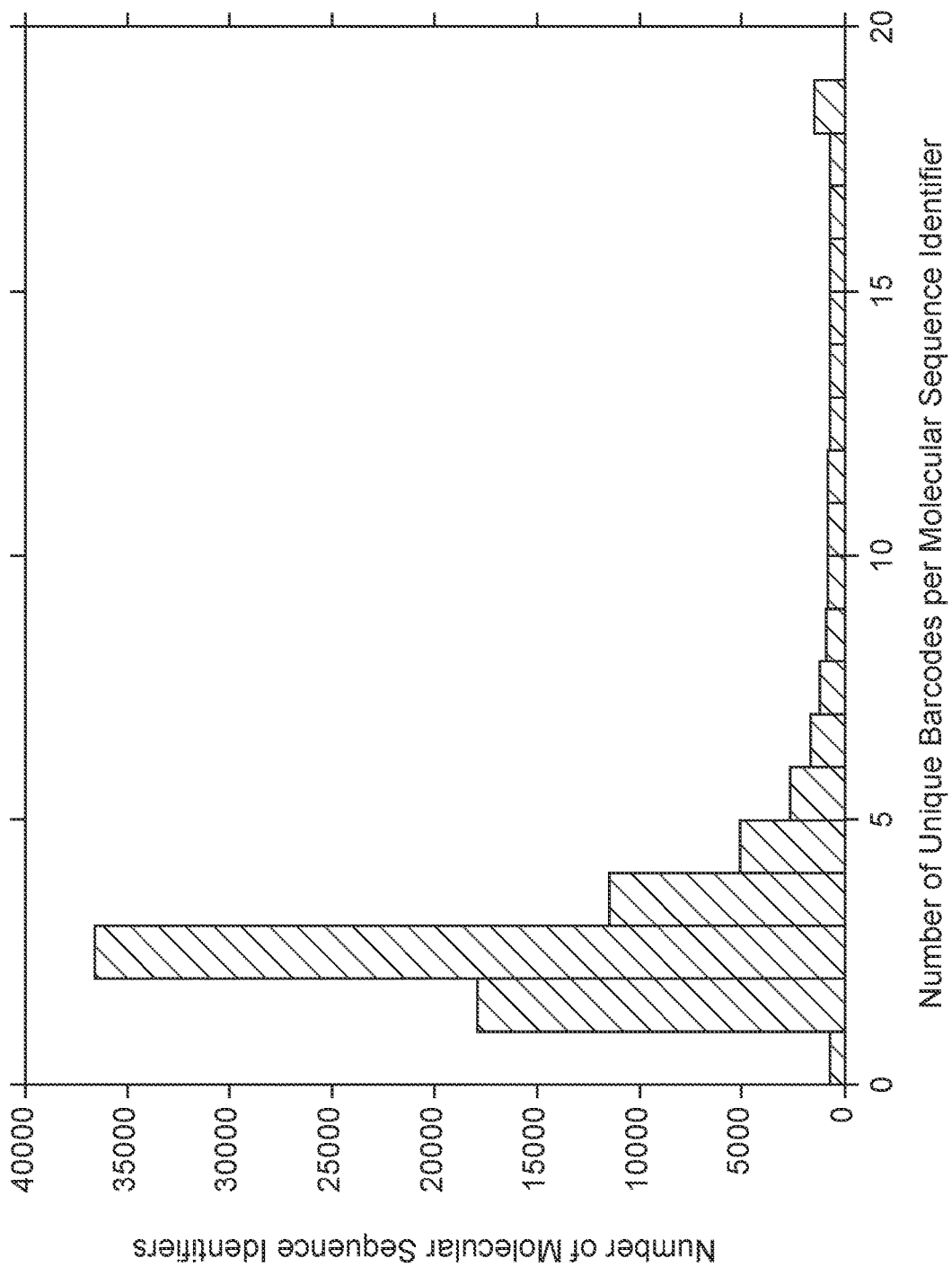
FIG. 13 is a graph showing the number of unique barcodes per molecular sequence identifier against the number of molecular sequence identifiers following the barcoding of synthetic DNA templates of known sequence with multimeric barcoding reagents containing barcoded oligonucleotides.

FIG. 13 shows the results of this analysis for Method 6 (Barcoding Synthetic DNA Templates of Known Sequence with Multimeric Barcoding Reagents Containing Barcoded Oligonucleotides). This figure makes clear that the majority of multimeric barcoding reagents are able to successfully label two or more of the tandemly-repeated copies of each molecular sequence identifier with which they are associated. A distribution from 1 to approximately 5 or 6 'labelling events' is observed, indicating that there may be a degree of stochastic interactions that occur with this system, perhaps due to incomplete enzymatic reactions, or steric hindrance at barcode reagent/synthetic template interface, or other factors.

Figure 14:
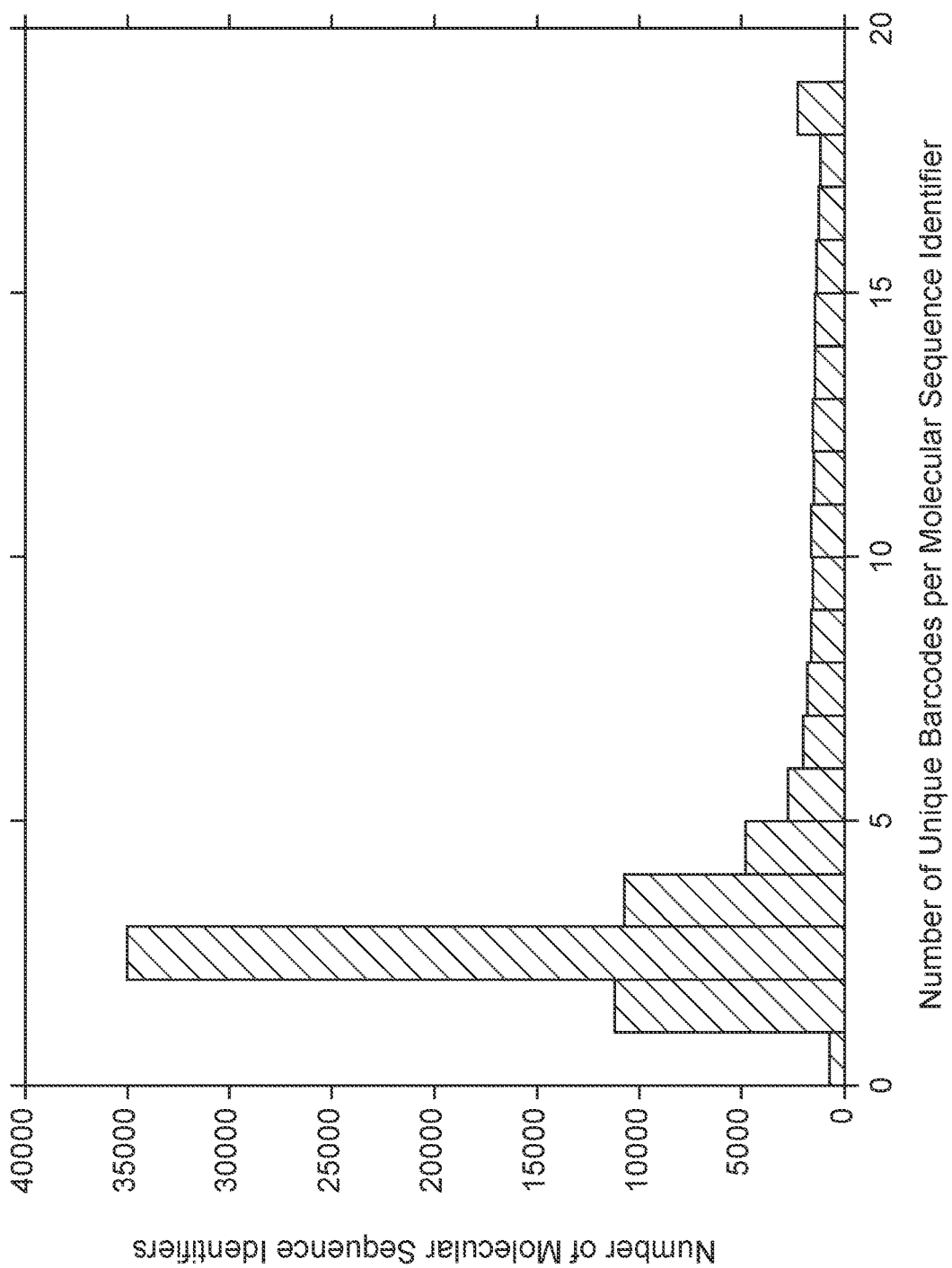
FIG. 14 is a graph showing the number of unique barcodes per molecular sequence identifier against the number of molecular sequence identifiers following the barcoding of synthetic DNA templates of known sequence with multimeric barcoding reagents and separate adapter oligonucleotides.

FIG. 14 shows the results of this same analysis conducted using Method 7 (Barcoding Oligonucleotides Synthetic DNA Templates of Known Sequence with Multimeric Barcode Molecules and Separate Adapter Oligonucleotides). This figure also clearly shows that the majority of multimeric barcoding reagents are able to successfully label two or more of the tandemly-repeated copies of each molecular sequence identifier with which they are associated, with a similar distribution to that observed for the previous analysis.

Together, these two figures show that this framework for multimeric molecular barcoding is an effective one, and furthermore that the framework can be configured in different methodologic ways. FIG. 13 shows results based on a method in which the framework is configured such that the multimeric barcode reagents already contain barcoded oligonucleotides, prior to their being contacted with a target (synthetic) DNA template. In contrast, FIG. 14 shows results based on an alternative method in which the adapter oligonucleotides first contact the synthetic DNA template, and then in a subsequent step the adapter oligonucleotides are barcoded through contact with a multimeric barcode reagent. Together these figures demonstrate both the multimeric barcoding ability of these reagents, and their versatility in different key laboratory protocols.

To analyse whether, and the extent to which, individual multimeric barcoding reagents successfully label two or more sub-sequences of the same synthetic DNA template, the groups of different barcodes on each individual multimeric barcoding reagent in the library (as predicted from the Networkx analysis described in the preceding paragraph and as illustrated in FIG. 12) was compared with the barcodes annealed and extended along single synthetic DNA templates (as described in Method 11). Each group of barcodes found on individual multimeric barcoding reagents was given a numeric 'reagent identifier label'. For each synthetic DNA template molecular sequence identifier (i.e., for each individual synthetic DNA template molecule) that was represented in the sequencing data of Method 11 by two or more barcodes (i.e., wherein two or more sub-sequences of the synthetic template molecule were annealed and extended by a barcoded oligonucleotide), the corresponding 'reagent identifier label' was determined. For each such synthetic template molecule, the total number of multimeric barcodes coming from the same, single multimeric barcoding reagent was then calculated (i.e., the number of different sub-sequences in the synthetic template molecule that were labeled by a different barcoded oligonucleotide but from the same, single multimeric barcoding reagent was calculated). This analysis was then repeated and compared with a 'negative control' condition, in which the barcodes assigned to each 'reagent identifier label' were randomized (i.e. the same barcode sequences remain present in the data, but they no longer correspond to the actual molecular linkage of different barcode sequences across the library of multimeric barcoding reagents).

The data from this analysis is shown in FIG. 17, for both the actual experimental data and for the control data with randomized barcode assignments (note the logarithmic scale of the vertical axis). As this figure shows, though the number of unique barcoding events per target synthetic DNA template molecule is small, they overlap almost perfectly with the known barcode content of individual multimeric barcoding reagents. That is, when compared with the randomized barcode data (which contains essentially no template molecules that appear to be 'multivalently barcoded'), the overwhelming majority (over 99.9%) of template molecules in the actual experiment that appear to be labeled by multiple barcoded oligonucleotides from the same, individual multimeric barcoding reagent, are in fact labeled multiply by the same, single reagents in solution. By contrast, if there were no non-random association between the different barcodes that labelled individual synthetic DNA templates (that is, if FIG. 17 showed no difference between the actual experimental data and the randomized data), then this would have indicated that the barcoding had not occurred in a spatially-constrained manner as directed by the multimeric barcoding reagents. However, as explained above, the data indicates convincingly that the desired barcoding reactions did occur, in which sub-sequences found on single synthetic DNA templates interacted with (and were then barcoded by) only single, individual multimeric barcoding reagents.

Figure 16:
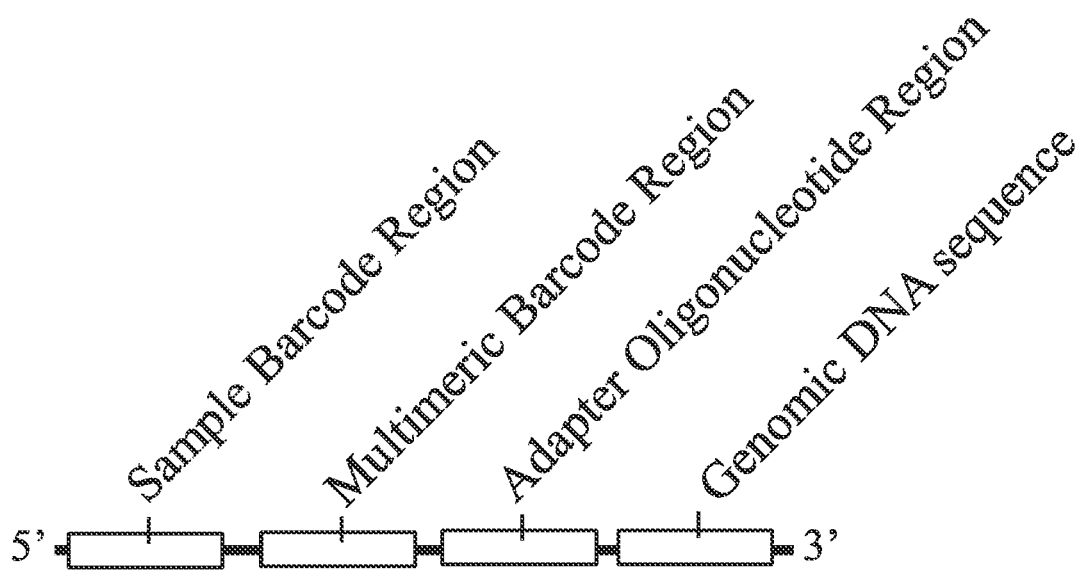
FIG. 16 is a schematic illustration of a sequence read obtained from barcoding genomic DNA loci with multimeric barcoding reagents containing barcoded oligonucleotides.

Barcoding Genomic DNA Loci with Multimeric Barcoding Reagents Containing Barcoded Oligonucleotides Sequence Extraction and Analysis As with other analysis, scripting was composed in Python and implemented in an Amazon Web Services (AWS) framework. For each sequence read following sample-demultiplexing, each barcode region from the given multimeric barcode reagent was isolated from its flanking upstream-adapter and downstream-adapter sequence and recorded independently for further analysis. Likewise, each sequence to the 3' end of the downstream region (representing sequence containing the barcoded oligonucleotide, and any sequences that the oligonucleotide had primed along during the experimental protocol) was isolated for further analysis. Each downstream sequence of each read was analysed for the presence of expected adapter oligonucleotide sequences (i.e. from the primers corresponding to one of the three genes to which the oligonucleotides were directed) and relevant additional downstream sequences. Each read was then recorded as being either 'on-target' (with sequence corresponding to one of the expected, targeted sequence) or 'off-target'. Furthermore, for each of the targeted regions, the total number of unique multimeric barcodes (i.e. with identical but duplicate barcodes merged into a single-copy representation) was calculated. A schematic of each expected sequence read, and the constituent components thereof, is shown in FIG. 16.

Discussion

FIG. 15 shows the results of this analysis for this method, for four different independent samples. These four samples represent a method wherein the process of annealing the multimeric barcode reagents took place for either 3 hours, or overnight (approximately 12 hours). Further, for each of these two conditions, the method was performed either with the multimeric barcode reagents retained intact as originally synthesized, or with a modified protocol in which the barcoded oligonucleotides are first denatured away from the barcode molecules themselves (through a high-temperature melting step). Each row represents a different amplicon target as indicated, and each cell represents the total number of unique barcode found associated with each amplicon in each of the four samples. Also listed is the total proportion of on-target reads, across all targets summed together, for each sample.

As seen in the figure, the majority of reads across all samples are on-target; however there is seen a large range in the number of unique barcode molecules observed for each amplicon target. These trends across different amplicons seem to be consistent across the different experimental conditions, and could be due to different priming (or mis-priming) efficiencies of the different oligonucleotides, or different amplification efficiencies, or different mapping efficiencies, plus potential other factors acting independently or in combination. Furthermore, it is clear that the samples that were annealed for longer have a larger number of barcodes observed, likely due to more complete overall annealing of the multimeric reagents to their cognate genomic targets. And furthermore, the samples where the barcoded oligonucleotides were first denatured from the barcode molecules show lower overall numbers of unique barcodes, perhaps owing to an avidity effect wherein fully assembled barcode molecules can more effectively anneal clusters of primers to nearby genomic targets at the same locus. In any case, taken together, this figure illustrates the capacity of multimeric reagents to label genomic DNA molecules, across a large number of molecules simultaneously, and to do so whether the barcoded oligonucleotides remain bound on the multimeric barcoding reagents or whether they have been denatured therefrom and thus potentially able to diffuse more readily in solution.

The invention claimed is:

1. A method of preparing a nucleic acid sample for sequencing, wherein the sample comprises at least 10 cells, wherein the sample of cells has been incubated with a pool of two or more different barcoded affinity probes, wherein the pool comprises a first barcoded affinity probe comprising a first affinity moiety and a first probe-barcode oligonucleotide, wherein the first affinity moiety is capable of binding to a first target protein, and a second barcoded affinity probe comprising a second affinity moiety and a second probe-barcode oligonucleotide, wherein the second affinity moiety is capable of binding to a second target protein, wherein each probe-barcode oligonucleotide comprises a barcode sequence associated with and/or identifying of the affinity moiety to which it is linked, and wherein the method comprises the steps of:

(a) contacting the sample with a library comprising at least two multimeric barcoding reagents, wherein each multimeric barcoding reagent comprises first and second barcoded oligonucleotides linked together and a cell-binding moiety, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library, wherein the cell-binding moiety of the first multimeric barcoding reagent binds to the cell membrane of a first cell prior to step (b), and wherein the cell-binding moiety of the second multimeric barcoding reagent binds to the cell membrane of a second cell prior to step (b);

(b) lysing the cells or permeabilizing the cell membranes of the cells; and (c) annealing or ligating the first and second barcoded oligonucleotides of the first multimeric barcoding reagent to first and second sub-sequences of a target nucleic acid of the first cell to produce first and second barcoded target nucleic acid molecules, and annealing or ligating the first and second barcoded oligonucleotides from the second multimeric barcoding reagent to first and second sub-sequences of a target nucleic acid of the second cell to produce first and second barcoded target nucleic acid molecules, wherein the cells are comprised within a single contiguous aqueous volume during steps (a), (b) and (c), and wherein the target nucleic acids comprise probe-barcode oligonucleotides within the barcoded affinity probes.

2. The method of claim 1, wherein step (c) comprises:
(i) annealing the first and second barcoded oligonucleotides of the first multimeric barcoding reagent to first and second sub-sequences of a target nucleic acid of the first cell, and annealing the first and second barcoded oligonucleotides of the second multimeric barcoding reagent to first and second sub-sequences of a target nucleic acid of the second cell; and
(ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the target nucleic acid as a template.

3. The method of claim 1, wherein the multimeric barcoding reagents each comprise:
(i) first and second hybridization molecules linked together, wherein each of the hybridization molecules comprises a nucleic acid sequence comprising a hybridization region; and
(ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule.

4. The method of claim 3, wherein the multimeric barcoding reagents each comprise:
(i) first and second barcode molecules linked together, wherein each of the barcode molecules comprises a nucleic acid sequence comprising a barcode region; and
(ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule.

5. The method of claim 1, wherein step (b) is performed by increasing the temperature of the sample.

6. The method of claim 1, wherein step (b) is performed in the presence of a chemical surfactant.

7. The method of claim 1, wherein step (b) is performed under hypotonic or hypertonic conditions.

8. The method of claim 1, wherein the target nucleic acids further comprise mRNA molecules comprised within the cells.

9. The method of claim 1, wherein a cell-binding moiety is attached to each of the barcoded oligonucleotides.

10. The method of claim 1, wherein the multimeric barcoding reagents each comprise a solid support or semi-solid support, and wherein a cell-binding moiety is attached to the solid support or semi-solid support.

11. The method of claim 1, wherein the sample of cells has been chemically crosslinked prior to the incubation of the sample of cells with the pool of barcoded affinity probes.

* * * * *

SEQUENCE LISTING

```
Sequence total quantity: 316
SEQ ID NO: 1            moltype = DNA  length = 38
FEATURE                 Location/Qualifiers
misc_feature            1..38
                        note = Primer
source                  1..38
                        mol_type = other DNA
                        organism = synthetic construct
SEQUENCE: 1
ctcgatgcta cgtgactact gcgtcgagga gtctatcc                          38

SEQ ID NO: 2            moltype = DNA  length = 96
FEATURE                 Location/Qualifiers
misc_feature            1..96
                        note = Primer
source                  1..96
                        mol_type = other DNA
                        organism = synthetic construct
SEQUENCE: 2
atacctgact gctcgtcagt tgagcgaatt ccgtatgggt agcaaggtcc aagagaggct   60
ccatcctcac tcgcctgact acgacaagac ctactg                            96

SEQ ID NO: 3            moltype = DNA  length = 98
FEATURE                 Location/Qualifiers
misc_feature            1..98
                        note = Primer
source                  1..98
                        mol_type = other DNA
                        organism = synthetic construct
SEQUENCE: 3
tccagtaggt cttgtcgtag tcaggcgagt gaggatggag cctctcttgg accttgctac   60
ccatacgaa ttcgctcaac tgacgagcag tcaggtat                           98

SEQ ID NO: 4            moltype = DNA  length = 22
FEATURE                 Location/Qualifiers
misc_feature            1..22
                        note = Primer
source                  1..22
```

```
                                mol_type = other DNA
                                organism = synthetic construct
SEQUENCE: 4
ctcgatgcta cgtgactact gc                                                  22

SEQ ID NO: 5                    moltype = DNA  length = 22
FEATURE                         Location/Qualifiers
misc_feature                    1..22
                                note = Primer
source                          1..22
                                mol_type = other DNA
                                organism = synthetic construct
SEQUENCE: 5
cagtaggtct tgtcgtagtc ag                                                  22

SEQ ID NO: 6                    moltype = DNA  length = 45
FEATURE                         Location/Qualifiers
misc_feature                    1..45
                                note = Primer
source                          1..45
                                mol_type = other DNA
                                organism = synthetic construct
SEQUENCE: 6
atggtacaca cctacactac tcggacgctc ttccgatctt gacct                         45

SEQ ID NO: 7                    moltype = DNA  length = 44
FEATURE                         Location/Qualifiers
misc_feature                    1..44
                                note = Primer
source                          1..44
                                mol_type = other DNA
                                organism = synthetic construct
SEQUENCE: 7
aggtcaagat cggaagagcg tccgagtagt gtaggtgtgt acca                          44

SEQ ID NO: 8                    moltype = DNA  length = 22
FEATURE                         Location/Qualifiers
misc_feature                    1..22
                                note = Primer
source                          1..22
                                mol_type = other DNA
                                organism = synthetic construct
SEQUENCE: 8
tggtacacac ctacactact cg                                                  22

SEQ ID NO: 9                    moltype = DNA  length = 20
FEATURE                         Location/Qualifiers
misc_feature                    1..20
                                note = Primer
source                          1..20
                                mol_type = other DNA
                                organism = synthetic construct
SEQUENCE: 9
ccatacggaa ttcgctcaac                                                     20

SEQ ID NO: 10                   moltype = DNA  length = 42
FEATURE                         Location/Qualifiers
misc_feature                    1..42
                                note = Primer
source                          1..42
                                mol_type = other DNA
                                organism = synthetic construct
SEQUENCE: 10
gttgagcgaa ttccgtatgg tggtacacac ctacactact cg                            42

SEQ ID NO: 11                   moltype = DNA  length = 46
FEATURE                         Location/Qualifiers
misc_feature                    1..46
                                note = Primer
source                          1..46
                                mol_type = other DNA
                                organism = synthetic construct
SEQUENCE: 11
taggacgata cgagtgtgta ctcgtggtac acacctacac tactcg                        46

SEQ ID NO: 12                   moltype = DNA  length = 42
FEATURE                         Location/Qualifiers
misc_feature                    1..42
                                note = Primer
```

```
                      source            1..42
                                        mol_type = other DNA
                                        organism = synthetic construct
SEQUENCE: 12
cgagtagtgt aggtgtgtac caccatacgg aattcgctca ac                         42

SEQ ID NO: 13           moltype = DNA   length = 44
FEATURE                 Location/Qualifiers
misc_feature            1..44
                        note = Primer
source                  1..44
                        mol_type = other DNA
                        organism = synthetic construct
SEQUENCE: 13
ctgtcaaggt agactagcat gctcccatac ggaattcgct caac                       44

SEQ ID NO: 14           moltype = DNA   length = 24
FEATURE                 Location/Qualifiers
misc_feature            1..24
                        note = Primer
source                  1..24
                        mol_type = other DNA
                        organism = synthetic construct
SEQUENCE: 14
taggacgata cgagtgtgta ctcg                                             24

SEQ ID NO: 15           moltype = DNA   length = 24
FEATURE                 Location/Qualifiers
misc_feature            1..24
                        note = Primer
source                  1..24
                        mol_type = other DNA
                        organism = synthetic construct
SEQUENCE: 15
ctgtcaaggt agactagcat gctc                                             24

SEQ ID NO: 16           moltype = DNA   length = 56
FEATURE                 Location/Qualifiers
misc_feature            1..56
                        note = Primer
source                  1..56
                        mol_type = other DNA
                        organism = synthetic construct
SEQUENCE: 16
ctcggcattc ctgctgaacc gctcttccga tctgctcaac tgacgagcag tcaggt          56

SEQ ID NO: 17           moltype = DNA   length = 39
FEATURE                 Location/Qualifiers
misc_feature            1..39
                        note = Primer
source                  1..39
                        mol_type = other DNA
                        organism = synthetic construct
SEQUENCE: 17
acactctttc cctacacgac gctcttccga tcttgacct                             39

SEQ ID NO: 18           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 18
aaacggatag actcctcgac                                                  20

SEQ ID NO: 19           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 19
aaagggatag actcctcgac                                                  20

SEQ ID NO: 20           moltype = DNA   length = 20
```

```
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 20
aaatggatag actcctcgac                                                    20

SEQ ID NO: 21           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 21
aacaggatag actcctcgac                                                    20

SEQ ID NO: 22           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 22
aaccggatag actcctcgac                                                    20

SEQ ID NO: 23           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 23
aacgggatag actcctcgac                                                    20

SEQ ID NO: 24           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 24
aactggatag actcctcgac                                                    20

SEQ ID NO: 25           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 25
aagaggatag actcctcgac                                                    20

SEQ ID NO: 26           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 26
aagcggatag actcctcgac                                                    20

SEQ ID NO: 27           moltype = DNA  length = 20
FEATURE                 Location/Qualifiers
misc_feature            1..20
```

```
                        note = Sequence used in the synthesis of sub-barcode
                         molecule library
source                  1..20
                        mol_type = other DNA
                        organism = synthetic construct
SEQUENCE: 27
aaggggatag actcctcgac                                                    20

SEQ ID NO: 28           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 28
aagtggatag actcctcgac                                                    20

SEQ ID NO: 29           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 29
aataggatag actcctcgac                                                    20

SEQ ID NO: 30           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 30
aatcggatag actcctcgac                                                    20

SEQ ID NO: 31           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 31
aatgggatag actcctcgac                                                    20

SEQ ID NO: 32           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 32
aattggatag actcctcgac                                                    20

SEQ ID NO: 33           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 33
acaaggatag actcctcgac                                                    20

SEQ ID NO: 34           moltype = DNA   length = 20
FEATURE                 Location/Qualifiers
misc_feature            1..20
                        note = Sequence used in the synthesis of sub-barcode
                         molecule library
```

```
source                  1..20
                        mol_type = other DNA
                        organism = synthetic construct
SEQUENCE: 34
acacggatag actcctcgac                                                    20

SEQ ID NO: 41           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 35
acagggatag actcctcgac                                                    20

SEQ ID NO: 36           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 36
acatggatag actcctcgac                                                    20

SEQ ID NO: 37           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 37
accaggatag actcctcgac                                                    20

SEQ ID NO: 38           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 38
acccggatag actcctcgac                                                    20

SEQ ID NO: 39           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 39
accgggatag actcctcgac                                                    20

SEQ ID NO: 40           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 40
acctggatag actcctcgac                                                    20

SEQ ID NO: 41           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
```

```
                              organism = synthetic construct
SEQUENCE: 41
acgaggatag actcctcgac                                                         20

SEQ ID NO: 42           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 42
acgcggatag actcctcgac                                                         20

SEQ ID NO: 43           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 43
acggggatag actcctcgac                                                         20

SEQ ID NO: 44           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 44
acgtggatag actcctcgac                                                         20

SEQ ID NO: 45           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 45
actaggatag actcctcgac                                                         20

SEQ ID NO: 46           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 46
actcggatag actcctcgac                                                         20

SEQ ID NO: 47           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 47
actgggatag actcctcgac                                                         20

SEQ ID NO: 48           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 48
```

```
acttggatag actcctcgac                                                 20

SEQ ID NO: 49           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 49
agaaggatag actcctcgac                                                 20

SEQ ID NO: 50           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 50
agacggatag actcctcgac                                                 20

SEQ ID NO: 51           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 51
agagggatag actcctcgac                                                 20

SEQ ID NO: 52           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 52
agatggatag actcctcgac                                                 20

SEQ ID NO: 53           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 53
agcaggatag actcctcgac                                                 20

SEQ ID NO: 54           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 54
agccggatag actcctcgac                                                 20

SEQ ID NO: 55           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 55
agcgggatag actcctcgac                                                 20
```

```
SEQ ID NO: 56           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 56
agctggatag actcctcgac                                                    20

SEQ ID NO: 57           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 57
aggaggatag actcctcgac                                                    20

SEQ ID NO: 58           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 58
aggcggatag actcctcgac                                                    20

SEQ ID NO: 59           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 59
agggggatag actcctcgac                                                    20

SEQ ID NO: 60           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 60
aggtggatag actcctcgac                                                    20

SEQ ID NO: 61           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 61
agtaggatag actcctcgac                                                    20

SEQ ID NO: 62           moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 62
agtcggatag actcctcgac                                                    20

SEQ ID NO: 63           moltype = DNA  length = 20
FEATURE                 Location/Qualifiers
```

```
misc_feature            1..20
                        note = Sequence used in the synthesis of sub-barcode
                         molecule library
source                  1..20
                        mol_type = other DNA
                        organism = synthetic construct
SEQUENCE: 63
agtgggatag actcctcgac                                                      20

SEQ ID NO: 64           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 64
agttggatag actcctcgac                                                      20

SEQ ID NO: 65           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 65
ataaggatag actcctcgac                                                      20

SEQ ID NO: 66           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 66
atacggatag actcctcgac                                                      20

SEQ ID NO: 67           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 67
ataggatag actcctcgac                                                       20

SEQ ID NO: 68           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 68
atatggatag actcctcgac                                                      20

SEQ ID NO: 69           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 69
atcaggatag actcctcgac                                                      20

SEQ ID NO: 70           moltype = DNA   length = 20
FEATURE                 Location/Qualifiers
misc_feature            1..20
                        note = Sequence used in the synthesis of sub-barcode
```

```
                           molecule library
source                     1..20
                           mol_type = other DNA
                           organism = synthetic construct
SEQUENCE: 70
atccggatag actcctcgac                                                    20

SEQ ID NO: 71              moltype = DNA  length = 20
FEATURE                    Location/Qualifiers
misc_feature               1..20
                           note = Sequence used in the synthesis of sub-barcode
                           molecule library
source                     1..20
                           mol_type = other DNA
                           organism = synthetic construct
SEQUENCE: 71
atcgggatag actcctcgac                                                    20

SEQ ID NO: 72              moltype = DNA  length = 20
FEATURE                    Location/Qualifiers
misc_feature               1..20
                           note = Sequence used in the synthesis of sub-barcode
                           molecule library
source                     1..20
                           mol_type = other DNA
                           organism = synthetic construct
SEQUENCE: 72
atctggatag actcctcgac                                                    20

SEQ ID NO: 73              moltype = DNA  length = 20
FEATURE                    Location/Qualifiers
misc_feature               1..20
                           note = Sequence used in the synthesis of sub-barcode
                           molecule library
source                     1..20
                           mol_type = other DNA
                           organism = synthetic construct
SEQUENCE: 73
atgaggatag actcctcgac                                                    20

SEQ ID NO: 74              moltype = DNA  length = 20
FEATURE                    Location/Qualifiers
misc_feature               1..20
                           note = Sequence used in the synthesis of sub-barcode
                           molecule library
source                     1..20
                           mol_type = other DNA
                           organism = synthetic construct
SEQUENCE: 74
atgcggatag actcctcgac                                                    20

SEQ ID NO: 75              moltype = DNA  length = 20
FEATURE                    Location/Qualifiers
misc_feature               1..20
                           note = Sequence used in the synthesis of sub-barcode
                           molecule library
source                     1..20
                           mol_type = other DNA
                           organism = synthetic construct
SEQUENCE: 75
atggggatag actcctcgac                                                    20

SEQ ID NO: 76              moltype = DNA  length = 20
FEATURE                    Location/Qualifiers
misc_feature               1..20
                           note = Sequence used in the synthesis of sub-barcode
                           molecule library
source                     1..20
                           mol_type = other DNA
                           organism = synthetic construct
SEQUENCE: 76
atgtggatag actcctcgac                                                    20

SEQ ID NO: 77              moltype = DNA  length = 20
FEATURE                    Location/Qualifiers
misc_feature               1..20
                           note = Sequence used in the synthesis of sub-barcode
                           molecule library
source                     1..20
```

```
                        mol_type = other DNA
                        organism = synthetic construct
SEQUENCE: 77
attaggatag actcctcgac                                                     20

SEQ ID NO: 78           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 78
attcggatag actcctcgac                                                     20

SEQ ID NO: 79           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 79
attgggatag actcctcgac                                                     20

SEQ ID NO: 80           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 80
atttggatag actcctcgac                                                     20

SEQ ID NO: 81           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 81
caaaggatag actcctcgac                                                     20

SEQ ID NO: 82           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 82
caacggatag actcctcgac                                                     20

SEQ ID NO: 83           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 83
caagggatag actcctcgac                                                     20

SEQ ID NO: 84           moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
```

```
SEQUENCE: 84
caatggatag actcctcgac                                                      20

SEQ ID NO: 85          moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 85
cacaggatag actcctcgac                                                      20

SEQ ID NO: 86          moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 86
caccggatag actcctcgac                                                      20

SEQ ID NO: 87          moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 87
cacgggatag actcctcgac                                                      20

SEQ ID NO: 88          moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 88
cactggatag actcctcgac                                                      20

SEQ ID NO: 89          moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 89
cagaggatag actcctcgac                                                      20

SEQ ID NO: 90          moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 90
cagcggatag actcctcgac                                                      20

SEQ ID NO: 91          moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 91
caggggatag actcctcgac                                                      20
```

```
SEQ ID NO: 92          moltype = DNA   length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 92
cagtggatag actcctcgac                                                  20

SEQ ID NO: 93          moltype = DNA   length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 93
cataggatag actcctcgac                                                  20

SEQ ID NO: 94          moltype = DNA   length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 94
catcggatag actcctcgac                                                  20

SEQ ID NO: 95          moltype = DNA   length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 95
catgggatag actcctcgac                                                  20

SEQ ID NO: 96          moltype = DNA   length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 96
cattggatag actcctcgac                                                  20

SEQ ID NO: 97          moltype = DNA   length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 97
ccaaggatag actcctcgac                                                  20

SEQ ID NO: 98          moltype = DNA   length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 98
ccacggatag actcctcgac                                                  20

SEQ ID NO: 99          moltype = DNA   length = 20
```

```
FEATURE              Location/Qualifiers
misc_feature         1..20
                     note = Sequence used in the synthesis of sub-barcode
                     molecule library
source               1..20
                     mol_type = other DNA
                     organism = synthetic construct
SEQUENCE: 99
ccagggatag actcctcgac                                                    20

SEQ ID NO: 100       moltype = DNA   length = 20
FEATURE              Location/Qualifiers
misc_feature         1..20
                     note = Sequence used in the synthesis of sub-barcode
                     molecule library
source               1..20
                     mol_type = other DNA
                     organism = synthetic construct
SEQUENCE: 100
ccatggatag actcctcgac                                                    20

SEQ ID NO: 101       moltype = DNA   length = 20
FEATURE              Location/Qualifiers
misc_feature         1..20
                     note = Sequence used in the synthesis of sub-barcode
                     molecule library
source               1..20
                     mol_type = other DNA
                     organism = synthetic construct
SEQUENCE: 101
cccaggatag actcctcgac                                                    20

SEQ ID NO: 102       moltype = DNA   length = 20
FEATURE              Location/Qualifiers
misc_feature         1..20
                     note = Sequence used in the synthesis of sub-barcode
                     molecule library
source               1..20
                     mol_type = other DNA
                     organism = synthetic construct
SEQUENCE: 102
cccgggatag actcctcgac                                                    20

SEQ ID NO: 103       moltype = DNA   length = 20
FEATURE              Location/Qualifiers
misc_feature         1..20
                     note = Sequence used in the synthesis of sub-barcode
                     molecule library
source               1..20
                     mol_type = other DNA
                     organism = synthetic construct
SEQUENCE: 103
ccctggatag actcctcgac                                                    20

SEQ ID NO: 104       moltype = DNA   length = 20
FEATURE              Location/Qualifiers
misc_feature         1..20
                     note = Sequence used in the synthesis of sub-barcode
                     molecule library
source               1..20
                     mol_type = other DNA
                     organism = synthetic construct
SEQUENCE: 104
ccgaggatag actcctcgac                                                    20

SEQ ID NO: 105       moltype = DNA   length = 20
FEATURE              Location/Qualifiers
misc_feature         1..20
                     note = Sequence used in the synthesis of sub-barcode
                     molecule library
source               1..20
                     mol_type = other DNA
                     organism = synthetic construct
SEQUENCE: 105
ccgcggatag actcctcgac                                                    20

SEQ ID NO: 106       moltype = DNA   length = 20
FEATURE              Location/Qualifiers
misc_feature         1..20
```

```
                    note = Sequence used in the synthesis of sub-barcode
                     molecule library
source              1..20
                    mol_type = other DNA
                    organism = synthetic construct
SEQUENCE: 106
ccggggatag actcctcgac                                                    20

SEQ ID NO: 107      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 107
ccgtggatag actcctcgac                                                    20

SEQ ID NO: 108      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 108
cctaggatag actcctcgac                                                    20

SEQ ID NO: 109      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 109
cctcggatag actcctcgac                                                    20

SEQ ID NO: 110      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 110
cctgggatag actcctcgac                                                    20

SEQ ID NO: 111      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 111
ccttggatag actcctcgac                                                    20

SEQ ID NO: 112      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 112
cgaaggatag actcctcgac                                                    20

SEQ ID NO: 113      moltype = DNA  length = 20
FEATURE             Location/Qualifiers
misc_feature        1..20
                    note = Sequence used in the synthesis of sub-barcode
                     molecule library
```

```
source                  1..20
                        mol_type = other DNA
                        organism = synthetic construct
SEQUENCE: 113
cgacggatag actcctcgac                                                   20

SEQ ID NO: 114          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 114
cgagggatag actcctcgac                                                   20

SEQ ID NO: 115          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 115
cgatggatag actcctcgac                                                   20

SEQ ID NO: 116          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 116
cgcaggatag actcctcgac                                                   20

SEQ ID NO: 117          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 117
cgccggatag actcctcgac                                                   20

SEQ ID NO: 118          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 118
cgcgggatag actcctcgac                                                   20

SEQ ID NO: 119          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 119
cgctggatag actcctcgac                                                   20

SEQ ID NO: 120          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
```

```
                        organism = synthetic construct
SEQUENCE: 120
cggaggatag actcctcgac                                                   20

SEQ ID NO: 121          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 121
cggcggatag actcctcgac                                                   20

SEQ ID NO: 122          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 122
cgggggatag actcctcgac                                                   20

SEQ ID NO: 123          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 123
cggtggatag actcctcgac                                                   20

SEQ ID NO: 124          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 124
cgtaggatag actcctcgac                                                   20

SEQ ID NO: 125          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 125
cgtcggatag actcctcgac                                                   20

SEQ ID NO: 126          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 126
cgtgggatag actcctcgac                                                   20

SEQ ID NO: 127          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 127
```

```
cgttggatag actcctcgac                                                  20

SEQ ID NO: 128         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 128
ctaaggatag actcctcgac                                                  20

SEQ ID NO: 129         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 129
ctacggatag actcctcgac                                                  20

SEQ ID NO: 130         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 130
ctagggatag actcctcgac                                                  20

SEQ ID NO: 131         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 131
ctatggatag actcctcgac                                                  20

SEQ ID NO: 132         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 132
ctcaggatag actcctcgac                                                  20

SEQ ID NO: 133         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 133
ctccggatag actcctcgac                                                  20

SEQ ID NO: 134         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 134
ctcgggatag actcctcgac                                                  20
```

```
SEQ ID NO: 135            moltype = DNA   length = 20
FEATURE                   Location/Qualifiers
misc_feature              1..20
                          note = Sequence used in the synthesis of sub-barcode
                          molecule library
source                    1..20
                          mol_type = other DNA
                          organism = synthetic construct
SEQUENCE: 135
ctctggatag actcctcgac                                                     20

SEQ ID NO: 136            moltype = DNA   length = 20
FEATURE                   Location/Qualifiers
misc_feature              1..20
                          note = Sequence used in the synthesis of sub-barcode
                          molecule library
source                    1..20
                          mol_type = other DNA
                          organism = synthetic construct
SEQUENCE: 136
ctgaggatag actcctcgac                                                     20

SEQ ID NO: 137            moltype = DNA   length = 20
FEATURE                   Location/Qualifiers
misc_feature              1..20
                          note = Sequence used in the synthesis of sub-barcode
                          molecule library
source                    1..20
                          mol_type = other DNA
                          organism = synthetic construct
SEQUENCE: 137
ctgcggatag actcctcgac                                                     20

SEQ ID NO: 138            moltype = DNA   length = 20
FEATURE                   Location/Qualifiers
misc_feature              1..20
                          note = Sequence used in the synthesis of sub-barcode
                          molecule library
source                    1..20
                          mol_type = other DNA
                          organism = synthetic construct
SEQUENCE: 138
ctgggatag actcctcgac                                                      20

SEQ ID NO: 139            moltype = DNA   length = 20
FEATURE                   Location/Qualifiers
misc_feature              1..20
                          note = Sequence used in the synthesis of sub-barcode
                          molecule library
source                    1..20
                          mol_type = other DNA
                          organism = synthetic construct
SEQUENCE: 139
ctgtggatag actcctcgac                                                     20

SEQ ID NO: 140            moltype = DNA   length = 20
FEATURE                   Location/Qualifiers
misc_feature              1..20
                          note = Sequence used in the synthesis of sub-barcode
                          molecule library
source                    1..20
                          mol_type = other DNA
                          organism = synthetic construct
SEQUENCE: 140
cttaggatag actcctcgac                                                     20

SEQ ID NO: 141            moltype = DNA   length = 20
FEATURE                   Location/Qualifiers
misc_feature              1..20
                          note = Sequence used in the synthesis of sub-barcode
                          molecule library
source                    1..20
                          mol_type = other DNA
                          organism = synthetic construct
SEQUENCE: 141
cttcggatag actcctcgac                                                     20

SEQ ID NO: 142            moltype = DNA   length = 20
FEATURE                   Location/Qualifiers
```

```
misc_feature              1..20
                          note = Sequence used in the synthesis of sub-barcode
                           molecule library
source                    1..20
                          mol_type = other DNA
                          organism = synthetic construct
SEQUENCE: 142
cttgggatag actcctcgac                                                   20

SEQ ID NO: 143            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 143
ctttggatag actcctcgac                                                   20

SEQ ID NO: 144            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 144
gaaaggatag actcctcgac                                                   20

SEQ ID NO: 145            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 145
gaacggatag actcctcgac                                                   20

SEQ ID NO: 146            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 146
gaagggatag actcctcgac                                                   20

SEQ ID NO: 147            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 147
gaatggatag actcctcgac                                                   20

SEQ ID NO: 148            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 148
gacaggatag actcctcgac                                                   20

SEQ ID NO: 149            moltype = DNA   length = 20
FEATURE                   Location/Qualifiers
misc_feature              1..20
                          note = Sequence used in the synthesis of sub-barcode
```

```
                              molecule library
source                        1..20
                              mol_type = other DNA
                              organism = synthetic construct
SEQUENCE: 149
gaccggatag actcctcgac                                                   20

SEQ ID NO: 150                moltype = DNA   length = 20
FEATURE                       Location/Qualifiers
misc_feature                  1..20
                              note = Sequence used in the synthesis of sub-barcode
                              molecule library
source                        1..20
                              mol_type = other DNA
                              organism = synthetic construct
SEQUENCE: 150
gacgggatag actcctcgac                                                   20

SEQ ID NO: 151                moltype = DNA   length = 20
FEATURE                       Location/Qualifiers
misc_feature                  1..20
                              note = Sequence used in the synthesis of sub-barcode
                              molecule library
source                        1..20
                              mol_type = other DNA
                              organism = synthetic construct
SEQUENCE: 151
gactggatag actcctcgac                                                   20

SEQ ID NO: 152                moltype = DNA   length = 20
FEATURE                       Location/Qualifiers
misc_feature                  1..20
                              note = Sequence used in the synthesis of sub-barcode
                              molecule library
source                        1..20
                              mol_type = other DNA
                              organism = synthetic construct
SEQUENCE: 152
gagaggatag actcctcgac                                                   20

SEQ ID NO: 153                moltype = DNA   length = 20
FEATURE                       Location/Qualifiers
misc_feature                  1..20
                              note = Sequence used in the synthesis of sub-barcode
                              molecule library
source                        1..20
                              mol_type = other DNA
                              organism = synthetic construct
SEQUENCE: 153
gagcggatag actcctcgac                                                   20

SEQ ID NO: 154                moltype = DNA   length = 20
FEATURE                       Location/Qualifiers
misc_feature                  1..20
                              note = Sequence used in the synthesis of sub-barcode
                              molecule library
source                        1..20
                              mol_type = other DNA
                              organism = synthetic construct
SEQUENCE: 154
gaggggatag actcctcgac                                                   20

SEQ ID NO: 155                moltype = DNA   length = 20
FEATURE                       Location/Qualifiers
misc_feature                  1..20
                              note = Sequence used in the synthesis of sub-barcode
                              molecule library
source                        1..20
                              mol_type = other DNA
                              organism = synthetic construct
SEQUENCE: 155
gagtggatag actcctcgac                                                   20

SEQ ID NO: 156                moltype = DNA   length = 20
FEATURE                       Location/Qualifiers
misc_feature                  1..20
                              note = Sequence used in the synthesis of sub-barcode
                              molecule library
source                        1..20
```

```
                        mol_type = other DNA
                        organism = synthetic construct
SEQUENCE: 156
gataggatag actcctcgac                                                   20

SEQ ID NO: 158          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 157
gatcggatag actcctcgac                                                   20

SEQ ID NO: 158          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 158
gatgggatag actcctcgac                                                   20

SEQ ID NO: 159          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 159
gattggatag actcctcgac                                                   20

SEQ ID NO: 160          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 160
gcaaggatag actcctcgac                                                   20

SEQ ID NO: 161          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 161
gcacggatag actcctcgac                                                   20

SEQ ID NO: 162          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 162
gcagggatag actcctcgac                                                   20

SEQ ID NO: 163          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
```

-continued

```
SEQUENCE: 163
gcatggatag actcctcgac                                              20

SEQ ID NO: 164          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 164
gccaggatag actcctcgac                                              20

SEQ ID NO: 165          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 165
gcccggatag actcctcgac                                              20

SEQ ID NO: 166          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 166
gccgggatag actcctcgac                                              20

SEQ ID NO: 167          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 167
gcctggatag actcctcgac                                              20

SEQ ID NO: 168          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 168
gcgaggatag actcctcgac                                              20

SEQ ID NO: 169          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 169
gcgcggatag actcctcgac                                              20

SEQ ID NO: 170          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 170
gcggggatag actcctcgac                                              20
```

```
SEQ ID NO: 171         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 171
gcgtggatag actcctcgac                                                20

SEQ ID NO: 172         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 172
gctaggatag actcctcgac                                                20

SEQ ID NO: 173         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 173
gctcggatag actcctcgac                                                20

SEQ ID NO: 174         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 174
gctgggatag actcctcgac                                                20

SEQ ID NO: 175         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 175
gcttggatag actcctcgac                                                20

SEQ ID NO: 176         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 176
ggaaggatag actcctcgac                                                20

SEQ ID NO: 177         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 177
ggacggatag actcctcgac                                                20

SEQ ID NO: 178         moltype = DNA  length = 20
```

```
FEATURE          Location/Qualifiers
misc_feature     1..20
                 note = Sequence used in the synthesis of sub-barcode
                 molecule library
source           1..20
                 mol_type = other DNA
                 organism = synthetic construct
SEQUENCE: 178
ggagggatag actcctcgac                                              20

SEQ ID NO: 179   moltype = DNA  length = 20
FEATURE          Location/Qualifiers
misc_feature     1..20
                 note = Sequence used in the synthesis of sub-barcode
                 molecule library
source           1..20
                 mol_type = other DNA
                 organism = synthetic construct
SEQUENCE: 179
ggatggatag actcctcgac                                              20

SEQ ID NO: 180   moltype = DNA  length = 20
FEATURE          Location/Qualifiers
misc_feature     1..20
                 note = Sequence used in the synthesis of sub-barcode
                 molecule library
source           1..20
                 mol_type = other DNA
                 organism = synthetic construct
SEQUENCE: 180
ggcaggatag actcctcgac                                              20

SEQ ID NO: 181   moltype = DNA  length = 20
FEATURE          Location/Qualifiers
misc_feature     1..20
                 note = Sequence used in the synthesis of sub-barcode
                 molecule library
source           1..20
                 mol_type = other DNA
                 organism = synthetic construct
SEQUENCE: 181
ggccggatag actcctcgac                                              20

SEQ ID NO: 182   moltype = DNA  length = 20
FEATURE          Location/Qualifiers
misc_feature     1..20
                 note = Sequence used in the synthesis of sub-barcode
                 molecule library
source           1..20
                 mol_type = other DNA
                 organism = synthetic construct
SEQUENCE: 182
ggcgggatag actcctcgac                                              20

SEQ ID NO: 183   moltype = DNA  length = 20
FEATURE          Location/Qualifiers
misc_feature     1..20
                 note = Sequence used in the synthesis of sub-barcode
                 molecule library
source           1..20
                 mol_type = other DNA
                 organism = synthetic construct
SEQUENCE: 183
ggctggatag actcctcgac                                              20

SEQ ID NO: 184   moltype = DNA  length = 20
FEATURE          Location/Qualifiers
misc_feature     1..20
                 note = Sequence used in the synthesis of sub-barcode
                 molecule library
source           1..20
                 mol_type = other DNA
                 organism = synthetic construct
SEQUENCE: 184
gggaggatag actcctcgac                                              20

SEQ ID NO: 185   moltype = DNA  length = 20
FEATURE          Location/Qualifiers
misc_feature     1..20
```

```
                    note = Sequence used in the synthesis of sub-barcode
                     molecule library
source              1..20
                    mol_type = other DNA
                    organism = synthetic construct
SEQUENCE: 185
gggcggatag actcctcgac                                                   20

SEQ ID NO: 186      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 186
gggtggatag actcctcgac                                                   20

SEQ ID NO: 187      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 187
ggtaggatag actcctcgac                                                   20

SEQ ID NO: 188      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 188
ggtcggatag actcctcgac                                                   20

SEQ ID NO: 189      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 189
ggtgggatag actcctcgac                                                   20

SEQ ID NO: 190      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 190
ggttggatag actcctcgac                                                   20

SEQ ID NO: 191      moltype = DNA  length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 191
gtaaggatag actcctcgac                                                   20

SEQ ID NO: 192      moltype = DNA  length = 20
FEATURE             Location/Qualifiers
misc_feature        1..20
                    note = Sequence used in the synthesis of sub-barcode
                     molecule library
```

| | |
|---|---|
| source | 1..20<br>mol_type = other DNA<br>organism = synthetic construct |
| SEQUENCE: 192 | |
| gtacggatag actcctcgac | 20 |
| SEQ ID NO: 193<br>FEATURE<br>misc_feature | moltype = DNA length = 20<br>Location/Qualifiers<br>1..20<br>note = Sequence used in the synthesis of sub-barcode<br>molecule library |
| source | 1..20<br>mol_type = other DNA<br>organism = synthetic construct |
| SEQUENCE: 193 | |
| gtagggatag actcctcgac | 20 |
| SEQ ID NO: 194<br>FEATURE<br>misc_feature | moltype = DNA length = 20<br>Location/Qualifiers<br>1..20<br>note = Sequence used in the synthesis of sub-barcode<br>molecule library |
| source | 1..20<br>mol_type = other DNA<br>organism = synthetic construct |
| SEQUENCE: 194 | |
| gtatggatag actcctcgac | 20 |
| SEQ ID NO: 195<br>FEATURE<br>misc_feature | moltype = DNA length = 20<br>Location/Qualifiers<br>1..20<br>note = Sequence used in the synthesis of sub-barcode<br>molecule library |
| source | 1..20<br>mol_type = other DNA<br>organism = synthetic construct |
| SEQUENCE: 195 | |
| gtcaggatag actcctcgac | 20 |
| SEQ ID NO: 196<br>FEATURE<br>misc_feature | moltype = DNA length = 20<br>Location/Qualifiers<br>1..20<br>note = Sequence used in the synthesis of sub-barcode<br>molecule library |
| source | 1..20<br>mol_type = other DNA<br>organism = synthetic construct |
| SEQUENCE: 196 | |
| gtccggatag actcctcgac | 20 |
| SEQ ID NO: 197<br>FEATURE<br>misc_feature | moltype = DNA length = 20<br>Location/Qualifiers<br>1..20<br>note = Sequence used in the synthesis of sub-barcode<br>molecule library |
| source | 1..20<br>mol_type = other DNA<br>organism = synthetic construct |
| SEQUENCE: 197 | |
| gtcgggatag actcctcgac | 20 |
| SEQ ID NO: 198<br>FEATURE<br>misc_feature | moltype = DNA length = 20<br>Location/Qualifiers<br>1..20<br>note = Sequence used in the synthesis of sub-barcode<br>molecule library |
| source | 1..20<br>mol_type = other DNA<br>organism = synthetic construct |
| SEQUENCE: 198 | |
| gtctggatag actcctcgac | 20 |
| SEQ ID NO: 199<br>FEATURE<br>misc_feature | moltype = DNA length = 20<br>Location/Qualifiers<br>1..20<br>note = Sequence used in the synthesis of sub-barcode<br>molecule library |
| source | 1..20<br>mol_type = other DNA |

```
                           organism = synthetic construct
SEQUENCE: 199
gtgaggatag actcctcgac                                                   20

SEQ ID NO: 200         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 200
gtgcggatag actcctcgac                                                   20

SEQ ID NO: 201         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 201
gtggggatag actcctcgac                                                   20

SEQ ID NO: 202         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 202
gtgtggatag actcctcgac                                                   20

SEQ ID NO: 203         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 203
gttaggatag actcctcgac                                                   20

SEQ ID NO: 204         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 204
gttcggatag actcctcgac                                                   20

SEQ ID NO: 205         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 205
gttgggatag actcctcgac                                                   20

SEQ ID NO: 206         moltype = DNA  length = 20
FEATURE                Location/Qualifiers
misc_feature           1..20
                       note = Sequence used in the synthesis of sub-barcode
                        molecule library
source                 1..20
                       mol_type = other DNA
                       organism = synthetic construct
SEQUENCE: 206
```

```
gtttggatag actcctcgac                                               20

SEQ ID NO: 207          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 207
taaaggatag actcctcgac                                               20

SEQ ID NO: 208          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 208
taacggatag actcctcgac                                               20

SEQ ID NO: 209          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 209
taagggatag actcctcgac                                               20

SEQ ID NO: 210          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 210
taatggatag actcctcgac                                               20

SEQ ID NO: 211          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 211
tacaggatag actcctcgac                                               20

SEQ ID NO: 212          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 212
taccggatag actcctcgac                                               20

SEQ ID NO: 213          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 213
tacgggatag actcctcgac                                               20
```

```
SEQ ID NO: 214           moltype = DNA   length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 214
tactggatag actcctcgac                                                   20

SEQ ID NO: 215           moltype = DNA   length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 215
tagaggatag actcctcgac                                                   20

SEQ ID NO: 216           moltype = DNA   length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 216
tagcggatag actcctcgac                                                   20

SEQ ID NO: 217           moltype = DNA   length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 217
taggggatag actcctcgac                                                   20

SEQ ID NO: 218           moltype = DNA   length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 218
tagtggatag actcctcgac                                                   20

SEQ ID NO: 219           moltype = DNA   length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 219
tataggatag actcctcgac                                                   20

SEQ ID NO: 220           moltype = DNA   length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 220
tatcggatag actcctcgac                                                   20

SEQ ID NO: 221           moltype = DNA   length = 20
FEATURE                  Location/Qualifiers
```

```
misc_feature            1..20
                        note = Sequence used in the synthesis of sub-barcode
                         molecule library
source                  1..20
                        mol_type = other DNA
                        organism = synthetic construct
SEQUENCE: 221
tatgggatag actcctcgac                                                    20

SEQ ID NO: 222          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 222
tattggatag actcctcgac                                                    20

SEQ ID NO: 223          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 223
tcaaggatag actcctcgac                                                    20

SEQ ID NO: 224          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 224
tcacggatag actcctcgac                                                    20

SEQ ID NO: 225          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 225
tcagggatag actcctcgac                                                    20

SEQ ID NO: 226          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 226
tcatggatag actcctcgac                                                    20

SEQ ID NO: 227          moltype = DNA  length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 227
tccaggatag actcctcgac                                                    20

SEQ ID NO: 228          moltype = DNA  length = 20
FEATURE                 Location/Qualifiers
misc_feature            1..20
                        note = Sequence used in the synthesis of sub-barcode
```

```
                         molecule library
source                   1..20
                         mol_type = other DNA
                         organism = synthetic construct
SEQUENCE: 228
tcccggatag actcctcgac                                                    20

SEQ ID NO: 229           moltype = DNA   length = 20
FEATURE                  Location/Qualifiers
misc_feature             1..20
                         note = Sequence used in the synthesis of sub-barcode
                         molecule library
source                   1..20
                         mol_type = other DNA
                         organism = synthetic construct
SEQUENCE: 229
tccgggatag actcctcgac                                                    20

SEQ ID NO: 230           moltype = DNA   length = 20
FEATURE                  Location/Qualifiers
misc_feature             1..20
                         note = Sequence used in the synthesis of sub-barcode
                         molecule library
source                   1..20
                         mol_type = other DNA
                         organism = synthetic construct
SEQUENCE: 230
tcctggatag actcctcgac                                                    20

SEQ ID NO: 231           moltype = DNA   length = 20
FEATURE                  Location/Qualifiers
misc_feature             1..20
                         note = Sequence used in the synthesis of sub-barcode
                         molecule library
source                   1..20
                         mol_type = other DNA
                         organism = synthetic construct
SEQUENCE: 231
tcgaggatag actcctcgac                                                    20

SEQ ID NO: 232           moltype = DNA   length = 20
FEATURE                  Location/Qualifiers
misc_feature             1..20
                         note = Sequence used in the synthesis of sub-barcode
                         molecule library
source                   1..20
                         mol_type = other DNA
                         organism = synthetic construct
SEQUENCE: 232
tcgcggatag actcctcgac                                                    20

SEQ ID NO: 233           moltype = DNA   length = 20
FEATURE                  Location/Qualifiers
misc_feature             1..20
                         note = Sequence used in the synthesis of sub-barcode
                         molecule library
source                   1..20
                         mol_type = other DNA
                         organism = synthetic construct
SEQUENCE: 233
tcggggatag actcctcgac                                                    20

SEQ ID NO: 234           moltype = DNA   length = 20
FEATURE                  Location/Qualifiers
misc_feature             1..20
                         note = Sequence used in the synthesis of sub-barcode
                         molecule library
source                   1..20
                         mol_type = other DNA
                         organism = synthetic construct
SEQUENCE: 234
tcgtggatag actcctcgac                                                    20

SEQ ID NO: 235           moltype = DNA   length = 20
FEATURE                  Location/Qualifiers
misc_feature             1..20
                         note = Sequence used in the synthesis of sub-barcode
                         molecule library
source                   1..20
```

```
                          mol_type = other DNA
                          organism = synthetic construct
SEQUENCE: 235
tctaggatag actcctcgac                                                  20

SEQ ID NO: 236            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 236
tctcggatag actcctcgac                                                  20

SEQ ID NO: 237            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 237
tctgggatag actcctcgac                                                  20

SEQ ID NO: 238            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 238
tcttggatag actcctcgac                                                  20

SEQ ID NO: 239            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 239
tgaaggatag actcctcgac                                                  20

SEQ ID NO: 240            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 240
tgacggatag actcctcgac                                                  20

SEQ ID NO: 241            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
SEQUENCE: 241
tgagggatag actcctcgac                                                  20

SEQ ID NO: 242            moltype = DNA   length = 20
FEATURE                   Location/Qualifiers
misc_feature              1..20
                          note = Sequence used in the synthesis of sub-barcode
                           molecule library
source                    1..20
                          mol_type = other DNA
                          organism = synthetic construct
```

```
SEQUENCE: 242
tgatggatag actcctcgac                                                    20

SEQ ID NO: 243          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 243
tgcaggatag actcctcgac                                                    20

SEQ ID NO: 244          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 244
tgccggatag actcctcgac                                                    20

SEQ ID NO: 245          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 245
tgcgggatag actcctcgac                                                    20

SEQ ID NO: 246          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 246
tgctggatag actcctcgac                                                    20

SEQ ID NO: 247          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 247
tggaggatag actcctcgac                                                    20

SEQ ID NO: 248          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 248
tggcggatag actcctcgac                                                    20

SEQ ID NO: 249          moltype = DNA   length = 20
FEATURE                 Location/Qualifiers
misc_feature            1..20
                        note = Sequence used in the synthesis of sub-barcode
                         molecule library
source                  1..20
                        mol_type = other DNA
                        organism = synthetic construct
SEQUENCE: 249
tgggggatag actcctcgac                                                    20
```

```
SEQ ID NO: 250           moltype = DNA  length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 250
tggtggatag actcctcgac                                                 20

SEQ ID NO: 251           moltype = DNA  length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 251
tgtaggatag actcctcgac                                                 20

SEQ ID NO: 252           moltype = DNA  length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 252
tgtcggatag actcctcgac                                                 20

SEQ ID NO: 253           moltype = DNA  length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 253
tgtgggatag actcctcgac                                                 20

SEQ ID NO: 254           moltype = DNA  length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 254
tgttggatag actcctcgac                                                 20

SEQ ID NO: 255           moltype = DNA  length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 255
ttaaggatag actcctcgac                                                 20

SEQ ID NO: 256           moltype = DNA  length = 20
FEATURE                  Location/Qualifiers
misc_feature             1..20
                         note = Sequence used in the synthesis of sub-barcode
                          molecule library
source                   1..20
                         mol_type = other DNA
                         organism = synthetic construct
SEQUENCE: 256
ttacggatag actcctcgac                                                 20

SEQ ID NO: 257           moltype = DNA  length = 20
```

| | | |
|---|---|---|
| FEATURE | Location/Qualifiers | |
| misc_feature | 1..20 | |
| | note = Sequence used in the synthesis of sub-barcode molecule library | |
| source | 1..20 | |
| | mol_type = other DNA | |
| | organism = synthetic construct | |
| SEQUENCE: 257 | | |
| ttagggatag actcctcgac | | 20 |
| | | |
| SEQ ID NO: 258 | moltype = DNA length = 20 | |
| FEATURE | Location/Qualifiers | |
| misc_feature | 1..20 | |
| | note = Sequence used in the synthesis of sub-barcode molecule library | |
| source | 1..20 | |
| | mol_type = other DNA | |
| | organism = synthetic construct | |
| SEQUENCE: 258 | | |
| ttatggatag actcctcgac | | 20 |
| | | |
| SEQ ID NO: 259 | moltype = DNA length = 20 | |
| FEATURE | Location/Qualifiers | |
| misc_feature | 1..20 | |
| | note = Sequence used in the synthesis of sub-barcode molecule library | |
| source | 1..20 | |
| | mol_type = other DNA | |
| | organism = synthetic construct | |
| SEQUENCE: 259 | | |
| ttcaggatag actcctcgac | | 20 |
| | | |
| SEQ ID NO: 260 | moltype = DNA length = 20 | |
| FEATURE | Location/Qualifiers | |
| misc_feature | 1..20 | |
| | note = Sequence used in the synthesis of sub-barcode molecule library | |
| source | 1..20 | |
| | mol_type = other DNA | |
| | organism = synthetic construct | |
| SEQUENCE: 260 | | |
| ttccggatag actcctcgac | | 20 |
| | | |
| SEQ ID NO: 261 | moltype = DNA length = 20 | |
| FEATURE | Location/Qualifiers | |
| misc_feature | 1..20 | |
| | note = Sequence used in the synthesis of sub-barcode molecule library | |
| source | 1..20 | |
| | mol_type = other DNA | |
| | organism = synthetic construct | |
| SEQUENCE: 261 | | |
| ttcgggatag actcctcgac | | 20 |
| | | |
| SEQ ID NO: 262 | moltype = DNA length = 20 | |
| FEATURE | Location/Qualifiers | |
| misc_feature | 1..20 | |
| | note = Sequence used in the synthesis of sub-barcode molecule library | |
| source | 1..20 | |
| | mol_type = other DNA | |
| | organism = synthetic construct | |
| SEQUENCE: 262 | | |
| ttctggatag actcctcgac | | 20 |
| | | |
| SEQ ID NO: 263 | moltype = DNA length = 20 | |
| FEATURE | Location/Qualifiers | |
| misc_feature | 1..20 | |
| | note = Sequence used in the synthesis of sub-barcode molecule library | |
| source | 1..20 | |
| | mol_type = other DNA | |
| | organism = synthetic construct | |
| SEQUENCE: 263 | | |
| ttgaggatag actcctcgac | | 20 |
| | | |
| SEQ ID NO: 264 | moltype = DNA length = 20 | |
| FEATURE | Location/Qualifiers | |
| misc_feature | 1..20 | |

```
                    note = Sequence used in the synthesis of sub-barcode
                     molecule library
source              1..20
                    mol_type = other DNA
                    organism = synthetic construct
SEQUENCE: 264
ttgcggatag actcctcgac                                                   20

SEQ ID NO: 265      moltype = DNA   length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 265
ttggggatag actcctcgac                                                   20

SEQ ID NO: 266      moltype = DNA   length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 266
ttgtggatag actcctcgac                                                   20

SEQ ID NO: 267      moltype = DNA   length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 267
tttaggatag actcctcgac                                                   20

SEQ ID NO: 268      moltype = DNA   length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 268
tttcggatag actcctcgac                                                   20

SEQ ID NO: 269      moltype = DNA   length = 20
FEATURE             Location/Qualifiers
misc_feature        1..20
                    note = Sequence used in the synthesis of sub-barcode
                     molecule library
source              1..20
                    mol_type = other DNA
                    organism = synthetic construct
SEQUENCE: 269
tttgggatag actcctcgac                                                   20

SEQ ID NO: 270      moltype = DNA   length = 47
FEATURE             Location/Qualifiers
misc_feature        1..47
                    note = Primer
source              1..47
                    mol_type = other DNA
                    organism = synthetic construct
SEQUENCE: 270
taatacgact cactataggg agataggacg atacgagtgt gtactcg                     47

SEQ ID NO: 271      moltype = DNA   length = 31
FEATURE             Location/Qualifiers
misc_feature        1..31
                    note = Primer
source              1..31
                    mol_type = other DNA
```

```
                            organism = synthetic construct
SEQUENCE: 271
ctgtcaaggt agactagcat gctcccatac g                                    31

SEQ ID NO: 272          moltype = DNA   length = 24
FEATURE                 Location/Qualifiers
misc_feature            1..24
                        note = Primer
source                  1..24
                        mol_type = other DNA
                        organism = synthetic construct
SEQUENCE: 272
ctgtcaaggt agactagcat gctc                                            24

SEQ ID NO: 273          moltype = DNA   length = 60
FEATURE                 Location/Qualifiers
misc_feature            1..60
                        note = Adaptor oligonucleotide
source                  1..60
                        mol_type = other DNA
                        organism = synthetic construct
SEQUENCE: 273
cctgactgct cgtcagttga ttaagtactc tgtgagatga tgatcagtag agcgagtcgt      60

SEQ ID NO: 274          moltype = DNA   length = 50
FEATURE                 Location/Qualifiers
misc_feature            1..50
                        note = Primer
source                  1..50
                        mol_type = other DNA
                        organism = synthetic construct
SEQUENCE: 274
caccgagatc tacactcttt ccctacacga cgctcttccg atcttgacct                 50

SEQ ID NO: 275          moltype = DNA   length = 59
FEATURE                 Location/Qualifiers
misc_feature            1..59
                        note = Synthetic template
misc_feature            22..39
                        note = n is a, c, g, or t
source                  1..59
                        mol_type = other DNA
                        organism = synthetic construct
SEQUENCE: 275
atgatcagta gagcgagtcg tnnnnnnnnn nnnnnnnnnt gctacgactt ccgagtcca       59

SEQ ID NO: 276          moltype = DNA   length = 27
FEATURE                 Location/Qualifiers
misc_feature            1..27
                        note = Primer
source                  1..27
                        mol_type = other DNA
                        organism = synthetic construct
SEQUENCE: 276
gctctactga tcattggact cggaagt                                         27

SEQ ID NO: 277          moltype = DNA   length = 28
FEATURE                 Location/Qualifiers
misc_feature            1..28
                        note = Primer
source                  1..28
                        mol_type = other DNA
                        organism = synthetic construct
SEQUENCE: 277
tccgatcttg gactcggaag tcgtagca                                        28

SEQ ID NO: 278          moltype = DNA   length = 39
FEATURE                 Location/Qualifiers
misc_feature            1..39
                        note = Primer
source                  1..39
                        mol_type = other DNA
                        organism = synthetic construct
SEQUENCE: 278
acactctttc cctacacgac gctcttccga tcttgacct                            39

SEQ ID NO: 279          moltype = DNA   length = 59
FEATURE                 Location/Qualifiers
misc_feature            1..59
```

```
                        note = BRCA1 adaptor oligonucleotide
source                  1..59
                        mol_type = other DNA
                        organism = synthetic construct
SEQUENCE: 279
cctgactgct cgtcagttga ttaagtactc tgtgagatgc ttggcccctc ttcggtaac    59

SEQ ID NO: 280          moltype = DNA  length = 60
FEATURE                 Location/Qualifiers
misc_feature            1..60
                        note = BRCA1 adaptor oligonucleotide
source                  1..60
                        mol_type = other DNA
                        organism = synthetic construct
SEQUENCE: 280
cctgactgct cgtcagttga ttaagtactc tgtgagatgc tgggagctca aaagatggct   60

SEQ ID NO: 281          moltype = DNA  length = 58
FEATURE                 Location/Qualifiers
misc_feature            1..58
                        note = BRCA1 adaptor oligonucleotide
source                  1..58
                        mol_type = other DNA
                        organism = synthetic construct
SEQUENCE: 281
cctgactgct cgtcagttga ttaagtactc tgtgagatgc agctgggctc aaaggacc     58

SEQ ID NO: 282          moltype = DNA  length = 60
FEATURE                 Location/Qualifiers
misc_feature            1..60
                        note = BRCA1 adaptor oligonucleotide
source                  1..60
                        mol_type = other DNA
                        organism = synthetic construct
SEQUENCE: 282
cctgactgct cgtcagttga ttaagtactc tgtgagatgc agacaaattc cccagcaggt   60

SEQ ID NO: 283          moltype = DNA  length = 58
FEATURE                 Location/Qualifiers
misc_feature            1..58
                        note = BRCA1 adaptor oligonucleotide
source                  1..58
                        mol_type = other DNA
                        organism = synthetic construct
SEQUENCE: 283
cctgactgct cgtcagttga ttaagtactc tgtgagatgc atggtgtgaa cccgggag     58

SEQ ID NO: 284          moltype = DNA  length = 60
FEATURE                 Location/Qualifiers
misc_feature            1..60
                        note = BRCA1 adaptor oligonucleotide
source                  1..60
                        mol_type = other DNA
                        organism = synthetic construct
SEQUENCE: 284
cctgactgct cgtcagttga ttaagtactc tgtgagatgc ccaaatccca agtcgtgtgt   60

SEQ ID NO: 285          moltype = DNA  length = 60
FEATURE                 Location/Qualifiers
misc_feature            1..60
                        note = BRCA1 adaptor oligonucleotide
source                  1..60
                        mol_type = other DNA
                        organism = synthetic construct
SEQUENCE: 285
cctgactgct cgtcagttga ttaagtactc tgtgagatgc tcatccctgg ttccttgagg   60

SEQ ID NO: 286          moltype = DNA  length = 60
FEATURE                 Location/Qualifiers
misc_feature            1..60
                        note = HLA-A adaptor oligonucleotide
source                  1..60
                        mol_type = other DNA
                        organism = synthetic construct
SEQUENCE: 286
cctgactgct cgtcagttga ttaagtactc tgtgaaaacg gcctctgtgg ggagaagcaa   60

SEQ ID NO: 287          moltype = DNA  length = 59
FEATURE                 Location/Qualifiers
```

```
misc_feature          1..59
                      note = HLA-A adaptor oligonucleotide
source                1..59
                      mol_type = other DNA
                      organism = synthetic construct
SEQUENCE: 287
cctgactgct cgtcagttga ttaagtactc tgtgagatgc actgggctga ccgtggggt      59

SEQ ID NO: 288        moltype = DNA  length = 60
FEATURE               Location/Qualifiers
misc_feature          1..60
                      note = HLA-A adaptor oligonucleotide
source                1..60
                      mol_type = other DNA
                      organism = synthetic construct
SEQUENCE: 288
cctgactgct cgtcagttga ttaagtactc tgcctgaatg wtctgactct tcccgtmaga     60

SEQ ID NO: 289        moltype = DNA  length = 60
FEATURE               Location/Qualifiers
misc_feature          1..60
                      note = DQB1 adaptor oligonucleotide
source                1..60
                      mol_type = other DNA
                      organism = synthetic construct
SEQUENCE: 289
cctgactgct cgtcagttga ttaagtactc tgggatcccc gcagaggatt cgtgtacca     60

SEQ ID NO: 290        moltype = DNA  length = 60
FEATURE               Location/Qualifiers
misc_feature          1..60
                      note = DQB1 adaptor oligonucleotide
source                1..60
                      mol_type = other DNA
                      organism = synthetic construct
SEQUENCE: 290
cctgactgct cgtcagttga ttaagtactc tgtgagatgg agcccacagt gaccatctcc     60

SEQ ID NO: 291        moltype = DNA  length = 60
FEATURE               Location/Qualifiers
misc_feature          1..60
                      note = BRCA1 reverse primer
source                1..60
                      mol_type = other DNA
                      organism = synthetic construct
SEQUENCE: 291
cggtctcggc attcctgctg aaccgctctt ccgatctgtt ctgagacacc tgatgacctg     60

SEQ ID NO: 292        moltype = DNA  length = 57
FEATURE               Location/Qualifiers
misc_feature          1..57
                      note = BRCA1 reverse primer
source                1..57
                      mol_type = other DNA
                      organism = synthetic construct
SEQUENCE: 292
cggtctcggc attcctgctg aaccgctctt ccgatcttga acccaggagt ttgaggc        57

SEQ ID NO: 293        moltype = DNA  length = 60
FEATURE               Location/Qualifiers
misc_feature          1..60
                      note = BRCA1 reverse primer
source                1..60
                      mol_type = other DNA
                      organism = synthetic construct
SEQUENCE: 293
cggtctcggc attcctgctg aaccgctctt ccgatcttgg agctttatct gctctgtgat     60

SEQ ID NO: 294        moltype = DNA  length = 57
FEATURE               Location/Qualifiers
misc_feature          1..57
                      note = BRCA1 reverse primer
source                1..57
                      mol_type = other DNA
                      organism = synthetic construct
SEQUENCE: 294
cggtctcggc attcctgctg aaccgctctt ccgatctttc actgtgatgg ccaggat        57

SEQ ID NO: 295        moltype = DNA  length = 57
```

```
FEATURE              Location/Qualifiers
misc_feature         1..57
                     note = BRCA1 reverse primer
source               1..57
                     mol_type = other DNA
                     organism = synthetic construct
SEQUENCE: 295
cggtctcggc attcctgctg aaccgctctt ccgatcttga cccaagcaag cctaaag      57

SEQ ID NO: 296       moltype = DNA  length = 57
FEATURE              Location/Qualifiers
misc_feature         1..57
                     note = BRCA1 reverse primer
source               1..57
                     mol_type = other DNA
                     organism = synthetic construct
SEQUENCE: 296
cggtctcggc attcctgctg aaccgctctt ccgatcttgc cacagtagat gctcagt      57

SEQ ID NO: 297       moltype = DNA  length = 58
FEATURE              Location/Qualifiers
misc_feature         1..58
                     note = BRCA1 reverse primer
source               1..58
                     mol_type = other DNA
                     organism = synthetic construct
SEQUENCE: 297
cggtctcggc attcctgctg aaccgctctt ccgatctccc agcaaccatt tcatttca     58

SEQ ID NO: 298       moltype = DNA  length = 60
FEATURE              Location/Qualifiers
misc_feature         1..60
                     note = HLA-A reverse primer
source               1..60
                     mol_type = other DNA
                     organism = synthetic construct
SEQUENCE: 298
cggtctcggc attcctgctg aaccgctctt ccgatcttgg atctcggacc cggagactgt   60

SEQ ID NO: 299       moltype = DNA  length = 58
FEATURE              Location/Qualifiers
misc_feature         1..58
                     note = HLA-A reverse primer
source               1..58
                     mol_type = other DNA
                     organism = synthetic construct
SEQUENCE: 299
cggtctcggc attcctgctg aaccgctctt ccgatctccc tggtaccvgt gcgctgca     58

SEQ ID NO: 300       moltype = DNA  length = 60
FEATURE              Location/Qualifiers
misc_feature         1..60
                     note = HLA-A reverse primer
source               1..60
                     mol_type = other DNA
                     organism = synthetic construct
SEQUENCE: 300
cggtctcggc attcctgctg aaccgctctt ccgatctgac cctgctaaag gtctccagag   60

SEQ ID NO: 301       moltype = DNA  length = 57
FEATURE              Location/Qualifiers
misc_feature         1..57
                     note = HLA-A reverse primer
source               1..57
                     mol_type = other DNA
                     organism = synthetic construct
SEQUENCE: 301
cggtctcggc attcctgctg aaccgctctt ccgatctgac cctgctaaag gtcagag      57

SEQ ID NO: 302       moltype = DNA  length = 60
FEATURE              Location/Qualifiers
misc_feature         1..60
                     note = DQB1 reverse primer
source               1..60
                     mol_type = other DNA
                     organism = synthetic construct
SEQUENCE: 302
cggtctcggc attcctgctg aaccgctctt ccgatctagg acgctcacct ctccgctgca   60
```

```
SEQ ID NO: 303          moltype = DNA  length = 57
FEATURE                 Location/Qualifiers
misc_feature            1..57
                        note = DQB1 reverse primer
source                  1..57
                        mol_type = other DNA
                        organism = synthetic construct
SEQUENCE: 303
cggtctcggc attcctgctg aaccgctctt ccgatctctg gggtgctcca cgtggca        57

SEQ ID NO: 304          moltype = DNA  length = 82
FEATURE                 Location/Qualifiers
misc_feature            1..82
                        note = synthetic sequence
source                  1..82
                        mol_type = other DNA
                        organism = synthetic construct
SEQUENCE: 304
atacctgact gctcgtcagt tgagcgaatt ccgtatggtg gtacacacct acactactcg     60
gacgctcttc cgatcttgac ct                                              82

SEQ ID NO: 305          moltype = DNA  length = 25
FEATURE                 Location/Qualifiers
misc_feature            1..25
                        note = synthetic sequence
source                  1..25
                        mol_type = other DNA
                        organism = synthetic construct
SEQUENCE: 305
gctcaactga cgagcagtca ggtat                                           25

SEQ ID NO: 306          moltype = DNA  length = 82
FEATURE                 Location/Qualifiers
misc_feature            1..82
                        note = synthetic sequence
source                  1..82
                        mol_type = other DNA
                        organism = synthetic construct
SEQUENCE: 306
aggtcaagat cggaagagcg tccgagtagt gtaggtgtgt accaccatac ggaattcgct     60
caactgacga gcagtcaggt at                                              82

SEQ ID NO: 307          moltype = DNA  length = 20
FEATURE                 Location/Qualifiers
misc_feature            1..20
                        note = synthetic sequence
source                  1..20
                        mol_type = other DNA
                        organism = synthetic construct
SEQUENCE: 307
ggcccagcct acacacccat                                                 20

SEQ ID NO: 308          moltype = DNA  length = 20
FEATURE                 Location/Qualifiers
misc_feature            1..20
                        note = synthetic sequence
source                  1..20
                        mol_type = other DNA
                        organism = synthetic construct
SEQUENCE: 308
ttacaagaat tatacacctc                                                 20

SEQ ID NO: 309          moltype = DNA  length = 20
FEATURE                 Location/Qualifiers
misc_feature            1..20
                        note = synthetic sequence
source                  1..20
                        mol_type = other DNA
                        organism = synthetic construct
SEQUENCE: 309
ggcccaacct atacgcccat                                                 20

SEQ ID NO: 310          moltype = DNA  length = 20
FEATURE                 Location/Qualifiers
misc_feature            1..20
                        note = synthetic sequence
source                  1..20
                        mol_type = other DNA
                        organism = synthetic construct
```

```
SEQUENCE: 310
taaccttgt atttgaacac                                                  20

SEQ ID NO: 311          moltype = DNA  length = 20
FEATURE                 Location/Qualifiers
misc_feature            1..20
                        note = synthetic sequence
source                  1..20
                        mol_type = other DNA
                        organism = synthetic construct
SEQUENCE: 311
ctatccactg attaactgtg                                                 20

SEQ ID NO: 312          moltype = DNA  length = 20
FEATURE                 Location/Qualifiers
misc_feature            1..20
                        note = synthetic sequence
source                  1..20
                        mol_type = other DNA
                        organism = synthetic construct
SEQUENCE: 312
taatcgggcc attaagcgat                                                 20

SEQ ID NO: 313          moltype = DNA  length = 20
FEATURE                 Location/Qualifiers
misc_feature            1..20
                        note = synthetic sequence
source                  1..20
                        mol_type = other DNA
                        organism = synthetic construct
SEQUENCE: 313
caagtaattt gctggaccta                                                 20

SEQ ID NO: 314          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 314
taccagagat acttgc                                                     16

SEQ ID NO: 315          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 315
atatccagca aagt                                                       14

SEQ ID NO: 316          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 316
ttacaagaat tat                                                        13
```